US008183349B2

(12) United States Patent
Qiu et al.

(10) Patent No.: US 8,183,349 B2
(45) Date of Patent: May 22, 2012

(54) MARKERS OF XMRV INFECTION AND USES THEREOF

(75) Inventors: Xiaoxing Qiu, Gurnee, IL (US); John R. Hackett, Jr., Libertyville, IL (US); Ka-Cheung X. Luk, Lake Bluff, IL (US); Priscilla Swanson, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 12/828,161

(22) Filed: Jun. 30, 2010

(65) Prior Publication Data

US 2011/0137015 A1    Jun. 9, 2011

Related U.S. Application Data

(63) Continuation of application No. 61/221,752, filed on Jun. 30, 2009.

(60) Provisional application No. 61/305,604, filed on Feb. 18, 2010.

(51) Int. Cl.
*C07K 16/18* (2006.01)
(52) U.S. Cl. .................................................. 530/387.3
(58) Field of Classification Search .................... None
See application file for complete search history.

(56) References Cited

U.S. PATENT DOCUMENTS

2010/0166797 A1    7/2010    Silverman et al.

FOREIGN PATENT DOCUMENTS

| WO | WO2006/110589 | * | 10/2006 |
| WO | WO2010075414 | | 7/2010 |
| WO | WO2010148323 | | 10/2010 |
| WO | WO2010132886 | | 11/2010 |
| WO | WO2011002936 | | 1/2011 |
| WO | WO2011041350 | | 4/2011 |

OTHER PUBLICATIONS

Sequence alignment of SEQ ID No. 83 with SEQ ID No. 93 of Silverman et al. Jan. 2007.*
Sequence alignment of SEQ ID No. 84 with SEQ ID No. 92 of Silverman et al. Jan. 2007.*
Sequence alignment of SEQ ID No. 85 with SEQ ID No. 93 of Silverman et al. Jan. 2007.*
U.S. Appl. No. 12/828,161, filed Jun. 30, 2010.
Urisman et al., "Identification of a novel gammaretrovirus in prostate tumors of patients homozygous for R462Q RNASEL variant",*PloS Pathog.*, Mar. 2006; 2(3):e25.
Dong et al., "An Infectious retrovirus susceptible to an IFN antiviral pathway from human prostate tumors", *Proc Natl Acad Sci U.S.A.*, Jan. 30, 2007; 104(5):1655-60.
McCormick et al., "Quantification of reverse transcriptase in ALS and elimination of a novel retroviral candidate", *Neurology*, Jan. 22, 2008; 70(4):278-83.

Kim et al., "Integration site preference of xenotropic murine leukemia virus-related virus, a new human retrovirus associated with prostate cancer", *J Virol*, Oct. 2008; 82(20):9964-77.
Fischer et al., "Prevalence of human gammaretrovirus XMRV in sporadic prostate cancer", *J clin Virol.*, Nov. 2008; 43(3):277-83.
Knouf et al., "Multiple integrated copies and high-level production of the human retrovirus XMRV (Xenotropic Murine Leukemia Virus-Related Virus) from 22Rv1 prostate carcinoma cells", *J Virol.*, Jul. 2009; 83(14):7353-6.
Hong et al., "Fibrils of prostatic acid phosphatase fragments boost infections with XMRV (Xenotropic Murine Leukemia Virus-Related Virus), a human retrovirus associated with prostate cancer", *J Virol.*, Jul. 2009; 83(14):6995-7003.
Schlaberg et al., "XMRV is present in malignant Prostatic epithelium and is associated with prostate cancer, Eepecially high-grade tumors", *Proc Natl Acad Sci U.S.A.*, Sep. 22, 2009; 106(38):16351-6.
Lombardi et al., "Detection of an infectious, XRMV, in blood cells of patients with chronic fatigue syndrome", *Science*, Oct. 23, 2009; 326(5952):585-9.
Mikovits et al., "Response to comments on Detection of an infectious retrovirus, XMRV, in blood cells of patients with chronic fatigue syndrome", *Science*, May 14, 2010; 328(5980):825-d.
Hohn et al., "Lack of evidence for xenotropic murine leukemia virus-related virus (XMRV) in German prostate cancer patients", *Retrovirology*, Oct. 16, 2009; 6:92.
Dong et al., "Androgen stimulates transcription and replication of xenotropic murine leukemia virus-related virus", *J Virol*, Feb. 2010; 84(3):1648-51.
Sakuma et al., "Xenotropic murine leukemia virus-related virus is susceptible to AZT", *Virology*, Feb. 5, 2010; 397(1):1-6.
Metzger et al., "The prostate cancer-associated human retrovirus XMRV lacks direct transforming activity but can induce low rates of transformation in cultured cells", *J Virol*, Feb. 2010; 84(4):1874-80.
Rodriguez et al., "Xenotropic murine leukemia virus-related virus establishes an efficient spreading infection and exhibits enhanced transcriptional activity in prostate carcinoma cell", *J Virol*, Mar. 2010; 84(5):2566-62.
Erlwein et al., "Failure to detect the novel retrovirus XMRV in chronic fatigue syndrome", *PloS One*, Jan. 6, 2010; 5(1):e8519.
Stieler et al., "Host range and cellular tropism of the human exogenous gammaretrovirus XMRV", *Virology*, Mar. 30, 2010; 399(1):23-30.
Lee et al., "The path well traveled: using mammalian retrovirus to guide research on XMRV", *Mol Interv*, Feb. 2010; 10(1):20-4.
Schlecht-Louf et al., "Retroviral infection in vivo requires an immune escpae virulence factor encrypted in the envelope protein of oncoretroviruses", *Retrovirology*, Feb. 15, 2010; 7(1):10.

(Continued)

*Primary Examiner* — Shanon A Foley
(74) *Attorney, Agent, or Firm* — Baker Botts, LLP

(57) ABSTRACT

The present invention relates generally to assays for the detection of Xenotropic Murine Leukemia Virus-related Retrovirus ("XMRV") and diseases associated with XMRV infection. Additionally, the invention relates to specific XMRV antigens capable of inducing an immunogenic response as well as XMRV-related nucleic acids having significant diagnostic, screening, and therapeutic utilities.

4 Claims, 38 Drawing Sheets

OTHER PUBLICATIONS van Kuppeveld et al., "Prevalence of xenotropic murine leukemia virus-related virus in patients with chronic fatigue syndrome in the Netherlands: retrospective analysis of samples from an established cohort", *BMJ*, Feb. 25, 2010; 340:c1018.

McClure et al., "Chronic fatigue syndrome and human retrovirus XMRV", *BMJ*, Feb. 25, 2010; 340:c1099.

Groom et al., "Susceptibility of xenotropic murine leukemia virus-related virus (XMRV) to retroviral restriction factors", *Proc Natl Acad Sci U.S.A.*, Mar. 1, 2010:1-6.

Denner, J., "Detection of a gammaretrovirus, XMRV, in the human population: Open questions and implications for xenotransplantation", *Retrovirology*, Mar. 10, 2010; 7(1):16.

Paprotka et al., "Inhibition of xenotropic murine leukemia virus-related virus by APOBEC3 proteins and antiviral drugs", *J Virol*, Mar. 24, 2010; 84(11):5719-29.

Arnold et al., "XMRV infection in patients with prostate cancer: novel serologic assay and correlation with PCR and FISH" *Urology*, Apr. 2010; 75(4):755-61.

Singh et al., "Raltegravir is a potent inhibitor of XMRV, a virus implicated in prostate cancer and chronic fatigue syndrome", *PloS One*, Apr. 1, 2010; 5(4):e9948.

Bhosle et al., "Evaluation of cellular determinants required for in vitro XMRV entry of human prostate cancer and non-cancerous cells", *J Virol*, Apr. 21, 2010, 84(13):6288-96.

Kim et al., "Fidelity of target site duplication and sequence preference during integration of xenotrpoic murine leukemia virus-related virus", *PloS One*, Apr. 20, 2010; 5(4): e10255.

Barabiuk, JN, "Xenotropic murine leukemia virus-related virus in chronic fatigue syndrome and prostate cancer", *Curr Allergy Asthma Rep.*, May 2010; 10(3): 210-4.

Sudlow et al., "Comment on Detection of an infectious retrovirus, XMRV, in blood cells of patients with chronic fatigue syndrome", *Science*, May 14, 2010; 328(5980): 825.

Lloyd et al., "Comment on Detection of an infectious retrovirus, XMRV, in blood cells of patients with chronic fatigue syndrome", *Science*, May 14, 2010; 328(5980): 825.

van der Meer at al., "Comment on Detection of an infectious retrovirus, XMRV, in blood cells of patients with chronic fatigue syndrome", *Science*, May 14, 2010; 328(5980): 825.

Fischer et al., "Xenotropic murine leukemia virus-related gammaretrovirus in respiratory tract", *Emerg Infect Dis.*, Jun. 2010; 16(6): 1000-2.

Metzger et al., "Acutely transforming retrovirus expressing Nras generated from HT-1080 fibrosarcoma cells infected with XMRV", *J Virol*, May 26, 2010: 1-14.

Silverman et al., "The human retrovirus XMRV in prostate cancer and chronic fatigue syndrome", *Nat. Rev. Urology*, Jun. 1, 2010:1-11.

van der Kuyl et al., "Of mice and men:on the origin of XMRV", *Frontiers in Microbiol*, Jan. 17, 2011; 1:1.

Hohn et al., "No evidence for XMRV in German CFS and MS patients with fatigue despite the ability of the virus to infect human blood cells in vitro", *PloS One*, Dec. 22, 2010; 5(12): e15632.

Kaiser, J., "Chronic fatigue syndrome. Studies point to possible contamination in XMRV findings", *Science*, Jan. 7, 2011; 331(6013): 17.

Stoye et al., "The xenotropic murine leukemia virus-related retrovirus debate continues at first international workshop", *Retrovirology*, Dec. 22, 2010; 7(1): 113.

Smith, RA, "Contamination of clinical specimens with MLV-encoding nucleic acids: implications for XMRV and other candidate human retroviruses", *Retrovirology*, Dec. 20, 2010; 7(1): 112.

Hué et al., "Disease-associated XMRV sequences are consistent with laboratory contamination", *Retrovirology*, Dec. 20, 2010; 7(1): 111.

Sato et al., "An endogenous murine leukemia viral genome contaminant in a commercial RT-PCR Kit is amplified using standard primers for XMRV", *Retrovirology*, Dec. 20, 2010; 7(1): 110.

Oakes et al., "Contamination of human DNA samples with mouse DNA can lead to false detection of XMRV-like sequences", *Retrovirology*, Dec. 20, 2010; 7(1): 109.

Robinson et al., "Mouse DNA contamination in human tissue tested for XMRV", *Retrovirology*, Dec. 20, 2010; 7: 108.

Gillette et al., "Purify first: Rapid expression and purification of proteins from XMRV", *Protein Expr Purif.*, Dec. 10, 2010; 76(2011):238-47.

Bogerd et al., "Human APOBEC3 proteins can inhibit xenotropic murine leukemia virus-related virus-infectivity", *Virology*, Dec. 3, 2010; 410(2011); 234-9.

Kearney et al., "Current status of xenotropic murine leukemia virus-related retrovirus in chronic fatigue syndrome and prostate cancer: Reach for a score card, not a prescription pad", *J Infect Dis.*, Nov. 15, 2010; 202: 1463.

Kozak, CA, "The mouse "xenotropic" gammaretroviruses and their XPR1 receptor", *Retrovirology*, Nov. 30, 2010; 7(1): 101.

Menéndez-Arias, L., "Evidence and controversies on the role of XMRV in prostate cancer and chronic fatigue syndrome", *Rev Med Virol.*, Nov. 26, 2010; 21:3-17.

Sakuma et al., "Early events in XMRV infection of wild-derived mouse, mus pahari", *J. Virol.*, Nov. 17, 2010; 85(3): 1205-13.

Tang et al., "Absence of detectable xenotropic murine leukemia virus-related virus in plasma or peripheral blood mononuclear cells of human immunodefiency virus type 1-infected blood donors or individuals in Africa", *Transfussion*, Nov. 15, 2010; 51: 463-68.

Aloia et al., "XMRV: A new virus in prostate cancer?" *Cancer Res.*, Oct. 21, 2010; 70(24): 10028-33.

Satterfield et al., "PCR and serology find no association between xenotropic murine leukemia virus-related virus (XMRV) and austism *Mol Austism*, Oct. 14, 2010; 1(1):14.

Barnes et al., "Failure to detect xenotropic murine leukemia virus-related virus in blood of individuals at high risk of blood-borne viral infections", *J Infect Dis.*, Oct. 11, 2010; 202:1482-85.

Henrich et al., "Xenotropic murine leukemia virus-related virus prevalence in patients with chronic fatigue syndrome or chronic immunomodulatory conditions", *J Infect Dis.*, Oct. 11, 2010; 202: 1478-81.

Danielson et al., "Detection of xenotropic murine leukemia virus-related virus in normal and tumor tissue of patients from the southern United States with prostate cancer is dependent on specific polymerase chain reaction conditions", *J Infect Dis.*, Sep. 3, 2010; 202: 1470-77.

Verhaegh et al., "Prevalence of human xenotropic murine leukemia virus-related gammaretrovirus (XMRV) in dutch prostate cancer patients", *Prostate*, Sep. 28, 2010; 71: 415-20.

Weiss, RA, "A cautionary tale of virus and disease", *BMC Biol.*, Sep. 27, 2010; 8: 124.

Kaiser, J., o meeting of minds on XMRV's role in chronic fatigue, cancer, *Science*, Sep. 17, 2010; 329(5995): 1454.

Mikovits et al., "Distribution of xenotropic murine leukemia virus-related virus (XMRV) infection in chronic fatigue syndrome and prostate cancer", *AIDS Rev.*, Jul.-Sep. 2010; 12(3): 149-52.

Hong et al., "Failure to detect xenotropic murine leukemia virus-related virus in Chinese patients with chronic fatigue syndrome", *Virol J.*, Sep. 13, 2010; 7(1): 224.

Smith et al., "Susceptibility of the human retrovirus XMRV to antiretroviral inhibitors", *Retrovirology*, Aug. 31, 2010; 7(1): 70.

Enserik, M., "Chronic fatigue syndrome. Nex XMRV paper looks good, skeptics admit-yet doubts linger", *Science*, Aug. 27, 2010; 329(5995): 1000.

Lo et al., "Detection of MLV-related virus gene sequences in blood of patients with chronic fatigue syndrome and healthy blood donors", *Proc Natl Acad Sci U.S.A.*, Sep. 7, 2010; 107(36); 15874-9.

Rusmevichientong et al., "Biology and pathophysiology of the new human retrovirus XMRV and its association with human disease", *Immunol Res.*, Aug. 18, 2010; DOI 10.1007/s12026-010-8165-y.

Qiu et al., "Characterization of antibodies elicited by XMRV infection and development of immunoassays useful for epidemiologic studies", *Retrovirology*, Aug. 17, 2010; 7(1): 68.

Cornelissen et al., "Lack of detection of XMRV in seminal plasma from HIV-1 infected men in the Netherlands", *PloS One*, Aug. 10, 2010; 5(8): pii:e12040.

Mikovits et al., "Detection of an infectious retrovirus, XMRV, in blood cells of patients with chronic fatigue syndrome", *Virulence*, Sep./Oct. 2010; 1(5): 1-5.

Dolgin, E., "Chronic controversy continues over mysterious XMRV virus", *Nat. Med.*, Aug. 2010; 16(8): 832.

Jeziorski et al., "No evidence for XMRV association in pediatric idiopathic diseases in France", *Retrovirology*, Aug. 2, 2010; 7:63.

Stieler et al., "Apobec 3G efficiently reduces infectivity of the human exogenous gammaretrovirus XMRV", *PloS One*, Jul. 23, 2010; 5(7): e11738.

McClure et al., "Can detection of xenotropic murine leukemia virus-related virus be linked to chronic fatigue syndrome?", *Expert Rev. Mol.*, Jul. 2010; 10(5): 537-39.

Switzer et al., "Absence of evidence of xenotropic murine leukemia virus-related virus infection in persons with chronic fatigue syndrome and healthy controls in the United States", *Retrovirology*, Jul. 2, 2010; 7(1): 57.

Sfanos et al., "A molecular analysis of prokaryotic and viral DNA sequences in prostate tissue from patients with prostates cancer indicates the presence of multiple and diverse microorganisms", *Prostate*, Feb. 15, 2008; 68(3): 306-20.

Martinez-Fierro et al., "Identification of viral infections in the prostate and evaluation of their association with cancer", *BMC Cancer*, Jun. 24, 2010; 10(1): 326.

Watts et al., "Combination of HOXB4 and delta-1 ligand improves expansion of cord blood cells", *Blood*, Dec. 26, 2010; 116(26): 5859-66.

Sakuma et al., "Characterization of retroviral and lentiviral vectors pseudotyped with xenotropic murine leukemia virus-related virus envelope glycoprotein", *Human Gene Therapy*, Dec. 2010; 12: 1665-73.

Kuang et al., "Phenylbutyric acid suppresses protein accumulation-mediated ER stress in retrovirus-infected astrocytes and delays onset of paralysis in infected mice", *Neurochemistry International*, Dec. 2010; 57(7): 738-48.

Briones et al., "A new functional role of HIV-1 integrase during uncoating of the viral core", *Immunologic Research*, Dec. 2010; 48(N1-3): 14-26.

Chu et al., "Human immunodefiency virus type-1 gag and host vesicular trafficking pathways", *Current Topics in Microbiology and Immunology*, Dec. 1, 2009; 339(1): 67-84.

Song, B., "HIV interactions with host cell proteins", *Current Topics in Microbiology and Immunology*, Dec. 1, 2009; 339(1): 47-66.

Mikovits et al., "Inactivation of XMRV by the intercept blood system (TM) in Platelet concentrates", *Transfussion*, Sep. 2010; 50(2): 211A-212A.

Khouzami et al., "Delayed cardiomyopathy in dystrophin deficient mdx mice relies on intrinsic glutathione resource", The *American Journal of Pathology*, Sep. 2010; 177(3): 1356-164.

Zimmerman et al., "Mouse models of human T lymphotropic virus type-1 associated adult t-cell leukemia/lymphoma", *Veterinary Pathology*, Jul. 2010; 47(4): 677-89.

Nater et al., "Criteria used to define chronic fatigue syndrome questioned the authors reply", *Psychosomatic Medicine*, Jun. 2010; 72(5): 507-509.

Pasquel, FJ, "Management of hyperglycemia in the hospitalized patient", *Medicina-Buenos Aires*, 2010, 70(3): 275-83 (English Absract Only).

Li et al., "Importance of macrophage inflammatory protein-la and splenic macrophages in neurodegeneration induced by PVC-211 murine leukemia virus", *Virology*, Jan. 20, 2011; 409(2): 198-203.

Boneva et al., "Gynelogical history in chronic fatigue syndrome: A population-based case-control study", *Journal of Womens Health*, Jan. 2010; 20(1): 21-28.

Makarova et al., "Antibody responses against xenotropic murine leukemia virus-related virus envelope in a murine model", *PloS One*, 6(4):e18272.

Koh et al., "Differential sensitivities of retroviruses to integrase strand transfer inhibitors", *Journal of Virilogy*, Apr. 2011; 85(7):3677-82.

Sakakibara et al., "NF-κB activation stimulates transcription and replication of retrovirus XMRV in human B-lineage and prostate carcinoma cells", *Journal of Virology*, Apr. 2011; 85(7): 3179-86.

Maillard et al, "Homology-based identification of capsid determinants that protect HIV1 from human TRIMα restriction", *The Journal of Biological Chemistry*, Mar. 11, 2011; 286(10): 8128-40.

Klein et al., "Xenotropic murine leukemia virus-related virus (XMRV) and blood transfusion: report of the AABB interorganizational XMRV task force", *Transfusion*, Mar. 2011; 51: 654-661.

Gray et al., "No evidence of XMRV or related retroviruses in a London HIV-1-Positive patient cohort", *PloS One*, Mar. 23, 2011; 6(3): e18096.

Sakuma et al., "No evidence of XMRV in prostate cancer cohorts in the Midwestern United States", *Retrovirology*, Mar. 29, 2001; 8(23): 1-11.

Furuta et al., "No association of xenotropic murin leukemia virus-related virus with prostate cancer or chronic fatigue syndrome in Japan", *Retrovirology*, Mar. 17, 2011; 8(20): 1-12.

Erlwein et al., "Investigation into the presence of and serological response to XMRV in CFS patients", *PloS One*, Mar. 9, 2011; 6(3): e17592.

Lintas et al., "Lack of infection with XMRV or other MLV-Related viruses in blood, post-mortem brains and paternal gametes of austistic individuals", *PloS One*, Feb. 23, 2011; 6(2): e16609.

Garson et al., "Analysis of XMRV integration sites from human prostate cancer tissues suggests PCR contamination rather than genuine human infection", *Retrovirology*, Feb. 25, 2011; 8:13.

Satterfield et al., "Serologic and PCR testing of persons with chronic fatigue syndrome in the United States shows no association with xenotropic or polytropic murine leukemia virus-related viruses", *Retrovirology*, Feb. 22, 2011; 8:12.

Luczkowiak et al., No xenotropic murine leukemia virus-related virus detected in fibromyalgia patients, *Emerg Infect Dis*, Feb. 2011; 17(2): 314-315.

Li et al., "Crystal structure of XMRV protease differs from the structures of other retropepsins", *Nat Struct Mol Biol.*, Jan. 23, 2011; 18(2): 227-229.

Hartman et al., "Evaluation of approved antivirals for inhibition of xenotropic murine leukemia-related virus (XMRV) in cell-based assyas", *Abstracts/Antiviral Research 90*, 2011; A21-A78.

Rahm et al., "Unique spectrum of activity of prosimian TRIM5α against exogenous and endogenous retroviruses", *Journal of Virology*, Jan. 12, 2011; 85(9): 4173-4183.

Chaipan et al., "Severe restriction of xenotropic murine leukemia virus-related virus replication and spread in cultured human peripheral blood mononuclear cells", *Journal of Virology*, Jan. 7, 2011; 85(10): 4888-4897.

Cohen, John, "More negative data for link between mouse virus and human disease", *Retrovirology*, Mar. 11, 2011; 331: 1253-1254.

Onlamoon et al., "Infection, viral dissemination, and antibody responses of rhesus macaques exposed to the human gammaretrovirus XMRV", *Journal of Virology*, May 2011;85(9):4547-4557.

Sabunciyan et al., No difference in antibody titers against xenotropic MLV related virus in prostate cancer cases and cancer-free controls, *Molecular and Cellular Probes 25*, Jan. 31, 2011; 134-136.

Schutzer et al., "Analysis of cerebrospinal fluid from chronic fatigue syndrome patients for multiple human ubiquitous viruses and xenotropic murine leukemia-related virus", *American Neurological Association*, Feb. 4, 2011;69: 735-738.

Shan, Hua, "What is XMRV and should we be worried about it?", *Transfussion*, Mar. 2011; 51: 450-453.

Wainberg et al., "XMRV as a human pathogen?", *Cell Host & Microbe*, Apr. 21, 2011; 9(4): 260-262.

Xu, et al., "Primate gammaretorviruses require an ancillary factor not required for murine gammaretroviruses to infect BHK cells", *Journal of Virology*, Apr. 2011; 85(7): 3498-3506.

* cited by examiner

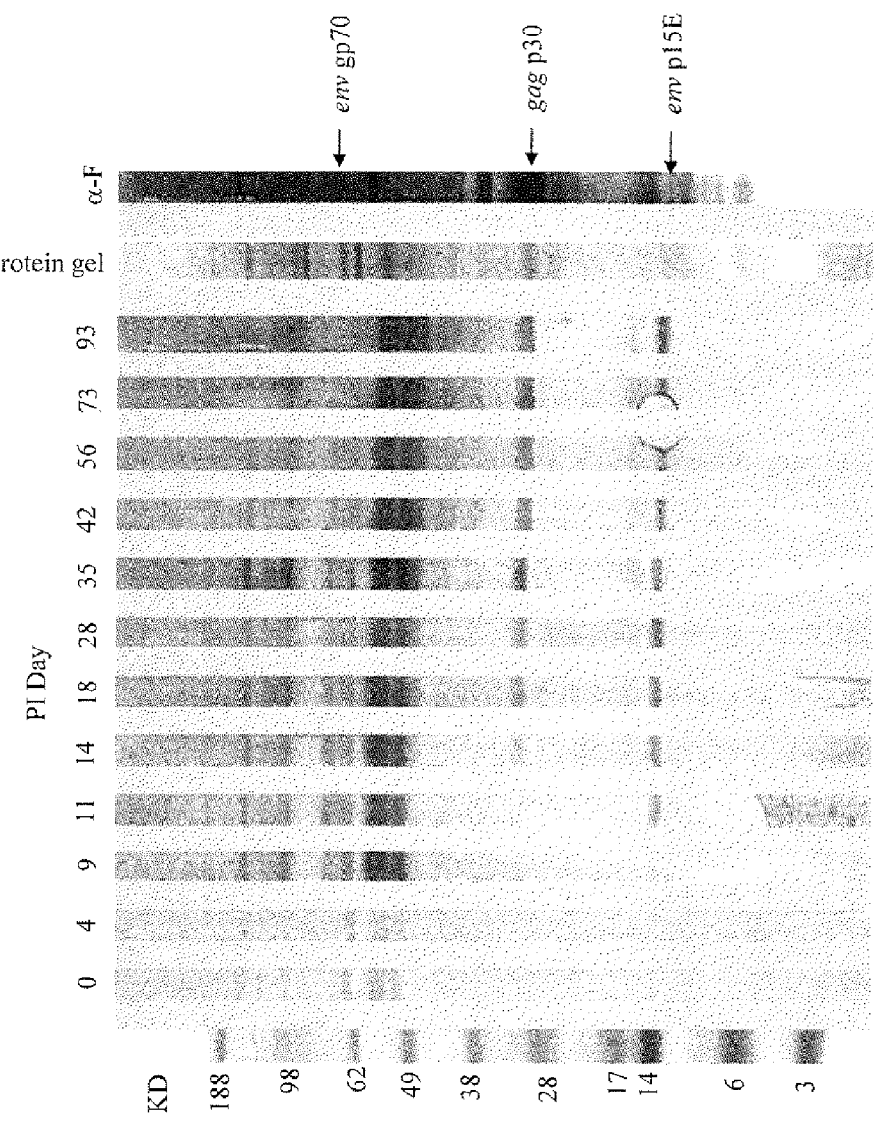
Figure 9A (IgG)

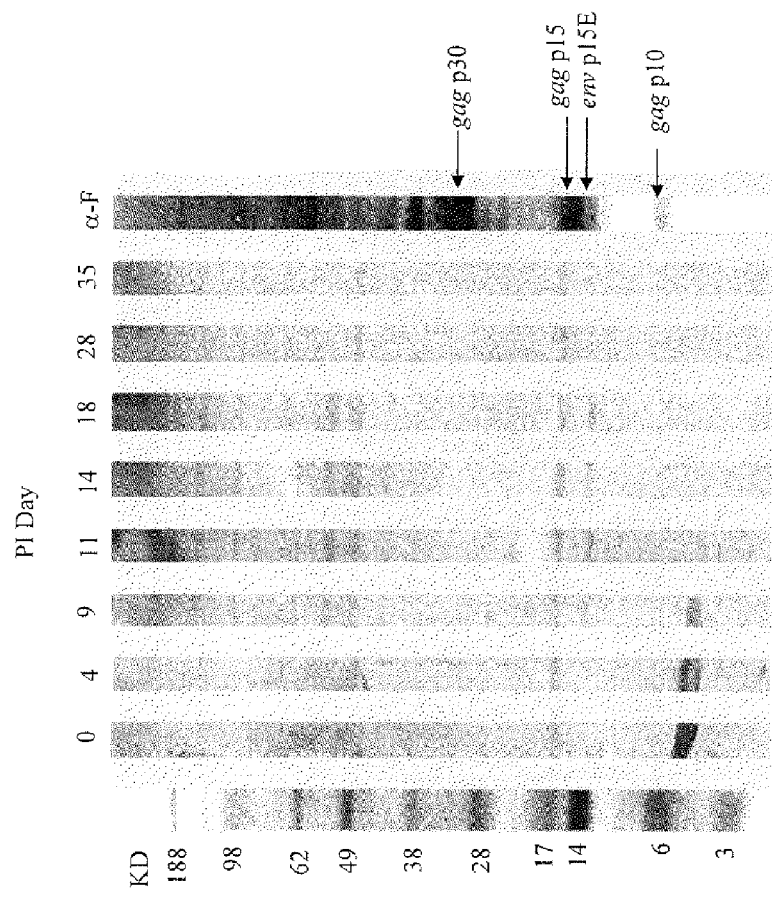
Figure 9A (IgM)

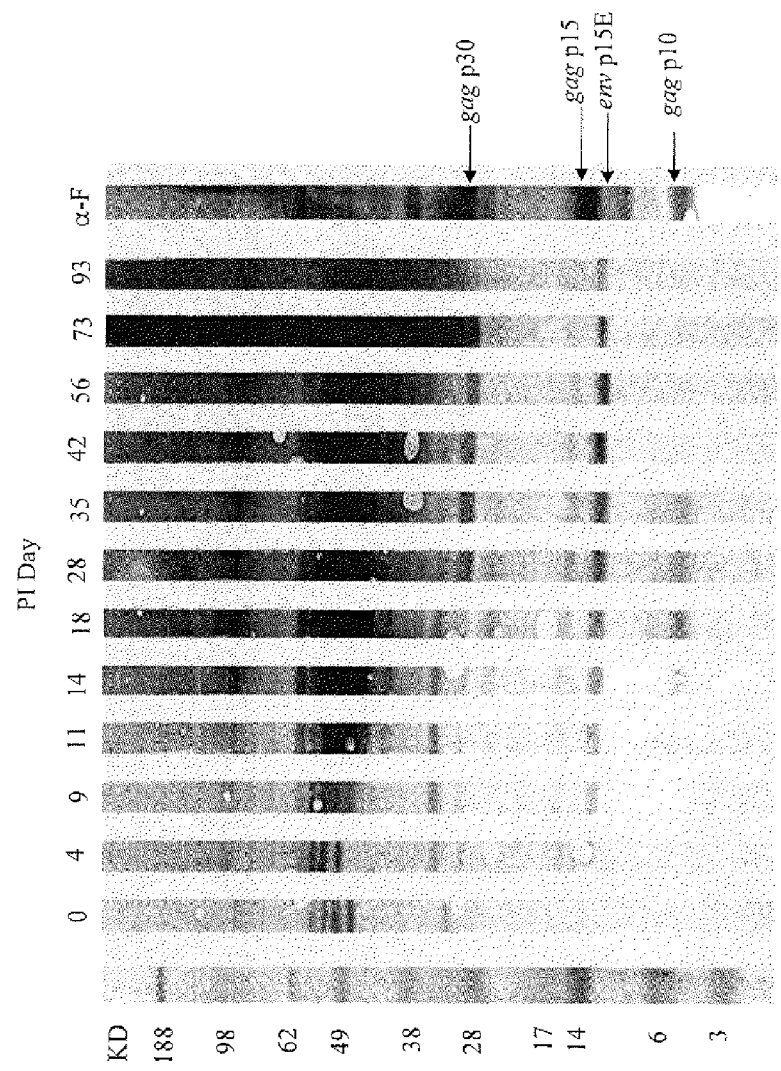
Figure 9B (IgG)

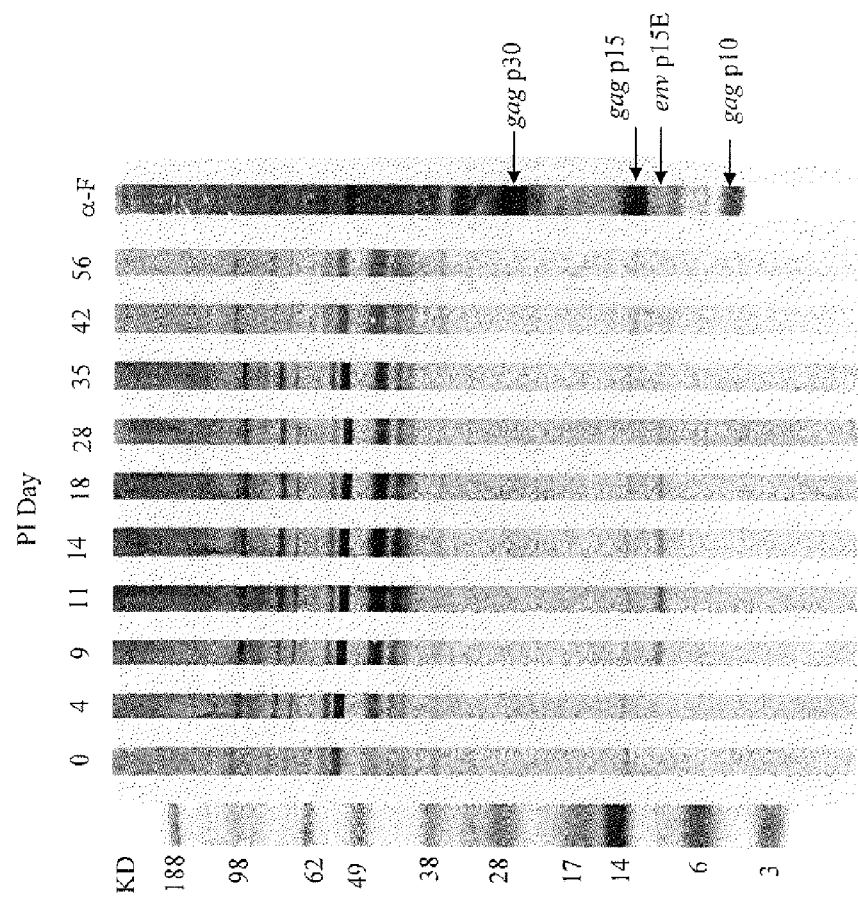
*Figure 9B (IgM)*

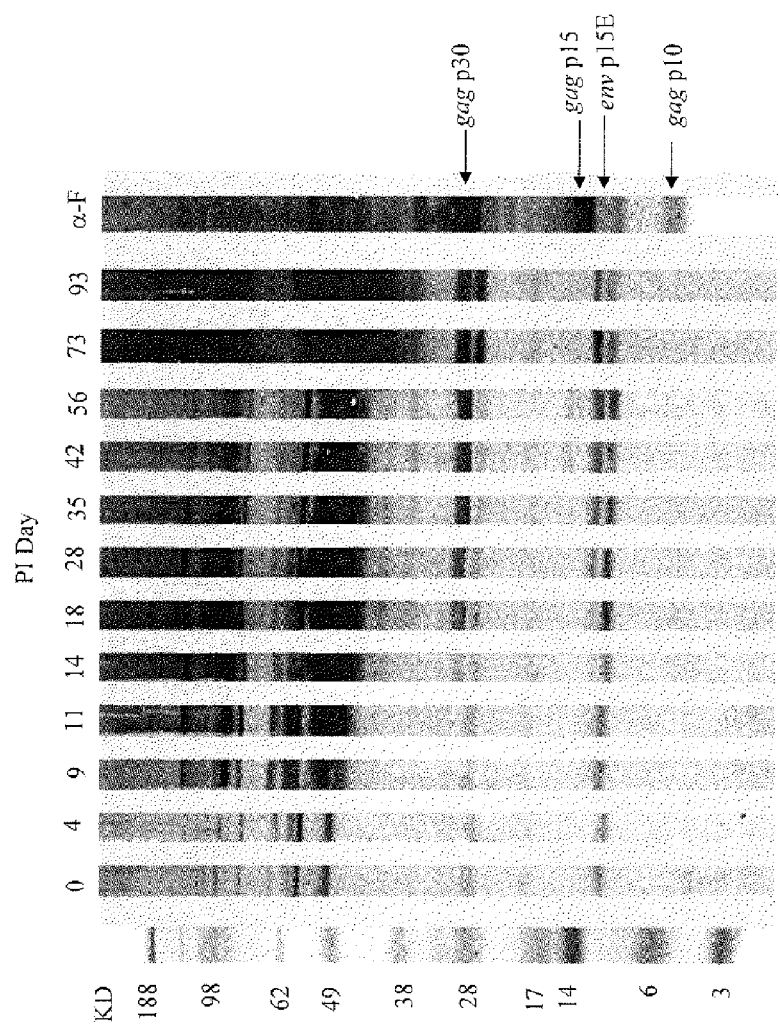
*Figure 9C (IgG)*

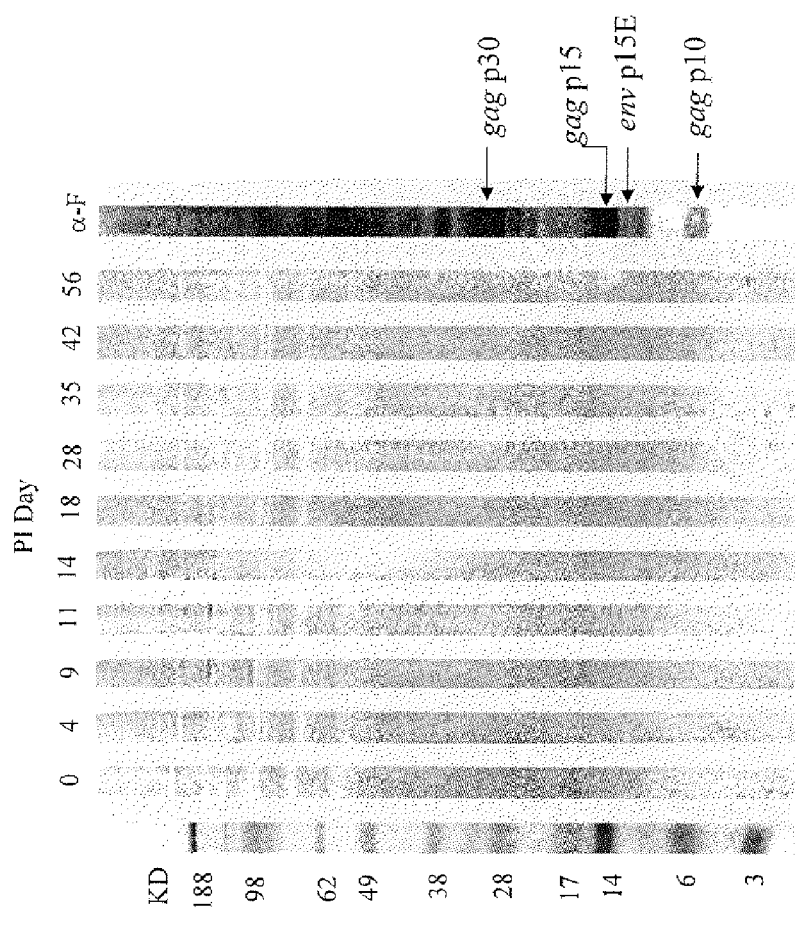
*Figure 9C (IgM)*

*Figure 17*
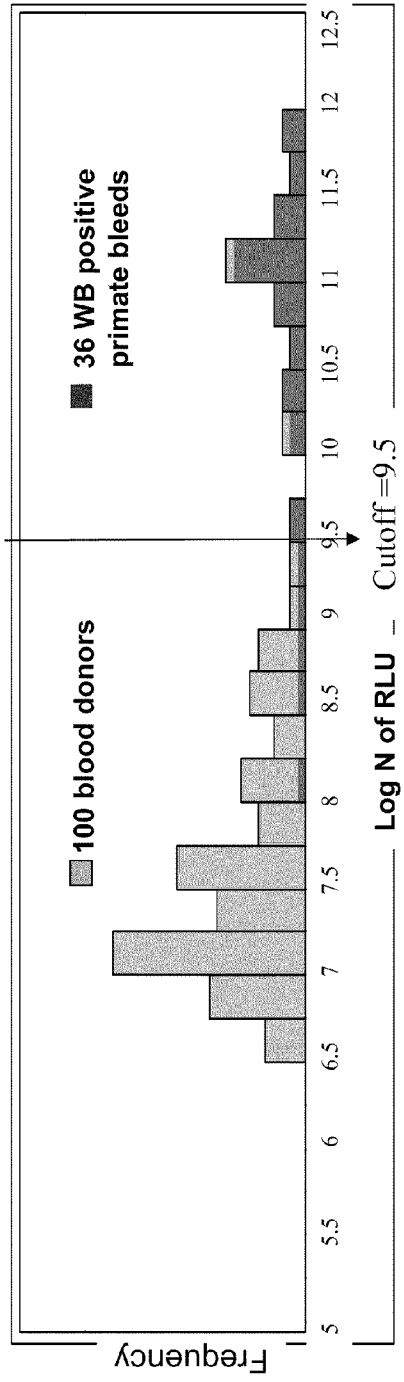
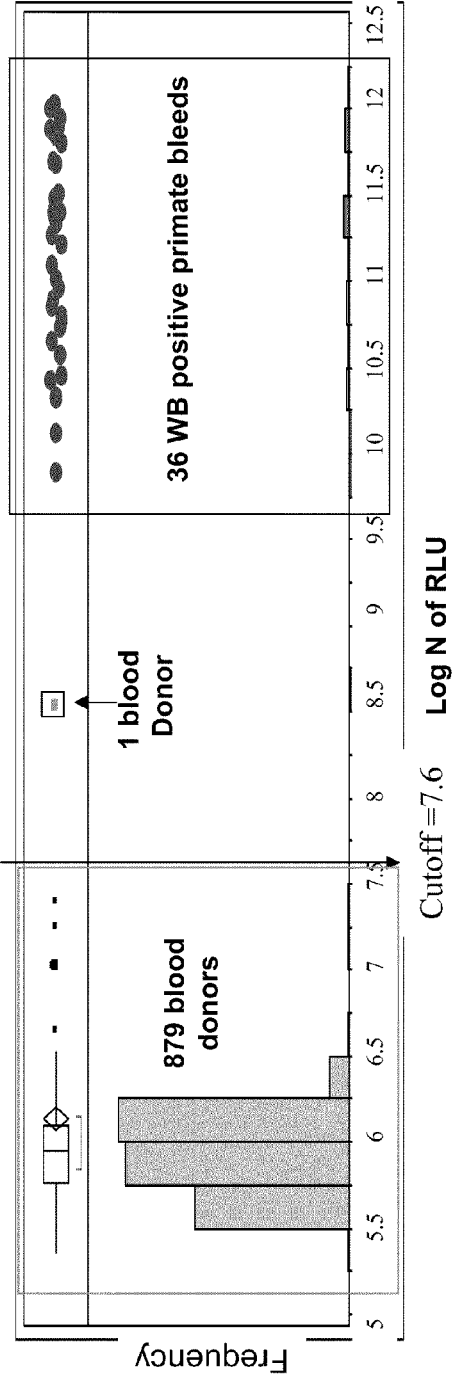

Figure 18

XMRV p15E sequence

```
EPVSLTLALLGGLTMGGIA AGVGTGTTALVATKQFEQLQAAIHT DLGALEKSVSALEKSLTSLS EVVLQNRRGLDLLFLKEGGL
CAALKEECCFYADHTGVVRD SMAKLRERLNQRQKLFESRQ GWFEGLFNRSPWFTTLISTIMGPLIVLLLILLFGPCILNRLVQFVKDRISVVQAL
```

Synthetic p15E peptides

|------ABTX2------|
|------ABTX3------|
|------ABTX4------|
|------ABTX5------|
|------ABTX6------|
|------ABTX7------|
|------ABTX8------|
|------ABTX10------|

Construction of pJVp70-E4/DH5α

Construction of pJVp30-D2/DH5α

SEQUENCE LISTING

```
<160> NUMBER OF SEQ ID NOS: 109

<210> SEQ ID NO 1
<211> LENGTH: 180
<212> TYPE: PRT
<213> ORGANISM: Artificial sequence
<220> FEATURE:
<223> OTHER INFORMATION: Synthetic polypeptide

<400> SEQUENCE: 1

Glu Pro Val Ser Leu Thr Leu Ala Leu Leu Gly Gly Leu Thr Met
1               5                   10                  15

Gly Gly Ile Ala Ala Gly Val Gly Thr Gly Thr Thr Ala Leu Val Ala
                20                  25                  30

Thr Lys Gln Phe Glu Gln Leu Gln Ala Ala Ile His Thr Asp Leu Gly
            35                  40                  45

Ala Leu Glu Lys Ser Val Ser Ala Leu Glu Lys Ser Leu Thr Ser Leu
    50                  55                  60

Ser Glu Val Val Leu Gln Asn Arg Arg Gly Leu Asp Leu Leu Phe Leu
65                  70                  75                  80

Lys Glu Gly Gly Leu Cys Ala Ala Leu Lys Glu Glu Cys Cys Phe Tyr
                85                  90                  95

Ala Asp His Thr Gly Val Val Arg Asp Ser Met Ala Lys Leu Arg Glu
                100                 105                 110

Arg Leu Asn Gln Arg Gln Lys Leu Phe Glu Ser Gly Gln Gly Trp Phe
            115                 120                 125

Glu Gly Leu Phe Asn Arg Ser Pro Trp Phe Thr Thr Leu Ile Ser Thr
    130                 135                 140

Ile Met Gly Pro Leu Ile Val Leu Leu Leu Ile Leu Leu Phe Gly Pro
145                 150                 155                 160

Cys Ile Leu Asn Arg Leu Val Gln Phe Val Lys Asp Arg Ile Ser Val
                165                 170                 175

Val Gln Ala Leu
            180

<210> SEQ ID NO 2
<211> LENGTH: 98
<212> TYPE: DNA
```

<213> ORGANISM: Artificial sequence
<220> FEATURE:
<223> OTHER INFORMATION: Synthetic oligonucleotide

<400> SEQUENCE: 2

```
gaaccggttt ctctgactct ggctctgctg ctgggtggtc tgactatggg tggcattgct    60
gctggcgtgg gtactggcac tactgcgctg gttgctac                            98
```

<210> SEQ ID NO 3
<211> LENGTH: 109
<212> TYPE: DNA
<213> ORGANISM: Artificial sequence
<220> FEATURE:
<223> OTHER INFORMATION: Synthetic oligonucleotide

<400> SEQUENCE: 3

```
gtcagggatt tttccagagc agacacagat ttttccagag cgcccaggtc agtgtgaatc    60
gccgcctgca gctgctcgaa ctgtttagta gcaaccagcg cagtagtgc               109
```

<210> SEQ ID NO 4
<211> LENGTH: 85
<212> TYPE: DNA
<213> ORGANISM: Artificial sequence
<220> FEATURE:
<223> OTHER INFORMATION: Synthetic oligonucleotide

<400> SEQUENCE: 4

```
gtctgctctg gaaaaatccc tgacctccct gtctgaagtt gttctgcaga accgtcgtgg    60
tctggacctg ctgtttctga agaa                                           85
```

<210> SEQ ID NO 5
<211> LENGTH: 107
<212> TYPE: DNA
<213> ORGANISM: Artificial sequence
<220> FEATURE:
<223> OTHER INFORMATION: Synthetic oligonucleotide

<400> SEQUENCE: 5

```
cagtttagcc atggagtcac gcacaacacc ggtgtggtcc gcataaaagc agcattcttc    60
tttcagagcc gcacacagac cgccttcttt cagaaacagc aggtcca                 107
```

<210> SEQ ID NO 6
<211> LENGTH: 81
<212> TYPE: DNA
<213> ORGANISM: Artificial sequence
<220> FEATURE:
<223> OTHER INFORMATION: Synthetic oligonucleotide

<400> SEQUENCE: 6

```
gtgcgtgact ccatggctaa actgcgtgag cgtctgaacc agcgtcagaa actgtttgag    60
tccggccagg gttggtttga a                                              81
```

<210> SEQ ID NO 7
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 7

```
ggtagagatc agagtggtga accacggaga acggttgaac agaccttcaa accaaccctg    60
gcc                                                                  63
```

```
<210> SEQ ID NO 8
<211> LENGTH: 70
<212> TYPE: DNA
<213> ORGANISM: Artificial sequence
<220> FEATURE:
<223> OTHER INFORMATION: Synthetic oligonucleeotide

<400> SEQUENCE: 8
ggttcaccac tctgatctct accattatgg gtccgctgat tgttctgctg ctgattctgc    60
tgttcggccc                                                          70

<210> SEQ ID NO 9
<211> LENGTH: 80
<212> TYPE: DNA
<213> ORGANISM: Artificial sequence
<220> FEATURE:
<223> OTHER INFORMATION: Synthetic oligonucleotide

<400> SEQUENCE: 9
cagcgcctga acaacagaga tacgatcttt cacgaactgc accaggcggt tcagaataca    60
cgggccgaac agcagaatca                                               80

<210> SEQ ID NO 10
<211> LENGTH: 89
<212> TYPE: DNA
<213> ORGANISM: Artificial sequence
<220> FEATURE:
<223> OTHER INFORMATION: Synthetic oligonucleotide

<400> SEQUENCE: 10
cagcgcctga acaacagaga tacgatcttt cacgaactgc accaggcggt tcagaataca    60
cgggccggta gagatcagag tggtgaacc                                     89

<210> SEQ ID NO 11
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 11
gaaccggttt ctctgactct ggctc                                         25

<210> SEQ ID NO 12
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 12
cagtttagcc atggagtcac gcacaa                                        26

<210> SEQ ID NO 13
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 13
gtgcgtgact ccatggctaa ac                                            22

<210> SEQ ID NO 14
```

```
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 14
cagcgcctga acaacagaga tac                                              23

<210> SEQ ID NO 15
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 15
ctacaagaat tccatggaac cggtttctct gac                                   33

<210> SEQ ID NO 16
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 16
atagtaggat cctattacag cgcctgaaca ac                                    32

<210> SEQ ID NO 17
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 17
gtgatacgaa acgaagcatt g                                                21

<210> SEQ ID NO 18
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 18
gatataggcg ccagcaac                                                    18

<210> SEQ ID NO 19
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 19
ctacaagaat tctgaaccgg tttctctgac                                       30

<210> SEQ ID NO 20
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 20
```

```
ctggcacagg tgtggatac                                                19
```

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 21

```
ccaaaattgg ctgaagtgtc                                               20
```

<210> SEQ ID NO 22
<211> LENGTH: 543
<212> TYPE: DNA
<213> ORGANISM: Artificial sequence
<220> FEATURE:
<223> OTHER INFORMATION: Synthetic oligonucleotide

<400> SEQUENCE: 22

```
atggaaccgg tttctctgac tctggctctg ctgctgggtg gtctgactat gggtggcatt     60
gctgctggcg tgggtactgg cactactgcg ctggttgcta ctaaacagtt cgagcagctg    120
caggcggcga ttcacactga cctgggcgct ctggaaaaat ctgtgtctgc tctggaaaaa    180
tccctgacct ccctgtctga agttgttctg cagaaccgtc gtggtctgga cctgctgttt    240
ctgaaagaag gcggtctgtg tgcggctctg aaagaagaat gctgcttta tgcggaccac    300
accggtgttg tgcgtgactc catggctaaa ctgcgtgagc gtctgaacca gcgtcagaaa    360
ctgtttgagt ccggccaggg ttggtttgaa ggtctgttca accgttctcc gtggttcacc    420
actctgatct ctaccattat gggtccgctg attgttctgc tgctgattct gctgttcggc    480
ccgtgtattc tgaaccgcct ggtgcagttc gtgaaagatc gtatctctgt tgttcaggcg    540
ctg                                                                  543
```

<210> SEQ ID NO 23
<211> LENGTH: 181
<212> TYPE: PRT
<213> ORGANISM: Artificial sequence
<220> FEATURE:
<223> OTHER INFORMATION: Synthetic polypeptide

<400> SEQUENCE: 23

Met Glu Pro Val Ser Leu Thr Leu Ala Leu Leu Leu Gly Gly Leu Thr
1               5                   10                  15

Met Gly Gly Ile Ala Ala Gly Val Gly Thr Gly Thr Thr Ala Leu Val
            20                  25                  30

Ala Thr Lys Gln Phe Glu Gln Leu Gln Ala Ala Ile His Thr Asp Leu
        35                  40                  45

Gly Ala Leu Glu Lys Ser Val Ser Ala Leu Glu Lys Ser Leu Thr Ser
    50                  55                  60

Leu Ser Glu Val Val Leu Gln Asn Arg Arg Gly Leu Asp Leu Leu Phe
65                  70                  75                  80

Leu Lys Glu Gly Gly Leu Cys Ala Ala Leu Lys Glu Glu Cys Cys Phe
                85                  90                  95

Tyr Ala Asp His Thr Gly Val Val Arg Asp Ser Met Ala Lys Leu Arg
            100                 105                 110

Glu Arg Leu Asn Gln Arg Gln Lys Leu Phe Glu Ser Gly Gln Gly Trp
        115                 120                 125

Phe Glu Gly Leu Phe Asn Arg Ser Pro Trp Phe Thr Thr Leu Ile Ser
    130                 135                 140

```
Thr Ile Met Gly Pro Leu Ile Val Leu Leu Ile Leu Leu Phe Gly
145                 150                 155                 160

Pro Cys Ile Leu Asn Arg Leu Val Gln Phe Val Lys Asp Arg Ile Ser
                165                 170                 175

Val Val Gln Ala Leu
            180

<210> SEQ ID NO 24
<211> LENGTH: 501
<212> TYPE: DNA
<213> ORGANISM: Artificial sequence
<220> FEATURE:
<223> OTHER INFORMATION: Synthetic oligonucleotide

<400> SEQUENCE: 24
atggaaccgg tttctctgac tctggctctg ctgctgggtg gtctgactat gggtggcatt      60
gctgctggcg tgggtactgg cactactgcg ctggttgcta ctaaacagtt cgagcagctg     120
caggcggcga ttcacactga cctgggcgct ctggaaaaat ctgtgtctgc tctggaaaaa     180
tccctgacct ccctgtctga agttgttctg cagaaccgtc gtggtctgga cctgctgttt     240
ctgaaagaag gcggtctgtg tgcggctctg aaagaagaat gctgttttta tgcggaccac     300
accggtgttg tgcgtgactc catggctaaa ctgcgtgagc gtctgaacca gcgtcagaaa     360
ctgtttgagt ccggccaggg ttggtttgaa ggtctgttca ccgttctccc gtggttcacc     420
actctgatct ctaccggccc cgtgtattct aaccgcctgg tgcagttcgt gaaagatcgt     480
atctctgttg ttcaggcgct g                                               501

<210> SEQ ID NO 25
<211> LENGTH: 167
<212> TYPE: PRT
<213> ORGANISM: Artificial sequence
<220> FEATURE:
<223> OTHER INFORMATION: Synthetic polypeptide

<400> SEQUENCE: 25

Met Glu Pro Val Ser Leu Thr Leu Ala Leu Leu Leu Gly Gly Leu Thr
1               5                   10                  15

Met Gly Gly Ile Ala Ala Gly Val Gly Thr Gly Thr Thr Ala Leu Val
                20                  25                  30

Ala Thr Lys Gln Phe Glu Gln Leu Gln Ala Ala Ile His Thr Asp Leu
            35                  40                  45

Gly Ala Leu Glu Lys Ser Val Ser Ala Leu Glu Lys Ser Leu Thr Ser
        50                  55                  60

Leu Ser Glu Val Val Leu Gln Asn Arg Arg Gly Leu Asp Leu Leu Phe
65                  70                  75                  80

Leu Lys Glu Gly Gly Leu Cys Ala Ala Leu Lys Glu Glu Cys Cys Phe
                85                  90                  95

Tyr Ala Asp His Thr Gly Val Val Arg Asp Ser Met Ala Lys Leu Arg
                100                 105                 110

Glu Arg Leu Asn Gln Arg Gln Lys Leu Phe Glu Ser Gly Gln Gly Trp
            115                 120                 125

Phe Glu Gly Leu Phe Asn Arg Ser Pro Trp Phe Thr Thr Leu Ile Ser
        130                 135                 140

Thr Gly Pro Cys Ile Leu Asn Arg Leu Val Gln Phe Val Lys Asp Arg
145                 150                 155                 160

Ile Ser Val Val Gln Ala Leu
                165
```

<210> SEQ ID NO 26
<211> LENGTH: 1278
<212> TYPE: DNA
<213> ORGANISM: Artificial sequence
<220> FEATURE:
<223> OTHER INFORMATION: Synthetic oligonucleotide

<400> SEQUENCE: 26

```
atgagttttg tggtcattat tcccgcgcgc tacgcgtcca cgcgtctgcc cggtaaacca     60
ttggttgata ttaacggcaa acccatgatt gttcatgttc ttgaacgcgc gcgtgaatca    120
ggtgccgagc gcatcatcgt ggcaaccgat catgaggatg ttgcccgcgc cgttgaagcc    180
gctggcggtg aagtatgtat gacgcgcgcc gatcatcagt caggaacaga acgtctggcg    240
gaagttgtcg aaaaatgcgc attcagcgac gacacgcgtga tcgttaatgt gcagggtgat    300
gaaccgatga tccctgcgac aatcattcgt caggttgctg ataacctcgc tcagcgtcag    360
gtgggtatga cgactctggc ggtgccaatc acaatgcgg aagaagcgtt taacccgaat    420
gcggtgaaag tggttctcga cgctgaaggg tatgcactgt acttctctcg cgccaccatt    480
ccttgggatc gtgatcgttt tgcagaaggc cttgaaaccg ttggcgataa cttcctgcgt    540
catcttggta tttatggcta ccgtgcaggc tttatccgtc gttacgtcaa ctggcagcca    600
agtccgttag aacacatcga aatgttagag cagcttcgtg ttctgtggta cggcgaaaaa    660
atccatgttg ctgttgctca ggaagttcct ggcacaggtg tggatacccc tgaagatctc    720
gacccgtcga cgaattctga accggtttct ctgactctgg ctctgctgct gggtggtctg    780
actatgggtg gcattgctgc tggcgtgggt actggcacta ctgcgctggt tgctactaaa    840
cagttcgagc agctgcaggc ggcgattcac actgacctgg cgctctggaa aaatctgtg    900
tctgctctgg aaaaatccct gacctccctg tctgaagttg ttctgcagaa ccgtcgtggt    960
ctggacctgc tgtttctgaa agaaggcggt ctgtgtgcgg ctctgaaaga gaatgctgc   1020
ttttatgcgg accacaccgg tgttgtgcgt gactccatgg ctaaactgcg tgagcgtctg   1080
aaccagcgtc agaaactgtt tgagtccggc cagggttggg ttgaaggtct gttcaaccgt   1140
tctccgtggt tcaccactct gatctctacc attatgggtc cgctgattgt tctgctgctg   1200
attctgctgt tcggcccgtg tattctgaac cgcctggtgc agttcgtgaa agatcgtatc   1260
tctgttgttc aggcgctg                                                1278
```

<210> SEQ ID NO 27
<211> LENGTH: 426
<212> TYPE: PRT
<213> ORGANISM: Artificial sequence
<220> FEATURE:
<223> OTHER INFORMATION: Synthetic polypeptide

<400> SEQUENCE: 27

Met Ser Phe Val Val Ile Ile Pro Ala Arg Tyr Ala Ser Thr Arg Leu
1               5                   10                  15

Pro Gly Lys Pro Leu Val Asp Ile Asn Gly Lys Pro Met Ile Val His
            20                  25                  30

Val Leu Glu Arg Ala Arg Glu Ser Gly Ala Glu Arg Ile Ile Val Ala
        35                  40                  45

Thr Asp His Glu Asp Val Ala Arg Ala Val Glu Ala Ala Gly Gly Glu
    50                  55                  60

Val Cys Met Thr Arg Ala Asp His Gln Ser Gly Thr Glu Arg Leu Ala
65                  70                  75                  80

```
Glu Val Val Glu Lys Cys Ala Phe Ser Asp Asp Thr Val Ile Val Asn
                85                   90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Thr Thr Leu Ala Val
            115                 120                 125

Pro Ile His Asn Ala Glu Glu Ala Phe Asn Pro Asn Ala Val Lys Val
            130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
            195                 200                 205

Leu Glu Gln Leu Arg Val Leu Trp Tyr Gly Glu Lys Ile His Val Ala
210                 215                 220

Val Ala Gln Glu Val Pro Gly Thr Gly Val Asp Thr Pro Glu Asp Leu
225                 230                 235                 240

Asp Pro Ser Thr Asn Ser Glu Pro Val Ser Leu Thr Leu Ala Leu Leu
                245                 250                 255

Leu Gly Gly Leu Thr Met Gly Gly Ile Ala Ala Gly Val Gly Thr Gly
            260                 265                 270

Thr Thr Ala Leu Val Ala Thr Lys Gln Phe Glu Gln Leu Gln Ala Ala
            275                 280                 285

Ile His Thr Asp Leu Gly Ala Leu Glu Lys Ser Val Ser Ala Leu Glu
290                 295                 300

Lys Ser Leu Thr Ser Leu Ser Glu Val Val Leu Gln Asn Arg Arg Gly
305                 310                 315                 320

Leu Asp Leu Leu Phe Leu Lys Glu Gly Gly Leu Cys Ala Ala Leu Lys
                325                 330                 335

Glu Glu Cys Cys Phe Tyr Ala Asp His Thr Gly Val Val Arg Asp Ser
            340                 345                 350

Met Ala Lys Leu Arg Glu Arg Leu Asn Gln Arg Gln Lys Leu Phe Glu
            355                 360                 365

Ser Gly Gln Gly Trp Phe Glu Gly Leu Phe Asn Arg Ser Pro Trp Phe
            370                 375                 380

Thr Thr Leu Ile Ser Thr Ile Met Gly Pro Leu Ile Val Leu Leu Leu
385                 390                 395                 400

Ile Leu Leu Phe Gly Pro Cys Ile Leu Asn Arg Leu Val Gln Phe Val
                405                 410                 415

Lys Asp Arg Ile Ser Val Val Gln Ala Leu
                420                 425

<210> SEQ ID NO 28
<211> LENGTH: 1236
<212> TYPE: DNA
<213> ORGANISM: Artificial sequence
<220> FEATURE:
<223> OTHER INFORMATION: Synthetic oligonucleotide

<400> SEQUENCE: 28
atgagttttg tggtcattat tcccgcgcgc tacgcgtcca cgcgtctgcc cggtaaacca      60
ttggttgata ttaacggcaa acccatgatt gttcatgttc tgaacgcgcg cgtgaatca     120
```

```
ggtgccgagc gcatcatcgt ggcaaccgat catgaggatg ttgcccgcgc cgttgaagcc    180
gctggcggtg aagtatgtat gacgcgcgcc gatcatcagt caggaacaga acgtctggcg    240
gaagttgtcg aaaaatgcgc attcagcgac acacggtga tcgttaatgt gcagggtgat    300
gaaccgatga tccctgcgac aatcattcgt caggttgctg ataacctcgc tcagcgtcag    360
gtgggtatga cgactctggc ggtgccaatc cacaatgcgg aagaagcgtt aacccgaat    420
gcggtgaaag tggttctcga cgctgaaggg tatgcactgt acttctctcg cgccaccatt    480
ccttgggatc gtgatcgttt tgcagaaggc cttgaaaccg ttggcgataa cttcctgcgt    540
catcttggta tttatggcta ccgtgcaggc tttatccgtc gttacgtcaa ctggcagcca    600
agtccgttag aacacatcga atgttagag cagcttcgtg ttctgtggta cggcgaaaaa     660
atccatgttg ctgttgctca ggaagttcct ggcacaggtg tggataccc tgaagatctc    720
gacccgtcga cgaattctga accggtttct ctgactctgg ctctgctgct gggtggtctg    780
actatgggtg gcattgctgc tggcgtgggt actggcacta ctgcgctggt tgctactaaa    840
cagttcgagc agctgcaggc ggcgattcac actgacctgg gcgctctgga aaaatctgtg    900
tctgctctgg aaaatcccct gacctccctg tctgaagttg ttctgcagaa ccgtcgtggt    960
ctggacctgc tgtttctgaa agaaggcggt ctgtgtgcgg ctctgaaaga agaatgctgc   1020
ttttatgcgg accacaccgg tgttgtgcgt gactccatgg ctaaactgcg tgagcgtctg   1080
aaccagcgtc agaaactgtt tgagtccggc cagggttggt ttgaaggtct gttcaaccgt   1140
tctccgtggt tcaccactct gatctctacc ggcccgtgta ttctgaaccg cctggtgcag   1200
ttcgtgaaag atcgtatctc tgttgttcag gcgctg                             1236
```

<210> SEQ ID NO 29
<211> LENGTH: 412
<212> TYPE: PRT
<213> ORGANISM: Artificial sequence
<220> FEATURE:
<223> OTHER INFORMATION: Synthetic polypeptide

<400> SEQUENCE: 29

```
Met Ser Phe Val Val Ile Ile Pro Ala Arg Tyr Ala Ser Thr Arg Leu
1               5                   10                  15

Pro Gly Lys Pro Leu Val Asp Ile Asn Gly Lys Pro Met Ile Val His
            20                  25                  30

Val Leu Glu Arg Ala Arg Glu Ser Gly Ala Glu Arg Ile Ile Val Ala
        35                  40                  45

Thr Asp His Glu Asp Val Ala Arg Ala Val Glu Ala Gly Gly Glu
    50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Asp Thr Val Ile Val Asn
                85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Thr Thr Leu Ala Val
        115                 120                 125

Pro Ile His Asn Ala Glu Glu Ala Phe Asn Pro Asn Ala Val Lys Val
    130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175
```

```
Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
        195                 200                 205

Leu Glu Gln Leu Arg Val Leu Trp Tyr Gly Glu Lys Ile His Val Ala
    210                 215                 220

Val Ala Gln Glu Val Pro Gly Thr Gly Val Asp Thr Pro Glu Asp Leu
225                 230                 235                 240

Asp Pro Ser Thr Asn Ser Glu Pro Val Ser Leu Thr Ala Leu Leu
            245                 250                 255

Leu Gly Gly Leu Thr Met Gly Gly Ile Ala Ala Gly Val Gly Thr Gly
            260                 265                 270

Thr Thr Ala Leu Val Ala Thr Lys Gln Phe Glu Gln Leu Gln Ala Ala
        275                 280                 285

Ile His Thr Asp Leu Gly Ala Leu Glu Lys Ser Val Ser Ala Leu Glu
    290                 295                 300

Lys Ser Leu Thr Ser Leu Ser Glu Val Val Leu Gln Asn Arg Arg Gly
305                 310                 315                 320

Leu Asp Leu Leu Phe Leu Lys Glu Gly Gly Leu Cys Ala Ala Leu Lys
            325                 330                 335

Glu Glu Cys Cys Phe Tyr Ala Asp His Thr Gly Val Val Arg Asp Ser
        340                 345                 350

Met Ala Lys Leu Arg Glu Arg Leu Asn Gln Arg Gln Lys Leu Phe Glu
    355                 360                 365

Ser Gly Gln Gly Trp Phe Glu Gly Leu Phe Asn Arg Ser Pro Trp Phe
370                 375                 380

Thr Thr Leu Ile Ser Thr Gly Pro Cys Ile Leu Asn Arg Leu Val Gln
385                 390                 395                 400

Phe Val Lys Asp Arg Ile Ser Val Val Gln Ala Leu
            405                 410

<210> SEQ ID NO 30
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 30
atgcagaatt cgcaagagcc ggtgtcatta act                          33

<210> SEQ ID NO 31
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 31
gtatctcgag ttattcacgt gattccactt cttc                         34

<210> SEQ ID NO 32
<211> LENGTH: 714
<212> TYPE: DNA
<213> ORGANISM: Artificial sequence
<220> FEATURE:
<223> OTHER INFORMATION: Synthetic oligonucleotide

<400> SEQUENCE: 32
```

-continued

```
atgggcagca gccatcatca tcatcatcac agcagcggcc tggtgccgcg cggcagccat    60
atggctagca tgactggtgg acagcaaatg ggtcgggatc cgaattcgca agagccggtg   120
tcattaactc tggccctgct gttgggagga cttactatgg cggcatagc tgcaggagtt    180
ggaacaggga ctacagccct agtggccacc aaacaattcg agcagctcca ggcagccata   240
catacagacc ttggggcctt agaaaaatca gtcagtgccc tagaaaagtc tctgacctcg   300
ttgtctgagg tggtcctaca gaaccggagg ggattagatc tactgttcct aaaagaagga   360
ggattatgtg ctgccctaaa agaagaatgc tgttttacg cggaccacac tggcgtagta    420
agagatagca tggcaaagct aagagaaagg ttaaaccaga dacaaaaatt gttcgaatca   480
ggacaagggt ggtttgaggg actgtttaac aggtccccat ggttcacgac cctgatatcc   540
accattatgg gccctctgat agtacttttta ttaatcctac tcttcggacc ctgtattctc   600
aaccgcttgg tccagtttgt aaaagacaga atttcggtag tgcaggccct ggttctgacc   660
caacagtatc accaactcaa atcaatagat ccagaagaag tggaatcacg tgaa         714
```

<210> SEQ ID NO 33
<211> LENGTH: 238
<212> TYPE: PRT
<213> ORGANISM: Artificial sequence
<220> FEATURE:
<223> OTHER INFORMATION: Synthetic polypeptide

<400> SEQUENCE: 33

```
Met Gly Ser Ser His His His His His His Ser Ser Gly Leu Val Pro
1               5                   10                  15

Arg Gly Ser His Met Ala Ser Met Thr Gly Gly Gln Gln Met Gly Arg
            20                  25                  30

Asp Pro Asn Ser Gln Glu Pro Val Ser Leu Thr Leu Ala Leu Leu Leu
        35                  40                  45

Gly Gly Leu Thr Met Gly Gly Ile Ala Ala Gly Val Gly Thr Gly Thr
    50                  55                  60

Thr Ala Leu Val Ala Thr Lys Gln Phe Glu Gln Leu Gln Ala Ala Ile
65                  70                  75                  80

His Thr Asp Leu Gly Ala Leu Glu Lys Ser Val Ser Ala Leu Glu Lys
                85                  90                  95

Ser Leu Thr Ser Leu Ser Glu Val Val Leu Gln Asn Arg Arg Gly Leu
            100                 105                 110

Asp Leu Leu Phe Leu Lys Glu Gly Gly Leu Cys Ala Ala Leu Lys Glu
        115                 120                 125

Glu Cys Cys Phe Tyr Ala Asp His Thr Gly Val Val Arg Asp Ser Met
    130                 135                 140

Ala Lys Leu Arg Glu Arg Leu Asn Gln Arg Gln Lys Leu Phe Glu Ser
145                 150                 155                 160

Gly Gln Gly Trp Phe Glu Gly Leu Phe Asn Arg Ser Pro Trp Phe Thr
                165                 170                 175

Thr Leu Ile Ser Thr Ile Met Gly Pro Leu Ile Val Leu Leu Leu Ile
            180                 185                 190

Leu Leu Phe Gly Pro Cys Ile Leu Asn Arg Leu Val Gln Phe Val Lys
        195                 200                 205

Asp Arg Ile Ser Val Val Gln Ala Leu Val Leu Thr Gln Gln Tyr His
    210                 215                 220

Gln Leu Lys Ser Ile Asp Pro Glu Glu Val Glu Ser Arg Glu
225                 230                 235
```

```
<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34
taatacgact cactataggg                                                    20

<210> SEQ ID NO 35
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 35
gctagttatt gctcagcgg                                                     19

<210> SEQ ID NO 36
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 36
ggctttgggg tgtgtgatac g                                                  21

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
gtcggcgata taggcgccag                                                    20

<210> SEQ ID NO 38
<211> LENGTH: 1263
<212> TYPE: DNA
<213> ORGANISM: Artificial sequence
<220> FEATURE:
<223> OTHER INFORMATION: Synthetic oligonucleotide

<400> SEQUENCE: 38
atggcatcag tacagcgtga tagcccgcat caagtgttta acgtgacatg gaaaatcacc        60
aatctgatga ccggccaaac cgcaaacgcc accagtctgc tgggcaccat gacggatacc       120
ttccctaaac tgtacttcga cctgtgcgat ctggtaggtg ataattggga tgacccggaa       180
ccggatattg gggatggttg ccgttcgccg ggcggccgca aacgcactcg cctgtatgac       240
ttttacgtgt gtccggggca cactgttctg accggctgcg gaggtccacg tgagggctat       300
tgcgggaaat ggggttgcga aaccacaggg caggcttatt ggaaaccgtc atctagctgg       360
gatctgatct ctctgaagcg tggtaatacg ccgaaaggcc aagtccatg ttttgattcg        420 tctgtcggct caggttcaat tcaaggtgcc acgccggggg gccgttgtaa tccgctggtg       480
ctggaattta ctgatgcagg caaacgcgca agttgggatg cgccgaaaac ctggggtctg       540
cgtctgtacc gttctacggg tgcagacccg gtgaccctgt ttagtctgac cgccaggtc        600 ctgaacgttg gcccgcgcgt gcctattgga ccgaacccgg tgatcaccga gcagctgccg       660
cctagtcaac ctgtccagat catgctgccg cgcccacctc gcccgccgcc atcggggcg        720
```

```
gcatccatgg taccaggtgc gccgccacca tcgcagcagc cgggcaccgg cgatcgcctg    780
ctgaatctgg ttgaaggcgc gtatcaggcg ctgaacctga cctctccaga taaaacccag    840
gaatgctggc tgtgcctggt ctccggtcct ccttattatg aaggtgtggc tgtactgggt    900
acctattcca atcacacctc agcccctgcg aattgtagtg tgacgagcca gcataaactg    960
acgctgtccg aagtgactgg tcagggcctg tgcattggtg cggtaccgaa aacgcatcag   1020
gccctgtgca ataccaccca gaaaacttcc gacggctcat attatctggc gtccccggct   1080
ggtaccattt gggcttgctc gaccggtctg accccgtgtc tgagcaccac tgttctgaac   1140
ctgacgaccg attactgcgt cctggtggag ctgtggccga agtcaccta ccacagtccg    1200 aactatgttt atggtcagtt tgaaaagaaa actaaatata agcgccacca tcatcatcat   1260
cat                                                                 1263
```

<210> SEQ ID NO 39
<211> LENGTH: 421
<212> TYPE: PRT
<213> ORGANISM: Artificial sequence
<220> FEATURE:
<223> OTHER INFORMATION: Synthetic polypeptide

<400> SEQUENCE: 39

```
Met Ala Ser Val Gln Arg Asp Ser Pro His Gln Val Phe Asn Val Thr
1               5                   10                  15

Trp Lys Ile Thr Asn Leu Met Thr Gly Gln Thr Ala Asn Ala Thr Ser
            20                  25                  30

Leu Leu Gly Thr Met Thr Asp Thr Phe Pro Lys Leu Tyr Phe Asp Leu
        35                  40                  45

Cys Asp Leu Val Gly Asp Asn Trp Asp Asp Pro Glu Pro Asp Ile Gly
    50                  55                  60

Asp Gly Cys Arg Ser Pro Gly Gly Arg Lys Arg Thr Arg Leu Tyr Asp
65                  70                  75                  80

Phe Tyr Val Cys Pro Gly His Thr Val Leu Thr Gly Cys Gly Gly Pro
                85                  90                  95

Arg Glu Gly Tyr Cys Gly Lys Trp Gly Cys Glu Thr Thr Gly Gln Ala
            100                 105                 110

Tyr Trp Lys Pro Ser Ser Ser Trp Asp Leu Ile Ser Leu Lys Arg Gly
        115                 120                 125

Asn Thr Pro Lys Gly Gln Gly Pro Cys Phe Asp Ser Ser Val Gly Ser
    130                 135                 140

Gly Ser Ile Gln Gly Ala Thr Pro Gly Gly Arg Cys Asn Pro Leu Val
145                 150                 155                 160

Leu Glu Phe Thr Asp Ala Gly Lys Arg Ala Ser Trp Asp Ala Pro Lys
                165                 170                 175

Thr Trp Gly Leu Arg Leu Tyr Arg Ser Thr Gly Ala Asp Pro Val Thr
            180                 185                 190

Leu Phe Ser Leu Thr Arg Gln Val Leu Asn Val Gly Pro Arg Val Pro
        195                 200                 205

Ile Gly Pro Asn Pro Val Ile Thr Glu Gln Leu Pro Pro Ser Gln Pro
    210                 215                 220

Val Gln Ile Met Leu Pro Arg Pro Pro Arg Pro Pro Ser Gly Ala
225                 230                 235                 240

Ala Ser Met Val Pro Gly Ala Pro Pro Ser Gln Pro Gly Thr
                245                 250                 255

Gly Asp Arg Leu Leu Asn Leu Val Glu Gly Ala Tyr Gln Ala Leu Asn
```

```
                   260                 265                 270
Leu Thr Ser Pro Asp Lys Thr Gln Glu Cys Trp Leu Cys Leu Val Ser
        275                 280                 285
Gly Pro Pro Tyr Tyr Glu Gly Val Ala Val Leu Gly Thr Tyr Ser Asn
    290                 295                 300
His Thr Ser Ala Pro Ala Asn Cys Ser Val Thr Ser Gln His Lys Leu
305                 310                 315                 320
Thr Leu Ser Glu Val Thr Gly Gln Gly Leu Cys Ile Gly Ala Val Pro
                325                 330                 335
Lys Thr His Gln Ala Leu Cys Asn Thr Thr Gln Lys Thr Ser Asp Gly
            340                 345                 350
Ser Tyr Tyr Leu Ala Ser Pro Ala Gly Thr Ile Trp Ala Cys Ser Thr
        355                 360                 365
Gly Leu Thr Pro Cys Leu Ser Thr Thr Val Leu Asn Leu Thr Thr Asp
    370                 375                 380
Tyr Cys Val Leu Val Glu Leu Trp Pro Lys Val Thr Tyr His Ser Pro
385                 390                 395                 400
Asn Tyr Val Tyr Gly Gln Phe Glu Lys Lys Thr Lys Tyr Lys Arg His
                405                 410                 415
His His His His His
            420

<210> SEQ ID NO 40
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 40
tcacaagaat tctgcatcag tacagcgtga tagc                              34

<210> SEQ ID NO 41
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 41
atagtaggat cctattaatg atgatgatga tggtggcgc                         39

<210> SEQ ID NO 42
<211> LENGTH: 1998
<212> TYPE: DNA
<213> ORGANISM: Artificial sequence
<220> FEATURE:
<223> OTHER INFORMATION: Synthetic oligonucleotide

<400> SEQUENCE: 42
atgagttttg tggtcattat tcccgcgcgc tacgcgtcca cgcgtctgcc cggtaaacca    60
ttggttgata ttaacggcaa acccatgatt gttcatgttc ttgaacgcgc gcgtgaatca   120
ggtgccgagc gcatcatcgt ggcaaccgat catgaggatg ttgcccgcgc cgttgaagcc   180
gctggcggtg aagtatgtat gacgcgcgcc gatcatcagt caggaacaga acgtctggcg   240
gaagttgtcg aaaaatgcgc attcagcgac gacacggtga tcgttaatgt gcagggtgat   300
gaaccgatga tccctgcgac aatcattcgt caggttgctg ataacctcgc tcagcgtcag   360
gtgggtatga cgactctggc ggtgccaatc cacaatgcgg aagaagcgtt taacccgaat   420
```

```
gcggtgaaag tggttctcga cgctgaaggg tatgcactgt acttctctcg cgccaccatt      480
ccttgggatc gtgatcgttt tgcagaaggc cttgaaaccg ttggcgataa cttcctgcgt      540
catcttggta tttatggcta ccgtgcaggc tttatccgtc gttacgtcaa ctggcagcca      600
agtccgttag aacacatcga aatgttagag cagcttcgtg ttctgtggta cggcgaaaaa      660
atccatgttg ctgttgctca ggaagttcct ggcacaggtg tggataccc tgaagatctc      720 gacccgtcga cgaattctgc atcagtacag cgtgatagcc cgcatcaagt gtttaacgtg      780
acatggaaaa tcaccaatct gatgaccggc caaaccgcaa acgccaccag tctgctgggc      840
accatgacgg ataccttccc taaactgtac ttcgacctgt gcgatctggt aggtgataat      900
tgggatgacc cggaaccgga tattggggat ggttgccgtt cgccgggcgg ccgcaaacgc      960
actcgcctgt atgacttta cgtgtgtccg gggcacactg ttctgaccgg ctgcggaggt     1020
ccacgtgagg gctattgcgg gaaatggggt tgcgaaacca cagggcaggc ttattggaaa     1080
ccgtcatcta gctgggatct gatctctctg aagcgtggta atacgccgaa aggccaaggt     1140
ccatgttttg attcgtctgt cggctcaggt tcaattcaag gtgccacgcc gggggggccgt     1200 tgtaatccgc tggtgctgga atttactgat gcaggcaaac gcgcaagttg ggatgcgccg     1260
aaaacctggg gtctgcgtct gtaccgttct acgggtgcag acccggtgac cctgtttagt     1320
ctgacccgcc aggtcctgaa cgttggcccg cgcgtgccta ttggaccgaa cccggtgatc     1380
accgagcagc tgccgcctag tcaacctgtc cagatcatgc tgccgcgccc acctcgcccg     1440
ccgccatcgg gggcggcatc catggtacca ggtgcgccgc caccatcgca gcagccgggc     1500
accggcgatc gcctgctgaa tctggttgaa ggcgcgtatc aggcgctgaa cctgacctct     1560
ccagataaaa cccaggaatg ctggctgtgc ctggtctccg gtcctcctta ttatgaaggt     1620
gtggctgtac tgggtaccta ttccaatcac acctcagccc ctgcgaattg tagtgtgacg     1680
agccagcata aactgacgct gtccgaagtg actggtcagg gctgtgcat tggtgcggta     1740 ccgaaaacgc atcaggccct gtgcaatacc acccagaaaa cttccgacgg ctcatattat     1800
ctggcgtccc cggctggtac catttgggct tgctcgaccg gtctgacccc gtgtctgagc     1860
accactgttc tgaacctgac gaccgattac tgcgtcctgg tggagctgtg gccgaaagtc     1920
acctaccaca gtccgaacta tgtttatggt cagtttgaaa agaaaactaa atataagcgc     1980
caccatcatc atcatcat                                                   1998
```

<210> SEQ ID NO 43
<211> LENGTH: 666
<212> TYPE: PRT
<213> ORGANISM: Artificial sequence
<220> FEATURE:
<223> OTHER INFORMATION: Synthetic polypeptide

<400> SEQUENCE: 43

```
Met Ser Phe Val Val Ile Ile Pro Ala Arg Tyr Ala Ser Thr Arg Leu
1               5                   10                  15

Pro Gly Lys Pro Leu Val Asp Ile Asn Gly Lys Pro Met Ile Val His
                20                  25                  30

Val Leu Glu Arg Ala Arg Glu Ser Gly Ala Glu Arg Ile Ile Val Ala
            35                  40                  45

Thr Asp His Glu Asp Val Ala Arg Ala Val Glu Ala Ala Gly Gly Glu
        50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Asp Thr Val Ile Val Asn
```

-continued

```
                85                  90                  95
Val Gln Gly Asp Glu Pro Met Ile Pro Ala Thr Ile Ile Arg Gln Val
            100                 105                 110
Ala Asp Asn Leu Ala Gln Arg Gln Val Gly Met Thr Thr Leu Ala Val
            115                 120                 125
Pro Ile His Asn Ala Glu Glu Ala Phe Asn Pro Asn Ala Val Lys Val
            130                 135                 140
Val Leu Asp Ala Glu Gly Tyr Ala Leu Tyr Phe Ser Arg Ala Thr Ile
145                 150                 155                 160
Pro Trp Asp Arg Asp Arg Phe Ala Glu Gly Leu Glu Thr Val Gly Asp
            165                 170                 175
Asn Phe Leu Arg His Leu Gly Ile Tyr Gly Tyr Arg Ala Gly Phe Ile
            180                 185                 190
Arg Arg Tyr Val Asn Trp Gln Pro Ser Pro Leu Glu His Ile Glu Met
            195                 200                 205
Leu Glu Gln Leu Arg Val Leu Trp Tyr Gly Lys Ile His Val Ala
            210                 215                 220
Val Ala Gln Glu Val Pro Gly Thr Gly Val Asp Thr Pro Glu Asp Leu
225                 230                 235                 240
Asp Pro Ser Thr Asn Ser Ala Ser Val Gln Arg Asp Ser Pro His Gln
            245                 250                 255
Val Phe Asn Val Thr Trp Lys Ile Thr Asn Leu Met Thr Gly Gln Thr
            260                 265                 270
Ala Asn Ala Thr Ser Leu Leu Gly Thr Met Thr Asp Thr Phe Pro Lys
            275                 280                 285
Leu Tyr Phe Asp Leu Cys Asp Leu Val Gly Asp Asn Trp Asp Asp Pro
            290                 295                 300
Glu Pro Asp Ile Gly Asp Gly Cys Arg Ser Pro Gly Gly Arg Lys Arg
305                 310                 315                 320
Thr Arg Leu Tyr Asp Phe Tyr Val Cys Pro Gly His Thr Val Leu Thr
            325                 330                 335
Gly Cys Gly Gly Pro Arg Glu Gly Tyr Cys Gly Lys Trp Gly Cys Glu
            340                 345                 350
Thr Thr Gly Gln Ala Tyr Trp Lys Pro Ser Ser Ser Trp Asp Leu Ile
            355                 360                 365
Ser Leu Lys Arg Gly Asn Thr Pro Lys Gly Gln Gly Pro Cys Phe Asp
            370                 375                 380
Ser Ser Val Gly Ser Gly Ser Ile Gln Gly Ala Thr Pro Gly Gly Arg
385                 390                 395                 400
Cys Asn Pro Leu Val Leu Glu Phe Thr Asp Ala Gly Lys Arg Ala Ser
            405                 410                 415
Trp Asp Ala Pro Lys Thr Trp Gly Leu Arg Leu Tyr Arg Ser Thr Gly
            420                 425                 430
Ala Asp Pro Val Thr Leu Phe Ser Leu Thr Arg Gln Val Leu Asn Val
            435                 440                 445
Gly Pro Arg Val Pro Ile Gly Pro Asn Pro Val Ile Thr Glu Gln Leu
            450                 455                 460
Pro Pro Ser Gln Pro Val Gln Ile Met Leu Pro Arg Pro Pro Arg Pro
465                 470                 475                 480
Pro Pro Ser Gly Ala Ala Ser Met Val Pro Gly Ala Pro Pro Ser
            485                 490                 495
Gln Gln Pro Gly Thr Gly Asp Arg Leu Leu Asn Leu Val Glu Gly Ala
            500                 505                 510
```

-continued

```
Tyr Gln Ala Leu Asn Leu Thr Ser Pro Asp Lys Thr Gln Glu Cys Trp
        515                 520                 525

Leu Cys Leu Val Ser Gly Pro Pro Tyr Tyr Glu Gly Val Ala Val Leu
530                 535                 540

Gly Thr Tyr Ser Asn His Thr Ser Ala Pro Ala Asn Cys Ser Val Thr
545                 550                 555                 560

Ser Gln His Lys Leu Thr Leu Ser Glu Val Thr Gly Gln Gly Leu Cys
            565                 570                 575

Ile Gly Ala Val Pro Lys Thr His Gln Ala Leu Cys Asn Thr Thr Gln
        580                 585                 590

Lys Thr Ser Asp Gly Ser Tyr Tyr Leu Ala Ser Pro Ala Gly Thr Ile
    595                 600                 605

Trp Ala Cys Ser Thr Gly Leu Thr Pro Cys Leu Ser Thr Thr Val Leu
610                 615                 620

Asn Leu Thr Thr Asp Tyr Cys Val Leu Val Glu Leu Trp Pro Lys Val
625                 630                 635                 640

Thr Tyr His Ser Pro Asn Tyr Val Tyr Gly Gln Phe Glu Lys Lys Thr
            645                 650                 655

Lys Tyr Lys Arg His His His His His His
            660                 665

<210> SEQ ID NO 44
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 44
atagtactcg agctattagc gcttatattt agttttcttt tc                           42

<210> SEQ ID NO 45
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 45
gcccgcgcgt gcctattg                                                     18

<210> SEQ ID NO 46
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 46
cagaaaactt ccgacggc                                                     18

<210> SEQ ID NO 47
<211> LENGTH: 19
<212> TYPE: DNA
<213> ORGANISM: Artificial sequence
<220> FEATURE:
<223> OTHER INFORMATION: Synthetic oligonucleeotide

<400> SEQUENCE: 47
gaggtgtgat tggaatagg                                                    19

<210> SEQ ID NO 48
```

```
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 48
caccagcgga ttacaacg                                                  18

<210> SEQ ID NO 49
<211> LENGTH: 1350
<212> TYPE: DNA
<213> ORGANISM: Artificial sequence
<220> FEATURE:
<223> OTHER INFORMATION: Synthetic oligonucleotide

<400> SEQUENCE: 49
atgggcagca gccatcatca tcatcatcac agcagcggcc tggtgccgcg cggcagccat      60
atggctagca tgactggtgg acagcaaatg ggtcgggatc cgaattctgc atcagtacag     120
cgtgatagcc cgcatcaagt gtttaacgtg acatggaaaa tcaccaatct gatgaccggc     180
caaaccgcaa cgccaccag tctgctgggc accatgacgg taccttccc taaactgtac      240 ttcgacctgt gcgatctggt aggtgataat tgggatgacc cggaaccgga tattggggat     300
ggttgccgtt cgccgggcgg ccgcaaacgc actcgcctgt atgactttta cgtgtgtccg     360
gggcacactg ttctgaccgg ctgcggaggt ccacgtgagg ctattgcgg gaaatggggt     420 tgcgaaacca cagggcaggc ttattggaaa ccgtcatcta gctgggatct gatctctctg     480
aagcgtggta atacgccgaa aggccaaggt ccatgttttg attcgtctgt cggctcaggt     540
tcaattcaag gtgccacgcc ggggggccgt tgtaatccgc tggtgctgga atttactgat     600
gcaggcaaac gcgcaagttg ggatgcgccg aaaacctggg gtctgcgtct gtaccgttct     660
acgggtgcag acccggtgac cctgtttagt ctgacccgcc aggtcctgaa cgttggcccg     720
cgcgtgccta ttggaccgaa cccggtgatc accgagcagc tgccgcctag tcaacctgtc     780
cagatcatgc tgccgcgccc acctcgcccg ccgccatcgg gggcggcatc catggtacca     840
ggtgcgccgc caccatcgca gcagccgggc accggcgatc gcctgctgaa tctggttgaa     900
ggcgcgtatc aggcgctgaa cctgacctct ccagataaaa cccaggaatg ctggctgtgc     960
ctggtctccg gtcctcctta ttatgaaggt gtggctgtac tgggtaccta ttccaatcac    1020
acctcagccc ctgcgaattg tagtgtgacg agccagcata aactgacgct gtccgaagtg    1080
actggtcagg gcctgtgcat tggtgcggta ccgaaaacgc atcaggccct gtgcaatacc    1140
acccagaaaa cttccgacgg ctcatattat ctggcgtccc cggctggtac catttgggct    1200
tgctcgaccg gtctgacccc cgtgtctgagc accactgttc tgaacctgac gaccgattac    1260
tgcgtcctgg tggagctgtg gccgaaagtc acctaccaca gtccgaacta gtttatggt    1320 cagtttgaaa agaaaactaa atataagcgc                                    1350

<210> SEQ ID NO 50
<211> LENGTH: 450
<212> TYPE: PRT
<213> ORGANISM: Artificial sequence
<220> FEATURE:
<223> OTHER INFORMATION: Synthetic polypeptide

<400> SEQUENCE: 50

Met Gly Ser Ser His His His His His His Ser Ser Gly Leu Val Pro
1               5                   10                  15

Arg Gly Ser His Met Ala Ser Met Thr Gly Gly Gln Gln Met Gly Arg
```

-continued

```
                20                  25                  30
Asp Pro Asn Ser Ala Ser Val Gln Arg Asp Ser Pro His Gln Val Phe
            35                  40                  45
Asn Val Thr Trp Lys Ile Thr Asn Leu Met Thr Gly Gln Thr Ala Asn
        50                  55                  60
Ala Thr Ser Leu Leu Gly Thr Met Thr Asp Thr Phe Pro Lys Leu Tyr
65                  70                  75                  80
Phe Asp Leu Cys Asp Leu Val Gly Asp Asn Trp Asp Asp Pro Glu Pro
                85                  90                  95
Asp Ile Gly Asp Gly Cys Arg Ser Pro Gly Gly Arg Lys Arg Thr Arg
            100                 105                 110
Leu Tyr Asp Phe Tyr Val Cys Pro Gly His Thr Val Leu Thr Gly Cys
        115                 120                 125
Gly Gly Pro Arg Glu Gly Tyr Cys Gly Lys Trp Gly Cys Glu Thr Thr
    130                 135                 140
Gly Gln Ala Tyr Trp Lys Pro Ser Ser Ser Trp Asp Leu Ile Ser Leu
145                 150                 155                 160
Lys Arg Gly Asn Thr Pro Lys Gly Gln Gly Pro Cys Phe Asp Ser Ser
                165                 170                 175
Val Gly Ser Gly Ser Ile Gln Gly Ala Thr Pro Gly Gly Arg Cys Asn
            180                 185                 190
Pro Leu Val Leu Glu Phe Thr Asp Ala Gly Lys Arg Ala Ser Trp Asp
        195                 200                 205
Ala Pro Lys Thr Trp Gly Leu Arg Leu Tyr Arg Ser Thr Gly Ala Asp
    210                 215                 220
Pro Val Thr Leu Phe Ser Leu Thr Arg Gln Val Leu Asn Val Gly Pro
225                 230                 235                 240
Arg Val Pro Ile Gly Pro Asn Pro Val Ile Thr Glu Gln Leu Pro Pro
                245                 250                 255
Ser Gln Pro Val Gln Ile Met Leu Pro Arg Pro Pro Arg Pro Pro Pro
            260                 265                 270
Ser Gly Ala Ala Ser Met Val Pro Gly Ala Pro Pro Ser Gln Gln
        275                 280                 285
Pro Gly Thr Gly Asp Arg Leu Leu Asn Leu Val Glu Gly Ala Tyr Gln
    290                 295                 300
Ala Leu Asn Leu Thr Ser Pro Asp Lys Thr Gln Glu Cys Trp Leu Cys
305                 310                 315                 320
Leu Val Ser Gly Pro Pro Tyr Tyr Glu Gly Val Ala Val Leu Gly Thr
                325                 330                 335
Tyr Ser Asn His Thr Ser Ala Pro Ala Asn Cys Ser Val Thr Ser Gln
            340                 345                 350
His Lys Leu Thr Leu Ser Glu Val Thr Gly Gln Gly Leu Cys Ile Gly
        355                 360                 365
Ala Val Pro Lys Thr His Gln Ala Leu Cys Asn Thr Thr Gln Lys Thr
    370                 375                 380
Ser Asp Gly Ser Tyr Tyr Leu Ala Ser Pro Ala Gly Thr Ile Trp Ala
385                 390                 395                 400
Cys Ser Thr Gly Leu Thr Pro Cys Leu Ser Thr Thr Val Leu Asn Leu
                405                 410                 415
Thr Thr Asp Tyr Cys Val Leu Val Glu Leu Trp Pro Lys Val Thr Tyr
            420                 425                 430
His Ser Pro Asn Tyr Val Tyr Gly Gln Phe Glu Lys Lys Thr Lys Tyr
        435                 440                 445
```

Lys Arg
    450

<210> SEQ ID NO 51
<211> LENGTH: 405
<212> TYPE: DNA
<213> ORGANISM: Artificial sequence
<220> FEATURE:
<223> OTHER INFORMATION: Synthetic oligonucleotide

<400> SEQUENCE: 51

```
atgggccaga ccgttaccac cccgctgagc ctgaccctgc agcattgggg cgatgtgcag      60
cgtattgcaa gtaaccagtc tgttgatgtg aaaaaacgcc gttgggtgac gttctgcagc     120
gcggaatggc cgacgtttaa cgttggttgg ccgcaggatg gcacgtttaa tctgggcgtt     180
attagtcagg tgaaaagccg cgtgttttgc ccgggcccgc acggccatcc ggatcaggtt     240
ccgtatatcg ttacctggga agcgctggcg tatgatccgc cgccgtgggt gaaaccgttt     300
gtgagtccga aaccgccgcc gctgccgacc gcaccggttc tgccgccggg tccgtctgcc     360
cagccgccga gtcgcagcgc gctgtatcac catcatcatc atcat                     405
```

<210> SEQ ID NO 52
<211> LENGTH: 135
<212> TYPE: PRT
<213> ORGANISM: Artificial sequence
<220> FEATURE:
<223> OTHER INFORMATION: Synthetic polypeptide

<400> SEQUENCE: 52

Met Gly Gln Thr Val Thr Thr Pro Leu Ser Leu Thr Leu Gln His Trp
1               5                   10                  15

Gly Asp Val Gln Arg Ile Ala Ser Asn Gln Ser Val Asp Val Lys Lys
            20                  25                  30

Arg Arg Trp Val Thr Phe Cys Ser Ala Glu Trp Pro Thr Phe Asn Val
        35                  40                  45

Gly Trp Pro Gln Asp Gly Thr Phe Asn Leu Gly Val Ile Ser Gln Val
    50                  55                  60

Lys Ser Arg Val Phe Cys Pro Gly Pro His Gly His Pro Asp Gln Val
65                  70                  75                  80

Pro Tyr Ile Val Thr Trp Glu Ala Leu Ala Tyr Asp Pro Pro Pro Trp
                85                  90                  95

Val Lys Pro Phe Val Ser Pro Lys Pro Pro Leu Pro Thr Ala Pro
            100                 105                 110

Val Leu Pro Pro Gly Pro Ser Ala Gln Pro Pro Ser Arg Ser Ala Leu
        115                 120                 125

Tyr His His His His His His
    130                 135

<210> SEQ ID NO 53
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 53

```
tcacaagaat tctatgggcc agaccgttac caccc                                 35
```

<210> SEQ ID NO 54
<211> LENGTH: 45
<212> TYPE: DNA

<210> SEQ ID NO 55
<211> LENGTH: 1143
<212> TYPE: DNA
<213> ORGANISM: Artificial sequence
<220> FEATURE:
<223> OTHER INFORMATION: Synthetic oligonucleotide

<400> SEQUENCE: 54

```
atagtaggat cctattaatg atgatgatga tggtgataca gcgcg                45
```

<210> SEQ ID NO 55
<211> LENGTH: 1143
<212> TYPE: DNA
<213> ORGANISM: Artificial sequence
<220> FEATURE:
<223> OTHER INFORMATION: Synthetic oligonucleotide

<400> SEQUENCE: 55

```
atgagttttg tggtcattat tcccgcgcgc tacgcgtcca cgcgtctgcc cggtaaacca     60
ttggttgata ttaacggcaa acccatgatt gttcatgttc ttgaacgcgc gcgtgaatca    120
ggtgccgagc gcatcatcgt ggcaaccgat catgaggatg ttgcccgcgc cgttgaagcc    180
gctggcggtg aagtatgtat gacgcgcgcc gatcatcagt caggaacaga acgtctggcg    240
gaagttgtcg aaaaatgcgc attcagcgac gacacggtga tcgttaatgt gcagggtgat    300
gaaccgatga tccctgcgac aatcattcgt caggttgctg ataacctcgc tcagcgtcag    360
gtgggtatga cgactctggc ggtgccaatc cacaatgcgg aagaagcgtt taacccgaat    420
gcggtgaaag tggttctcga cgctgaaggg tatgcactgt acttctctcg cgccaccatt    480
ccttgggatc gtgatcgttt tgcagaaggc cttgaaaccg ttggcgataa cttcctgcgt    540
catcttggta tttatggcta ccgtgcaggc tttatccgtc gttacgtcaa ctggcagcca    600
agtccgttag aacacatcga atgttagag cagcttcgtg ttctgtggta cggcgaaaaa    660
atccatgttg ctgttgctca ggaagttcct ggcacaggtg tggatacccc tgaagatctc    720
gacccgtcga cgaattccat gggccagacc gttaccaccc cgctgagcct gaccctgcag    780
cattggggcg atgtgcagcg tattgcaagt aaccagtctg ttgatgtgaa aaaacgccgt    840
tgggtgacgt tctgcagcgc ggaatggccg acgtttaacg ttggttggcc gcaggatggc    900
acgtttaatc tgggcgttat tagtcaggtg aaaagccgcg tgttttgccc gggccccgcac    960
ggccatccgg atcaggttcc gtatatcgtt acctgggaag cgctggcgta tgatccgccg   1020
ccgtgggtga aaccgtttgt gagtccgaaa ccgccgccgc tgccgaccgc accggttctg   1080
ccgccgggtc cgtctgccca gccgccgagt cgcagcgcgc tgtatcacca tcatcatcat   1140
cat                                                                 1143
```

<210> SEQ ID NO 56
<211> LENGTH: 381
<212> TYPE: PRT
<213> ORGANISM: Artificial sequence
<220> FEATURE:
<223> OTHER INFORMATION: Synthetic polypeptide

<400> SEQUENCE: 56

```
Met Ser Phe Val Val Ile Ile Pro Ala Arg Tyr Ala Ser Thr Arg Leu
1               5                   10                  15

Pro Gly Lys Pro Leu Val Asp Ile Asn Gly Lys Pro Met Ile Val His
            20                  25                  30

Val Leu Glu Arg Ala Arg Glu Ser Gly Ala Glu Arg Ile Ile Val Ala
        35                  40                  45

Thr Asp His Glu Asp Val Ala Arg Ala Val Glu Ala Ala Gly Gly Glu
    50                  55                  60
```

```
Val Cys Met Thr Arg Ala Asp His Gln Ser Gly Thr Glu Arg Leu Ala
 65                  70                  75                  80

Glu Val Val Glu Lys Cys Ala Phe Ser Asp Thr Val Ile Val Asn
                 85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Thr Thr Leu Ala Val
            115                 120                 125

Pro Ile His Asn Ala Glu Glu Ala Phe Asn Pro Asn Ala Val Lys Val
        130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
            195                 200                 205

Leu Glu Gln Leu Arg Val Leu Trp Tyr Gly Glu Lys Ile His Val Ala
    210                 215                 220

Val Ala Gln Glu Val Pro Gly Thr Gly Val Asp Thr Pro Glu Asp Leu
225                 230                 235                 240

Asp Pro Ser Thr Asn Ser Met Gly Gln Thr Val Thr Pro Leu Ser
                245                 250                 255

Leu Thr Leu Gln His Trp Gly Asp Val Gln Arg Ile Ala Ser Asn Gln
            260                 265                 270

Ser Val Asp Val Lys Lys Arg Arg Trp Val Thr Phe Cys Ser Ala Glu
            275                 280                 285

Trp Pro Thr Phe Asn Val Gly Trp Pro Gln Asp Gly Thr Phe Asn Leu
        290                 295                 300

Gly Val Ile Ser Gln Val Lys Ser Arg Val Phe Cys Pro Gly Pro His
305                 310                 315                 320

Gly His Pro Asp Gln Val Pro Tyr Ile Val Thr Trp Glu Ala Leu Ala
                325                 330                 335

Tyr Asp Pro Pro Pro Trp Val Lys Pro Phe Val Ser Pro Lys Pro Pro
            340                 345                 350

Pro Leu Pro Thr Ala Pro Val Leu Pro Pro Gly Pro Ser Ala Gln Pro
        355                 360                 365

Pro Ser Arg Ser Ala Leu Tyr His His His His His
    370                 375                 380

<210> SEQ ID NO 57
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 57
tcacaagaat tctccggcgc tgaccccgag c                            31

<210> SEQ ID NO 58
<211> LENGTH: 49
<212> TYPE: DNA
<213> ORGANISM: Artificial sequence
<220> FEATURE:
<223> OTHER INFORMATION: Synthetic oligonucleotide
```

-continued

<400> SEQUENCE: 58
atagtaggat cctattaatg atgatgatga tgatgaaacg cctggctgg                49

<210> SEQ ID NO 59
<211> LENGTH: 1008
<212> TYPE: DNA
<213> ORGANISM: Artificial sequence
<220> FEATURE:
<223> OTHER INFORMATION: Synthetic oligonucleotide

<400> SEQUENCE: 59

```
atgagttttg tggtcattat tcccgcgcgc tacgcgtcca cgcgtctgcc cggtaaacca      60
ttggttgata ttaacggcaa acccatgatt gttcatgttc tgaacgcgc gcgtgaatca     120
ggtgccgagc gcatcatcgt ggcaaccgat catgaggatg ttgcccgcgc cgttgaagcc    180
gctggcggtg aagtatgtat gacgcgcgcc gatcatcagt caggaacaga acgtctggcg    240
gaagttgtcg aaaaatgcgc attcagcgac gacacggtga tcgttaatgt gcagggtgat    300
gaaccgatga tccctgcgac aatcattcgt caggttgctg ataacctcgc tcagcgtcag    360
gtgggtatga cgactctggc ggtgccaatc cacaatgcgg aagaagcgtt taacccgaat    420
gcggtgaaag tggttctcga cgctgaaggg tatgcactgt acttctctcg cgccaccatt    480
ccttgggatc gtgatcgttt tgcagaaggc cttgaaaccg ttggcgataa cttcctgcgt    540
catcttggta tttatggcta ccgtgcaggc tttatccgtc gttacgtcaa ctggcagcca    600
agtccgttag aacacatcga aatgttagag cagcttcgtg ttctgtggta cggcgaaaaa    660
atccatgttg ctgttgctca ggaagttcct ggcacaggtg tggataccc tgaagatctc    720
gacccgtcga cgaattctcc ggcgctgacc ccgagcatta aaagcaaacc gccgaaaccg    780
caggtgctgc cggatagcgg cggcccgctg attgatctgc tgaccgaaga tccgccgccg    840
tatggcgcgc agccgagcag cagcgcgcgt gaaaacaacg aagaagaagc ggcgaccacc    900
agcgaagtga gcccgccgag cccgatggtg agccgtctgc gtggccgtcg cgatccgccg    960
gcggcggata gcaccaccag ccaggcgttt catcatcatc atcatcat              1008
```

<210> SEQ ID NO 60
<211> LENGTH: 336
<212> TYPE: PRT
<213> ORGANISM: Artificial sequence
<220> FEATURE:
<223> OTHER INFORMATION: Synthetic polypeptide

<400> SEQUENCE: 60

Met Ser Phe Val Val Ile Ile Pro Ala Arg Tyr Ala Ser Thr Arg Leu
1               5                   10                  15

Pro Gly Lys Pro Leu Val Asp Ile Asn Gly Lys Pro Met Ile Val His
            20                  25                  30

Val Leu Glu Arg Ala Arg Glu Ser Gly Ala Glu Arg Ile Ile Val Ala
        35                  40                  45

Thr Asp His Glu Asp Val Ala Arg Ala Val Ala Ala Gly Gly Glu
    50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Asp Thr Val Ile Val Asn
                85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Thr Thr Leu Ala Val

```
                 115                 120                 125
Pro Ile His Asn Ala Glu Glu Ala Phe Asn Pro Asn Ala Val Lys Val
    130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
        195                 200                 205

Leu Glu Gln Leu Arg Val Leu Trp Tyr Gly Glu Lys Ile His Val Ala
    210                 215                 220

Val Ala Gln Glu Val Pro Gly Thr Gly Val Asp Thr Pro Glu Asp Leu
225                 230                 235                 240

Asp Pro Ser Thr Asn Ser Pro Ala Leu Thr Pro Ser Ile Lys Ser Lys
                245                 250                 255

Pro Pro Lys Pro Gln Val Leu Pro Asp Ser Gly Gly Pro Leu Ile Asp
            260                 265                 270

Leu Leu Thr Glu Asp Pro Pro Tyr Gly Ala Gln Pro Ser Ser Ser
        275                 280                 285

Ala Arg Glu Asn Asn Glu Glu Ala Ala Thr Thr Ser Glu Val Ser
    290                 295                 300

Pro Pro Ser Pro Met Val Ser Arg Leu Arg Gly Arg Arg Asp Pro Pro
305                 310                 315                 320

Ala Ala Asp Ser Thr Thr Ser Gln Ala Phe His His His His His
                325                 330                 335

<210> SEQ ID NO 61
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 61
atagtactcg agctattaaa acgcctggct ggtggtgc                       38

<210> SEQ ID NO 62
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 62
atgggcagca gccatcatca tcatcatcac agcagcggcc tggtgccgcg cggcagccat    60
atggctagca tgactggtgg acagcaaatg ggtcgggatc cgaattctcc ggcgctgacc   120
ccgagcatta aaagcaaacc gccgaaaccg caggtgctgc ggatagcgg cggcccgctg    180 attgatctgc tgaccgaaga tccgccgccg tatggcgcgc agccgagcag cagcgcgcgt   240
gaaaacaacg aagaagaagc ggcgaccacc agcgaagtga gcccgccgag cccgatggtg   300
agccgtctgc gtggccgtcg cgatccgccg gcggcggata gcaccaccag ccaggcgttt   360

<210> SEQ ID NO 63
<211> LENGTH: 120
<212> TYPE: PRT
<213> ORGANISM: Artificial sequence
```

<220> FEATURE:
<223> OTHER INFORMATION: Synthetic polypeptide

<400> SEQUENCE: 63

```
Met Gly Ser Ser His His His His His His Ser Ser Gly Leu Val Pro
1               5                   10                  15
Arg Gly Ser His Met Ala Ser Met Thr Gly Gly Gln Gln Met Gly Arg
            20                  25                  30
Asp Pro Asn Ser Pro Ala Leu Thr Pro Ser Ile Lys Ser Lys Pro Pro
        35                  40                  45
Lys Pro Gln Val Leu Pro Asp Ser Gly Gly Pro Leu Ile Asp Leu Leu
    50                  55                  60
Thr Glu Asp Pro Pro Tyr Gly Ala Gln Pro Ser Ser Ser Ala Arg
65                  70                  75                  80
Glu Asn Asn Glu Glu Ala Ala Thr Thr Ser Glu Val Ser Pro Pro
                85                  90                  95
Ser Pro Met Val Ser Arg Leu Arg Gly Arg Arg Asp Pro Pro Ala Ala
            100                 105                 110
Asp Ser Thr Thr Ser Gln Ala Phe
        115                 120
```

<210> SEQ ID NO 64
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 64
tcacaagaat tctccgctgc gtatgggcgg cg                              32

<210> SEQ ID NO 65
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 65
atagtaggat cctattaatg atgatgatga tgatgcagca gtttgctc             48

<210> SEQ ID NO 66
<211> LENGTH: 1545
<212> TYPE: DNA
<213> ORGANISM: Artificial sequence
<220> FEATURE:
<223> OTHER INFORMATION: Synthetic oligonucleotide

<400> SEQUENCE: 66
atgagttttg tggtcattat tcccgcgcgc tacgcgtcca cgcgtctgcc cggtaaacca    60
ttggttgata ttaacggcaa acccatgatt gttcatgttc tgaacgcgc gcgtgaatca   120 ggtgccgagc gcatcatcgt ggcaaccgat catgaggatg ttcccgcgc cgttgaagcc   180 gctggcggtg aagtatgtat gacgcgcgcc gatcatcagt caggaacaga acgtctggcg   240
gaagttgtcg aaaaatgcgc attcagcgac gacacggtga tcgttaatgt gcagggtgat   300
gaaccgatga tccctgcgac aatcattcgt caggttgctg ataacctcgc tcagcgtcag   360
gtgggtatga cgactctggc ggtgccaatc cacaatgcgg aagaagcgtt aacccgaat   420 gcggtgaaag tggttctcga cgctgaaggg tatgcactgt acttctctcg cgccaccatt   480
ccttgggatc gtgatcgttt tgcagaaggc cttgaaaccg ttggcgataa cttcctgcgt   540
```

-continued

```
catcttggta tttatggcta ccgtgcaggc tttatccgtc gttacgtcaa ctggcagcca    600
agtccgttag aacacatcga aatgttagag cagcttcgtg ttctgtggta cggcgaaaaa    660
atccatgttg ctgttgctca ggaagttcct ggcacaggtg tggataccCC tgaagatctc    720
gacccgtcga cgaattctcc gctgcgtatg ggcggcgatg ccagctgca gtattggccg    780 tttagcagca gcgatctgta taactggaaa acaacaacc cgagctttag cgaagatccg    840
ggcaaactga ccgcgctgat tgaaagcgtg ctgattaccc atcagccgac ctgggatgat    900
tgccagcagc tgctgggtac cctgctgacc ggcgaagaaa acagcgcgt gctgctggaa    960 gcgcgtaaag cggtgcgcgg caatgatggc cgtccgaccc agctgccgaa cgaagtgaac   1020
gcggcgtttc cgctggaacg tccggattgg gattatacca ccaccgaagg tcgcaaccat   1080
ctggtgctgt atcgtcagct gctgctggcg ggcctgcaga acgcgggccg cagcccgacc   1140
aacctggcga agtgaaagg cattacccag ggcccgaatg aaagcccgag cgcgtttctg   1200
gaacgtctga agaagcgta tcgccgttat acccCgtatg atccggaaga tccgggccag   1260
gaaaccaacg tgagcatgag ctttatttgg cagagcgcgc cggatattgg ccgtaaactg   1320
gaacgtctga agatctgaa agcaaaacc ctgggcgatc tggtgcgcga agcggaaaaa   1380
atttttaata acgcgaaac cccggaagaa cgtgaagaac gcattcgtcg cgaaattgaa   1440 gaaaagaag aacgccgtcg tgcggaagat gaacagcgcg aacgcgaacg cgatcgccgt   1500
cgtcatcgcg aaatgagcaa actgctgcat catcatcatc atcat                   1545
```

<210> SEQ ID NO 67
<211> LENGTH: 515
<212> TYPE: PRT
<213> ORGANISM: Artificial sequence
<220> FEATURE:
<223> OTHER INFORMATION: Synthetic polypeptide

<400> SEQUENCE: 67

```
Met Ser Phe Val Val Ile Ile Pro Ala Arg Tyr Ala Ser Thr Arg Leu
1               5                  10                  15

Pro Gly Lys Pro Leu Val Asp Ile Asn Gly Lys Pro Met Ile Val His
            20                  25                  30

Val Leu Glu Arg Ala Arg Glu Ser Gly Ala Glu Arg Ile Ile Val Ala
        35                  40                  45

Thr Asp His Glu Asp Val Ala Arg Ala Val Glu Ala Ala Gly Gly Glu
    50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Asp Thr Val Ile Val Asn
                85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Thr Thr Leu Ala Val
        115                 120                 125

Pro Ile His Asn Ala Glu Glu Ala Phe Asn Pro Asn Ala Val Lys Val
    130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190
```

```
Arg Arg Tyr Val Asn Trp Gln Pro Ser Pro Leu Glu His Ile Glu Met
        195                 200                 205
Leu Glu Gln Leu Arg Val Leu Trp Tyr Gly Glu Lys Ile His Val Ala
    210                 215                 220
Val Ala Gln Glu Val Pro Gly Thr Gly Val Asp Thr Pro Glu Asp Leu
225                 230                 235                 240
Asp Pro Ser Thr Asn Ser Pro Leu Arg Met Gly Gly Asp Gly Gln Leu
                245                 250                 255
Gln Tyr Trp Pro Phe Ser Ser Ser Asp Leu Tyr Asn Trp Lys Asn Asn
            260                 265                 270
Asn Pro Ser Phe Ser Glu Asp Pro Gly Lys Leu Thr Ala Leu Ile Glu
        275                 280                 285
Ser Val Leu Ile Thr His Gln Pro Thr Trp Asp Cys Gln Gln Leu
    290                 295                 300
Leu Gly Thr Leu Leu Thr Gly Glu Glu Lys Gln Arg Val Leu Leu Glu
305                 310                 315                 320
Ala Arg Lys Ala Val Arg Gly Asn Asp Gly Arg Pro Thr Gln Leu Pro
                325                 330                 335
Asn Glu Val Asn Ala Ala Phe Pro Leu Glu Arg Pro Asp Trp Asp Tyr
            340                 345                 350
Thr Thr Thr Glu Gly Arg Asn His Leu Val Leu Tyr Arg Gln Leu Leu
        355                 360                 365
Leu Ala Gly Leu Gln Asn Ala Gly Arg Ser Pro Thr Asn Leu Ala Lys
    370                 375                 380
Val Lys Gly Ile Thr Gln Gly Pro Asn Glu Ser Pro Ser Ala Phe Leu
385                 390                 395                 400
Glu Arg Leu Lys Glu Ala Tyr Arg Arg Tyr Thr Pro Tyr Asp Pro Glu
                405                 410                 415
Asp Pro Gly Gln Glu Thr Asn Val Ser Met Ser Phe Ile Trp Gln Ser
            420                 425                 430
Ala Pro Asp Ile Gly Arg Lys Leu Glu Arg Leu Glu Asp Leu Lys Ser
        435                 440                 445
Lys Thr Leu Gly Asp Leu Val Arg Glu Ala Glu Lys Ile Phe Asn Lys
    450                 455                 460
Arg Glu Thr Pro Glu Glu Arg Glu Glu Arg Ile Arg Arg Glu Ile Glu
465                 470                 475                 480
Glu Lys Glu Glu Arg Arg Ala Glu Asp Glu Gln Arg Glu Arg Glu
                485                 490                 495
Arg Asp Arg Arg Arg His Arg Glu Met Ser Lys Leu Leu His His His
            500                 505                 510
His His His
        515

<210> SEQ ID NO 68
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 68
tcacaagaat tccatggcat tcccactccg catg                              34

<210> SEQ ID NO 69
<211> LENGTH: 56
<212> TYPE: DNA
```

<213> ORGANISM: Artificial sequence
<220> FEATURE:
<223> OTHER INFORMATION: Synthetic oligonucleotide

<400> SEQUENCE: 69
atagtaggat ccttactagt ggtggtggtg gtggtgcaag agcttgctca tctctc        56

<210> SEQ ID NO 70
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 70
ggcagtccgg ggcaatgatg gacg        24

<210> SEQ ID NO 71
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 71
tccgatatcc ggggcagact gccag        25

<210> SEQ ID NO 72
<211> LENGTH: 816
<212> TYPE: DNA
<213> ORGANISM: Artificial sequence
<220> FEATURE:
<223> OTHER INFORMATION: Synthetic oligonucleotide

<400> SEQUENCE: 72
atggcattcc cactccgcat gggggagat ggccagcttc agtactggcc gttttcctcc        60
tctgatttat ataattggaa aaataataac ccttcctttt ctgaagatcc aggtaaattg       120
acggccttga ttgagtccgt cctcatcacc caccagccca cctgggacga ctgtcagcag       180
ttgttgggga ccctgctgac cggagaagaa agcagcgggt tgctcctaga ggctagaaag       240
gcagtccggg gcaatgatgg acgccccact cagttgccta atgaagtcaa tgctgctttt       300
cccctTgagc gccccgattg ggattacacc actacagaag gtaggaacca cctagtcctc       360
taccgccagt tgctcttagc gggtctccaa aacgcgggca ggagccccac caatttggcc       420
aaggtaaaag gataacccca gggacctaat gagtctccct cagcctttt agagagactc       480
aaggaggcct atcgcaggta cactccttat gaccctgagg acccagggca agaaaccaat       540
gtgtccatgt cattcatctg gcagtctgcc ccggatatcg gacgaaagtt agagcggtta       600
gaagatttaa agagcaagac cttaggagac ttagtgaggg aagctgaaaa gatctttaat       660
aagcgagaaa ccccggaaga agagaggaa cgtatcagga gaaaataga ggaaaaagaa        720
gaacgccgta gggcagagga tgagcagaga gagagagaaa gggaccgcag aagacataga       780
gagatgagca agctcttgca ccaccaccac caccac        816

<210> SEQ ID NO 73
<211> LENGTH: 272
<212> TYPE: PRT
<213> ORGANISM: Artificial sequence
<220> FEATURE:
<223> OTHER INFORMATION: Synthetic polypeptide

<400> SEQUENCE: 73

-continued

```
Met Ala Phe Pro Leu Arg Met Gly Gly Asp Gly Gln Leu Gln Tyr Trp
1               5                   10                  15

Pro Phe Ser Ser Ser Asp Leu Tyr Asn Trp Lys Asn Asn Pro Ser
            20                  25                  30

Phe Ser Glu Asp Pro Gly Lys Leu Thr Ala Leu Ile Glu Ser Val Leu
        35                  40                  45

Ile Thr His Gln Pro Thr Trp Asp Asp Cys Gln Gln Leu Leu Gly Thr
    50                  55                  60

Leu Leu Thr Gly Glu Glu Lys Gln Arg Val Leu Leu Glu Ala Arg Lys
65              70                  75                  80

Ala Val Arg Gly Asn Asp Gly Arg Pro Thr Gln Leu Pro Asn Glu Val
                85                  90                  95

Asn Ala Ala Phe Pro Leu Glu Arg Pro Asp Trp Asp Tyr Thr Thr Thr
            100                 105                 110

Glu Gly Arg Asn His Leu Val Leu Tyr Arg Gln Leu Leu Leu Ala Gly
        115                 120                 125

Leu Gln Asn Ala Gly Arg Ser Pro Thr Asn Leu Ala Lys Val Lys Gly
130             135                 140

Ile Thr Gln Gly Pro Asn Glu Ser Pro Ser Ala Phe Leu Glu Arg Leu
145                 150                 155                 160

Lys Glu Ala Tyr Arg Arg Tyr Thr Pro Tyr Asp Pro Glu Asp Pro Gly
                165                 170                 175

Gln Glu Thr Asn Val Ser Met Ser Phe Ile Trp Gln Ser Ala Pro Asp
            180                 185                 190

Ile Gly Arg Lys Leu Glu Arg Leu Glu Asp Leu Lys Ser Lys Thr Leu
        195                 200                 205

Gly Asp Leu Val Arg Glu Ala Glu Lys Ile Phe Asn Lys Arg Glu Thr
210                 215                 220

Pro Glu Glu Arg Glu Glu Arg Ile Arg Arg Glu Ile Glu Glu Lys Glu
225                 230                 235                 240

Glu Arg Arg Arg Ala Glu Asp Glu Gln Arg Glu Arg Glu Arg Asp Arg
                245                 250                 255

Arg Arg His Arg Glu Met Ser Lys Leu Leu His His His His His His
            260                 265                 270
```

<210> SEQ ID NO 74
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 74
tcacaagaat tctgcgaccg tggtgattgg c             31

<210> SEQ ID NO 75
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 75
atagtaggat cctattaatg atgatgatga tgatgcagca ggc            43

<210> SEQ ID NO 76
<211> LENGTH: 924
<212> TYPE: DNA
<213> ORGANISM: Artificial sequence
<220> FEATURE:
<223> OTHER INFORMATION: Synthetic oligonucleotide

<400> SEQUENCE: 76

```
atgagttttg tggtcattat tcccgcgcgc tacgcgtcca cgcgtctgcc cggtaaacca    60
ttggttgata ttaacggcaa acccatgatt gttcatgttc ttgaacgcgc gcgtgaatca   120
ggtgccgagc gcatcatcgt ggcaaccgat catgaggatg ttgcccgcgc cgttgaagcc   180
gctggcggtg aagtatgtat gacgcgcgcc gatcatcagt caggaacaga acgtctggcg   240
gaagttgtcg aaaaatgcgc attcagcgac gacacggtga tcgttaatgt gcagggtgat   300
gaaccgatga tccctgcgac aatcattcgt caggttgctg ataacctcgc tcagcgtcag   360
gtgggtatga cgactctggc ggtgccaatc cacaatgcgg aagaagcgtt taacccgaat   420
gcggtgaaag tggttctcga cgctgaaggg tatgcactgt acttctctcg cgccaccatt   480
ccttgggatc gtgatcgttt tgcagaaggc cttgaaaccg ttggcgataa cttcctgcgt   540
catcttggta tttatggcta ccgtgcaggc tttatccgtc gttacgtcaa ctggcagcca   600
agtccgttag aacacatcga atgttagag cagcttcgtg ttctgtggta cggcgaaaaa   660
atccatgttg ctgttgctca ggaagttcct ggcacaggtg tggataccccc tgaagatctc   720
gacccgtcga cgaattctgc gaccgtggtg attggccagc gtcaggatcg tcagggcggc   780
gaacgtcgcc gtccgcagct ggataaagat cagtgcgcgt attgcaaaga aaaaggccat   840
tgggcgaaag attgcccgaa aaaccgcgc ggcccgcgcg gcccgcgtcc gcagaccagc   900
ctgctgcatc atcatcatca tcat                                          924
```

<210> SEQ ID NO 77
<211> LENGTH: 308
<212> TYPE: PRT
<213> ORGANISM: Artificial sequence
<220> FEATURE:
<223> OTHER INFORMATION: Synthetic polypeptide

<400> SEQUENCE: 77

```
Met Ser Phe Val Val Ile Ile Pro Ala Arg Tyr Ala Ser Thr Arg Leu
1               5                   10                  15

Pro Gly Lys Pro Leu Val Asp Ile Asn Gly Lys Pro Met Ile Val His
                20                  25                  30

Val Leu Glu Arg Ala Arg Glu Ser Gly Ala Glu Arg Ile Ile Val Ala
            35                  40                  45

Thr Asp His Glu Asp Val Ala Arg Ala Val Glu Ala Ala Gly Gly Glu
        50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Asp Thr Val Ile Val Asn
                85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Thr Thr Leu Ala Val
        115                 120                 125

Pro Ile His Asn Ala Glu Glu Ala Phe Asn Pro Asn Ala Val Lys Val
    130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175
```

```
Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
        195                 200                 205

Leu Glu Gln Leu Arg Val Leu Trp Tyr Gly Lys Ile His Val Ala
    210                 215                 220

Val Ala Gln Glu Val Pro Gly Thr Gly Val Asp Thr Pro Glu Asp Leu
225                 230                 235                 240

Asp Pro Ser Thr Asn Ser Ala Thr Val Val Ile Gly Gln Arg Gln Asp
                245                 250                 255

Arg Gln Gly Gly Glu Arg Arg Pro Gln Leu Asp Lys Asp Gln Cys
    260                 265                 270

Ala Tyr Cys Lys Glu Lys Gly His Trp Ala Lys Asp Cys Pro Lys Lys
        275                 280                 285

Pro Arg Gly Pro Arg Gly Pro Arg Pro Gln Thr Ser Leu Leu His His
        290                 295                 300

His His His His
305

<210> SEQ ID NO 78
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 78
atagtactcg agctattaca gcaggctggt ctgcgg                              36

<210> SEQ ID NO 79
<211> LENGTH: 276
<212> TYPE: DNA
<213> ORGANISM: Artificial sequence
<220> FEATURE:
<223> OTHER INFORMATION: Synthetic oligonucleotide

<400> SEQUENCE: 79
atgggcagca gccatcatca tcatcatcac agcagcggcc tggtgccgcg cggcagccat    60
atggctagca tgactggtgg acagcaaatg ggtcgggatc cgaattctgc gaccgtggtg   120
attggccagc gtcaggatcg tcagggcggc gaacgtcgcc gtccgcagct ggataaagat   180
cagtgcgcgt attgcaaaga aaaaggccat tgggcgaaag attgcccgaa aaaaccgcgc   240
ggcccgcgcg gcccgcgtcc gcagaccagc ctgctg                             276

<210> SEQ ID NO 80
<211> LENGTH: 92
<212> TYPE: PRT
<213> ORGANISM: Artificial sequence
<220> FEATURE:
<223> OTHER INFORMATION: Synthetic polypeptide

<400> SEQUENCE: 80

Met Gly Ser Ser His His His His His His Ser Ser Gly Leu Val Pro
1               5                   10                  15

Arg Gly Ser His Met Ala Ser Met Thr Gly Gly Gln Gln Met Gly Arg
            20                  25                  30

Asp Pro Asn Ser Ala Thr Val Val Ile Gly Gln Arg Gln Asp Arg Gln
        35                  40                  45

Gly Gly Glu Arg Arg Pro Gln Leu Asp Lys Asp Gln Cys Ala Tyr
    50                  55                  60
```

```
Cys Lys Glu Lys Gly His Trp Ala Lys Asp Cys Pro Lys Lys Pro Arg
 65                  70                  75                  80

Gly Pro Arg Gly Pro Arg Pro Gln Thr Ser Leu Leu
                 85                  90
```

<210> SEQ ID NO 81
<211> LENGTH: 498
<212> TYPE: DNA
<213> ORGANISM: Artificial sequence
<220> FEATURE:
<223> OTHER INFORMATION: Synthetic oligonucleotide

<400> SEQUENCE: 81

```
gaaccggttt ctctgactct ggctctgctg ctgggtggtc tgactatggg tggcattgct     60
gctggcgtgg gtactggcac tactgcgctg gttgctacta acagttcga gcagctgcag    120
gcggcgattc acactgacct gggcgctctg gaaaaatctg tgtctgctct ggaaaaatcc    180
ctgacctccc tgtctgaagt tgttctgcag aaccgtcgtg gtctggacct gctgtttctg    240
aaagaaggcg gtctgtgtgc ggctctgaaa gaagaatgct gcttttatgc ggaccacacc    300
ggtgttgtgc gtgactccat ggctaaactg cgtgagcgtc tgaaccagcg tcagaaactg    360
tttgagtccg gccagggttg gtttgaaggt ctgttcaacc gttctccgtg gttcaccact    420
ctgatctcta ccggcccgtg tattctgaac cgcctggtgc agttcgtgaa agatcgtatc    480
tctgttgttc aggcgctg                                                 498
```

<210> SEQ ID NO 82
<211> LENGTH: 166
<212> TYPE: PRT
<213> ORGANISM: Artificial sequence
<220> FEATURE:
<223> OTHER INFORMATION: Synthetic polypeptide

<400> SEQUENCE: 82

```
Glu Pro Val Ser Leu Thr Leu Ala Leu Leu Leu Gly Gly Leu Thr Met
 1               5                  10                  15

Gly Gly Ile Ala Ala Gly Val Gly Thr Gly Thr Thr Ala Leu Val Ala
             20                  25                  30

Thr Lys Gln Phe Glu Gln Leu Gln Ala Ala Ile His Thr Asp Leu Gly
         35                  40                  45

Ala Leu Glu Lys Ser Val Ser Ala Leu Glu Lys Ser Leu Thr Ser Leu
     50                  55                  60

Ser Glu Val Val Leu Gln Asn Arg Arg Gly Leu Asp Leu Leu Phe Leu
 65                  70                  75                  80

Lys Glu Gly Gly Leu Cys Ala Ala Leu Lys Glu Glu Cys Cys Phe Tyr
                 85                  90                  95

Ala Asp His Thr Gly Val Val Arg Asp Ser Met Ala Lys Leu Arg Glu
            100                 105                 110

Arg Leu Asn Gln Arg Gln Lys Leu Phe Glu Ser Gly Gln Gly Trp Phe
        115                 120                 125

Glu Gly Leu Phe Asn Arg Ser Pro Trp Phe Thr Thr Leu Ile Ser Thr
    130                 135                 140

Gly Pro Cys Ile Leu Asn Arg Leu Val Gln Phe Val Lys Asp Arg Ile
145                 150                 155                 160

Ser Val Val Gln Ala Leu
                165
```

<210> SEQ ID NO 83

```
<211> LENGTH: 25
<212> TYPE: PRT
<213> ORGANISM: Artificial sequence
<220> FEATURE:
<223> OTHER INFORMATION: Synthetic polypeptide

<400> SEQUENCE: 83

Gly Val Val Arg Asp Ser Met Ala Lys Leu Arg Glu Arg Leu Asn Gln
1               5                   10                  15

Arg Gln Lys Leu Phe Glu Ser Arg Gln
            20                  25

<210> SEQ ID NO 84
<211> LENGTH: 25
<212> TYPE: PRT
<213> ORGANISM: Artificial sequence
<220> FEATURE:
<223> OTHER INFORMATION: Synthetic polypeptide

<400> SEQUENCE: 84

Leu Thr Ser Leu Ser Glu Val Val Leu Gln Asn Arg Arg Gly Leu Asp
1               5                   10                  15

Leu Leu Phe Leu Lys Glu Gly Gly Leu
            20                  25

<210> SEQ ID NO 85
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 85

Phe Tyr Ala Asp His Thr Gly Val Val Arg Asp Ser Met Ala Lys Leu
1               5                   10                  15

Arg Glu Arg Leu Asn Gln Arg Gln
            20

<210> SEQ ID NO 86
<211> LENGTH: 738
<212> TYPE: DNA
<213> ORGANISM: Artificial sequence
<220> FEATURE:
<223> OTHER INFORMATION: Synthetic oligonucleotide

<400> SEQUENCE: 86
atgagttttg tggtcattat tcccgcgcgc tacgcgtcca cgcgtctgcc cggtaaacca      60
ttggttgata ttaacggcaa acccatgatt gttcatgttc ttgaacgcgc gcgtgaatca     120
ggtgccgagc gcatcatcgt ggcaaccgat catgaggatg ttcccgcgc cgttgaagcc     180
gctggcggtg aagtatgtat gacgcgcgcc gatcatcagt caggaacaga acgtctggcg     240
gaagttgtcg aaaaatgcgc attcagcgac gacacggtga tcgttaatgt gcagggtgat     300
gaaccgatga tccctgcgac aatcattcgt caggttgctg ataacctcgc tcagcgtcag     360
gtgggtatga cgactctggc ggtgccaatc acaatgcgg aagaagcgtt taacccgaat      420
gcggtgaaag tggttctcga cgctgaaggg tatgcactgt acttctctcg cgccaccatt     480
ccttgggatc gtgatcgttt tgcagaaggc cttgaaccg ttggcgataa cttcctgcgt      540
catcttggta tttatggcta ccgtgcaggc tttatccgtc gttacgtcaa ctggcagcca     600
agtccgttag aacacatcga aatgttagag cagcttcgtg ttctgtggta cggcgaaaaa     660
atccatgttg ctgttgctca ggaagttcct ggcacaggtg tggataccc tgaagatctc     720
```

-continued gacccgtcga cgaattct                                                    738

<210> SEQ ID NO 87
<211> LENGTH: 246
<212> TYPE: PRT
<213> ORGANISM: Artificial sequence
<220> FEATURE:
<223> OTHER INFORMATION: Synthetic polypeptide

<400> SEQUENCE: 87

Met Ser Phe Val Val Ile Ile Pro Ala Arg Tyr Ala Ser Thr Arg Leu
1               5                   10                  15

Pro Gly Lys Pro Leu Val Asp Ile Asn Gly Lys Pro Met Ile Val His
            20                  25                  30

Val Leu Glu Arg Ala Arg Glu Ser Gly Ala Glu Arg Ile Ile Val Ala
        35                  40                  45

Thr Asp His Glu Asp Val Ala Arg Ala Val Glu Ala Ala Gly Gly Glu
    50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Asp Thr Val Ile Val Asn
                85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Thr Thr Leu Ala Val
        115                 120                 125

Pro Ile His Asn Ala Glu Glu Ala Phe Asn Pro Asn Ala Val Lys Val
    130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
        195                 200                 205

Leu Glu Gln Leu Arg Val Leu Trp Tyr Gly Glu Lys Ile His Val Ala
    210                 215                 220

Val Ala Gln Glu Val Pro Gly Thr Gly Val Asp Thr Pro Glu Asp Leu
225                 230                 235                 240

Asp Pro Ser Thr Asn Ser
                245

<210> SEQ ID NO 88
<211> LENGTH: 108
<212> TYPE: DNA
<213> ORGANISM: Artificial sequence
<220> FEATURE:
<223> OTHER INFORMATION: Synthetic oligonucleotide

<400> SEQUENCE: 88
atgggcagca gccatcatca tcatcatcac agcagcggcc tggtgccgcg cggcagccat        60
atggctagca tgactggtgg acagcaaatg ggtcgggatc cgaattct                    108

<210> SEQ ID NO 89
<211> LENGTH: 36
<212> TYPE: PRT
<213> ORGANISM: Artificial sequence
<220> FEATURE:

<223> OTHER INFORMATION: Synthetic polypeptide

<400> SEQUENCE: 89

```
Met Gly Ser Ser His His His His His His Ser Ser Gly Leu Val Pro
1               5                   10                  15

Arg Gly Ser His Met Ala Ser Met Thr Gly Gly Gln Gln Met Gly Arg
            20                  25                  30

Asp Pro Asn Ser
        35
```

<210> SEQ ID NO 90
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 90
tcacaatcgc gatgctcagt acaacgtgac agc                           33

<210> SEQ ID NO 91
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 91
atagtagcgg ccgcttacta atggtgatgg tgatgatgtc ttttatattt agttttcttt    60
tcaaactgg                                                            69

<210> SEQ ID NO 92
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 92
gagtgacaat gacatccact ttgc                                     24

<210> SEQ ID NO 93
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 93
ctgcattcta gttgtggttt gtcc                                     24

<210> SEQ ID NO 94
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 94
tggccgcgtc catctg                                              16

<210> SEQ ID NO 95
<211> LENGTH: 31
<212> TYPE: DNA
<213> ORGANISM: Artificial sequence -continued

```
<220> FEATURE:
<223> OTHER INFORMATION: Synthetic oligonucleotide

<400> SEQUENCE: 95
agcttataat ggttacaaat aaagcaatag c                                    31

<210> SEQ ID NO 96
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 96
cgatattgga gatggttgcc g                                               21

<210> SEQ ID NO 97
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 97
gcctgatggg ttttgggaac tg                                              22

<210> SEQ ID NO 98
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 98
ctactacgaa ggggtggccg tc                                              22

<210> SEQ ID NO 99
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 99
ggagtgtttc ctcgcttaag gg                                              22

<210> SEQ ID NO 100
<211> LENGTH: 441
<212> TYPE: PRT
<213> ORGANISM: Artificial sequence
<220> FEATURE:
<223> OTHER INFORMATION: Synthetic polypeptide

<400> SEQUENCE: 100

Met Asp Met Arg Val Pro Ala Gln Leu Leu Gly Leu Leu Leu Leu Trp
  1               5                  10                  15

Phe Pro Gly Ser Arg Cys Ser Val Gln Arg Asp Ser Pro His Gln Val
             20                  25                  30

Phe Asn Val Thr Trp Lys Ile Thr Asn Leu Met Thr Gly Gln Thr Ala
         35                  40                  45

Asn Ala Thr Ser Leu Leu Gly Thr Met Thr Asp Thr Phe Pro Lys Leu
     50                  55                  60

Tyr Phe Asp Leu Cys Asp Leu Val Gly Asp Asn Trp Asp Asp Pro Glu
 65                  70                  75                  80
```

Pro Asp Ile Gly Asp Gly Cys Arg Ser Pro Gly Gly Arg Lys Arg Thr
                85                  90                  95

Arg Leu Tyr Asp Phe Tyr Val Cys Pro Gly His Thr Val Leu Thr Gly
            100                 105                 110

Cys Gly Gly Pro Arg Glu Gly Tyr Cys Gly Lys Trp Gly Cys Glu Thr
        115                 120                 125

Thr Gly Gln Ala Tyr Trp Lys Pro Ser Ser Trp Asp Leu Ile Ser
    130                 135                 140

Leu Lys Arg Gly Asn Thr Pro Lys Gly Gln Gly Pro Cys Phe Asp Ser
145                 150                 155                 160

Ser Val Gly Ser Gly Ser Ile Gln Gly Ala Thr Pro Gly Gly Arg Cys
                165                 170                 175

Asn Pro Leu Val Leu Glu Phe Thr Asp Ala Gly Lys Arg Ala Ser Trp
            180                 185                 190

Asp Ala Pro Lys Thr Trp Gly Leu Arg Leu Tyr Arg Ser Thr Gly Ala
        195                 200                 205

Asp Pro Val Thr Leu Phe Ser Leu Thr Arg Gln Val Leu Asn Val Gly
    210                 215                 220

Pro Arg Val Pro Ile Gly Pro Asn Pro Val Ile Thr Glu Gln Leu Pro
225                 230                 235                 240

Pro Ser Gln Pro Val Gln Ile Met Leu Pro Arg Pro Arg Pro Pro
                245                 250                 255

Pro Ser Gly Ala Ala Ser Met Val Pro Gly Ala Pro Pro Ser Gln
            260                 265                 270

Gln Pro Gly Thr Gly Asp Arg Leu Leu Asn Leu Val Gly Ala Tyr
        275                 280                 285

Gln Ala Leu Asn Leu Thr Ser Pro Asp Lys Thr Gln Glu Cys Trp Leu
290                 295                 300

Cys Leu Val Ser Gly Pro Pro Tyr Tyr Glu Gly Val Ala Val Leu Gly
305                 310                 315                 320

Thr Tyr Ser Asn His Thr Ser Ala Pro Ala Asn Cys Ser Val Thr Ser
                325                 330                 335

Gln His Lys Leu Thr Leu Ser Glu Val Thr Gly Gln Gly Leu Cys Ile
            340                 345                 350

Gly Ala Val Pro Lys Thr His Gln Ala Leu Cys Asn Thr Thr Gln Lys
        355                 360                 365

Thr Ser Asp Gly Ser Tyr Tyr Leu Ala Ser Pro Ala Gly Thr Ile Trp
    370                 375                 380

Ala Cys Ser Thr Gly Leu Thr Pro Cys Leu Ser Thr Thr Val Leu Asn
385                 390                 395                 400

Leu Thr Thr Asp Tyr Cys Val Leu Val Glu Leu Trp Pro Lys Val Thr
                405                 410                 415

Tyr His Ser Pro Asn Tyr Val Tyr Gly Gln Phe Glu Lys Lys Thr Lys
            420                 425                 430

Tyr Lys Arg His His His His His His
        435                 440

<210> SEQ ID NO 101
<211> LENGTH: 1323
<212> TYPE: DNA
<213> ORGANISM: Artificial sequence
<220> FEATURE:
<223> OTHER INFORMATION: Synthetic oligonucleotide

<400> SEQUENCE: 101
atggacatgc gcgtgcccgc ccagctgctg ggcctgctgc tgctgtggtt ccccggctcg    60

```
cgatgctcag tacaacgtga cagccctcac caggtcttta atgtcacttg gaaaattacc    120
aacctaatga caggacaaac agctaatgct acctccctcc tggggacgat gacagacact    180
ttccctaaac tatattttga cttgtgtgat ttagttggag acaactggga tgacccggaa    240
cccgatattg gagatggttg ccgctctccc ggggaagaa aaaggacaag actatatgat     300
ttctatgttt gccccggtca tactgtatta acagggtgtg gagggccgag agagggctac    360
tgtggcaaat ggggatgtga gaccactgga caggcatact ggaagccatc atcatcatgg    420
gacctaattt cccttaagcg aggaaacact cctaagggtc agggcccctg ttttgattcc    480
tcagtgggct ccggtagcat ccagggtgcc acaccggggg gtcgatgcaa cccctagtc    540 ctagaattca ctgacgcggg taaaagggcc agctgggatg ccccaaaac atggggacta    600 agactgtatc gatccactgg ggccgacccg gtgaccctgt tctctctgac ccgccaggtc    660
ctcaatgtag gccccgcgt ccccattggg cctaatcccg tgatcactga acagctaccc    720
ccctcccaac ccgtgcagat catgctcccc aggcctcctc gtcctcctcc ttcaggcgcg    780
gcctctatgg tgcctggggc tccccgcct tctcaacaac ctgggacggg agacaggctg    840
ctaaacctgg tagaaggagc ctaccaagcc ctcaacctca ccagtcccga caaaaccccaa   900 gagtgctggc tgtgtctagt atcgggaccc ccctactacg aaggggtggc cgtcctaggt    960
acttactcca accatacctc tgccccggct aactgctccg tgacctccca acacaagctg   1020
accctgtccg aagtgaccgg gcagggactc tgcataggag cagttcccaa aacccatcag   1080
gccctgtgta ataccaccca gaagacgagc gacgggtcct actatttggc ctctcccgcc   1140
gggaccattt gggcttgcag caccgggctc actccctgtc tatctactac tgtgcttaac   1200
ttaaccactg attactgtgt cctggttgaa ctctggccaa aggtaaccta ccactcccct   1260
aattatgttt atggccagtt tgaaaagaaa actaaatata aagacatca tcaccatcac   1320 cat                                                                 1323
```

<210> SEQ ID NO 102
<211> LENGTH: 224
<212> TYPE: PRT
<213> ORGANISM: Artificial sequence
<220> FEATURE:
<223> OTHER INFORMATION: Synthetic polypeptide

<400> SEQUENCE: 102

```
Arg Gln Val Leu Asn Val Gly Pro Arg Val Pro Ile Gly Pro Asn Pro
1               5                   10                  15

Val Ile Thr Glu Gln Leu Pro Pro Ser Gln Pro Val Gln Ile Met Leu
            20                  25                  30

Pro Arg Pro Pro Arg Pro Pro Ser Gly Ala Ala Ser Met Val Pro
        35                  40                  45

Gly Ala Pro Pro Ser Gln Gln Pro Gly Thr Gly Asp Arg Leu Leu
    50                  55                  60

Asn Leu Val Glu Gly Ala Tyr Gln Ala Leu Asn Leu Thr Ser Pro Asp
65                  70                  75                  80

Lys Thr Gln Glu Cys Trp Leu Cys Leu Val Ser Gly Pro Pro Tyr Tyr
                85                  90                  95

Glu Gly Val Ala Val Leu Gly Thr Tyr Ser Asn His Thr Ser Ala Pro
            100                 105                 110

Ala Asn Cys Ser Val Thr Ser Gln His Lys Leu Thr Leu Ser Glu Val
        115                 120                 125

Thr Gly Gln Gly Leu Cys Ile Gly Ala Val Pro Lys Thr His Gln Ala
```

```
                130                 135                 140
Leu Cys Asn Thr Thr Gln Lys Thr Ser Asp Gly Ser Tyr Tyr Leu Ala
145                 150                 155                 160

Ser Pro Ala Gly Thr Ile Trp Ala Cys Ser Thr Gly Leu Thr Pro Cys
                165                 170                 175

Leu Ser Thr Thr Val Leu Asn Leu Thr Thr Asp Tyr Cys Val Leu Val
                180                 185                 190

Glu Leu Trp Pro Lys Val Thr Tyr His Ser Pro Asn Tyr Val Tyr Gly
                195                 200                 205

Gln Phe Glu Lys Lys Thr Lys Tyr Lys Arg His His His His His His
    210                 215                 220

<210> SEQ ID NO 103
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 103
tcacaatcgc gatgcccact ccgcatggg                                    29

<210> SEQ ID NO 104
<211> LENGTH: 56
<212> TYPE: DNA
<213> ORGANISM: Artificial sequence
<220> FEATURE:
<223> OTHER INFORMATION: Synthetic oligonucleotide

<400> SEQUENCE: 104
atagtagcgg ccgcttacta atggtgatgg tgatgatgca agagcttgct catctc      56

<210> SEQ ID NO 105
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 105
ggcagtccgg ggcaatgatg gacg                                         24

<210> SEQ ID NO 106
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 106
tccgatatcc ggggcagact gccag                                        25

<210> SEQ ID NO 107
<211> LENGTH: 291
<212> TYPE: PRT
<213> ORGANISM: Artificial sequence
<220> FEATURE:
<223> OTHER INFORMATION: Synthetic polypeptide

<400> SEQUENCE: 107

Met Asp Met Arg Val Pro Ala Gln Leu Leu Gly Leu Leu Leu Leu Trp
1               5                   10                  15

Phe Pro Gly Ser Arg Cys Pro Leu Arg Met Gly Gly Asp Gly Gln Leu
                20                  25                  30
```

Gln Tyr Trp Pro Phe Ser Ser Ser Asp Leu Tyr Asn Trp Lys Asn Asn
                35                  40                  45

Asn Pro Ser Phe Ser Glu Asp Pro Gly Lys Leu Thr Ala Leu Ile Glu
 50                  55                  60

Ser Val Leu Ile Thr His Gln Pro Thr Trp Asp Cys Gln Gln Leu
 65                  70                  75                  80

Leu Gly Thr Leu Leu Thr Gly Glu Glu Lys Gln Arg Val Leu Glu
                 85                  90                  95

Ala Arg Lys Ala Val Arg Gly Asn Asp Gly Arg Pro Thr Gln Leu Pro
                100                 105                 110

Asn Glu Val Asn Ala Ala Phe Pro Leu Glu Arg Pro Asp Trp Asp Tyr
                115                 120                 125

Thr Thr Thr Glu Gly Arg Asn His Leu Val Leu Tyr Arg Gln Leu Leu
                130                 135                 140

Leu Ala Gly Leu Gln Asn Ala Gly Arg Ser Pro Thr Asn Leu Ala Lys
145                 150                 155                 160

Val Lys Gly Ile Thr Gln Gly Pro Asn Glu Ser Pro Ser Ala Phe Leu
                165                 170                 175

Glu Arg Leu Lys Glu Ala Tyr Arg Arg Tyr Thr Pro Tyr Asp Pro Glu
                180                 185                 190

Asp Pro Gly Gln Glu Thr Asn Val Ser Met Ser Phe Ile Trp Gln Ser
                195                 200                 205

Ala Pro Asp Ile Gly Arg Lys Leu Glu Arg Leu Glu Asp Leu Lys Ser
210                 215                 220

Lys Thr Leu Gly Asp Leu Val Arg Glu Ala Glu Lys Ile Phe Asn Lys
225                 230                 235                 240

Arg Glu Thr Pro Glu Glu Arg Glu Arg Ile Arg Arg Glu Ile Glu
                245                 250                 255

Glu Lys Glu Glu Arg Arg Ala Glu Asp Glu Gln Arg Glu Arg Glu
                260                 265                 270

Arg Asp Arg Arg Arg His Arg Glu Met Ser Lys Leu Leu His His His
                275                 280                 285

His His His
    290

<210> SEQ ID NO 108
<211> LENGTH: 873
<212> TYPE: DNA
<213> ORGANISM: Artificial sequence
<220> FEATURE:
<223> OTHER INFORMATION: Synthetic oligonucleotide

<400> SEQUENCE: 108
atggacatgc gcgtgcccgc ccagctgctg ggcctgctgc tgctgtggtt ccccggctcg    60
cgatgcccac tccgcatggg gggagatggc cagcttcagt actggccgtt ttcctcctct   120
gatttatata attggaaaaa taataaccct tccttttctg aagatccagg taaattgacg   180
gccttgattg agtccgtcct catcacccac cagcccacct gggacgactg tcagcagttg   240
ttggggaccc tgctgaccgg agaagaaaag cagcgggtgc tcctagaggc tagaaaggca   300
gtccggggca atgatggacg ccccactcag ttgcctaatg aagtcaatgc tgcttttccc   360
cttgagcgcc ccgattggga ttacaccact acagaaggta ggaaccacct agtcctctac   420
cgccagttgc tcttagcggg tctccaaaac gcgggcagga gccccaccaa tttggccaag   480
gtaaaaggga taccccaggg acctaatgag tctccctcag cctttttaga gagactcaag   540

```
gaggcctatc gcaggtacac tccttatgac cctgaggacc cagggcaaga aaccaatgtg    600
tccatgtcat tcatctggca gtctgccccg gatatcggac gaaagttaga gcggttagaa    660
gatttaaaga gcaagacctt aggagactta gtgagggaag ctgaaaagat ctttaataag    720
cgagaaaccc cggaagaaag agaggaacgt atcaggagag aaatagagga aaagaagaa    780 cgccgtaggg cagaggatga gcagagagag agagaaaggg accgcagaag acatagagag    840
atgagcaagc tcttgcatca tcaccatcac cat                                 873
```

<210> SEQ ID NO 109
<211> LENGTH: 269
<212> TYPE: PRT
<213> ORGANISM: Artificial sequence
<220> FEATURE:
<223> OTHER INFORMATION: Synthetic polypeptide

<400> SEQUENCE: 109

```
Pro Leu Arg Met Gly Gly Asp Gly Gln Leu Gln Tyr Trp Pro Phe Ser
1               5                   10                  15

Ser Ser Asp Leu Tyr Asn Trp Lys Asn Asn Pro Ser Phe Ser Glu
            20                  25                  30

Asp Pro Gly Lys Leu Thr Ala Leu Ile Glu Ser Val Leu Ile Thr His
        35                  40                  45

Gln Pro Thr Trp Asp Asp Cys Gln Gln Leu Leu Gly Thr Leu Leu Thr
    50                  55                  60

Gly Glu Glu Lys Gln Arg Val Leu Leu Glu Ala Arg Lys Ala Val Arg
65                  70                  75                  80

Gly Asn Asp Gly Arg Pro Thr Gln Leu Pro Asn Glu Val Asn Ala Ala
                85                  90                  95

Phe Pro Leu Glu Arg Pro Asp Trp Asp Tyr Thr Thr Thr Glu Gly Arg
            100                 105                 110

Asn His Leu Val Leu Tyr Arg Gln Leu Leu Leu Ala Gly Leu Gln Asn
        115                 120                 125

Ala Gly Arg Ser Pro Thr Asn Leu Ala Lys Val Lys Gly Ile Thr Gln
    130                 135                 140

Gly Pro Asn Glu Ser Pro Ser Ala Phe Leu Glu Arg Leu Lys Glu Ala
145                 150                 155                 160

Tyr Arg Arg Tyr Thr Pro Tyr Asp Pro Glu Asp Pro Gly Gln Glu Thr
                165                 170                 175

Asn Val Ser Met Ser Phe Ile Trp Gln Ser Ala Pro Asp Ile Gly Arg
            180                 185                 190

Lys Leu Glu Arg Leu Glu Asp Leu Lys Ser Lys Thr Leu Gly Asp Leu
        195                 200                 205

Val Arg Glu Ala Glu Lys Ile Phe Asn Lys Arg Glu Thr Pro Glu Glu
    210                 215                 220

Arg Glu Glu Arg Ile Arg Arg Glu Ile Glu Glu Lys Glu Glu Arg Arg
225                 230                 235                 240

Arg Ala Glu Asp Glu Gln Arg Glu Arg Glu Arg Asp Arg Arg His
                245                 250                 255

Arg Glu Met Ser Lys Leu Leu His His His His His
            260                 265
```

MARKERS OF XMRV INFECTION AND USES THEREOF

This application claims priority to U.S. Provisional Application Ser. No. 61/221,752, filed on Jun. 30, 2009, and U.S. Provisional Application Ser. No. 61/305,604, filed on Feb. 18, 2010, the contents of each of which are hereby incorporated herein by reference in their entirety.

BACKGROUND OF THE INVENTION

1. Technical Field

The present invention relates generally to assays for the detection of Xenotropic Murine Leukemia Virus-related Retrovirus ("XMRV") and diseases associated with XMRV infection. Additionally, the invention relates to specific XMRV antigens capable of inducing an immunogenic response as well as XMRV-related nucleic acids having significant diagnostic, screening, and therapeutic utilities.

2. Background Information

XMRV is a newly identified gammaretrovirus discovered in prostate cancer tissue using Virochip DNA microarray technology (A. Urisman et al., *PloS Pathog.* 2:e25, 2006; International Application No. PCT/US2006/013167). Using PCR-cloned cDNAs full-length genomic sequences were generated from several prostate tumors (A. Urisman et al., *PloS Pathog.* 2:e25, 2006). Analysis revealed a potentially replication-competent retrovirus most closely related to xenotropic murine leukemia viruses. Initial screening using a nested reverse transcription-PCR (RT-PCR) assay found that XMRV was detectable in 40% (8/20) of tumor tissues from prostate cancer patients homozygous for the reduced activity R462Q variant of RNase L, as compared to just 1.5% (1/66) of patients heterozygous (RQ) or homozygous wild-type (RR) for this allele (A. Urisman et al., *PloS Pathog.* 2:e25, 2006). Consistent with this observation, XMRV was detected in only 1 of 105 non-familial prostate cancer patients and 1 of 70 tissue samples from men without prostate cancer (N. Fischer et al., *J. Clin. Virol.* 43:277, 2008).

Subsequent studies by Dong et al. (*Proc. Nat'l Acad. Sci. USA* 104:1655, 2007), revealed several important insights regarding XMRV: (1) infectious virus was produced from prostate cancer cell lines transfected with an XMRV genome derived from 2 cDNA clones. Moreover, the virus replicated in both prostate and non-prostate cell lines; (2) XMRV replication in the prostate cancer-derived cell line, DU145, is interferon sensitive; and (3) the human cell surface receptor required for infection with XMRV is xenotropic and polytropic retrovirus receptor 1 ("Xpr1"). Finally, characterization of integration sites in human prostate DNA provided unequivocal evidence for the capacity of XMRV to infect humans (Dong et al., *Proc. Nat'l Acad. Sci. USA* 104:1655, 2007; Kim et al., *J. Viral.* 82:9964, 2008). More recently, XMRV was identified in patients with chronic fatigue syndrome (Lombardi et al., *Science* 326:585-589, 2009; Oct. 23, 2009).

An alternative to detecting or screening for the virus directly is to detect or screen for an indirect or surrogate marker such as antibodies elicited due to infection with XMRV. Immunoassays designed to detect specific antibodies to other viruses are known and offer several advantages: (1) bodily fluids (e.g., plasma, serum, cerebrospinal fluid, saliva, tears, urine, or aqueous extracts of tissues and cells), generally more accessible than, for example, prostate tissue, can be screened; (2) immunoassays are amenable to automation facilitating high-throughput screening; (3) antibodies are intrinsically relatively stable so are amenable for storage and testing; (4) titers of antibodies induced by infection with XMRV may persist longer than XMRV polypeptides in the compartments being measured; and (5) would provide a method to distinguish between recent and chronic infections based on antibody isotype present in the sample. Availability of a high throughput serological assay (immunoassay) that detects XMRV-specific antibodies elicited by infection with the virus in bodily fluids (e.g., plasma, serum, cerebrospinal fluid, saliva, tears, urine, or aqueous extracts of tissues and cells) would thus greatly facilitate studies to establish the etiologic role of XMRV in prostate cancer or other diseases.

All patents and publications referred to herein are hereby incorporated in their entirety by reference.

SUMMARY OF THE INVENTION

The present invention encompasses an isolated nucleic acid sequence or fragment thereof comprising or complementary to a nucleotide sequence encoding a polypeptide, wherein the amino acid sequence of said polypeptide has at least 95% identity to an amino acid sequence selected from the group consisting of SEQ ID NO:23, SEQ ID NO:25, SEQ ID NO:27, SEQ ID NO:29, SEQ ID NO:33, SEQ ID NO:39, SEQ ID NO:43, SEQ ID NO:50, SEQ ID NO:52, SEQ ID NO:56, SEQ ID NO:60, SEQ ID NO:63, SEQ ID NO:67, SEQ ID NO:73, SEQ ID NO:77, SEQ ID NO:80, SEQ ID NO:82, SEQ ID NO:83, SEQ ID NO:84, SEQ ID NO:85, SEQ ID NO:102 and SEQ ID NO:109. Further, the present invention also includes an isolated nucleic acid sequence or fragment thereof comprising or complementary to a nucleotide sequence having at least 70% identity to a nucleotide sequence selected from the group consisting of SEQ ID NO:22, SEQ ID NO:24, SEQ ID NO:26, SEQ ID NO:28, SEQ ID NO:38, SEQ ID NO:42, SEQ ID NO:49, SEQ ID NO:51, SEQ ID NO:55, SEQ ID NO:59, SEQ ID NO:62, SEQ ID NO:66, SEQ ID NO:76, SEQ ID NO:79 and SEQ ID NO:81. The nucleic acid sequences may be isolated from or prepared using Xenotropic Murine Leukemia Virus-related Retrovirus (XMRV) or may be prepared synthetically. Further, such nucleic acid sequences may be used as probes and/or primers (e.g., in controls or calibrators in DNA-based molecular assays). The invention also encompasses purified proteins or fragments thereof encoded by the nucleic acid sequences referred to above.

Additionally, the present invention encompasses a purified protein or fragment thereof comprising an amino acid sequence having at least 95% or at least 97% identity to an amino acid sequence selected from the group consisting of SEQ ID NO:29, SEQ ID NO:25 and SEQ ID:82.

Moreover, the present invention also includes a method of producing a protein comprising the steps of: a) isolating a nucleic acid sequence selected from the group consisting of SEQ ID NO:22, SEQ ID NO:24, SEQ ID NO:26, SEQ ID NO:28, SEQ ID NO:38, SEQ ID NO:42, SEQ ID NO:49, SEQ ID NO:51, SEQ ID NO:55, SEQ ID NO:59, SEQ ID NO:62, SEQ ID NO:66, SEQ ID NO:76, SEQ ID NO:79 and SEQ ID NO:81; b) constructing a vector comprising the isolated nucleic acid sequence operably linked to a regulatory sequence; and c) introducing the vector into a host cell for a time and under conditions sufficient for expression of the protein.

Additionally, the present invention includes a vector comprising a nucleotide sequence selected from the group consisting of SEQ ID NO:22, SEQ ID NO:24, SEQ ID NO:26, SEQ ID NO:28, SEQ ID NO:38, SEQ ID NO:42, SEQ ID NO:49, SEQ ID NO:51, SEQ ID NO:55, SEQ ID NO:59, SEQ ID NO:62, SEQ ID NO:66, SEQ ID NO:76, SEQ ID NO:79 and SEQ ID NO:81, operably linked to a regulatory sequence. The invention also includes a host cell comprising this vector.

Furthermore, the present invention also encompasses a method of detecting anti-XMRV antibody in a test sample suspected of containing an anti-XMRV antibody comprising the steps of: (a) contacting said test sample with an antigen comprising an amino acid sequence selected from the group consisting of SEQ ID NO:23, SEQ ID NO:25, SEQ ID NO:27, SEQ ID NO:29, SEQ ID NO:33, SEQ ID NO:39, SEQ ID NO:43, SEQ ID NO:50, SEQ ID NO:52, SEQ ID NO:56, SEQ ID NO:60, SEQ ID NO:63, SEQ ID NO:67, SEQ ID NO:73, SEQ ID NO:77, SEQ ID NO:80 and SEQ ID NO:82, SEQ ID NO:83, SEQ ID NO:84, SEQ ID NO:85, SEQ ID NO:102 and SEQ ID NO:109, for a time and under conditions sufficient for the formation of antigen/anti-XMRV antibody complexes; and (b) detecting presence of anti-XMRV antibody present in the test sample by detecting presence of said antigen/anti-XMRV antibody complexes.

Moreover, the present invention includes a method of detecting anti-XMRV antibody in a test sample suspected of containing the anti-XMRV antibody comprising the steps of: (a) contacting the test sample with a first antigen comprising an amino acid sequence selected from the group consisting of SEQ ID NO:23, SEQ ID NO:25, SEQ ID NO:27, SEQ ID NO:29, SEQ ID NO:33, SEQ ID NO:39, SEQ ID NO:43, SEQ ID NO:50, SEQ ID NO:52, SEQ ID NO:56, SEQ ID NO:60, SEQ ID NO:63, SEQ ID NO:67, SEQ ID NO:73, SEQ ID NO:77, SEQ ID NO:80, SEQ ID NO:82, SEQ ID NO:83, SEQ ID NO:84, SEQ ID NO:85, SEQ ID NO:102 and SEQ ID NO:109, for a time and under conditions sufficient to allow for the formation of first antigen/anti-XMRV antibody complexes; (b) contacting an antibody conjugate to the antigen/anti-XMRV antibody complexes for a time and under conditions sufficient to allow the conjugate to bind to the bound anti-XMRV antibody, wherein the antibody conjugate comprises an antibody, against the anti-XMRV antibody, attached to a signal-generating compound capable of generating a detectable signal; and (c) detecting the presence of anti-XMRV antibody present in the test sample by detecting the presence of said signal generated by the signal-generating compound, the presence of the signal indicating the presence of anti-XMRV antibody in the test sample.

Additionally, the method of detecting anti-XMRV antibody in a test sample suspected of containing said anti-XMRV antibody may comprise the steps of: (a) contacting the test sample with antibody, for a time and under conditions sufficient to allow for the formation of antibody/anti-XMRV antibody complexes; and (b) detecting the presence of XMRV antibodies which may be present in the test sample by detecting the presence of the antibody/anti-XMRV antibody complexes. The antibody may be, for example, an anti-human antibody.

Also, the invention includes a method of detecting anti-XMRV antibody in a test sample suspected of containing the anti-XMRV antibody comprising the steps of: (a) contacting the test sample with antibody for a time and under conditions sufficient to allow for formation of antibody/anti-XMRV antibody complexes; (b) contacting an antigen conjugate to the antibody/anti-XMRV antibody complexes for a time and under conditions sufficient to allow the antigen conjugate to bind to the bound anti-XMRV antibody, wherein the conjugate comprises an antigen comprising an amino acid sequence selected from the group consisting of SEQ ID NO:23, SEQ ID NO:25, SEQ ID NO:27, SEQ ID NO:29, SEQ ID NO:33, SEQ ID NO:39, SEQ ID NO:43, SEQ ID NO:50, SEQ ID NO:52, SEQ ID NO:56, SEQ ID NO:60, SEQ ID NO:63, SEQ ID NO:67, SEQ ID NO:73, SEQ ID NO:77, SEQ ID NO:80, SEQ ID NO:82, SEQ ID NO:83, SEQ ID NO:84, SEQ ID NO:85, SEQ ID NO:102 and SEQ ID NO:109, attached to a signal-generating compound capable of generating a detectable signal; and (c) detecting the presence of anti-XMRV antibody which may be present in the test sample by detecting presence of the signal generated by the signal-generating compound, presence of the signal indicating presence of anti-XMRV antibody in the test sample. In certain embodiments the antigen portion of the antigen conjugate is identical to the antigen employed to initially bind the anti-XMRV antibody, or the antigen portion of the antigen conjugate can be distinct, yet capable of being bound by the same anti-XMRV antibody.

The present invention encompasses yet another method for detecting the presence of anti-XMRV antibodies in a test sample. This method comprises the steps of: (a) contacting the test sample suspected of containing the antibodies with an isolated protein or antigen comprising an amino acid sequence selected from the group consisting of p15E-CKS (SEQ ID NO:27), p15EΔ-CKS (SEQ ID NO:29), p15E-PET (SEQ ID NO:33), p15E-PL (SEQ ID NO:23), p15EΔ-PL (SEQ ID NO:25), p15EΔ (SEQ ID NO:82) and epitopes thereof (i.e., SEQ ID NOs: 83, 84 and 85), p70-PL (SEQ ID NO:39), p70-CKS (SEQ ID NO:43), p70-PET (SEQ ID NO:50), p30-CKS (SEQ ID NO:67), p30-PL (SEQ ID NO:73), p15-PL (SEQ ID NO:52), p15-CKS (SEQ ID NO:56), p12-CKS (SEQ ID NO:60), p12-PET (SEQ ID NO:63), p10-CKS (SEQ ID NO:77), p10-PET (SEQ ID NO:80), gp70 (SEQ ID NO:102) and p30 (SEQ ID NO:109), for a time and under conditions sufficient to allow the formation of antigen/anti-XMRV antibody complexes; (b) adding a XMRV antigen conjugate comprising an amino acid sequence selected from the group consisting of p15E-CKS (SEQ ID NO:27), p15EΔ-CKS (SEQ ID NO:29), p15E-PET (SEQ ID NO:33), p15EΔ-PL (SEQ ID NO:23), p15EΔ-PL (SEQ ID NO:25), p15EΔ (SEQ ID NO:82) and epitopes thereof (i.e., SEQ ID NOs: 83, 84 and 85), p70-PL (SEQ ID NO:39), p70-CKS (SEQ ID NO:43), p70-PET (SEQ ID NO:50), p30-CKS (SEQ ID NO:67), p30-PL (SEQ ID NO:73), p15-PL (SEQ ID NO:52), p15-CKS (SEQ ID NO:56), p12-CKS (SEQ ID NO:60), p12-PET (SEQ ID NO:63), p10-CKS (SEQ ID NO:77), p10-PET (SEQ ID NO:80), gp70 (SEQ ID NO:102) and p30 (SEQ ID NO:109) to the resulting antigen/XMRV antibody complexes for a time and under conditions sufficient to allow the antigen to bind to the bound XMRV antibody, the XMRV antigen conjugate being operably linked to a ligand binding moiety, and (c) detecting the presence of anti-XMRV antibodies which may be present in the test sample by detecting the signal generated by a signal-generating compound operably linked to the ligand bound by the ligand binding moiety operably linked to antigen conjugate. In certain embodiments the antigen portion of the antigen conjugate is identical to the antigen employed to initially bind the anti-XMRV antibody, or the antigen portion of the antigen conjugate can be distinct, yet capable of being bound by the same anti-XMRV antibody. Again, a control or calibrator may be used which comprises antibody to XMRV.

Additionally, the present invention includes a kit for determining the presence of anti-XMRV antibody in a test sample comprising at least one antigen comprising an amino acid sequence selected from the group consisting of SEQ ID NO:23, SEQ ID NO:25, SEQ ID NO:27, SEQ ID NO:29, SEQ ID NO:33, SEQ ID NO:39, SEQ ID NO:43, SEQ ID NO:50, SEQ ID NO:52, SEQ ID NO:56, SEQ ID NO:60, SEQ ID NO:63, SEQ ID NO:67, SEQ ID NO:73, SEQ ID NO:77, SEQ ID NO:80 and SEQ ID NO:82, SEQ ID NO:83, SEQ ID NO:84, SEQ ID NO:85, SEQ ID NO:102 and SEQ ID NO:109.

Moreover, the present invention also includes a kit for determining the presence of anti-XMRV antibody in a test sample comprising: a) at least one antigen comprising an amino acid sequence selected from the group consisting of SEQ ID NO:23, SEQ ID NO:25, SEQ ID NO:27, SEQ ID NO:29, SEQ ID NO:33, SEQ ID NO:39, SEQ ID NO:43, SEQ ID NO:50, SEQ ID NO:52, SEQ ID NO:56, SEQ ID NO:60, SEQ ID NO:63, SEQ ID NO:67, SEQ ID NO:73, SEQ ID NO:77, SEQ ID NO:80 and SEQ ID NO:82, SEQ ID NO:83, SEQ ID NO:84, SEQ ID NO:85, SEQ ID NO:102 and SEQ ID NO:1095; and b) a conjugate comprising: 1) an antibody to anti-XMRV antibody attached to 2) a signal-generating compound capable of generating a detectable signal.

Furthermore, the present invention also includes a kit for detecting anti-XMRV antibody in a test sample comprising: a) at least one antigen comprising an amino acid sequence selected from the group consisting of SEQ ID NO:23, SEQ ID NO:25, SEQ ID NO:27, SEQ ID NO:29, SEQ ID NO:33, SEQ ID NO:39, SEQ ID NO:43, SEQ ID NO:50, SEQ ID NO:52, SEQ ID NO:56, SEQ ID NO:60, SEQ ID NO:63, SEQ ID NO:67, SEQ ID NO:73, SEQ ID NO:77, SEQ ID NO:80 and SEQ ID NO:82, SEQ ID NO:83, SEQ ID NO:84, SEQ ID NO:85, SEQ ID NO:102 and SEQ ID NO:109 bound on a solid phase; and b) a conjugate comprising: 1) an antigen comprising an amino acid sequence selected from the group consisting of SEQ ID NO:23, SEQ ID NO:25, SEQ ID NO:27, SEQ ID NO:29, SEQ ID NO:33, SEQ ID NO:39, SEQ ID NO:43, SEQ ID NO:50, SEQ ID NO:52, SEQ ID NO:56, SEQ ID NO:60, SEQ ID NO:63, SEQ ID NO:67, SEQ ID NO:73, SEQ ID NO:77, SEQ ID NO:80 and SEQ ID NO:82, SEQ ID NO:83, SEQ ID NO:84, SEQ ID NO:85, SEQ ID NO:102 and SEQ ID NO:109 attached to 2) a signal-generating compound capable of generating a detectable signal. At least one antigen may comprise any of the amino acid sequences or proteins of the conjugate.

Additionally, the present invention encompasses a kit for detecting anti-XMRV antibody in a test sample comprising: a) an antibody to anti-XMRV antibody and b) a conjugate comprising: 1) an antigen comprising an amino acid sequence selected from the group consisting of SEQ ID NO:23, SEQ ID NO:25, SEQ ID NO:27, SEQ ID NO:29, SEQ ID NO:33, SEQ ID NO:39, SEQ ID NO:43, SEQ ID NO:50, SEQ ID NO:52, SEQ ID NO:56, SEQ ID NO:60, SEQ ID NO:63, SEQ ID NO:67, SEQ ID NO:73, SEQ ID NO:77, SEQ ID NO:80 and SEQ ID NO:82, SEQ ID NO:83, SEQ ID NO:84, SEQ ID NO:85, SEQ ID NO:102 and SEQ ID NO:109 attached to 2) a signal-generating compound capable of generating a detectable signal.

Further, the present invention also includes a kit for detecting anti-XMRV antibody in a test sample comprising: a) a first antibody against anti-XMRV antibody and b) a conjugate comprising: 1) a second antibody against anti-XMRV antibody attached to 2) a signal-generating compound capable of generating a detectable signal.

Additionally, the present invention encompasses an isolated protein comprising an amino acid sequence selected from the group consisting of SEQ ID NO:83, SEQ ID NO:84 and SEQ ID NO:85.

Further, the present invention includes a method of detecting XMRV infection in a mammal comprising the steps of: (a) isolating a test sample from the mammal; (b) contacting the test sample with an antigen comprising an amino acid sequence selected from the group consisting of SEQ ID NO:23, SEQ ID NO:25, SEQ ID NO:27, SEQ ID NO:29, SEQ ID NO:33, SEQ ID NO:39, SEQ ID NO:43, SEQ ID NO:50, SEQ ID NO:52, SEQ ID NO:56, SEQ ID NO:60, SEQ ID NO:63, SEQ ID NO:67, SEQ ID NO:73, SEQ ID NO:77, SEQ ID NO:80, SEQ ID NO:82, SEQ ID NO:83, SEQ ID NO:84, SEQ ID NO:85, SEQ ID NO:102 and SEQ ID NO:109, for a time and under conditions sufficient for the formation of antigen/anti-XMRV antibody complexes; and (c) detecting presence of anti-XMRV antibody present in the test sample by detecting presence of the antigen/anti-XMRV antibody complexes, presence of the complexes indicating past or present XMRV infection in the mammal.

Moreover, the present invention encompasses a method of detecting XMRV infection in a mammal comprising the steps of: (a) isolating a test sample from the mammal; (b) contacting the test sample with a first antigen comprising an amino acid sequence selected from the group consisting of SEQ ID NO:23, SEQ ID NO:25, SEQ ID NO:27, SEQ ID NO:29, SEQ ID NO:33, SEQ ID NO:39, SEQ ID NO:43, SEQ ID NO:50, SEQ ID NO:52, SEQ ID NO:56, SEQ ID NO:60, SEQ ID NO:63, SEQ ID NO:67, SEQ ID NO:73, SEQ ID NO:77, SEQ ID NO:80, SEQ ID NO:82, SEQ ID NO:83, SEQ ID NO:84, SEQ ID NO:85, SEQ ID NO:102 and SEQ ID NO:109, for a time and under conditions sufficient to allow for the formation of first antigen/anti-XMRV antibody complexes; (c) contacting an antibody conjugate to the antigen/anti-XMRV antibody complexes for a time and under conditions sufficient to allow the antibody conjugate to bind to the bound anti-XMRV antibody, wherein the antibody conjugate comprises an antibody, against the anti-XMRV antibody, attached to a signal-generating compound capable of generating a detectable signal; and (d) detecting presence of anti-XMRV antibody present in the test sample by detecting presence of the signal generated by the signal-generating compound, presence of the signal indicating past or present XMRV infection in the mammal.

Additionally, the present invention includes a method of detecting XMRV infection in a mammal comprising the steps of: (a) obtaining a test sample from the mammal; (b) contacting the test sample with an antibody, for a time and under conditions sufficient to allow for the formation of antibody/anti-XMRV antibody complexes; and (c) detecting presence of XMRV antibodies which may be present in the test sample by detecting presence of the antibody/anti-XMRV antibody complexes, presence of the complexes indicating past or present XMRV infection in the mammal.

Moreover, the present invention also includes a method of detecting XMRV infection in a mammal comprising the steps of: (a) isolating a test sample from the mammal; (b) contacting the test sample with an antibody for a time and under conditions sufficient to allow for formation of antibody/anti-XMRV antibody complexes; (c) contacting an antigen conjugate to the resulting antibody/anti-XMRV antibody complexes for a time and under conditions sufficient to allow the conjugate to bind to the bound anti-XMRV antibody, wherein the antigen conjugate comprises an amino acid sequence selected from the group consisting of SEQ ID NO:23, SEQ ID NO:25, SEQ ID NO:27, SEQ ID NO:29, SEQ ID NO:33, SEQ ID NO:39, SEQ ID NO:43, SEQ ID NO:50, SEQ ID NO:52, SEQ ID NO:56, SEQ ID NO:60, SEQ ID NO:63, SEQ ID NO:67, SEQ ID NO:73, SEQ ID NO:77, SEQ ID NO:80, SEQ ID NO:82, SEQ ID NO:83, SEQ ID NO:84, SEQ ID NO:85, SEQ ID NO:102 and SEQ ID NO:109, attached to a signal-generating compound capable of generating a detectable signal; and (d) detecting the presence of an anti-XMRV antibody which may be present in the test sample by detecting presence of the signal generated by said signal-generating compound, presence of the signal indicating past or present XMRV infection in the mammal.

Furthermore, the present invention also includes a method of detecting XMRV infection in a mammal comprising the steps of: (a) obtaining a test sample from the mammal; (b) contacting the test sample with a first antigen comprising an amino acid sequence selected from the group consisting of SEQ ID NO:23, SEQ ID NO:25, SEQ ID NO:27, SEQ ID NO:29, SEQ ID NO:33, SEQ ID NO:39, SEQ ID NO:43, SEQ ID NO:50, SEQ ID NO:52, SEQ ID NO:56, SEQ ID NO:60, SEQ ID NO:63, SEQ ID NO:67, SEQ ID NO:73, SEQ ID NO:77, SEQ ID NO:80, SEQ ID NO:82, SEQ ID NO:83, SEQ ID NO:84, SEQ ID NO:85, SEQ ID NO:102 and SEQ ID NO:109, for a time and under conditions sufficient to allow for the formation of first antigen/anti-XMRV antibody complexes; (c) contacting an antigen conjugate to the antigen/anti-XMRV antibody complexes for a time and under conditions sufficient to allow the antigen conjugate to bind to the bound anti-XMRV antibody, wherein the antigen conjugate comprises an amino acid sequence selected from the group consisting of SEQ ID NO:23, SEQ ID NO:25, SEQ ID NO:27, SEQ ID NO:29, SEQ ID NO:33, SEQ ID NO:39, SEQ ID NO:43, SEQ ID NO:50, SEQ ID NO:52, SEQ ID NO:56, SEQ ID NO:60, SEQ ID NO:63, SEQ ID NO:67, SEQ ID NO:73, SEQ ID NO:77, SEQ ID NO:80, SEQ ID NO:82, SEQ ID NO:83, SEQ ID NO:84, SEQ ID NO:85, SEQ ID NO:102 and SEQ ID NO:109, attached to a signal-generating compound capable of generating a detectable signal; and (d) detecting presence of anti-XMRV antibody present in the test sample by detecting presence of the signal generated by the signal-generating compound, presence of the anti-XMRV antibody indicating past or present XMRV infection in the mammal.

Also, the present invention encompasses a method of detecting XMRV infection in a mammal comprising the steps of: (a) obtaining a test sample from the mammal; (b) contacting the test sample with a first antibody against anti-XMRV antibody, for a time and under conditions sufficient to allow for formation of first antibody/anti-XMRV antibody complexes; (c) adding a conjugate to said first antibody/anti-XMRV antibody complexes for a time and under conditions sufficient for the conjugate to bind to the bound anti-XMRV antibody, wherein the conjugate comprises a second antibody, against the anti-XMRV antibody, attached to a signal-generating compound capable of generating a detectable signal; and (d) detecting the presence of anti-XMRV antibody which may be present in the test sample by detecting presence of the signal generated by the signal-generating compound, presence of the signal indicating presence of past or present XMRV infection in the mammal.

Furthermore, the present invention also includes a method of detecting XMRV infection in a mammal comprising the steps of: (a) obtaining a test sample from the mammal; (b) contacting the test sample with a first antigen comprising an amino acid sequence selected from the group consisting of SEQ ID NO:23, SEQ ID NO:25, SEQ ID NO:27, SEQ ID NO:29, SEQ ID NO:33, SEQ ID NO:39, SEQ ID NO:43, SEQ ID NO:50, SEQ ID NO:52, SEQ ID NO:56, SEQ ID NO:60, SEQ ID NO:63, SEQ ID NO:67, SEQ ID NO:73, SEQ ID NO:77, SEQ ID NO:80, SEQ ID NO:82, SEQ ID NO:83, SEQ ID NO:84, SEQ ID NO:85, SEQ ID NO:102 and SEQ ID NO:109, for a time and under conditions sufficient to allow for the formation of first antigen/anti-XMRV antibody complexes; (c) contacting an antigen conjugate to the antigen/anti-XMRV antibody complexes for a time and under conditions sufficient to allow the antigen conjugate to bind to the bound anti-XMRV antibody, wherein the conjugate comprises a second antigen comprising an amino acid sequence selected from the group consisting of SEQ ID NO:23, SEQ ID NO:25, SEQ ID NO:27, SEQ ID NO:29, SEQ ID NO:33, SEQ ID NO:39, SEQ ID NO:43, SEQ ID NO:50, SEQ ID NO:52, SEQ ID NO:56, SEQ ID NO:60, SEQ ID NO:63, SEQ ID NO:67, SEQ ID NO:73, SEQ ID NO:77, SEQ ID NO:80, SEQ ID NO:82, SEQ ID NO:83, SEQ ID NO:84, SEQ ID NO:85, SEQ ID NO:102 and SEQ ID NO:109, operably linked to a ligand binding moiety, and (d) detecting the presence of anti-XMRV antibodies which may be present in the test sample by detecting the signal generated by a signal-generating compound operably linked to the ligand bound by the ligand binding moiety operably linked to antigen conjugate. In certain embodiments the XMRV antigen portion of the antigen conjugate is identical to the XMRV antigen employed to initially bind the XMRV antibody, or the antigen portion of the antigen conjugate can be distinct, yet capable of being bound by the same XMRV antibody. Again, a control or calibrator may be used which comprises antibody to XMRV.

Also, the present invention encompasses a method of detecting XMRV infection in a mammal comprising one or more of (a) detecting the presence of anti-XMRV antibody in a sample obtained from the mammal, (b) contacting a test sample obtained from the mammal with a FISH probe; and (c) contacting a test sample obtained from the mammal with nucleic acid compositions capable of hybridizing to XMRV nucleic acids and under conditions sufficient to amplify any such XMRV nucleic acid, wherein the presence of one or more of: an anti-XMRV antibody, a signal indicative of fluorescent in situ hybridization (FISH) of an XMRV FISH probe, and a signal indicative of amplification of an XMRV nucleic acid sequence indicates the presence of past or present XMRV infection in the mammal.

The present invention also provides methods for detecting XMRV antibodies that are indicative of XMRV infection, prostate cancer, cervical cancer, uterine cancer, or chronic fatigue syndrome. In addition, the present invention provides methods for detecting XMRV antibodies that are indicative of a propensity to develop prostate cancer, cervical cancer, uterine cancer, or chronic fatigue syndrome.

The present invention also provides methods for monitoring the progression of XMRV infection by detecting antibodies to specific XMRV proteins. For example, but not by way of limitation, progression of XMRV infection can be monitored by detecting the presence of antibodies to one or more of the following XMRV proteins: gp70, p15E, p30, p15, p12, and p10.

The present invention also provides methods for detecting XMRV nucleic acids that are indicative of XMRV infection, prostate cancer, cervical cancer, uterine cancer, or chronic fatigue syndrome. In addition, the present invention provides methods for detecting XMRV nucleic acids that are indicative of a propensity to develop prostate cancer, cervical cancer, uterine cancer, or chronic fatigue syndrome. The present invention is further directed to antigenic XMRV amino acid sequences that are capable of eliciting an immune response.

The present invention is also directed to inhibitory nucleic acids capable of decreasing XMRV gene expression, including, but not limited to, antisense nucleic acids, ribozymes, and siRNA nucleic acids.

In the above embodiments, SEQ ID NO:23, SEQ ID NO:25, SEQ ID NO:27, SEQ ID NO:29, SEQ ID NO:33, SEQ ID NO:39, SEQ ID NO:43, SEQ ID SEQ ID NO:52, SEQ ID NO:56, SEQ ID NO:60, SEQ ID NO:63, SEQ ID NO:67, SEQ ID NO:73, SEQ ID NO:77, SEQ ID NO:80, SEQ ID NO:82, SEQ ID NO:83, SEQ ID NO:84, SEQ ID NO:85, SEQ ID NO:102 and SEQ ID NO:109 may optionally each be comprised in a larger peptide, which may comprise XMRV or non-XMRV amino acid sequence, where the percentage of XMRV amino acid sequence outside of the above-recited sequences may be 0%, up to 10%, up to 20%, up to 30%, up to 40%, up to 50%, up to 60%, up to 70%, up to 80%, up to 90%, up to 95%, up to 99%, or up to 100%, and where the entire peptide, comprising an above-recited sequence, may constitute up to 10%, up to 20%, up to 30%, up to 40%, up to 50%, up to 60%, up to 70%, up to 80%, up to 90%, up to 95%, up to 99%, or up to 100% of a native XMRV protein or of the entire XMRV-encoded polyprotein.

BRIEF DESCRIPTION OF THE DRAWINGS

FIGS. 9A through 9C are Western Blot analyses of IgG and IgM responses in rhesus macaques RIl-10 (A), RLq-10 (B) and RYh-10 (C) using native XMRV lysate proteins. Blood samples were listed on strips as days post inoculation (PI) with XMRV (0-93). The goat anti-Friend MuLV (α-F) was used as a positive control.

FIG. 17 compares assay performance (sensitivity and specificity) between the anti-human and sandwich p15E assay format based CMIAs on XMRV positive primate bleeds and blood donors.

FIG. 18 illustrates the location of eight p15E mapping peptides. The p15E protein sequence is based on Genbank, accession number EF185282.

DETAILED DESCRIPTION OF THE INVENTION

Figure 1:
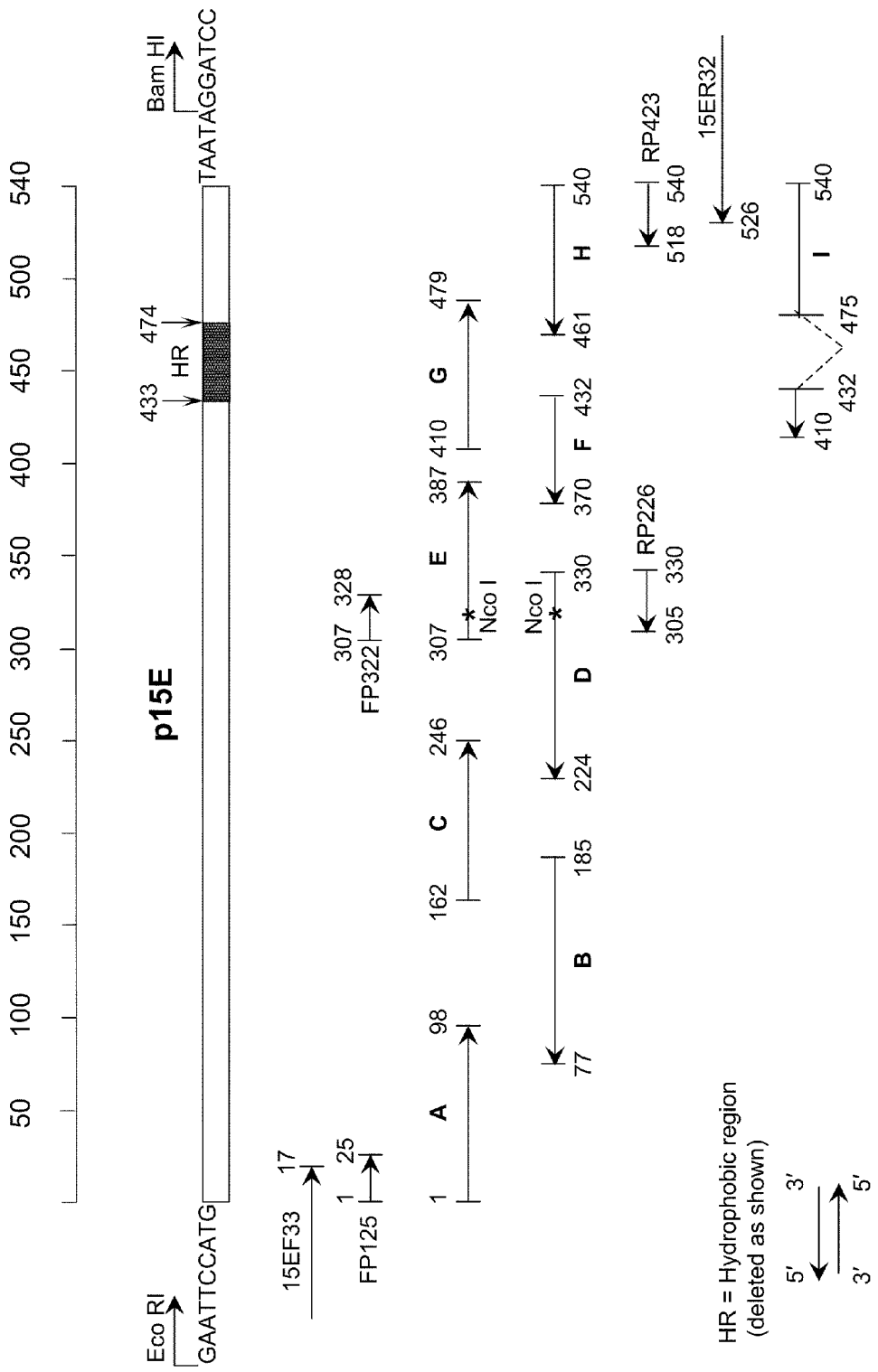
FIG. 1 illustrates the oligonucleotides used to generate synthetic XMRV env p15E gene constructs, wherein a set of eight overlapping oligonucleotides (A-H) builds a full-length p15E gene, and another set of seven overlapping oligonucleotides (A-F and I) produces a p15E gene with a deletion of hydrophobic region (HR) as shown.

The present invention relates to the identification of markers (e.g., anti-XMRV specific antibodies elicited by infection with XMRV or XMRV nucleic acid) for detection of XMRV infection as well as to methods of identifying such markers. Further, the present invention describes characterization of XMRV virions derived from a prostate cancer cell line, experimental infection of primates with the viral particles and the monitoring of seroconversion patterns of the XMRV infected primate. Additionally, the present invention shows that all primates developed detectable antibodies against envelope (env) and core (gag) proteins, providing direct evidence of XMRV infection and seroconversion in primates. More specifically, antibody to the env p15E, env gp70 and gag p30 proteins were identified to be the most dominant and persistent responses; thus, antibodies to these proteins can be utilized as sensitive serological markers to indicate XMRV infection. Although antibody responses elicited to other XMRV proteins (i.e., gag p15, gag p12 and gag p10) are weaker and of shorter duration as compared to the anti-env p15E, env p70 and gag p30 antibody responses, antibodies to these viral proteins may still have utility as additional serological markers to detect and/or confirm XMRV infection.

Further, the subject invention relates to isolated and purified nucleic acid sequences or molecules (and the proteins encoded thereby) which may be utilized in the detection and treatment of XMRV. These utilities, as well as others, will be described, in detail, below.

The Nucleic Acid Sequences and Encoded Proteins

In certain embodiments, the present invention is directed to isolated XMRV antigens and the nucleic acids encoding those antigens. Such antigens include, but are not limited to, the following XMRV proteins: gp70, p15E, p30, p15, p12, and p10, as well as fragments thereof.

SEQ ID NO:81 represents the nucleotide sequence of the gene (i.e., isolated nucleic acid molecule) encoding the amino acid sequence of the XMRV env p15E variant identified as "p15EΔ". The p15EΔ amino acid sequence is identical to the wild type XMRV p15E amino acid sequence, except that the p15EΔ sequence includes a deletion of the wild type XMRV env p15E sequence's hydrophobic putative transmembrane domain. SEQ ID NO:82 represents the amino acid sequence of the encoded, purified protein. SEQ ID NO:24 illustrates the nucleotide sequence of the gene encoding the amino acid sequence of p15EΔ with the PL fusion protein (see, e.g., U.S. Pat. Nos. 5,322,769, 5,312,737 and 5,854,001 for use of PL in the creation of fusion proteins using PL), and SEQ ID NO:25 represents the amino acid sequence of the encoded, purified protein. SEQ ID NO:28 represents the nucleotide sequence of the gene encoding the amino acid sequence of p15EΔ with CKS fusion protein (SEQ ID NO:86=nucleotide sequence of CKS; SEQ ID NO:87=amino acid sequence of CKS), and SEQ ID NO:29 represents the amino acid sequence of the encoded, purified protein. Additionally, SEQ ID NOs: 83, 84 and 85 represent the amino acid sequences of immunodominant epitopes within the p15E protein.

SEQ ID NO:38 represents the nucleotide sequence of the gene encoding the amino acid sequence of env gp70, and SEQ ID NO:39 represents the amino acid sequence of the encoded, purified protein. SEQ ID NO:42 represents the nucleotide sequence of the gene encoding the amino acid sequence of gp70 with CKS fusion protein, and SEQ ID NO:43 represents the amino acid sequence of the encoded, purified protein. SEQ ID NO:49 represents the nucleotide sequence of the gene encoding the amino acid sequence of gp70 with PET fusion protein, and SEQ ID NO:50 represents the amino acid sequence of the encoded, purified protein.

SEQ ID NO:72 represents the nucleotide sequence of the gene encoding the amino acid sequence of p30. SEQ ID NO:73 represents the amino acid sequence of the encoded, purified protein. SEQ ID NO:66 represents the nucleotide sequence of the gene encoding the amino acid sequence of p30 with CKS fusion protein, and SEQ ID NO:67 represents the amino acid sequence of the encoded, purified protein.

SEQ ID NO:51 represents the nucleotide sequence of the gene encoding the amino acid sequence of p15. SEQ ID NO:52 represents the amino acid sequence of the encoded, purified protein. SEQ ID NO:55 represents the nucleotide sequence of the gene encoding the amino acid sequence of p15 with CKS fusion protein, and SEQ ID NO:56 represents the amino acid sequence of the encoded, purified protein.

SEQ ID NO:62 illustrates the nucleotide sequence of the gene encoding the amino acid sequence of p12 with the PET fusion protein, and SEQ ID NO:63 represents the amino acid sequence of the encoded, purified protein. SEQ ID NO:59 represents the nucleotide sequence of the gene encoding the amino acid sequence of p12 with CKS fusion protein, and SEQ ID NO:60 represents the amino acid sequence of the encoded, purified protein.

SEQ ID NO:79 illustrates the nucleotide sequence of the gene encoding the amino acid sequence of p10 with the PET fusion protein, and SEQ ID NO:80 represents the amino acid sequence of the encoded, purified protein. SEQ ID NO:76 represents the nucleotide sequence of the gene encoding the amino acid sequence of p10 with CKS fusion protein, and SEQ ID NO:77 represents the amino acid sequence of the encoded, purified protein.

It should be noted that the present invention also encompasses nucleic acid sequences or molecules comprising nucleotide sequences which are at least about 70% identical to, preferably at least about 80% identical to, or at least about 90% identical to, and more preferably at least about 95% identical to, or at least about 97% identical to, or at least about 99% identical to, the nucleotide sequence of SEQ ID NO:22, SEQ ID NO:24, SEQ ID NO:26, SEQ ID NO:28, SEQ ID NO:38, SEQ ID NO:42, SEQ ID NO:49, SEQ ID NO:51, SEQ ID NO:55, SEQ ID NO:59, SEQ ID NO:62, SEQ ID NO:66, SEQ ID NO:76, SEQ ID NO:79 or SEQ ID NO:81. As noted above, such nucleic acid sequences may be used, for example, in production of the polypeptides of interest described herein; however, they may also be utilized as probes or primers in controls or calibrators used to ensure the safety and efficacy of molecular-based assays. (Fragments of the nucleotide sequences described herein as well as fragments of the sequences having the above-described identity are also included within the scope of the present invention.) Complements of these sequences are also encompassed by the present invention as well as fragments of these complements. (All integers within the range of 70 to 100 (in terms of percent identity) are also included within the scope of the invention (i.e., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100%).

It should be noted that the present invention also encompasses proteins or polypeptides comprising amino acid sequences which are at least about 70% identical to, preferably at least about 80% identical to, or at least about 90% identical to, and more preferably at least about 95% identical to, or at least about 97% identical to, or at least about 99% identical to, the amino acid sequence of SEQ ID NO:23, SEQ ID NO:25, SEQ ID NO:27, SEQ ID NO:29, SEQ ID NO:33, SEQ ID NO:39, SEQ ID NO:43, SEQ ID NO:50, SEQ ID NO:52, SEQ ID NO:56, SEQ ID NO:60, SEQ ID NO:63, SEQ ID NO:67, SEQ ID NO:73, SEQ ID NO:77, SEQ ID NO:80, SEQ ID NO:82, SEQ ID NO:102 or SEQ ID NO:109. (Again, all integers within the range of 70 to 100 (in terms of percent identity) are also included within the scope of the invention (i.e., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100%).

Additionally, the present invention encompasses "fragments or peptides" of the full-length polypeptides described herein. Such peptides as SEQ ID NO:83, SEQ ID NO:84 and SEQ ID NO:85 represent portions of the polypeptide that may, for example, have specific immunogenic or binding properties. The fragment may be, for example, between 3-10 amino acids in length, 10-20 amino acids in length, 20-40 amino acids in length, 40-80 amino acids in length, 80-160 amino acids in length or even longer. Amino acid sequences having at least 70% amino acid identity, preferably at least 80% amino acid identity, or at least 90% identity to, and more preferably at least about 95% identical to, or at least about 97% identical to, or at least about 99% identical to, the fragments described herein are also included within the scope of the present invention. (Further, all integers between the range of 70 to 100 percent identity, as recited above, are also considered to fall within the scope of the present invention.)

An "epitope" is an antigenic determinant of a polypeptide. An epitope may comprise at least three amino acids in a spatial conformation that is unique to the epitope. Generally, an epitope consists of at least five such amino acids, and more usually, consists of at least eight to ten amino acids.

The nucleotide or amino acids sequences having the above-described percent identity (or complementary sequences with respect with nucleotide sequences) may be derived from one or more sources other than XMRV. Such sequences may be derived from, for example, non-XMRV viruses, mammalian cell lines, insects, parasites, bacteria or fungi.

Furthermore, as mentioned above, the present invention also encompasses fragments and derivatives of the nucleic acid sequences of the present invention as well as fragments and portions of the amino acid sequences of the present invention. Corresponding sequences derived from non-XMRV, as described above, and having the above-described complementarity or identity, as appropriate, are also considered to fall within the scope of the present invention. Functional equivalents of the above-sequences (i.e., nucleotide sequences encoding proteins having, for example, the same binding affinities, epitopes, etc. of the encoded proteins) are also encompassed by the present invention.

For purposes of the present invention, "complementarity" is defined as the degree of relatedness between two DNA segments. It is determined by measuring the ability of the sense strand of one DNA segment to hybridize with the antisense strand of the other DNA segment, under appropriate conditions, to form a double helix. In the double helix, wherever adenine appears in one strand, thymine appears in the other strand. Similarly, wherever guanine is found in one strand, cytosine is found in the other. The greater the relatedness between the nucleotide sequences of two DNA segments, the greater the ability to form hybrid duplexes between the strands of two DNA segments.

The term "identity" refers to the relatedness of two sequences on a nucleotide-by-nucleotide basis over a particular comparison window or segment. Thus, identity is defined as the degree of sameness, correspondence or equivalence between the same strands (either sense or antisense) of two DNA segments (or two amino acid sequences). "Percentage of sequence identity" is calculated by comparing two optimally aligned sequences over a particular region, determining the number of positions at which the identical base or amino acid occurs in both sequences in order to yield the number of matched positions, dividing the number of such positions by the total number of positions in the segment being compared and multiplying the result by 100. Optimal alignment of sequences may be conducted by the algorithm of Smith & Waterman, Appl. Math. 2:482 (1981), by the algorithm of Needleman & Wunsch, J. Mol. Biol. 48:443 (1970), by the method of Pearson & Lipman, Proc. Natl. Acad. Sci. (USA) 85:2444 (1988) and by computer programs which implement the relevant algorithms (e.g., Clustal Macaw Pileup (http://cmgm.stanford.edu/biochem218/11Multiple.pdf; Higgins et al., CABIOS. 5L151-153 (1989)), FASTDB (Intelligenetics), BLAST (National Center for Biomedical Information; Altschul et al., Nucleic Acids Research 25:3389-3402 (1997)), PILEUP (Genetics Computer Group, Madison, Wis.) or GAP, BESTFIT, FASTA and TFASTA (Wisconsin Genetics Software Package Release 7.0, Genetics Computer Group, Madison, Wis.). (See U.S. Pat. No. 5,912,120.)

"Identity between two amino acid sequences" is defined as the presence of a series of exactly alike or invariant amino acid residues in both sequences (see above definition for identity between nucleic acid sequences). The definitions of "complementarity" and "identity" are well known to those of ordinary skill in the art.

"Encoded by" refers to a nucleic acid sequence which codes for a polypeptide sequence, wherein the polypeptide sequence or a portion thereof contains an amino acid sequence of at least 3 amino acids, more preferably at least 8 amino acids, and even more preferably at least 15 amino acids from a polypeptide encoded by the nucleic acid sequence.

The present invention also encompasses an isolated nucleic acid sequence which encodes a protein or antigen having functional activity that is similar to or equivalent to those proteins represented by SEQ ID NO:24, SEQ ID NO:28 or SEQ ID NO:81, and that is hybridizable, under moderately stringent conditions, to a nucleic acid molecule having a nucleotide sequence comprising or complementary to the nucleotide sequences described above. A nucleic acid molecule is "hybridizable" to another nucleic acid molecule when a single-stranded form of the nucleic acid molecule can anneal to the other nucleic acid molecule under the appropriate conditions of temperature and ionic strength (see Sambrook et al., "Molecular Cloning: A Laboratory Manual, Second Edition (1989), Cold Spring Harbor Laboratory Press, Cold Spring Harbor, N.Y.). The conditions of temperature and ionic strength determine the "stringency" of the hybridization. "Hybridization" requires that two nucleic acids contain complementary sequences. However, depending on the stringency of the hybridization, mismatches between bases may occur. The appropriate stringency for hybridizing nucleic acids depends on the length of the nucleic acids and the degree of complementation. Such variables are well known in the art. More specifically, the greater the degree of similarity, identity or homology between two nucleotide sequences, the greater the value of Tm for hybrids of nucleic acids having those sequences. For hybrids of greater than 100 nucleotides in length, equations for calculating Tm have been derived (see Sambrook et al., supra (1989)). For hybridization with shorter nucleic acids, the position of mismatches becomes more important, and the length of the oligonucleotide determines its specificity (see Sambrook et al., supra (1989)).

As used herein, an "isolated nucleic acid fragment or sequence" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. (A "fragment" of a specified polynucleotide refers to a polynucleotide sequence which comprises a contiguous sequence of approximately at least about 6 nucleotides, preferably at least about 8 nucleotides, more preferably at least about 10 nucleotides, and even more preferably at least about 15 nucleotides, and most preferably at least about 25 nucleotides, and may be up to the full length of the reference sequence, up to the full length sequence minus one nucleotide, or up to 50 nucleotides, 100 nucleotides, 500 nucleotides, 1000 nucleotides, 2000 nucleotides, 3000 nucleotides, 4000 nucleotides, 5000 nucleotides, 6000 nucleotides, 7000 nucleotides, or 8000 nucleotides, identical or complementary to a region of the specified nucleotide sequence.) Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "fragment or subfragment that is functionally equivalent" and "functionally equivalent fragment or subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric constructs to produce the desired phenotype in a transformed plant. Chimeric constructs can be designed for use in co-suppression or antisense by linking a nucleic acid fragment or subfragment thereof, whether or not it encodes an active protein, in the appropriate orientation relative to a promoter sequence.

The terms "homology", "homologous", "substantially similar" and "corresponding substantially" are used interchangeably herein. They refer to nucleic acid fragments wherein changes in one or more nucleotide bases does not affect the ability of the nucleic acid fragment to mediate gene expression or produce a certain phenotype. These terms also refer to modifications of the nucleic acid fragments of the present invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences described herein.

"Gene" refers to a nucleic acid fragment that expresses a specific protein, including regulatory sequences preceding (5' non-coding sequences) and following (3' non-coding sequences) the coding sequence.

"Native gene" refers to a gene as found in nature with its own regulatory sequences. In contrast, "chimeric construct" refers to a combination of nucleic acid fragments that are not normally found together in nature. Accordingly, a chimeric construct may comprise regulatory sequences and coding sequences that are derived from different sources, or regulatory sequences and coding sequences derived from the same source, but arranged in a manner different than that normally found in nature. (The term "isolated" means that the sequence is removed from its natural environment.)

A "foreign" gene refers to a gene not normally found in the host organism, but that is introduced into the host organism by gene transfer. Foreign genes can comprise native genes inserted into a non-native organism, or chimeric constructs. A "transgene" is a gene that has been introduced into the genome by a transformation procedure.

A "probe" or "primer" as used herein is a polynucleotide that is at least 8 nucleotides, at least 10 nucleotides, at least 15 nucleotides, at least 20 nucleotides, or at least 25 nucleotides in length and forms a hybrid structure with a target sequence, due to complementarity of at least one sequence in the probe or primer with a sequence in the target region. The polynucleotide regions of the probe can be composed of DNA and/or RNA and/or synthetic nucleotide analogs. Preferably, the probe does not contain a sequence that is complementary to the sequence or sequences used to prime for a target sequence during the polymerase chain reaction. In alternative embodiments, such as, but not limited to, fluorescence in situ hybridization assays, the term "probe" or "FISH probe" is used herein to refer to a polynucleotide that is at least 10 nucleotides, at least 100 nucleotides, at least 1000 nucleotides, at least 2000 nucleotides, at least 3000 nucleotides, at least 4000 nucleotides, at least 5000 nucleotides, at least 6000 nucleotides, at least 7000 nucleotides, or at least 8000 nucleotides.

"Coding sequence" refers to a DNA sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" (or "regulatory sequence") refers to a DNA sequence capable of controlling the expression of a coding sequence or functional RNA. The promoter sequence, for example, consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue-specificity of a promoter. Regulatory sequences (e.g., a promoter) can also be located within the transcribed portions of genes, and/or downstream of the transcribed sequences. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most host cell types, at most times, are commonly referred to as "constitutive promoters". New promoters of various types useful in plant cells are constantly being discovered; numerous examples may be found in the compilation by Okamuro and Goldberg, (1989) *Biochemistry of Plants* 15:1-82. It is further recognized that since, in most cases, the exact boundaries of regulatory sequences have not been completely defined, DNA fragments of some variation may have identical promoter activity.

An "intron" is an intervening sequence in a gene that does not encode a portion of the protein sequence. Thus, such sequences are transcribed into RNA but are then excised and are not translated. The term is also used for the excised RNA sequences. An "exon" is a portion of the gene sequence that is transcribed and is found in the mature messenger RNA derived from the gene, but is not necessarily a part of the sequence that encodes the final gene product.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a DNA that is complementary to and synthesized from a mRNA template using the enzyme reverse transcriptase. The cDNA can be single-stranded or converted into the double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "endogenous RNA" refers to any RNA which is encoded by any nucleic acid sequence present in the genome of the host prior to transformation with the recombinant construct of the present invention, whether naturally-occurring or non-naturally occurring, i.e., introduced by recombinant means, mutagenesis, etc.

The term "non-naturally occurring" means artificial, not consistent with what is normally found in nature.

The term "operably linked" refers to the association of two moieties. For example, but not by way of limitation, the association of two or more nucleic acid sequences on a single nucleic acid fragment so that the function of one is regulated by the other. In one such non-limiting example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another non-limiting example, the complementary RNA regions of the invention can be operably linked, either directly or indirectly, 5' to the target mRNA, or 3' to the target mRNA, or within the target mRNA, or a first complementary region is 5' and its complement is 3' to the target mRNA. Alternative examples of operable linkage include, but are not limited to covalent and noncovalent associations, e.g., the biotinylation of a polypeptide (a covalent linkage) and hybridization of two complementary nucleic acids (a non-covalent linkage).

The term "expression", as used herein, refers to the production of a functional end-product. Expression of a gene involves transcription of the gene and translation of the mRNA into a precursor or mature protein. "Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020).

"Mature" protein refers to a post-translationally processed polypeptide; i.e., one from which any pre- or pro-peptides present in the primary translation product have been removed. "Precursor" protein refers to the primary product of translation of mRNA; i.e., with pre- and pro-peptides still present. Pre- and pro-peptides may be but are not limited to intracellular localization signals.

"Stable transformation" refers to the transfer of a nucleic acid fragment into a genome of a host organism, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms. The term "transformation" as used herein refers to both stable transformation and transient transformation.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

The term "recombinant" refers to an artificial combination of two otherwise separated segments of sequence, e.g., by chemical synthesis or by the manipulation of isolated segments of nucleic acids by genetic engineering techniques.

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double-stranded DNA is heat denatured, the two primers complementary to the 3' boundaries of the target segment are annealed at low temperature and then extended at an intermediate temperature. One set of these three consecutive steps is referred to as a cycle.

Polymerase chain reaction ("PCR") is a powerful technique used to amplify DNA millions of fold, by repeated replication of a template, in a short period of time. (Mullis et al., *Cold Spring Harbor Symp. Quant. Biol.* 51:263-273 (1986); Erlich et al., European Patent Application No. 50,424; European Patent Application No. 84,796; European Patent Application No. 258,017, European Patent Application No. 237,362; European Patent Application No. 201,184, U.S. Pat. No. 4,683,202; U.S. Pat. No. 4,582,788; and U.S. Pat. No. 4,683,194). The process utilizes sets of specific in vitro synthesized oligonucleotides to prime DNA synthesis. The design of the primers is dependent upon the sequences of DNA that are to be analyzed. The technique is carried out through many cycles (usually 20-50) of melting the template at high temperature, allowing the primers to anneal to complementary sequences within the template and then replicating the template with DNA polymerase.

The products of PCR reactions are analyzed by separation in agarose gels followed by ethidium bromide staining and visualization with UV transillumination. Alternatively, radioactive dNTPs can be added to the PCR in order to incorporate label into the products. In this case the products of PCR are visualized by exposure of the gel to x-ray film. The added advantage of radiolabeling PCR products is that the levels of individual amplification products can be quantitated.

The terms "recombinant construct", "expression construct" and "recombinant expression construct" are used interchangeably herein. These terms refer to a functional unit of genetic material that can be inserted into the genome of a cell using standard methodology well known to one skilled in the art. Such a construct may be itself or may be used in conjunction with a vector. If a vector is used, then the choice of vector is dependent upon the method that will be used to transform host plants, as is well known to those skilled in the art. For example, a plasmid can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., (1985) *EMBO J.* 4:2411-2418; De Almeida et al., (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

The term "serological marker" as used herein is defined as an antibody specific for XMRV (i.e., anti-XMRV specific antibody) elicited by infection with XMRV.

The terms "peptide" and "peptide sequence", as used herein, refer to polymers of amino acid residues. In certain embodiments the peptide sequences of the present invention will comprise 1-30, 1-50, 1-100, 1-150, or 1-300 amino acid residues. In certain embodiments the peptides of the present invention comprise XMRV or non-XMRV sequences. For example, but not by way of limitation, the peptide sequences of the present invention can comprise up to 10%, or 20%, or 30%, or 40%, or 50%, or 60%, or 70%, or 80%, or 90%, or 95%, or 96%, or 97%, or 98%, or 99% identity to an XMRV peptide sequence.

In certain embodiments, the invention also encompasses peptide sequences that are "substantially similar" to XMRV peptide sequences indentified herein. Such peptide sequences include, but are not limited to, those that retain certain structural and functional features of the reference peptide sequence, yet differ from that reference peptide sequence at one or more amino acid position (i.e., by amino acid substitutions).

A variant peptide sequence can be prepared by substituting amino acid residues of a reference peptide sequence and selecting for a peptide sequence that retains the reference sequence's structure and/or activity. For example, amino acid residues of the reference peptide sequence can be systematically substituted with other residues and the substituted peptide sequence can then be tested in standard assays for evaluating the effects of such substitutions on the ability of the peptide sequence to perform activities of the reference peptide sequence.

In some embodiments, to retain functional activity, conservative amino acid substitutions are made. As used herein, the language a "conservative amino acid substitution" is intended to include a substitution in which the amino acid residue is replaced with an amino acid residue having a similar side chain. Families of amino acid residues having similar side chains have been defined in the art, including: basic side chains (e.g., lysine, arginine, histidine); acidic side chains (e.g., aspartic acid, glutamic acid); uncharged polar side chains (e.g., glycine, asparagine, glutamine, serine, threonine, tyrosine, cysteine); nonpolar side chains (e.g., alanine, valine, leucine, isoleucine, proline, phenylalanine, methionine, tryptophan); β-branched side chains (e.g., threonine, valine, isoleucine); and aromatic side chains (e.g., tyrosine, phenylalanine, tryptophan, histidine). Other generally preferred substitutions involve replacement of an amino acid residue with another residue having a small side chain, such as alanine or glycine. Amino acid substituted peptide sequences can be prepared by standard techniques, such as automated chemical synthesis.

Production of the Proteins

Once the gene encoding the protein of interest has been isolated, it may then be introduced into either a prokaryotic or eukaryotic host cell, through the use of a vector or construct, in order for the host cell to express the protein of interest. The vector, for example, a bacteriophage, cosmid or plasmid, may comprise the nucleic acid sequence encoding the enzyme, as well as any regulatory sequence (e.g., promoter) that is functional in the host cell and is able to elicit expression of the protein encoded by the nucleic acid sequence. The regulatory sequence (e.g., promoter) is in operable association with, or operably linked to, the nucleotide sequence. (A regulatory sequence (e.g., promoter) is said to be "operably linked" with a coding sequence if the regulatory sequence affects transcription or expression of the coding sequence.) Suitable promoters include, for example, those from genes encoding alcohol dehydrogenase, glyceraldehyde-3-phosphate dehydrogenase, phosphoglucoisomerase, phosphoglycerate kinase, acid phosphatase, T7, TPI, lactase, metallothionein, cytomegalovirus immediate early, whey acidic protein, glucoamylase, promoters activated in the presence of galactose, for example, GAL1 and GAL10, as well as any other promoters involved in prokaryotic and eukaryotic expression systems. Additionally, nucleic acid sequences that encode other proteins may also be included within the vector as well as other non-promoter regulatory sequences such as, for example, a polyadenylation signal (e.g., the poly-A signal of SV-40T-antigen, ovalbumin or bovine growth hormone). The choice of sequences present in the construct is dependent upon the desired expression products as well as the nature of the host cell.

As noted above, once the vector has been constructed, it may then be introduced into the host cell of choice by methods known to those of ordinary skill in the art including, for example, transfection, transformation and electroporation (see *Molecular Cloning: A Laboratory Manual*, $2^{nd}$ ed., Vol. 1-3, ed. Sambrook et al., Cold Spring Harbor Laboratory Press (1989)). The host cell is then cultured under suitable conditions permitting expression of the desired protein that is then recovered and purified.

Examples of suitable prokaryotic host cells include, for example, bacteria such as *Escherichia coli, Bacillus subtilis, Actinomycetes* such as *Streptomyces coelicolor, Streptomyces lividans*, as well as cyanobacteria such as *Spirulina* spp. (i.e., blue-green algae). Examples of suitable eukaryotic host cells include, for example, mammalian cells, plant cells, yeast cells such as *Saccharomyces* spp., *Lipomyces* spp., *Candida* spp. such as *Yarrowia* (Candida) spp., *Kluyveromyces* spp., *Pichia* spp., *Trichoderma* spp. or *Hansenula* spp., or fungal cells such as filamentous fungal cells, for example, *Aspergillus, Neurospora* and *Penicillium*. Preferably, *Saccharomyces cerevisiae* (baker's yeast) cells are utilized.

Expression in a host cell can be accomplished in a transient or stable fashion. Transient expression can occur from introduced constructs which contain expression signals functional in the host cell, but which constructs do not replicate and rarely integrate in the host cell, or where the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a construct that can integrate into the host genome or that autonomously replicates in the host cell. Stable expression of the gene of interest can be selected for through the use of a selectable marker located on or transfected with the expression construct, followed by selection for cells expressing the marker. When stable expression results from integration, the site of the construct's integration can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

A transgenic mammal may also be used in order to express the protein of interest encoded by one or both of the above-described nucleic acid sequences. More specifically, once the above-described construct is created, it may be inserted into the pronucleus of an embryo. The embryo may then be implanted into a recipient female. Alternatively, a nuclear transfer method could also be utilized (Schnieke et al., *Science* (1997) 278:2130-2133). Gestation and birth are then permitted to occur (see, e.g., U.S. Pat. No. 5,750,176 and U.S. Pat. No. 5,700,671), and milk, tissue or other fluid samples from the offspring should then contain the protein of interest. The mammal utilized as the host may be selected from the group consisting of, for example, a mouse, a rat, a rabbit, a pig, a goat, a sheep, a horse and a cow. However, any mammal may be used provided it has the ability to incorporate DNA encoding the protein of interest into its genome.

In view of the above, the present invention also encompasses a method of producing one or more of the proteins described above comprising the steps of: 1) isolating the desired nucleic acid sequence(s) of the gene encoding the protein(s) (i.e., SEQ ID NO:24 and/or SEQ ID NO:28; 2) constructing a vector comprising said nucleic acid sequence(s); and 3) introducing said vector into a host cell for a time and conditions sufficient for the production of the protein(s).

Uses of the Genes and Proteins Encoded Thereby

As noted above, the isolated nucleic acid sequences (or genes) and the corresponding proteins (or purified polypeptides) encoded thereby have many beneficial uses. For example, there is significant need to discover antigens that could be used as diagnostic agents in immunoassays that could accurately detect the presence of anti-XMRV specific antibodies elicited in the infected individual. The present invention provides such needed immunoassays and, in particular, sole antigens or combinations of antigens which accurately detect the presence of antibodies to XMRV in human body fluids. The presence of antibodies to such antigens can aid in the proper diagnosis of prostate or other cancer(s)/diseases and eliminate other related conditions (e.g., benign prostatic hyperplasia). In addition, such antigens can be used to elicit an immune response in an individual. For example, but not by way of limitation, immune responses elicited in such a manner in the context of treating or preventing XMRV infection.

The present invention also includes polyclonal and monoclonal antibodies raised against the above-described proteins. Such antibodies may be used, for example, in an immunoassay, a kit, or for research purposes. Such antibodies may also have utility as therapeutic agents.

The present invention is also directed to compositions and methods relating to the molecular detection of XMRV infection and related conditions. For example, but not by way of limitation, the present invention includes numerous nucleic acid sequences that can be employed in hybridization and/or amplification-based assays to detect the presence of XMRV. These nucleic acids can also find use in therapeutic contexts, for example, as the basis for antisense or siRNA inhibitors of XMRV activity.

The uses noted above are described, in detail, in the sections that follow.

Immunoassays

There are two basic types of immunoassays, competitive and non-competitive (e.g., immunometric and sandwich, respectively). In both assays, antibody or antigen reagents are covalently or non-covalently attached to the solid phase. (See *The Immunoassay Handbook*, 2$^{nd}$ Edition, edited by David Wild, Nature Publishing Group, London 2001.) Linking agents for covalent attachment are known and may be part of the solid phase or derivatized to it prior to coating. Examples of solid phases used in immunoassays are porous and non-porous materials, latex particles, magnetic particles, microparticles, strips, beads, membranes, microtiter wells and plastic tubes. The choice of solid phase material and method of labeling the antigen or antibody reagent are determined based upon desired assay format performance characteristics. For some immunoassays, no label is required. For example, if, the antigen is on a detectable particle such as a red blood cell, reactivity can be established based upon agglutination. Alternatively, an antigen-antibody reaction may result in a visible change (e.g., radial immunodiffusion). In most cases, one of the antibody or antigen reagents used in an immunoassay is attached to a signal-generating compound or "label". This signal-generating compound or "label" is in itself detectable or may be reacted with one or more additional compounds to generate a detectable product (see also U.S. Pat. No. 6,395,472 B1). Examples of such signal generating compounds include chromogens, radioisotopes (e.g., 125I, 131I, 32P, 3H, 35S, and 14C), fluorescent compounds (e.g., fluorescein and rhodamine), chemiluminescent compounds, particles (visible or fluorescent), nucleic acids, complexing agents, or catalysts such as enzymes (e.g., alkaline phosphatase, acid phosphatase, horseradish peroxidase, beta-galactosidase, and ribonuclease). In the case of enzyme use, addition of chromo-, fluoro-, or lumo-genic substrate results in generation of a detectable signal. Other detection systems such as time-resolved fluorescence, internal-reflection fluorescence, amplification (e.g., polymerase chain reaction) and Raman spectroscopy are also useful.

There are three general formats commonly used to monitor specific antibody titer and type in humans: (1) the indirect anti-human assay format, where antigen is presented on a solid phase, as described above, the human biological fluid containing the specific antibodies is allowed to react with the antigen forming an antigen/antibody complex, and then antibody bound to antigen is detected with an anti-human antibody coupled to a signal-generating compound, (2) the semi-direct anti-human assay format, where an anti-human antibody is bound to the solid phase, the human biological fluid containing specific antibodies is allowed to react with the bound anti-human antibody forming an anti-human antibody/antibody complex, and then antigen attached to a signal-generating compound is added to detect specific antibody present in the fluid sample, and (3) the direct double antigen sandwich assay format, where antigen is presented both as capture antigen and as detection conjugate, as described in format (1), antigen is presented on a solid phase, the human biological fluid containing the specific antibodies is allowed to react with the antigen bound on solid phase forming an antigen/antibody complex, and then antibody bound to antigen is detected with the antigen coupled to a signal-generating compound. In formats (1) and (2), the anti-human antibody reagent may recognize all antibody classes, or alternatively, be specific for a particular class or subclass of antibody, depending upon the intended purpose of the assay.

Format (3) has advantages over formats (1) and (2) in that it detects all antibody classes and antibodies derived from all mammalian species. These assay formats as well as other known formats are intended to be within the scope of the present invention and are well-known to those of ordinary skill in the art.

Of course, any of the exemplary formats described herein and any assay or kit according to the invention can be adapted or optimized for use in automated and semi-automated systems (including those in which there is a solid phase comprising a microparticle), as described, e.g., in U.S. Pat. Nos. 5,089,424 and 5,006,309, and as, e.g., commercially marketed by Abbott Laboratories (Abbott Park, Ill.) including but not limited to Abbott's ARCHITECT®, AxSYM, IMX, PRISM, and Quantum II platforms, as well as other platforms.

Additionally, the assays and kits of the present invention optionally can be adapted or optimized for point of care assay systems, including Abbott's Point of Care (i-STAT™) electrochemical immunoassay system. Immunosensors and methods of manufacturing and operating them in single-use test devices are described, for example in U.S. Pat. No. 5,063,081 and published U.S. Patent Application Publication Nos. 20030170881, 20040018577, 20050054078, and 20060160164 (incorporated by reference herein for their teachings regarding same).

In view of the above, the present invention includes, for example, a method of detecting antibodies to XMRV in a test sample comprising the steps of: (a) contacting the test sample suspected of containing antibodies with an isolated protein or antigen comprising an amino acid sequence selected from the group consisting of p15E-CKS (SEQ ID NO:27), p15EΔ-CKS (SEQ ID NO:29), p15E-PET (SEQ ID NO:33), p15E-PL (SEQ ID NO:23), p15EΔ-PL (SEQ ID NO:25), p15EΔ (SEQ ID NO:82) and epitopes thereof (i.e., SEQ ID NOs: 83, 84 and 85), p70-PL (SEQ ID NO:39), p70-CKS (SEQ ID NO:43), p70-PET (SEQ ID NO:50), p30-CKS (SEQ ID NO:67), p30-PL (SEQ ID NO:73), p15-PL (SEQ ID NO:52), p15-CKS (SEQ ID NO:56), p12-CKS (SEQ ID NO:60), p12-PET (SEQ ID NO:63), p10-CKS (SEQ ID NO:77), p10-PET (SEQ ID NO:80), gp70 (SEQ ID NO:102) and p30 (SEQ ID NO:109) for a time and under conditions sufficient for the formation of antigen/anti-XMRV antibody complexes and (b) detecting the presence of antibodies present in the test sample. More specifically, the present invention includes a method of detecting antibodies to XMRV in a test sample comprising the steps of: (a) contacting the test sample suspected of containing the antibodies with an isolated protein or antigen comprising an amino acid sequence selected from the group consisting of p15E-CKS (SEQ ID NO:27), p15EΔ-CKS (SEQ ID NO:29), p15E-PET (SEQ ID NO:33), p15E-PL (SEQ ID NO:23), p15EΔ-PL (SEQ ID NO:25), p15EΔ (SEQ ID NO:82) and epitopes thereof (SEQ ID NOs: 83, 84 and 85), p70-PL (SEQ ID NO:39), p70-CKS (SEQ ID NO:43), p70-PET (SEQ ID NO:50), p30-CKS (SEQ ID NO:67), p30-PL (SEQ ID NO:73), p15-PL (SEQ ID NO:52), p15-CKS (SEQ ID NO:56), p12-CKS (SEQ ID NO:60), p12-PET (SEQ ID NO:63), p10-CKS (SEQ ID NO:77), p10-PET (SEQ ID NO:80), gp70 (SEQ ID NO:102) and p30 (SEQ ID NO:109), for a time and under conditions sufficient to allow the formation of antigen/anti-XMRV antibody complexes; (b) adding a conjugate to the resulting antigen/anti-XMRV antibody complexes for a time and under conditions sufficient to allow the conjugate to bind to the bound antibody, the conjugate comprising, for example, an anti-human antibody attached to a signal-generating compound capable of generating a detectable signal and (c) detecting the presence of the antibody which may be present in the test sample by detecting the signal generated by the signal-generating compound. A control or calibrator may also be used which comprises antibody to XMRV.

The present invention further includes a different method for detecting the presence of antibodies which may be present in a test sample. This method comprises the steps of: (a) contacting the test sample suspected of containing the antibodies with anti-human antibody, for a time and under conditions sufficient to allow for the formation of anti-human antibody/anti-XMRV antibody complexes; (b) adding an antigen conjugate comprising an amino acid sequence selected from the group consisting of p15E-CKS (SEQ ID NO:27), p15EΔ-CKS (SEQ ID NO:29), p15E-PET (SEQ ID NO:33), p15E-PL (SEQ ID NO:23), p15EΔ-PL (SEQ ID NO:25), p15EΔ (SEQ ID NO:82) and epitopes thereof (i.e., SEQ ID NOs:83, 84 and 85), p70-PL (SEQ ID NO:39), p70-CKS (SEQ ID NO:43), p70-PET (SEQ ID NO:50), p30-CKS (SEQ ID NO:67), p30-PL (SEQ ID NO:73), p15-PL (SEQ ID NO:52), p15-CKS (SEQ ID NO:56), p12-CKS (SEQ ID NO:60), p12-PET (SEQ ID NO:63), p10-CKS (SEQ ID NO:77), p10-PET (SEQ ID NO:80), gp70 (SEQ ID NO:102) and p30 (SEQ ID NO:109) to the resulting anti-human antibody/anti-XMRV antibody complexes for a time and under conditions sufficient to allow the antigen to bind to the bound antibody, the XMRV antigen conjugate being attached to a signal-generating compound capable of generating a detectable signal, and (c) detecting the presence of anti-XMRV antibodies which may be present in the test sample by detecting the signal generated by the signal generating compound. Again, a control or calibrator may be used which comprises antibody to XMRV.

The present invention also encompasses another method for detecting the presence of anti-XMRV antibodies in a test sample. This method comprises the steps of (a) contacting the test sample suspected of containing the antibodies with an isolated protein or antigen comprising an amino acid sequence selected from the group consisting of p15E-CKS (SEQ ID NO:27), p15EΔ-CKS (SEQ ID NO:29), p15E-PET (SEQ ID NO:33), p15E-PL (SEQ ID NO:23), p15EΔ-PL (SEQ ID NO:25), p15EΔ (SEQ ID NO:82) and epitopes thereof (i.e., SEQ ID NOs: 83, 84 and 85), p70-PL (SEQ ID NO:39), p70-CKS (SEQ ID NO:43), p70-PET (SEQ ID NO:50), p30-CKS (SEQ ID NO:67), p30-PL (SEQ ID NO:73), p15-PL (SEQ ID NO:52), p15-CKS (SEQ ID NO:56), p12-CKS (SEQ ID NO:60), p12-PET (SEQ ID NO:63), p10-CKS (SEQ ID NO:77), p10-PET (SEQ ID NO:80), gp70 (SEQ ID NO:102) and p30 (SEQ ID NO:109), for a time and under conditions sufficient to allow the formation of antigen/anti-XMRV antibody complexes; (b) adding a XMRV antigen conjugate comprising an amino acid sequence selected from the group consisting of p15E-CKS (SEQ ID NO:27), p15EΔ-CKS (SEQ ID NO:29), p15E-PET (SEQ ID NO:33), p15E-PL (SEQ ID NO:23), p15EΔ-PL (SEQ ID NO:25), p15EΔ (SEQ ID NO:82) and epitopes thereof (i.e., SEQ ID NOs: 83, 84 and 85), p70-PL (SEQ ID NO:39), p70-CKS (SEQ ID NO:43), p70-PET (SEQ ID NO:50), p30-CKS (SEQ ID NO:67), p30-PL (SEQ ID NO:73), p15-PL (SEQ ID NO:52), p15-CKS (SEQ ID NO:56), p12-CKS (SEQ ID NO:60), p12-PET (SEQ ID NO:63), p10-CKS (SEQ ID NO:77), p10-PET (SEQ ID NO:80), gp70 (SEQ ID NO:102) and p30 (SEQ ID NO:109) to the resulting antigen/XMRV antibody complexes for a time and under conditions sufficient to allow the antigen to bind to the bound XMRV antibody, the XMRV antigen conjugate being attached to a signal-generating compound capable of generating a detectable signal, and (c) detecting the presence of anti-XMRV antibodies which may be present in the test sample by detecting the signal generated by the signal-generating compound. Again, a control or calibrator may be used which comprises antibody to XMRV. The present invention encompasses yet another method for detecting the presence of anti-XMRV antibodies in a test sample. This method comprises the steps of: (a) contacting the test sample suspected of containing the antibodies with an isolated protein or antigen comprising an amino acid sequence selected from the group consisting of p15E-CKS (SEQ ID NO:27), p15EΔ-CKS (SEQ ID NO:29), p15E-PET (SEQ ID NO:33), p15E-PL (SEQ ID NO:23), p15EΔ-PL (SEQ ID NO:25), p15EΔ (SEQ ID NO:82) and epitopes thereof (i.e., SEQ ID NOs: 83, 84 and 85), p70-PL (SEQ ID NO:39), p70-CKS (SEQ ID NO:43), p70-PET (SEQ ID NO:50), p30-CKS (SEQ ID NO:67), p30-PL (SEQ ID NO:73), p15-PL (SEQ ID NO:52), p15-CKS (SEQ ID NO:56), p12-CKS (SEQ ID NO:60), p12-PET (SEQ ID NO:63), p10-CKS (SEQ ID NO:77), p10-PET (SEQ ID NO:80), gp70 (SEQ ID NO:102) and p30 (SEQ ID NO:109), for a time and under conditions sufficient to allow the formation of antigen/anti-XMRV antibody complexes; (b) contacting an XMRV antigen conjugate comprising an amino acid sequence selected from the group consisting of p15E-CKS (SEQ ID NO:27), p15EΔ-CKS (SEQ ID NO:29), p15E-PET (SEQ ID NO:33), p15E-PL (SEQ ID NO:23), p15EΔ-PL (SEQ ID NO:25), p15EΔ (SEQ ID NO:82) and epitopes thereof (i.e., SEQ ID NOs: 83, 84 and 85), p70-PL (SEQ ID NO:39), p70-CKS (SEQ ID NO:43), p70-PET (SEQ ID NO:50), p30-CKS (SEQ ID NO:67), p30-PL (SEQ ID NO:73), p15-PL (SEQ ID NO:52), p15-CKS (SEQ ID NO:56), p12-CKS (SEQ ID NO:60), p12-PET (SEQ ID NO:63), p10-CKS (SEQ ID NO:77), p10-PET (SEQ ID NO:80), gp70 (SEQ ID NO:102) and p30 (SEQ ID NO:109) to the resulting antigen/XMRV antibody complexes for a time and under conditions sufficient to allow the antigen conjugate to bind to the bound XMRV antibody, the XMRV antigen conjugate being operably linked to a ligand binding moiety, and (c) detecting the presence of anti-XMRV antibodies which may be present in the test sample by detecting the signal generated by a signal-generating compound operably linked to the ligand bound by the ligand binding moiety operably linked to antigen conjugate. In certain embodiments the XMRV antigen portion of the antigen conjugate is identical to the XMRV antigen employed to initially bind the XMRV antibody, or the antigen portion of the antigen conjugate can be distinct, yet capable of being bound by the same XMRV antibody. Again, a control or calibrator may be used which comprises antibody to XMRV.

In certain embodiments, the above-described ligand binding moiety is avidin and the ligand is biotin. In alternative embodiments, the ligand binding moiety is streptavidin. Additional ligands and ligand binding moieties that can find use in the context of the present invention include, but are not limited to: digoxigenin/anti-digoxigenin; anti-fluorescein/ fluorescein; anti-2,4-dinitrophenol (DNF)/DNP; and anti-peroxidase/peroxidase. Additional alternative embodiments can employ any receptor/ligand or antibody/antigen interaction sufficiently specific to allow for reliable detection.

In certain embodiments, the present invention provides methods for detecting XMRV antibodies that are indicative of XMRV infection, prostate cancer, cervical cancer, uterine cancer, or chronic fatigue syndrome. In certain embodiments the present invention provides methods for detecting XMRV antibodies that are indicative of a propensity to develop prostate cancer, cervical cancer, uterine cancer, or chronic fatigue syndrome.

In certain embodiments, the present invention provides methods for monitoring the progression of XMRV infection by detecting antibodies to specific XMRV proteins. For example, but not by way of limitation, progression of XMRV infection can be monitored by detecting the presence of antibodies to one or more of the following XMRV proteins: gp70, p15E, p30, p15, p12, and p10. In certain embodiments such monitoring is achieved by detecting the presence of antibodies to p30. In certain embodiments such detection is achieved by detecting the presence of antibodies gp70 and p30. In certain embodiments such detection is achieved by detecting the presence of antibodies p15E and p30.

In certain embodiments, the above-described monitoring of the progression of XMRV infection is accomplished by detecting the presence of one or more anti-XMRV antibodies over one or more periods of time. Examples of such time periods include, but are not limited to, detecting the presence of one or more anti-XMRV antibodies in samples obtained from a subject every 6 hrs, 12 hrs, 24 hrs, 36 hrs, 48 hrs, 72 hrs, weekly, or monthly.

In additional embodiments, the present invention provides methods for detecting XMRV infection that combine one or more anti-XMRV immunodetection technique with one or more XMRV molecular detection technique, for example, but not limited to, LCR, SDA, RT-PCR, FISH, or NASBA.

In certain embodiments the present invention provides methods for detecting XMRV infection, prostate cancer, cervical cancer, uterine cancer, or chronic fatigue syndrome that involve the use of one or more anti-XMRV immunodetection technique in the context of assaying a panel of XMRV infection, prostate cancer, cervical cancer, uterine cancer, or chronic fatigue syndrome markers. Such panels can include one or more markers of XMRV infection, prostate cancer, cervical cancer, uterine cancer, or chronic fatigue syndrome. Such markers include, but are not limited to, elevated PSA levels, prostate cancer-specific gene expression (See, e.g., Bradford et al., Molecular markers of prostate cancer (2006), Urol. Oncol. 24(6), 538-551), cervical cancer-specific gene expression (See. e.g., Bachtiary et al., Gene Expression Profiling in Cervical Cancer: An Exploration of Intratumor Heterogeneity (2006) Clin Cancer Res 2006; 12(19) 5632-5640), uterine cancer-specific gene expression (See, e.g, Smid-Koopman et al., (2003) Gene expression profiling in human endometrial cancer tissue samples: utility and diagnostic value, Gynecologic Oncology, 93(2): 292-300), and chronic fatigue syndrome-specific gene expression (See, e.g., Fletcher et al. (2010) Biomarkers in Chronic Fatigue Syndrome: Evaluation of Natural Killer Cell Function and Dipeptidyl Peptidase IV/CD26. PLoS ONE 5(5): e10817). In certain embodiments the present invention provides methods for detecting a propensity to develop prostate cancer, cervical cancer, uterine cancer, or chronic fatigue syndrome that involve the use of one or more anti-XMRV immunodetection techniques in the context of assaying a panel of prostate cancer, cervical cancer, uterine cancer, or chronic fatigue syndrome markers.

A positive result using any of the above-described methods, indicative of the presence of XMRV, may optionally be followed by a corroborative or confirmative diagnostic procedure, such as but not limited to a tissue biopsy, histologic evaluation, radiographic study, MRI study, ultrasound study, PET scan, etc.

Molecular Detection

In certain embodiments, the present invention provides compositions and methods for the detection of XMRV nucleic acids using nucleic acid hybridization and/or amplification-based assays.

In certain embodiments, the methods for detection via hybridization and/or nucleic acid amplification of the present invention include, but are not limited to: real-time PCR (for example see Mackay, Clin. Microbiol. Infect. 10(3):190-212, 2004), Strand Displacement Amplification (SDA) (for example see Jolley and Nasir, Comb. Chem. High Throughput Screen. 6(3):235-44, 2003), self-sustained sequence replication reaction (3SR) (for example see Mueller et al., Histochem. Cell. Biol. 108(4-5):431-7, 1997), ligase chain reaction (LCR) (for example see Laffler et al., Ann. Biol. Clin. (Paris).51(9):821-6, 1993), transcription mediated amplification (TMA) (for example see Prince et al., J. Viral Hepat. 11(3):236-42, 2004), or nucleic acid sequence based amplification (NASBA) (for example see Romano et al., Clin. Lab. Med. 16(1):89-103, 1996).

In certain embodiments, the present invention provides methods for the detection of XMRV nucleic acids involving Fluorescence in situ Hybridization (FISH). The term "in situ hybridization" generally refers to hybridization of a nucleic acid probe to a nucleic acid target that is part of a cytological or histological preparation. Typically, FISH methods involve the following steps: (a) fixing the tissue or other biological material under investigation to a support (e.g., glass slide or wall of a micro titer well), (b) treatment of the tissue or material to increase accessibility of FISH probe to target nucleic acid, (c) contacting the tissue or material containing the target nucleic acid with probes to form specific hybridization complexes, (d) post hybridization washes of the complexes to selectively remove probes that are not specifically hybridized to the target, and (e) detection of probes that have formed hybridization complexes with target nucleic acid molecules. Such methods are described in a number of sources, including: Gall and Pardue, (1981) Methods of Enzymology 21:470-480; Henderson, (1982) International Review of Cytology, 76:1-46; and Angerer, et al., (1985) in Genetic Engineering: Principles and Methods (Setlow and Hollaender, Eds.) vol. 7, pp. 43-65, Plenum Press, New York.

In certain embodiments of the above-described methods for detection via hybridization and/or nucleic acid amplification comprise the use of nucleic acids (e.g., FISH probes, amplification primers, or RT-PCR probes) comprising, or otherwise derived from, one or more of the following sequences: SEQ ID NO.: 16; SEQ ID NO.: 19; SEQ ID NO.: 30; SEQ ID NO.: 31; SEQ ID NO.: 40; SEQ ID NO.: 44; SEQ ID NO.: 53; SEQ ID NO.: 54; SEQ ID NO.: 57; SEQ ID NO.: 58; SEQ ID NO.: 64; SEQ ID NO.: 65; SEQ ID NO.: 68; SEQ ID NO.: 69; SEQ ID NO.: 70; SEQ ID NO.: 71; SEQ ID NO.: 74; SEQ ID NO.: 75; SEQ ID NO.: 78; SEQ ID NO.: 90; SEQ ID NO.: 91; SEQ ID NO.: 96; SEQ ID NO.: 97; SEQ ID NO.: 98; SEQ ID NO.: 99; SEQ ID NO.: 103; SEQ ID NO.: 104; SEQ ID NO.: 105; and SEQ ID NO.: 106, or a complement thereof.

In certain embodiments, the present invention provides methods for detecting XMRV nucleic acids that are indicative of XMRV infection, prostate cancer, cervical cancer, uterine cancer, or chronic fatigue syndrome. In certain embodiments the present invention provides methods for detecting XMRV nucleic acids that are indicative of a propensity to develop prostate cancer, cervical cancer, uterine cancer, or chronic fatigue syndrome.

In further embodiments, the present invention provides methods for detecting XMRV infection that incorporate the use of one or more molecular detection technique, e.g., LCR, SDA, RT-PCR, FISH, or NASBA, with one or more immunodetection technique, including, but not limited to the immunodetection techniques described above.

In certain embodiments the present invention provides methods for detecting XMRV infection, prostate cancer, cervical cancer, uterine cancer, or chronic fatigue syndrome that involve the use of one or more anti-XMRV molecular detection technique in the context of assaying a panel of XMRV infection, prostate cancer, cervical cancer, uterine cancer, or chronic fatigue syndrome markers. Such panels can include one or more markers of XMRV infection, prostate cancer, cervical cancer, uterine cancer, or chronic fatigue syndrome. Such markers include, but are not limited to, elevated PSA levels, prostate cancer-specific gene expression (See, e.g., Bradford et al., Molecular markers of prostate cancer (2006), Urol. Oncol. 24(6), 538-551), cervical cancer-specific gene expression (See. e.g., Bachtiary et al., Gene Expression Profiling in Cervical Cancer: An Exploration of Intratumor Heterogeneity (2006) Clin Cancer Res 2006; 12(19) 5632-5640), uterine cancer-specific gene expression (See, e.g, Smid-Koopman et al., (2003) Gene expression profiling in human endometrial cancer tissue samples: utility and diagnostic value, Gynecologic Oncology, 93(2): 292-300), and chronic fatigue syndrome-specific gene expression (See, e.g., Fletcher et al. (2010) Biomarkers in Chronic Fatigue Syndrome: Evaluation of Natural Killer Cell Function and Dipeptidyl Peptidase IV/CD26. PLoS ONE 5(5): e10817). In certain embodiments the present invention provides methods for detecting a propensity to develop prostate cancer, cervical cancer, uterine cancer, or chronic fatigue syndrome that involve the use of one or more anti-XMRV molecular detection technique in the context of assaying a panel of prostate cancer, cervical cancer, uterine cancer, or chronic fatigue syndrome markers.

A positive result using any of the above-described methods, indicative of the presence of XMRV, may optionally be followed by a corroborative or confirmative diagnostic procedure, such as but not limited to a tissue biopsy, histologic evaluation, radiographic study, MRI study, ultrasound study, PET scan, etc.

Diagnostic Kits

Diagnostic kits are also included within the scope of the present invention. More specifically, the present invention includes kits for determining the presence of antibodies to XMRV in a test sample as well as diagnostic kits for determining the presence of XMRV nucleic acids in a test sample.

Kits directed to determining the presence of antibodies to XMRV in a sample may comprise: a) at least one XMRV antigen comprising an amino acid sequence selected from the group consisting of p70-PL (SEQ ID NO:39), p70-CKS (SEQ ID NO:43), p70-PET (SEQ ID NO:50), p30-CKS (SEQ ID NO:67), p30-PL (SEQ ID NO:73), p15-PL (SEQ ID NO:52), p15-CKS (SEQ ID NO:56), p12-CKS (SEQ ID NO:60), p12-PET (SEQ ID NO:63), p10-CKS (SEQ ID NO:77), p10-PET (SEQ ID NO:80), gp70 (SEQ ID NO:102), p30 (SEQ ID NO:109), p15EΔ-CKS (SEQ ID NO:29), p15EΔ-PL (SEQ ID NO:25), p15EΔ (SEQ ID NO:82) and epitopes thereof (i.e., SEQ ID NOs:83, 84 and 85) and b) a conjugate comprising an antibody attached to a signal-generating compound capable of generating a detectable signal. The kit may also contain a control or calibrator that comprises a reagent which binds to the antigen as well as an instruction sheet describing the manner of utilizing the kit.

The present invention also includes another type of kit for detecting antibodies to XMRV in a test sample. This kit may comprise: a) an anti-human antibody and b) at least one XMRV antigen comprising an amino acid sequence selected from the group consisting of p70-PL (SEQ ID NO:39), p70-CKS (SEQ ID NO:43), p70-PET (SEQ ID NO:50), p30-CKS (SEQ ID NO:67), p30-PL (SEQ ID NO:73), p15-PL (SEQ ID NO:52), p15-CKS (SEQ ID NO:56), p12-CKS (SEQ ID NO:60), p12-PET (SEQ ID NO:63), p10-CKS (SEQ ID NO:77), p10-PET (SEQ ID NO:80), gp70 (SEQ ID NO:102), p30 (SEQ ID NO:109), p15EΔ-CKS (SEQ ID NO:29), p15EΔ-PL (SEQ ID NO:25), p15EΔ (SEQ ID NO:82) and epitopes thereof (i.e., SEQ ID NOs: 83, 84 and 85). A control or calibrator comprising a reagent which binds to the XMRV antigen may also be included. More specifically, the kit may comprise: a) an anti-human antibody and b) a conjugate comprising at least one XMRV antigen comprising an amino acid sequence selected from the group consisting of p70-PL (SEQ ID NO:39), p70-CKS (SEQ ID NO:43), p70-PET (SEQ ID NO:50), p30-CKS (SEQ ID NO:67), p30-PL (SEQ ID NO:73), p15-PL (SEQ ID NO:52), p15-CKS (SEQ ID NO:56), p12-CKS (SEQ ID NO:60), p12-PET (SEQ ID NO:63), p10-CKS (SEQ ID NO:77), p10-PET (SEQ ID NO:80), gp70 (SEQ ID NO:102), p30 (SEQ ID NO:109), p15EΔ-CKS (SEQ ID NO:29), p15EΔ-PL (SEQ ID NO:25), p15EΔ (SEQ ID NO:82) and epitopes thereof (i.e., SEQ ID NOs: 83, 84 and 85), the conjugate being attached to a signal-generating compound capable of generating a detectable signal. Again, the kit may also comprise a control or calibrator comprising a reagent that binds to the XMRV antigen.

The present invention also includes another type of kit for detecting antibodies to XMRV in a test sample. The kit may comprise: a) at least one XMRV antigen comprising an amino acid sequence selected from the group consisting of p70-PL (SEQ ID NO:39), p70-CKS (SEQ ID NO:43), p70-PET (SEQ ID NO:50), p30-CKS (SEQ ID NO:67), p30-PL (SEQ ID NO:73), p15-PL (SEQ ID NO:52), p15-CKS (SEQ ID NO:56), p12-CKS (SEQ ID NO:60), p12-PET (SEQ ID NO:63), p10-CKS (SEQ ID NO:77), p10-PET (SEQ ID NO:80), gp70 (SEQ ID NO:102), p30 (SEQ ID NO:109), p15EΔ-CKS (SEQ ID NO:29), p15EΔ-PL (SEQ ID NO:25), p15EΔ (SEQ ID NO:82) and epitopes thereof (i.e., SEQ ID NOs: 83, 84 and 85) bound on a solid phase and b) a conjugate comprising: 1) an antigen comprising an amino acid sequence selected from the group consisting of p70-PL (SEQ ID NO:39), p70-CKS (SEQ ID NO:43), p70-PET (SEQ ID NO:50), p30-CKS (SEQ ID NO:67), p30-PL (SEQ ID NO:73), p15-PL (SEQ ID NO:52), p15-CKS (SEQ ID NO:56), p12-CKS (SEQ ID NO:60), p12-PET (SEQ ID NO:63), p10-CKS (SEQ ID NO:77), p10-PET (SEQ ID NO:80), gp70 (SEQ ID NO:102), p30 (SEQ ID NO:109), SEQ ID NO:25, SEQ ID NO:29, SEQ ID NO:82, SEQ ID NO:83, SEQ ID NO:84 and SEQ ID NO:85 attached to 2) a signal-generating compound capable of generating a detectable signal. A control or calibrator comprising a reagent which binds to the XMRV antigen may also be included. More specifically, the kit may comprise: a) at least one XMRV antigen comprising an amino acid sequence selected from the group consisting of p70-PL (SEQ ID NO:39), p70-CKS (SEQ ID NO:43), p70-PET (SEQ ID NO:50), p30-CKS (SEQ ID NO:67), p30-PL (SEQ ID NO:73), p15-PL (SEQ ID NO:52), p15-CKS (SEQ ID NO:56), p12-CKS (SEQ ID NO:60), p12-PET (SEQ ID NO:63), p10-CKS (SEQ ID NO:77), p10-PET (SEQ ID NO:80), gp70 (SEQ ID NO:102), p30 (SEQ ID NO:109), p15EΔ-CKS (SEQ ID NO:29), p15EΔ-PL (SEQ ID NO:25), p15EΔ (SEQ ID NO:82) and epitopes thereof (i.e., SEQ ID NOs: 83, 84 and 85), bound on a solid phase and b) a conjugate comprising at least one XMRV antigen comprising an amino acid sequence selected from the group consisting of p70-PL (SEQ ID NO:39), p70-CKS (SEQ ID NO:43), p70-PET (SEQ ID NO:50), p30-CKS (SEQ ID NO:67), p30-PL (SEQ ID NO:73), p15-PL (SEQ ID NO:52), p15-CKS (SEQ ID NO:56), p12-CKS (SEQ ID NO:60), p12-PET (SEQ ID NO:63), p10-CKS (SEQ ID NO:77), p10-PET (SEQ ID NO:80), gp70 (SEQ ID NO:102), p30 (SEQ ID NO:109), p15EΔ-CKS (SEQ ID NO:29), p15EΔ-PL (SEQ ID NO:25), p15EΔ (SEQ ID NO:82) and epitopes thereof (i.e., SEQ ID NOs: 83, 84 and 85), the conjugate being attached to a signal-generating compound capable of generating a detectable signal. Again, the kit may also comprise a control or calibrator comprising a reagent that binds to the XMRV antigen.

In certain embodiments, the present invention is directed to kits and compositions useful for the detection of XMRV nucleic acids. In certain embodiments, such kits comprise nucleic acids capable of hybridizing to XMRV nucleic acids. For example, but not by way of limitation, such kits can be used in connection with hybridization and/or nucleic acid amplification assays to detect XMRV nucleic acids.

In certain embodiments the hybridization and/or nucleic acid amplification assays that can be employed using the kits of the present invention include, but are not limited to: real-time PCR (for example see Mackay, Clin. Microbiol. Infect. 10(3):190-212, 2004), Strand Displacement Amplification (SDA) (for example see Jolley and Nasir, Comb. Chem. High Throughput Screen. 6(3):235-44, 2003), self-sustained sequence replication reaction (3SR) (for example see Mueller et al., Histochem. Cell. Biol. 108(4-5):431-7, 1997), ligase chain reaction (LCR) (for example see Laffler et al., Ann. Biol. Clin. Paris).51(9):821-6, 1993), transcription mediated amplification (TMA) (for example see Prince et al., J. Viral Hepat. 11(3):236-42, 2004), or nucleic acid sequence based amplification (NASBA) (for example see Romano et al., Clin. Lab. Med. 16(1):89-103, 1996).

In certain embodiments of the present invention, a kit for detection of XMRV nucleic acids comprises: (1) a nucleic acid sequence comprising a target-specific sequence that hybridizes specifically to an XMRV nucleic acid target, and (ii) a detectable label. Such kits can further comprise one or more additional nucleic acid sequence that can function as primers, including nested and/or hemi-nested primers, to mediate amplification of the target sequence. In certain embodiments, the kits of the present invention can further comprise additional nucleic acid sequences function as indicators of amplification, such as labeled probes employed in the context of a real time polymerase chain reaction assay.

The kits of the invention are also useful for detecting multiple XMRV nucleic acid targets. In such situations, the kit can comprise, for each different nucleic acid target, a different set of primers and one or more distinct labels.

In certain embodiments the kit comprises nucleic acids (e.g., hybridization probes, primers, or RT-PCR probes) comprising or otherwise derived from one or more of the following sequences: SEQ ID NO.: 16; SEQ ID NO.: 19; SEQ ID NO.: 30; SEQ ID NO.: 31; SEQ ID NO.: 40; SEQ ID NO.: 44; SEQ ID NO.: 53; SEQ ID NO.: 54; SEQ ID NO.: 57; SEQ ID NO.: 58; SEQ ID NO.: 64; SEQ ID NO.: 65; SEQ ID NO.: 68;

SEQ ID NO.: 69; SEQ ID NO.: 70; SEQ ID NO.: 71; SEQ ID NO.: 74; SEQ ID NO.: 75; SEQ ID NO.: 78; SEQ ID NO.: 90; SEQ ID NO.: 91; SEQ ID NO.: 96; SEQ ID NO.: 97; SEQ ID NO.: 98; SEQ ID NO.: 99; SEQ ID NO.: 103; SEQ ID NO.: 104; SEQ ID NO.: 105; and SEQ ID NO.: 106, or a complement thereof.

Therapeutics

XMRV Sequences Capable of Eliciting Immune Responses

In certain embodiments, the present invention is directed to antigenic XMRV amino acid sequences that are capable of eliciting an immune response. The XMRV amino acid sequence can include, or be derived from, any material that raises a cell-mediated immune response, a humoral immune response, or both, against at least a portion of an XMRV amino acid sequence. Suitable antigenic material can include, for example, but not by way of limitation, an XMRV protein, an XMRV polyprotein, or an antigenic polypeptide fragment of any XMRV protein or XMRV polyprotein. In certain embodiments the antigenic XMRV amino acid sequence is selected from the group consisting of p15EΔ-CKS (SEQ ID NO:29), p15EΔ-PL (SEQ ID NO:25), p15EΔ (SEQ ID NO:82) and epitopes thereof (SEQ ID Nos. 83, 84, and 85).

In certain embodiments, the amino acid sequence capable of eliciting an immune response is administered in combination with an adjuvant. In certain embodiments, the adjuvant is an immunostimulating adjuvant, more preferably a saponin-based adjuvant, and even more particularly an immunostimulating complex (or ISCOM™), such as ISCOMATRIX™ adjuvant. However, the present invention also encompasses the use of other immunostimulating adjuvants, either individually or in combination with another adjuvant such as an immunostimulating complex, including for example liposomes, oil-in-water adjuvants such as MF59, aluminium salt adjuvants such as aluminium hydroxide and aluminium phosphate, lipopolysaccharide adjuvants such as lipid A and monophosphoryl lipid A (MPL), oligonucleotide adjuvants such as CpG oligonucleotide adjuvant, and mucosal adjuvants such as cholera toxin. Suitable immunostimulating adjuvants are described by way of example by Cox and Coulter, Vaccine (1997), 15(3):248-256.

In certain embodiments the amino acid sequence capable of eliciting an immune response is prepared in the form of an immunogenic composition. The subject immunogenic composition is provided in any of a variety of formulations. For example, but not by way of limitation, the immunogenic composition of the present invention may be employed in such forms, both sterile and non-sterile, such as capsules, liquid solutions, liquid drops, emulsions, suspensions, elixirs, creams, suppositories, gels, soft capsules, sprays, inhalants, aerosols, powders, tablets, coated tablets, lozenges, microcapsules, suppositories, dragees, syrups, slurries, granules, enemas or pills. Any inert carrier can be used, such as saline, or phosphate buffered saline, stabilizers, propellants, encased in gelatin capsule or in a microcapsule or vector that aids administration or any such carrier in which the compounds used in the method of the present invention have suitable solubility properties for use in the methods of the present invention.

In a further embodiment, the subject immunogenic composition can be delivered alone or in conjunction with a dispersion system. In some embodiments the dispersion system is selected from the group consisting of, but not limited to: macromolecular complexes, nanocapsules, microspheres, beads and lipid based systems. Lipid-based systems optionally include oil-in-water emulsions, micelles, mixed micelles, or liposomes.

In certain embodiments a subject immunogenic composition is in the form of a pharmaceutically acceptable solution, which may routinely contain pharmaceutically acceptable concentrations of salt, buffering agents, preservatives, compatible carriers, adjuvants and optionally other therapeutic ingredients. Such composition can contain additives for example: disintegrants, binders, coating agents, swelling agents, lubricants, flavorings, sweeteners or solubilizers and the like. In certain embodiments a subject immunogenic composition is administered in its neat form or in the form of a pharmaceutically acceptable salt.

In certain embodiments, the immunogenic composition is freeze-dried (lyophilized) for long term stability and storage in a solid form. The freeze-dried method is known to those skilled in the art.

In certain embodiments, the immunogenic compositions of the present invention are employed in the prevention or treatment of one or more of the following: XMRV infection, prostate cancer, cervical cancer, uterine cancer, and chronic fatigue syndrome Inhibitory Nucleic Acids In certain embodiments, the present invention is directed to inhibitory nucleic acids capable of decreasing XMRV gene expression. Such inhibitory nucleic acids include, but are not limited to, antisense nucleic acids, ribozymes, and siRNA nucleic acids. In certain embodiments, the inhibitory nucleic acids of the present invention function by inhibiting either transcription or translation of a particular target gene.

In certain embodiments, the inhibitory nucleic acid of the present invention is an antisense nucleic acid molecule, i.e., a molecule which is complementary to a sense nucleic acid of the invention, e.g., complementary to the coding strand of an XMRV protein. An antisense oligonucleotide can be, for example, but not by way of limitation, about 5, 10, 15, 20, 25, 30, 35, 40, 45, or 50 or more nucleotides in length. An antisense nucleic acid of the invention can be constructed using chemical synthesis or by enzymatic synthesis reactions using procedures known in the art. For example, an antisense nucleic acid (e.g., an antisense oligonucleotide) can be chemically synthesized using naturally occurring nucleotides or modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

In certain embodiments, the inhibitory nucleic acid is a ribozyme. Ribozymes are catalytic RNA molecules that exhibit ribonuclease activity, and which are capable of cleaving a single-stranded nucleic acid, such as an mRNA, to which they have a complementary region. Thus, ribozymes (e.g., hammerhead ribozymes as described in Haseloff and Gerlach, 1988, Nature 334:585-591) can be used to catalytically cleave mRNA transcripts to thereby inhibit translation of the protein encoded by the mRNA. A ribozyme having specificity for a nucleic acid molecule encoding an XMRV protein of interest can be designed based upon the nucleotide sequence of that XMRV protein. For example, and not by way of limitation, a derivative of a Tetrahymena L-19 IVS RNA can be constructed in which the nucleotide sequence of the active site is complementary to the nucleotide sequence to be cleaved (see Cech et al. U.S. Pat. No. 4,987,071; and Cech et al. U.S. Pat. No. 5,116,742).

In certain embodiments, the inhibitory nucleic acid is a siRNA. siRNA-mediated transcript "knockdown," is a technique which has emerged as a standard way of specifically and potently inhibiting the expression of large numbers of genes. The siRNA of the invention can comprise partially purified RNA, substantially pure RNA, synthetic RNA, or recombinantly produced RNA, as well as altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides.

In certain embodiments, one or both strands of the siRNA of the invention can also comprise a 3' overhang. As used herein, a "3' overhang" refers to at least one unpaired nucleotide extending from the 3'-end of a duplexed RNA strand. Thus in one embodiment, the siRNA of the invention comprises at least one 3' overhang of from 1 to about 6 nucleotides (which includes ribonucleotides or deoxyribonucleotides) in length, preferably from 1 to about 5 nucleotides in length, more preferably from 1 to about 4 nucleotides in length, and particularly preferably from about 2 to about 4 nucleotides in length.

The siRNA of the invention can be targeted to any stretch of approximately 19-25 contiguous nucleotides in any of the target mRNA sequences. Techniques for selecting target sequences for siRNA are given, for example, in Tuschl T et al., "The siRNA User Guide," revised Oct. 11, 2002, the entire disclosure of which is herein incorporated by reference. Generally, a target sequence on the target mRNA can be selected from a given cDNA sequence corresponding to the target mRNA, preferably beginning 50 to 100 nt downstream (i.e., in the 3' direction) from the start codon. The target sequence can, however, be located in the 5' or 3' untranslated regions, or in the region nearby the start codon.

In certain embodiments the inhibitory nucleic acid sequence is prepared in the form of a pharmaceutical composition. Such pharmaceutical compositions can be provided in any of a variety of formulations. For example, but not by way of limitation, the inhibitory nucleic acid-containing pharmaceutical composition of the present invention may be employed in such forms, both sterile and non-sterile, such as capsules, liquid solutions, liquid drops, emulsions, suspensions, elixirs, creams, suppositories, gels, soft capsules, sprays, inhalants, aerosols, powders, tablets, coated tablets, lozenges, microcapsules, suppositories, dragees, syrups, slurries, granules, enemas or pills. Any inert carrier can be used, such as saline, or phosphate buffered saline, stabilizers, propellants, encased in gelatin capsule or in a microcapsule or vector that aids administration or any such carrier in which the compounds used in the method of the present invention have suitable solubility properties for use in the methods of the present invention.

The inhibitory nucleic acid-containing pharmaceutical compositions can contain pharmaceutically acceptable concentrations of salt, buffering agents, preservatives, compatible carriers, adjuvants and optionally other therapeutic ingredients. Such composition can contain additives for example: disintegrants, binders, coating agents, swelling agents, lubricants, flavorings, sweeteners or solubilizers and the like. In certain embodiments the inhibitory nucleic acid-containing pharmaceutical composition is administered in its neat form or in the form of a pharmaceutically acceptable salt.

In certain embodiments, the inhibitory nucleic acid-containing pharmaceutical composition is freeze-dried (lyophilized) for long term stability and storage in a solid form.

In certain embodiments, the inhibitory nucleic acid-containing compositions of the present invention are employed in the prevention or treatment of one or more of the following: XMRV infection, prostate cancer, cervical cancer, uterine cancer, and chronic fatigue syndrome.

The present invention may be illustrated by the use of the following non-limiting examples:

EXAMPLE 1

Production of XMRV Virions

XMRV particles were produced and purified by Advanced Biotechnologies, Inc. (ABI, Columbia, Md.). Briefly, XMRV-infected DU145 prostate cancer cells obtained from the Cleveland Clinic (Cleveland, Ohio) were cultured in RPMI medium 1640 supplemented with 10% fetal bovine serum, 2 mM L-glutamine, 200 units penicillin G and 200 ug/ml streptomycin. Virus particles from the culture supernatants were purified using a sucrose gradient density method. (Mahy, B. W. J. Virology: A Practical Approach; IRL Press: Oxford, 1985, pp. 36-37.)

EXAMPLE 2

General Cloning Procedures

Oligonucleotides for gene construction, gene cloning and sequencing were synthesized at MWG Biotech (High Point, N.C.), TriLink BioTechnologies (San Diego, Calif.), or Invitrogen (Carlsbad, Calif.). Genes were synthesized by GenScript Corporation (Piscataway, N.J.). Polymerase chain reaction (PCR) reagents, including AmpliTaq DNA polymerase and dNTPs from Applied Biosystems (Foster City, Calif.), SuperScript One-Step RT-PCR for Long Templates from Invitrogen, QIAGEN OneStep RT-PCR Kit from Qiagen (Valencia, Calif.), and Pfu DNA polymerase from Stratagene (La Jolla, Calif.) were used according to the manufacturer's instructions unless otherwise indicated. PCR amplifications were performed on GeneAmp 9700 thermal cyclers (Applied Biosystems, Foster City, Calif.). Restriction enzymes and ligases were purchased from Invitrogen and used as recommended by the manufacturer. Digested DNAs were either gel-purified using a QIAquick Gel Extraction Kit (Qiagen, or a Wizard SV Gel and PCR Clean-Up System (Promega, Madison, Wis.), or purified by passing through Chroma Spin-100 DEPC-$H_2O$ columns from Clontech (Palo Alto, Calif.) following the manufacturer's protocols.

Bacterial transformations were performed using competent cells of Subcloning Efficiency DH5α (Invitrogen), XL1-Blue (Stratagene) or BL21(DE3) (Novagen, Madison, Wis.)

based on the manufacturer's instructions. Transformations and bacterial restreaks were done on LB agar plates (Sigma-Aldrich, St. Louis, Mo.) with 100 µg/ml ampicillin or 50 µg/ml kanamycin, or on LB+antibiotic agar plates supplemented with a final concentration of 1% glucose. Bacteria were incubated overnight at 30° C. or 37° C., as noted.

Bacterial colony PCR was used to screen transformants in order to identify desired clones. Individual colonies were picked from agar plates, first streaked on a LB+antibiotic agar plate and then suspended in a well of 25 µl water in a 96-well PCR plate (Bio-Rad, Richmond, Calif.). The inoculated agar plates were incubated overnight at 30° C. or 37° C. as master plates for future use. Seventy-five µl of PCR master mix containing 10 µl of 10×PCR buffer, 10 µl of 10 mM dNTP (0.25 mM each), 2 µl of 20 µM forward primer (0.4 µM), 2 µl of 20 µM reverse primer (0.4 µM), 0.5 µl of 5 units/µl Ampli-Taq DNA polymerase (2.5 units), and 50.5 µl water were added to each 25 µl of bacterial suspension in the 96-well plate. Cycling conditions were 5 min at 94° C., followed by 40 cycles of 15 sec at 94° C., 30 sec at 50° C., and 60 sec at 72° C. The PCR reactions were then incubated at 72° C. for 7 min and held at 4° C. PCR products and miniprep plasmid DNA were examined by agarose gel electrophoresis and purified through a QIAquick PCR Purification Kit (Qiagen) or a Wizard SV Gel and PCR Clean-Up System (Promega) following the manufacturer's protocols. Miniprep plasmid DNA from an overnight bacterial culture was isolated and purified by using QIAprep Spin Miniprep Kit (Qiagen) according to the manufacturer's instructions.

An automated 3130×1 Genetic Analyzer (Applied Biosystems) was used for DNA sequence analysis. Sequencing reactions were performed with a BigDye Terminator v3.1 RR-1000 Cycle Sequencing Kit (Applied Biosystems), as recommended by the manufacturer. Sequence reactions were purified according to the manufacturer's instructions using Centri-Sep Spin Columns or Centri-Sep 96-Well Plates (Princeton Separations, Adelphia, N.J.). Sequence data were analyzed using Sequencher 4.8 (Gene Codes Corporation, Ann Arbor, Mich.) and DNASTAR Lasergene 7.1.1 or 7.2.1 (DNASTAR, Madison, Wis.).

EXAMPLE 3

Construction of Plasmid Clones Carrying a Synthetic XMRV Env p15E Gene

FIG. 1 illustrates the strategy employed to generate synthetic XMRV env p15E gene constructs. The env p15E amino acid sequence (SEQ ID NO:1) was deduced from the genomic DNA sequence of XMRV strain VP62 (GenBank accession EF185282). Eight overlapping oligonucleotides (A-H) were designed to make a full-length (i.e., 180 amino acids) synthetic env p15E gene, in which nucleotide #1 is the first base of the first codon of p15E and nucleotide #540 is the third base of the last codon. Seven overlapping oligonucleotides (A-F and I) were designed to construct a truncated p15E gene that carries a deletion of 14 amino acids (nucleotides #433 through #474), encompassing the highly hydrophobic region (transmembrane domain) of p15E. As a result, the shortened p15E gene (p15EΔ) encodes 166 amino acids.

In all nine overlapping oligonucleotides, the native XMRV viral codons were altered to conform to *E. coli* codon bias in an effort to increase the expression level of recombinant protein in *E. coli* host. (See, for example, M. Gouy and C. Gautier, *Nucleic Acids Research* 10:7055 (1982); H. Grosjean and W. Fiers, *Gene* 18:199 (1982); J. Watson et al. (eds.), *Molecular Biology of the Gene,* 4th Ed., Benjamin Kumming Publishing Co., pp. 440 (1987).)

In the process of gene construction, the complementary ends of the nine overlapping oligonucleotides, when annealed, served as primers for the extension of the complementary strand. This process (i.e., "PCR knitting" of oligonucleotides) was repeated to progressively lengthen the gene fragment. The knitted fragments were then amplified by PCR (oligonucleotide primer set FP125/RP226 or FP322/RP423). Outermost PCR primer 15EF33 was designed for cloning into a PL vector pKRR826. The expression vector, pKRR826, is a modified form of the bacteriophage lambda pL promoter vector pSDKR816, described in U.S. Ser. No. 08/314,570, incorporated herein by reference. pKRR826 is a high copy number derivative of pBR322 that contains the temperature sensitive lambda cI repressor gene (Benard et al., *Gene* 5:59 [1979]). However, pKRR826 lacks the translational terminator rrnBt1 and has the lambda pL and pR promoters in the reverse orientation, relative to pSDKR816. The polylinker region of pKRR826 contains EcoRI and BamHI restriction enzyme sites but lacks an ATG translational start codon. Optimal expression is obtained when the 5' end of the gene insert (including an N-terminal methionine) is cloned into the EcoRI site. The 5' end sense (or forward) primer 15EF33 (SEQ ID NO:15) was designed to contain an EcoRI restriction site for cloning and an ATG codon (methionine) to provide for proper translational initiation of the recombinant protein. The corresponding 3' end antisense (or reverse) primer 15ER32 (SEQ ID NO:16) contains two sequential translational termination codons (TAA, TAG) and a BamHI restriction site. Primers 15EF33 and 15ER32 were used to amplify the knitted fragment containing oligonucleotides A-H, encoding a full-length env p15E gene product of 180 amino acids (excluding the N-terminal methionine) that was designated as pK121F (SEQ ID NO:23). Primers 15EF33 and 15ER32 were also used to amplify a second knitted fragment composed of oligonucleotides A-F and I resulting in a truncated env p15E gene product, which excluding the N-terminal methionine, encodes for 166 amino acids (pK1310B; SEQ ID NO:25).

The full-length and truncated p15E genes were also expressed as CMP-KDO synthetase (CKS) fusion proteins. PCR-mediated transfer of the two synthetic genes from pKRR826 into a CKS expression vector pJO200 (described in U.S. Serial No. 6,593,083 B1 and incorporated herein by reference) was accomplished by employing an alternative 5' end sense PCR primer, 15EF30 (SEQ ID NO:19). Primer 15EF30 contained an EcoRI site and resulted in the in-frame fusion of the gene insert to CKS in pJO200. The 3' end antisense primer 15ER32 (SEQ ID NO:16) was used in combination with 15EF30 to generate plasmid construct pJ1F2A (SEQ ID NO:27) carrying the full-length (180 amino acids) p15E gene, or pJ10B9A (SEQ ID NO:29) having the truncated (166 amino acids) p15E gene.

The above-mentioned cloning steps are detailed below:

A. PCR Knitting of Synthetic Oligonucleotides

As outlined in FIGS. 2A and 3A, three PCR reactions (50 μl volume each) were set up as follows:

(1) Reaction K1: RT/Platinum Taq HiFi enzyme mix (Invitrogen) in 1× reaction buffer containing 0.2 mM each dNTP 1.2 mM $MgSO_4$, 0.1 μM each of oligonucleotides A (SEQ ID NO:2), B (SEQ ID NO:3), C (SEQ ID NO:4) and D (SEQ ID NO:5), and 0.4 μM each of primers FP125 (SEQ ID NO:11) and RP226 (SEQ ID NO:12);

(2) Reaction K2: RT/Platinum Taq HiFi enzyme mix (Invitrogen) in 1× reaction buffer containing 0.2 mM each dNTP+1.2 mM $MgSO_4$, 0.1 μM each of oligonucleotides E (SEQ ID NO:6), F (SEQ ID NO:7), G (SEQ ID NO:8) and H (SEQ ID NO:9), and 0.4 μM each of primers FP322 (SEQ ID NO:13) and RP423 (SEQ ID NO:14); and (3) Reaction K3: RT/Platinum Taq HiFi enzyme mix (Invitrogen) in 1× reaction buffer containing 0.2 mM each dNTP+1.2 mM MgSO$_4$, 0.1 μM each of oligonucleotides E (SEQ ID NO:6), F (SEQ ID NO:7) and I (SEQ ID NO:10), and 0.4 μM each of primers FP322 (SEQ ID NO:13) and RP423 (SEQ ID NO:14).

The PCR thermal profile consisted of an initial step of 2 min at 94° C., followed by 30 cycles of 15 sec at 94° C., 30 sec at 55° C., and 60 sec at 68° C. Reactions were then incubated at 72° C. for 7 min and held at 4° C. Amplified products were evaluated by agarose gel electrophoresis and purified through a QIAquick PCR Purification Kit (Qiagen).

B. PCR Knitting of PCR Products from Reactions K1 and K2 or Reactions K1 and K3

Figure 2A:
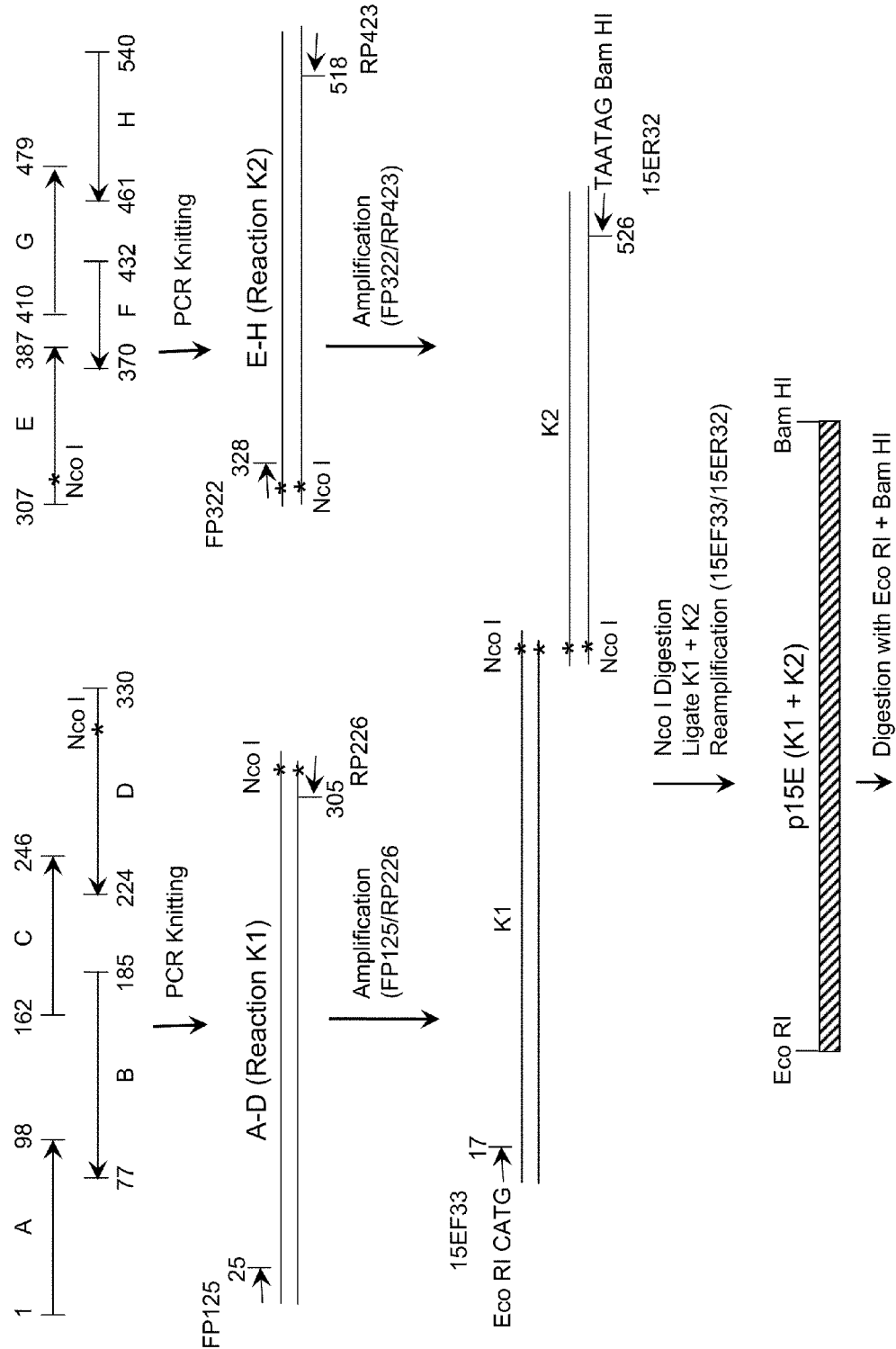
FIGS. 2A through 2C represent a diagrammatic description of the steps involved in construction of plasmid clones pK121F/DH5α and pJ1F2A/XL1 that carry a full-length synthetic XMRV env p15E gene.
Figure 3A:
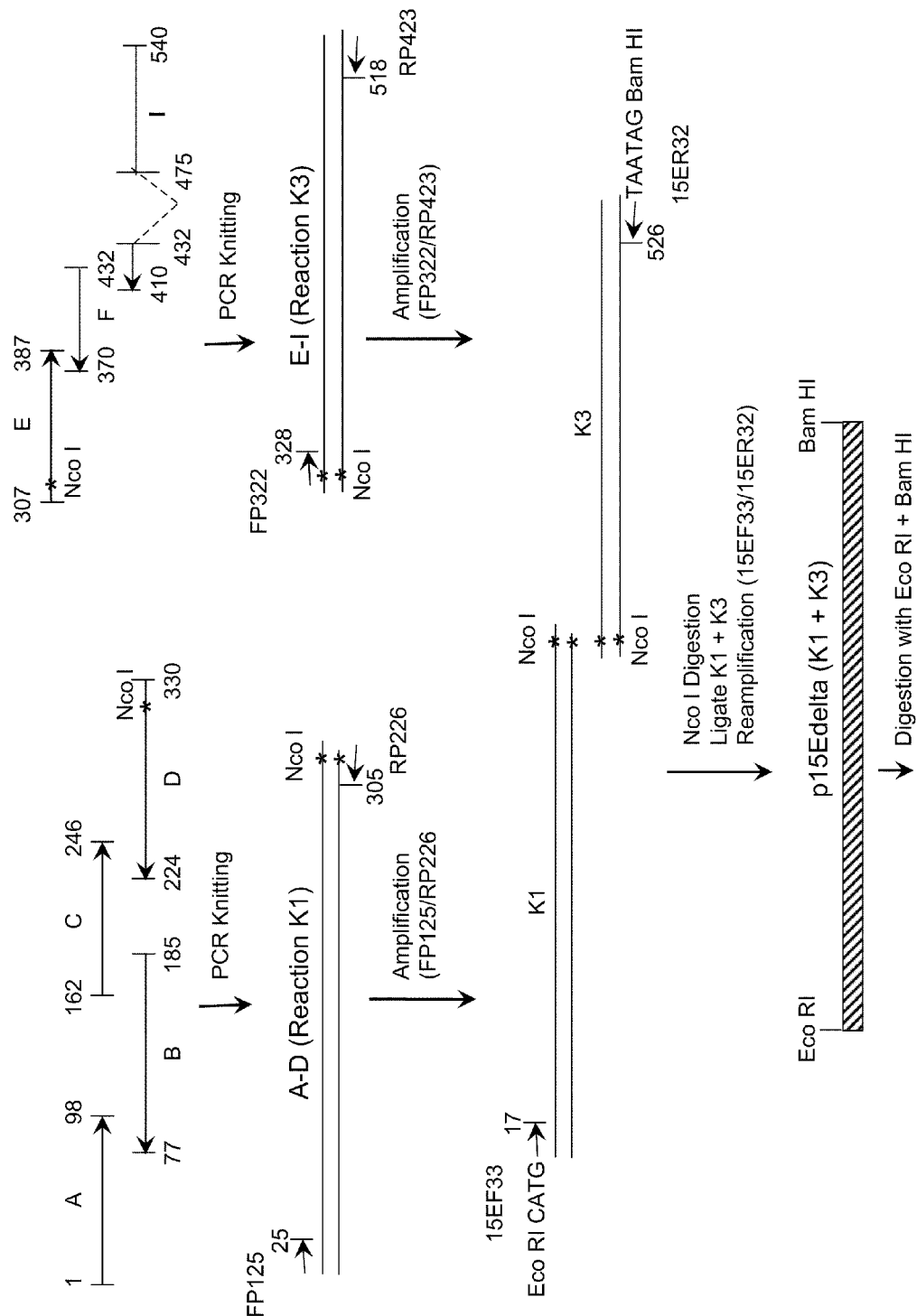
FIGS. 3A through 3C show a diagrammatic representation of the steps involved in construction of plasmid clones pK1310B/DH5α and pJ10B9A/XL1 that contain a synthetic XMRV env p15E gene with a deletion.

PCR products from reactions K1, K2 and K3 were digested with a restriction endonuclease Nco I (Invitrogen), purified by passing through a Chroma Spin-100 DEPC—H$_2$O column (Clontech), and ligated (K1+K2 or K1+K3) with T4 DNA ligase (Invitrogen) (see FIGS. 2A and 3A). The two ligation reactions, K1+K2 and K1+K3, were then purified through a Chroma Spin Column, and separately amplified using primers 15EF33 (SEQ ID NO:15) and 15ER32 (SEQ ID NO:16) with SuperScript One-Step RT-PCR Kit (Invitrogen) according to the manufacturer's instructions. The two 15EF33-15ER32 amplified products (K1+K2 and K1+K3) were later visualized by agarose gel electrophoresis and purified with QIAquick PCR Purification Kit.

C. Cloning of the 15EF33-15ER32 PCR Products into pKRR826

Figure 2B:
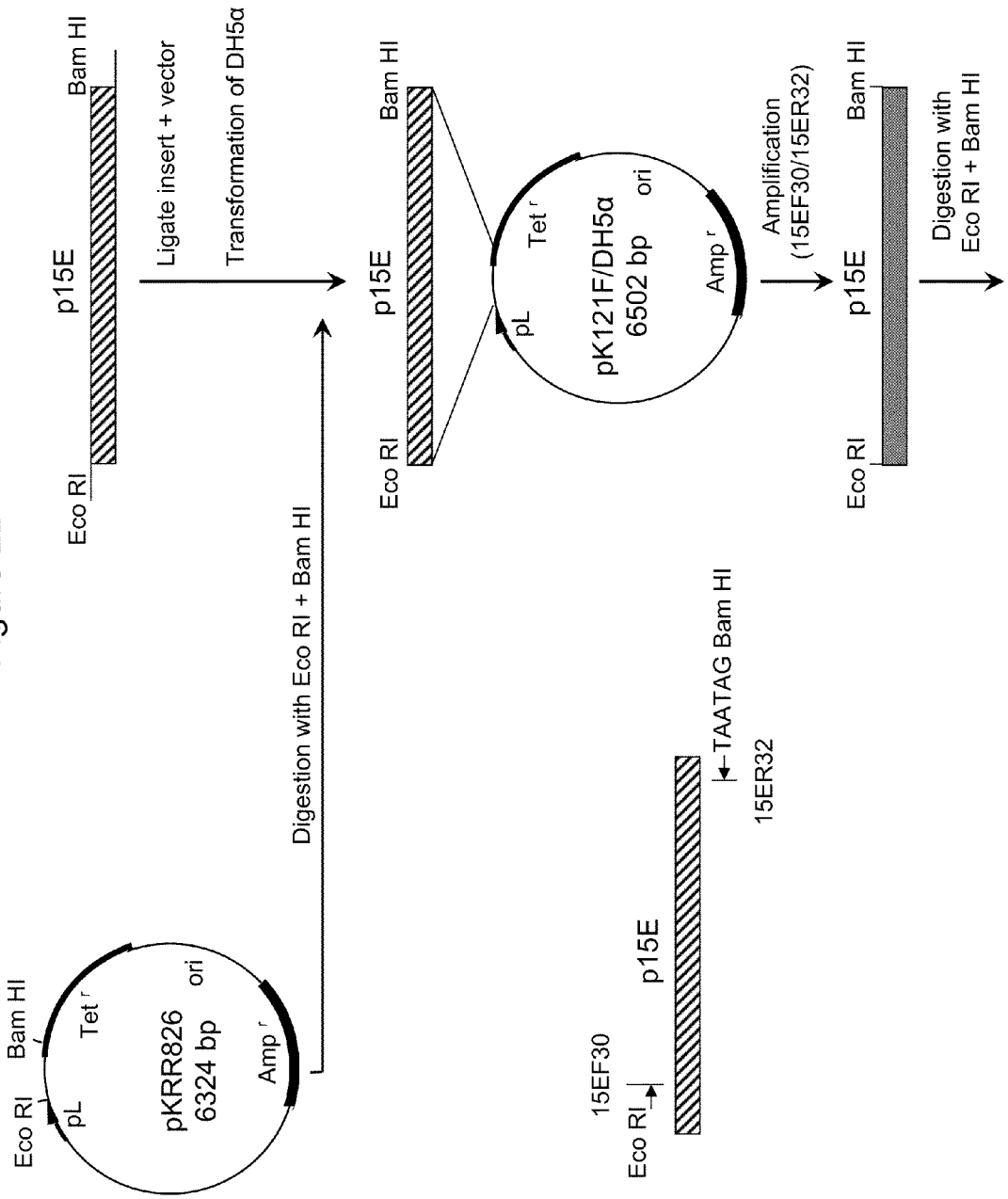
Figure 3B:
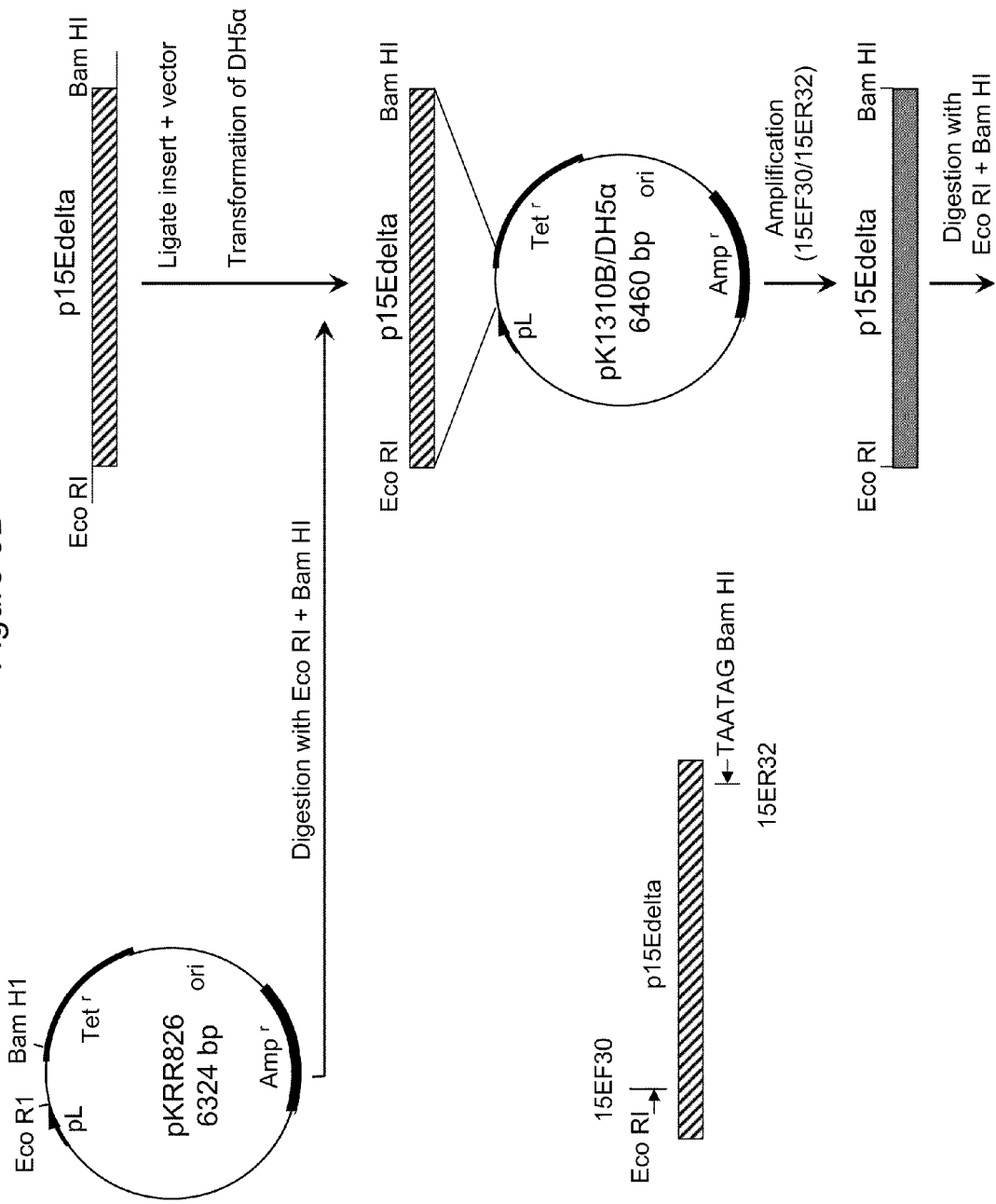

As shown in FIGS. 2B and 3B, the two 15EF33-15ER32 amplification products (K1+K2 and K1+K3) and the PL expression vector, pKRR826, were digested with restriction enzymes Eco RI+Bam HI, purified using Chroma Spin Columns, and ligated overnight at 14° C. with T4 DNA ligase (Invitrogen). The ligation products were transformed into DH5α competent cells, and the transformed cells were incubated at 30° C. on LB+ampicillin agar plates. Individual colonies were screened by colony PCR using two flanking plasmid primers KR21 (SEQ ID NO:17) and KR18 (SEQ ID NO:18) to amplify the plasmid inserts. The amplified insert products were analyzed by agarose gel electrophoresis, purified using QIAquick PCR Purification Kit, and sequenced with primers KR21 and KR18. Two sequence verified clones were identified: (1) pK121F/DH5α that carries the K1+K2 insert encoding the full-length (180 amino acids) p15E gene (p15E), and (2) pK1310B/DH5α that possesses the K1+K3 insert encoding the truncated (166 amino acids) p15E gene (p15EΔ). Miniprep plasmid DNA was prepared from an overnight culture of each clone and was sequence verified using primers KR21 and KR18. SEQ ID NO:22 presents the nucleotide sequence of the full-length p15E recombinant protein in clone pK121F/DH5α; SEQ ID NO:23 shows the corresponding amino acid sequence. This recombinant protein (p15E-PL) consists of an N-terminal methionine and 180 amino acids of env p15E. SEQ ID NO:24 depicts the nucleotide sequence of the truncated p15E (p15EΔ) recombinant protein in clone pK1310B/DH5α. SEQ ID NO:25 lists the corresponding amino acid sequence. This recombinant protein (p15EΔ-PL) consists of an N-terminal methionine and 166 amino acids of env p15E.

D. Cloning of the 15EF30-15ER32 PCR Products into the CKS Expression Vector, pJO200

Figure 2C:
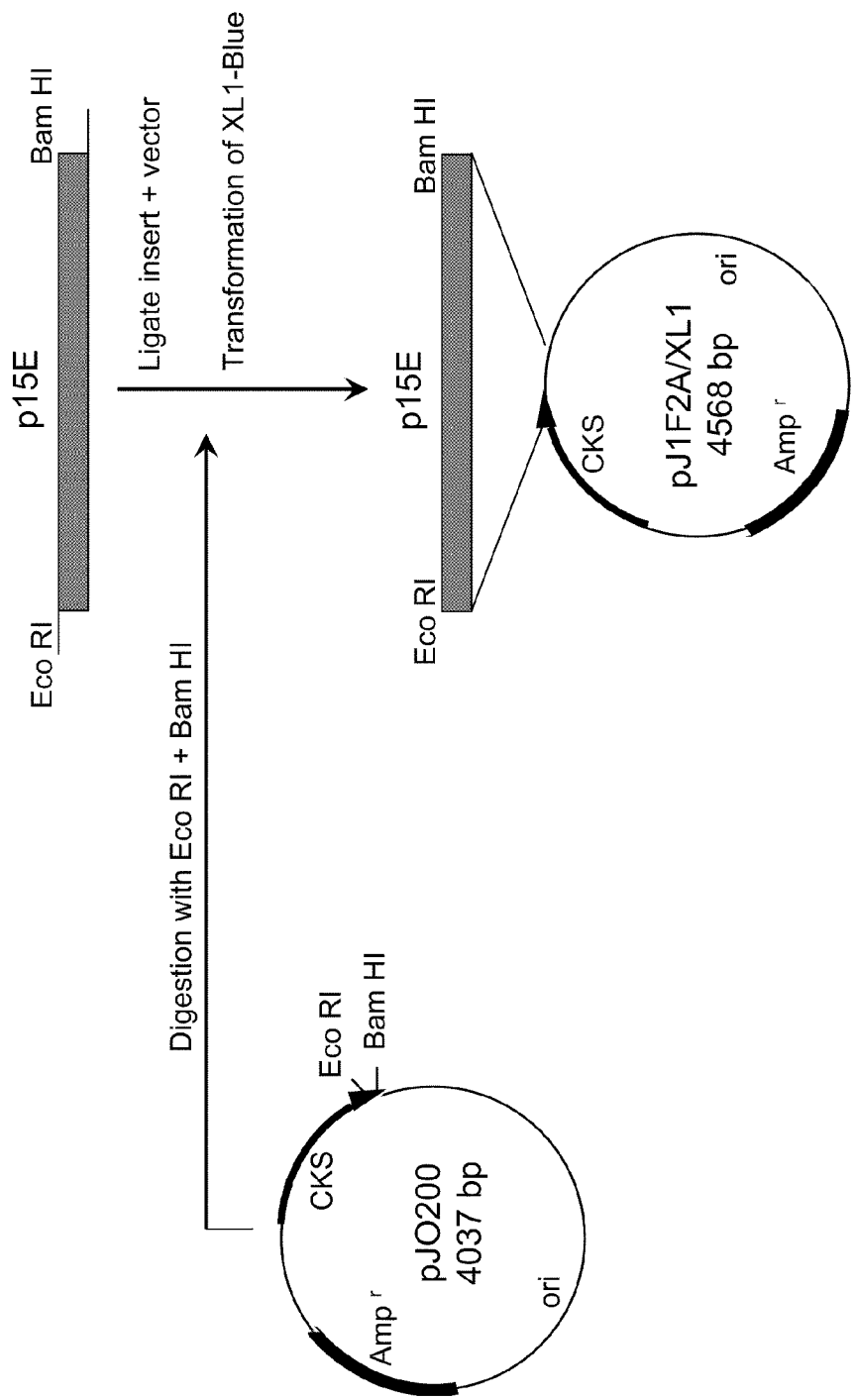
Figure 3C:
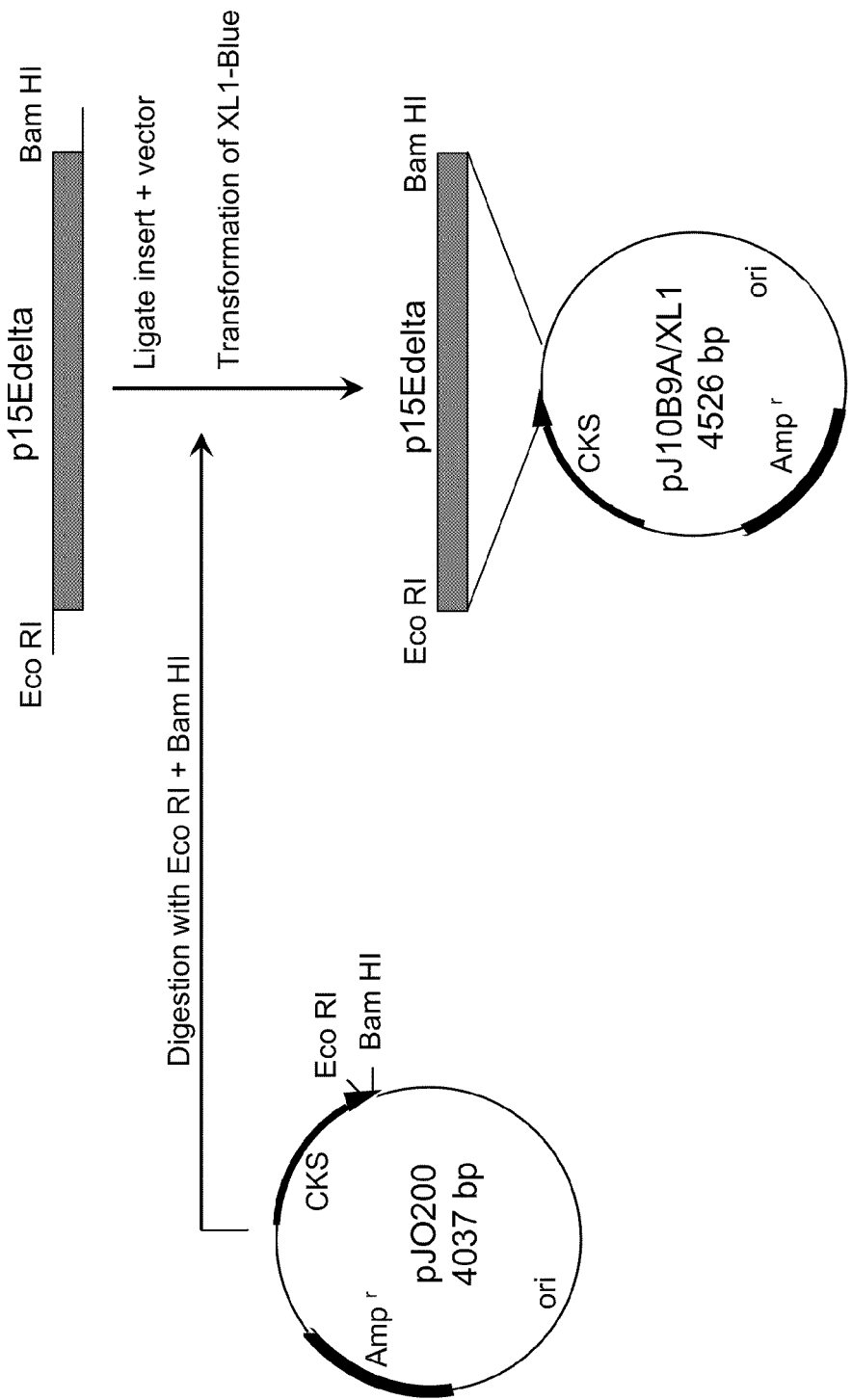

FIGS. 2A through 2C show a diagrammatic representation of the steps involved in construction of pJ1F2A/XL1, and FIGS. 3A through 3C show those steps utilized in construction of pJ10B9A/XL1. Construction of clones pJ1F2A/XL1 and pJ10B9A/XL1 was achieved as follows:

Two PCR reactions (50 μl each) were prepared with RT/Platinum Taq HiFi enzyme mix (Invitrogen) in 1× reaction buffer containing 0.2 mM each dNTP+1.2 mM MgSO$_4$, 60 ng plasmid DNA pK121F/DH5α or pK1310B/DH5α, Example 2, Section C), and 0.4 μM each of primers 15EF30 (SEQ ID NO:19) and 15ER32 (SEQ ID NO:16). Cycling conditions consisted of an initial step of 2 min at 94° C., followed by 30 cycles of 15 sec at 94° C., 30 sec at 55° C., and 60 sec at 68° C. Reactions were then incubated at 72° C. for 7 min and held at 4° C. Amplified products were evaluated by agarose gel electrophoresis and purified using QIAquick PCR Purification Kit. The two purified 15EF30-15ER32 PCR products (p15E and p15EΔ) and the expression vector, pJO200, were digested with Eco RI+Bam HI, purified on Chroma Spin Columns, and ligated using T4 DNA ligase (14° C. overnight). The ligation products were transformed into XL1-Blue competent cells, and the transformed cells were incubated at 37° C. on LB+ampicillin+1% glucose agar plates. Individual colonies were screened by colony PCR using two flanking primers JF19 (SEQ ID NO:20) and JR20 (SEQ ID NO:21) to amplify the plasmid inserts. The amplified insert products were evaluated by agarose gel electrophoresis, purified using QIAquick PCR Purification Kit, and sequenced with primers JF19 and JR20. Two sequence-verified clones were identified: (1) pJ1F2A/XL1 that carries the full-length (180 amino acids) p15E gene (p15E), and (2) pJ10B9A/XL1 containing the truncated p15E gene (p15EΔ; 166 amino acids). Miniprep plasmid DNA was prepared from an overnight culture of each clone and the p15E gene inserts were sequence verified with primers JF19 and JR20. SEQ ID NO:26 displays the nucleotide sequence of the coding region of the p15E-CKS recombinant fusion protein in clone pJ1F2A/XL1. The corresponding amino acid sequence of p15E-CKS (SEQ ID NO:27) is composed of 246 amino acids of CKS/polylinker followed by 180 amino acids of env p15E. SEQ ID NO:28 depicts the nucleotide sequence of the coding region of the recombinant fusion protein, 15EΔ-CKS, in clone pJ10B9A/XL1. The recombinant p15EΔ-CKS fusion protein (SEQ ID NO:29) contains 246 amino acids of CKS/polylinker followed by 166 amino acids of env p15E.

EXAMPLE 4

Construction of a Plasmid Clone Carrying a Native XMRV Env p15E Gene

Figure 4:
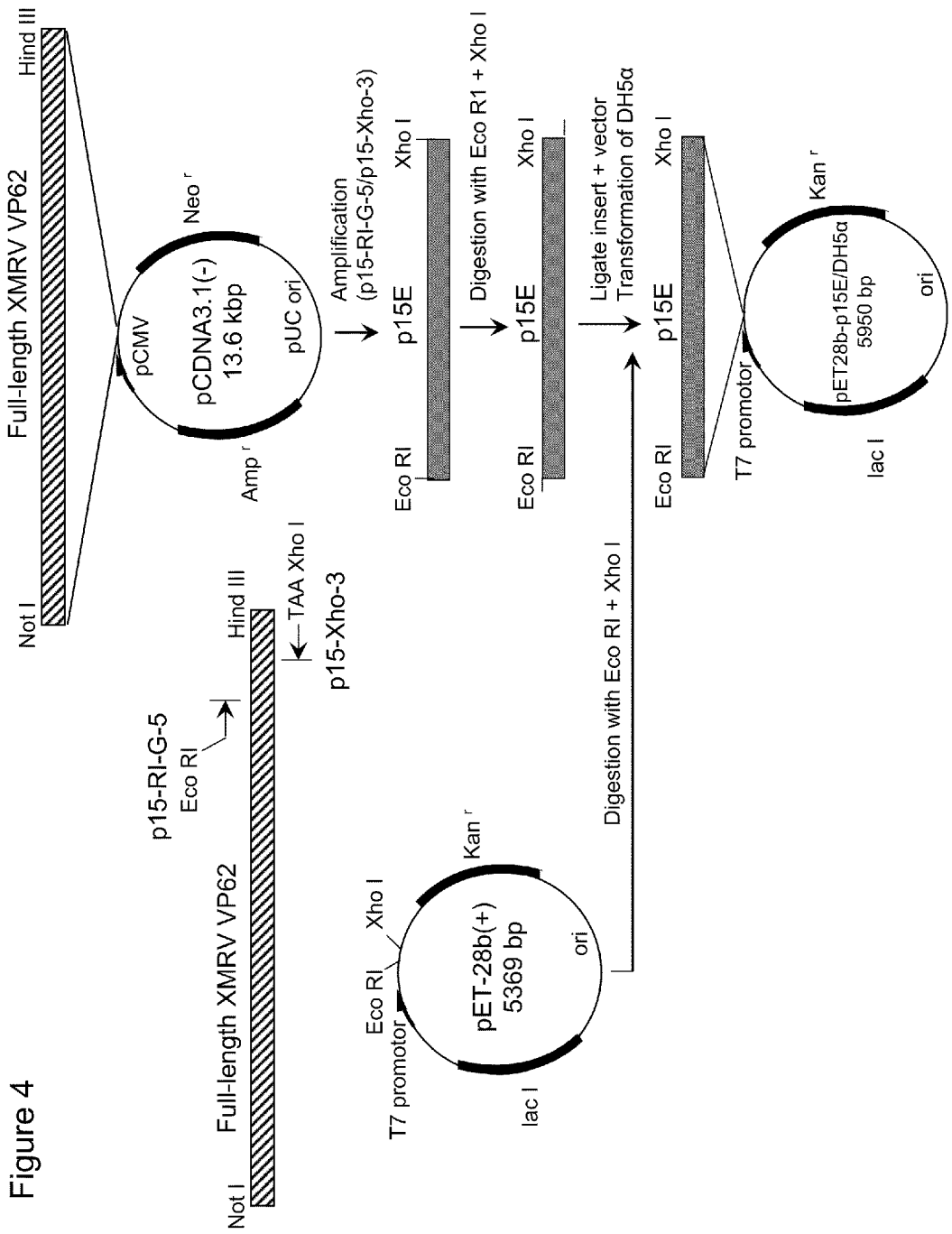
FIG. 4 illustrates the steps involved in construction of plasmid clone pET28b-p15E/DH5α that has a full-length native XMRV env p15E gene.

FIG. 4 illustrates the steps involved in construction of p15E-PET/DH5α, a plasmid clone that carries a native XMRV env p15E gene. This plasmid construct produces a recombinant protein p15E-PET, the amino acid sequence of which is shown in SEQ ID NO:33. This recombinant protein consists of 37 amino acids of plasmid his-tag/polylinker fused to 201 amino acids of the XMRV env p15E protein. SEQ ID NO:32 displays the nucleotide sequence of this recombinant fusion protein. The DNA sequence contains 111 base pairs from the plasmid followed by 603 base pairs of the env p15E gene derived from native XMRV viral RNA. Plasmid clone pET28b-p15E/DH5α was constructed as follows:

A pcDNA3.1-based plasmid clone carrying a full-length XMRV strain VP62 was constructed and described by B.

Dong et al., *Proc. Natl. Acad. Sci.* 104:1655 (2007). The full-length XMRV VP62 DNA insert was generated by RT-PCR amplification of viral RNA. A PCR reaction (50 µl) was set up with Pfu DNA polymerase (Stratagene) in 1× reaction buffer containing 2 mM MgSO$_4$ and 0.25 mM each dNTP, 10$^5$ copies of VP62 plasmid clone DNA, and 0.2 µM each of primers p15-RI-G-5 (SEQ ID NO:30) and p15-Xho-3 (SEQ ID NO:31). Cycling conditions consisted of an initial step of 2 min at 95° C., followed by 39 cycles of 30 sec at 95° C., 30 sec at 55° C., and 4.5 min at 68° C. The reaction was then incubated at 68° C. for 10 min and held at 4° C. The amplified product was evaluated by agarose gel electrophoresis and purified using Wizard SV Gel and PCR Clean-Up System (Promega). The purified p15-RI-G-5/p15-Xho-3 PCR product (env p15E gene) and pET-28b(+) expression vector were digested with restriction enzymes Eco RI+Xho I, gel-purified using Wizard SV Gel and PCR Clean-Up System (Promega), and ligated into the PET expression vector pET-28b(+) (Novagen) that was digested with Eco RI+Xho I and gel-purified using Wizard SV Gel and PCR Clean-Up System (Promega). The purified p15E gene inserts and digested pET-28b(+) vector were ligated with T4 DNA ligase. The ligation product was transformed into DH5α competent cells, and the transformed cells were incubated at 37° C. on LB+kanamycin agar plates. Individual colonies were screened by colony PCR using two flanking plasmid primers T7 promoter (SEQ ID NO:34) and T7 terminator (SEQ ID NO:35) to amplify the plasmid inserts. The amplified insert products were analyzed by agarose gel electrophoresis, purified using Wizard SV Gel and PCR Clean-Up System (Promega), and sequenced with T7 promoter and terminator primers. A clone designated as pET28b-p15E/DH5α was identified. Miniprep plasmid DNA was prepared from an overnight culture of this clone, and the integrity of the p15B gene insert was sequence confirmed using T7 promoter and terminator primers. SEQ ID NO:32 displays the nucleotide sequence of the p15E-PET recombinant fusion protein expressed by clone pET28b-p15E/DH5α, and SEQ ID NO:33 shows its corresponding amino acid sequence.

EXAMPLE 5

Construction of Plasmid Clones Carrying a Synthetic XMRV Env gp70 Gene

Figure 5A:
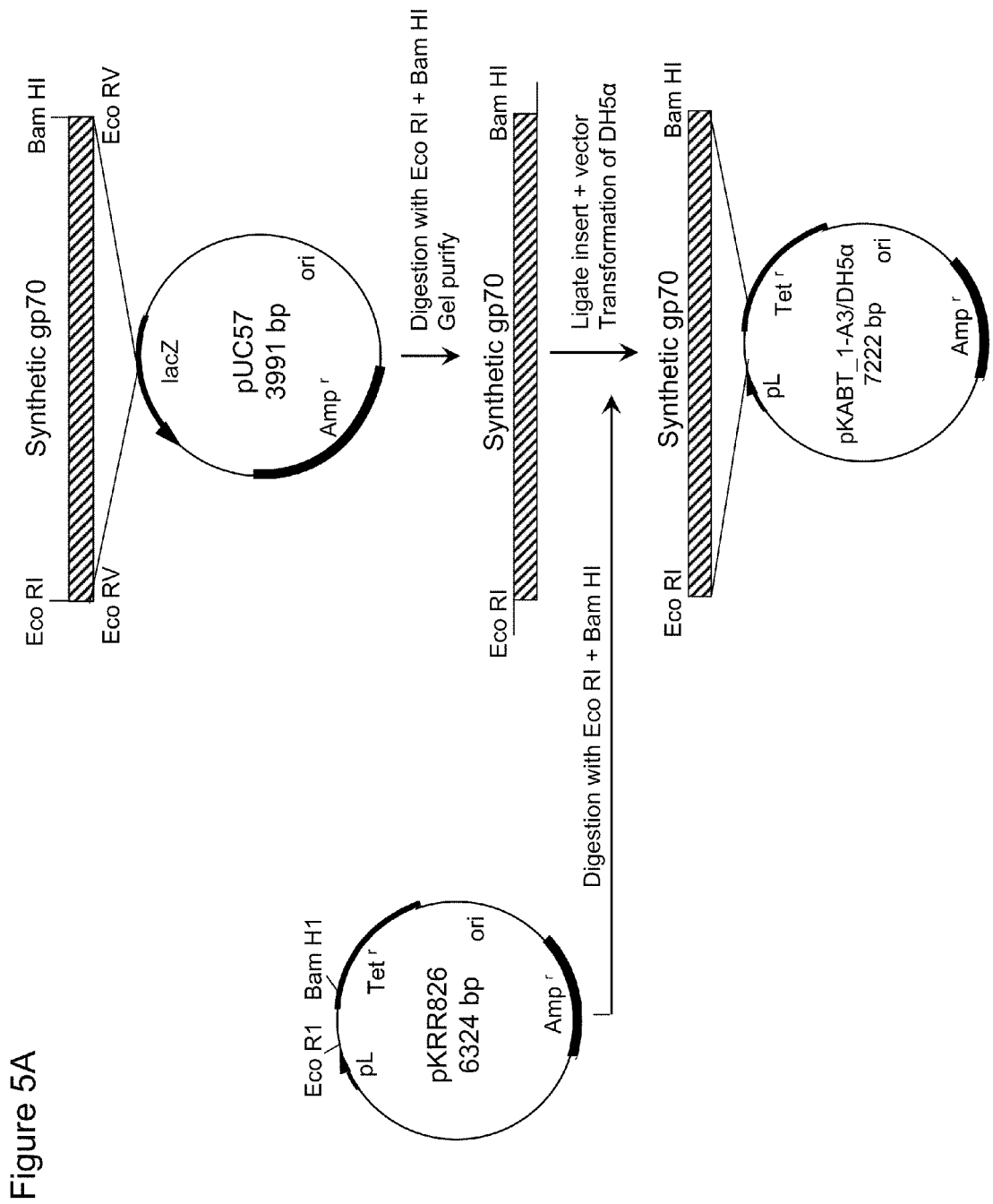
FIGS. 5A through 5C outline the schematic steps involved in construction of plasmid clones pKABT_1-A3/DH5α, pJABT_1-B2/XL1, and pEABT_1-D2/DH5α, respectively, wherein all three clones have a copy of full-length synthetic XMRV env gp70 gene.
Figure 5B:
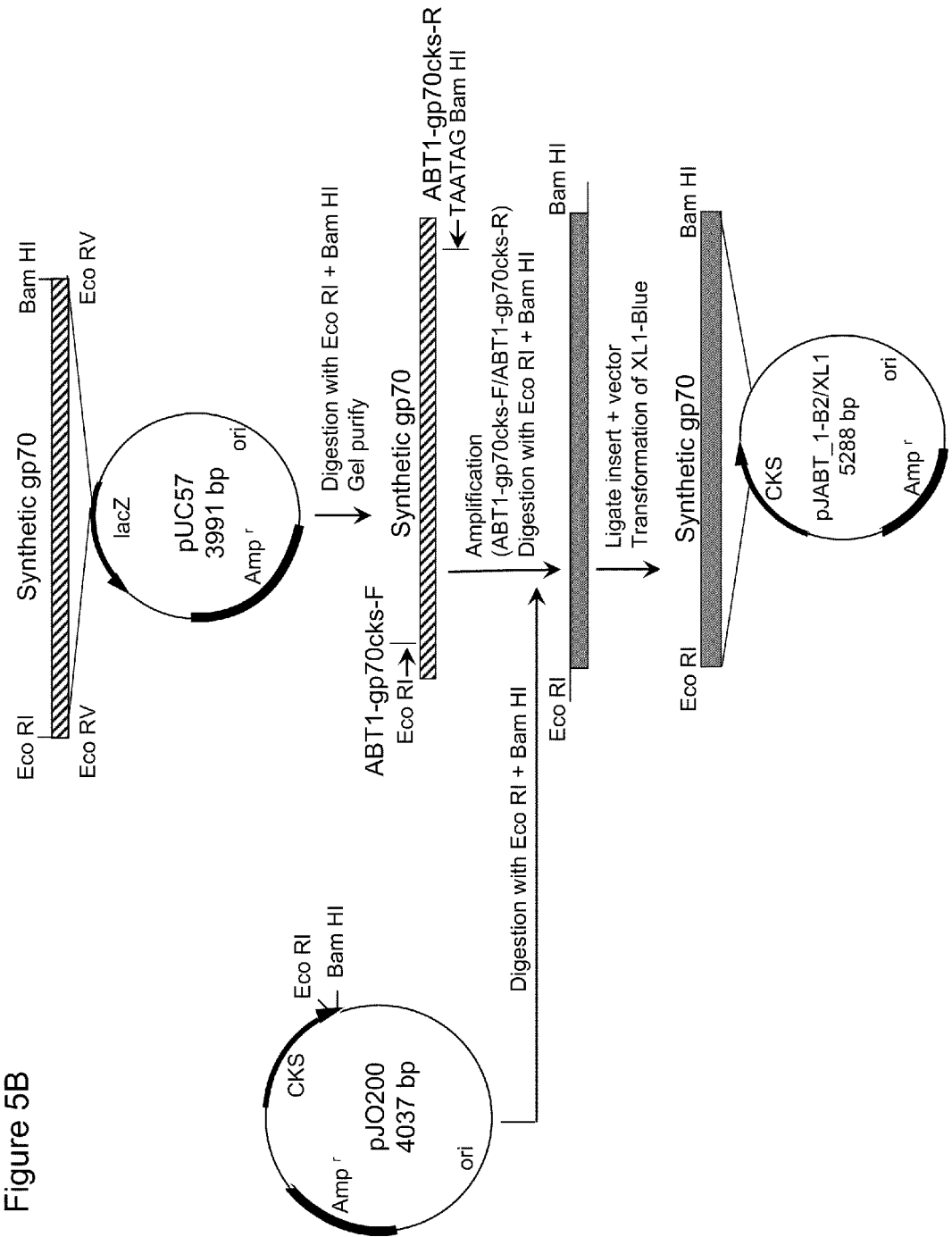
Figure 5C:
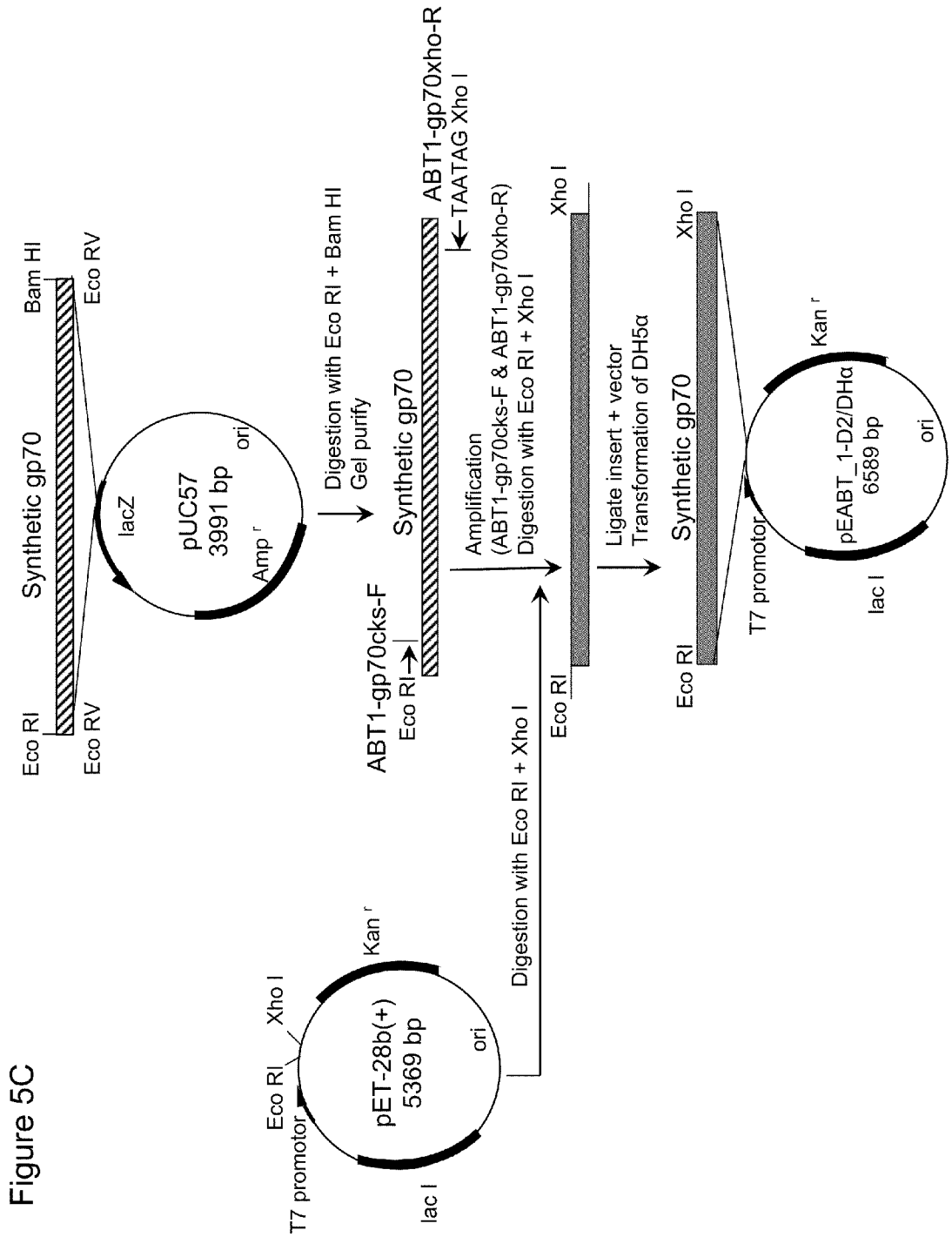

FIGS. 5A through 5C show the steps involved in construction of three plasmid clones carrying a full-length synthetic XMRV env gp70 gene. The gp70 gene was synthesized by GenScript Corporation (Piscataway, N.J.), and the native XMRV viral codons were modified to conform to *E. coli* codon bias in an effort to increase the expression level of recombinant gp70 protein in *E. coli* host. The synthetic gene was then cloned into a plasmid vector pUC57, and this plasmid construct was used to make three env gp70 expression constructs.

A. Construction of pKABT_1-A3/DH5α

As shown in FIG. 5A, the pUC57-based plasmid clone received from GenScript carrying the full-length synthetic gp70 gene and the vector pKRR826 were digested with Eco RI+Bam HI. The gp70 insert was gel-purified using QIAquick Gel Extraction Kit (Qiagen). The digested vector was purified through a Chroma Spin Column. The purified gp70 insert and pKRR826 vector were ligated with T4 DNA ligase. The ligation product was transformed into DH5α, and the transformed cells were incubated at 30° C. on LB+ampicillin agar plates. Individual colonies were screened by colony PCR using two flanking plasmid primers pKR34-F (SEQ ID NO:36) and pKR51-R (SEQ ID NO:37) to amplify the plasmid inserts. The amplified insert products were analyzed by agarose gel electrophoresis, purified using a QIAquick PCR Purification Kit, and sequenced with primers pKR34-F and pKR51-R. Based on the sequencing results, a desired clone designated as pKABT_1-A3/DH5Δ was identified. Miniprep plasmid DNA was prepared from an overnight culture of this clone, and the gp70 gene insert was sequence confirmed using primers pKR34-F and pKR51-R. SEQ ID NO:38 shows the nucleotide sequence of the expressed gp70 recombinant protein in clone pKABT_1-A3/DH5α. The recombinant protein (p70-PL) encoded by pKABT_1-A3/DH5α is composed of an N-terminal methionine followed by 414 amino acids of env gp70 viral protein and six histidine residues (SEQ ID NO:39).

B. Construction of pJABT_1-B2/XL1

As presented in FIG. 5B, the gel-purified gp70 gene insert from pUC57 was amplified using QIAGEN OneStep RT-PCR Kit (Qiagen) using primers ABT1-gp70cks-F (SEQ ID NO:40) and ABT1-gp70cks-R (SEQ ID NO:41), according to the manufacturer's protocol. Amplified product was later analyzed by agarose gel electrophoresis and purified through QIAquick PCR Purification Kit. The purified PCR product and pJO200 vector DNA were digested with Eco RI+Bam HI, purified on Chroma Spin Columns, and ligated using T4 DNA ligase. The ligation product was transformed into XL1-Blue, and the transformed cells were incubated at 37° C. on LB+ampicillin+1% glucose agar plates. Individual colonies were screened by colony PCR using two flanking plasmid primers JF19 (SEQ ID NO:20) and JR20 (SEQ ID NO:21) to amplify the plasmid inserts. The amplified insert products were evaluated by agarose gel electrophoresis, purified using QIAquick PCR Purification Kit, and sequenced with primers JF19, JR20, ABT1-gp70cks-F and ABT1-gp70cks-R. Based on the sequencing results, a desired clone designated as pJABT_1-B2/XL1 was identified. Miniprep plasmid DNA was prepared from an overnight culture of this clone, and the gp70 gene insert was sequence verified. SEQ ID NO:42 shows the nucleotide sequence of the expressed p70-CKS fusion protein in clone pJABT_1-B2/XL1. The p70-CKS fusion recombinant protein (p70-CKS) encoded by pJABT_1-B2/XL1 consists of 246 amino acids of CKS/polylinker fused to 414 amino acids of env gp70 viral protein followed by six histidine residues (SEQ ID N°:43).

C. Construction of pEABT_1-D2/DH5α

As illustrated in FIG. 5C, the gel-purified gp70 gene insert from pUC57 was amplified using QIAGEN OneStep RT-PCR Kit (Qiagen) and primers ABT1-gp70cks-F (SEQ ID NO:40) and ABT1-gp70xho-R (SEQ ID NO:44). Amplified product was analyzed by agarose gel electrophoresis and purified using QIAquick PCR Purification Kit. The purified PCR product and pET-28b(+) vector were digested with Eco RI+Xho I, purified on Chroma Spin Columns, and ligated using T4 DNA ligase. The ligation product was transformed into DH5α, and the transformed cells were incubated at 37° C. on LB kanamycin agar plates. Individual colonies were screened by colony PCR using two flanking plasmid primers T7 promoter (SEQ ID NO:34) and T7 terminator (SEQ ID NO:35) to amplify the plasmid inserts. The amplified insert products were evaluated by agarose gel electrophoresis, purified using QIAquick PCR Purification Kit, and sequenced with primers T7 promoter, T7 terminator, ABT_1-seq2-F (SEQ ID NO:45), ABT_1-seq3-F (SEQ ID NO:46), ABT_1-seq1-R (SEQ ID NO:47) and ABT_1-seq2-R (SEQ ID NO:48). Based on the sequencing results, a desired clone designated as pEABT_1-D2/DH5α was identified. Miniprep plasmid DNA was prepared from an overnight culture of this clone, and the gp70 gene insert was sequence confirmed. SEQ ID NO:49 shows the nucleotide sequence of the expressed gp70-PET fusion protein in clone pEABT_1-D2/DH5α. The recombinant p70-PET fusion protein (p70-PET) encoded by pEABT_1-D2/DH5α consists of 36 amino acids of plasmid his-tag/polylinker followed by 414 amino acids of env gp70 viral protein (SEQ ID NO:50).

EXAMPLE 6

Construction of Plasmid Clones Carrying a Synthetic XMRV Gag p15 Gene

A full-length XMRV gag p15 gene was synthesized by GenScript
Corporation and was inserted into pUC57 as described in Example 5. In this synthetic p15 gene the native XMRV viral codons were modified to conform to *E. coli* codon bias in an effort to increase the expression level of the recombinant p15 protein in a bacterial host. The pUC57-based plasmid clone was used to clone two gag p15 expression constructs.
A. Construction of pKABT_2-D5/DH5α
As diagrammed in FIG. 5A, the pUC57-based plasmid clone carrying the full-length synthetic gag p15 gene obtained from GenScript was digested with Eco RI+Bam HI. The digested p15 gene insert was gel-purified using QIAquick Gel Extraction Kit (Qiagen). The vector pKRR826 was digested with Eco RI+Bam HI and purified on a Chroma Spin Column. The digested gag p15 insert and pKRR826 vector preparation were ligated with T4 DNA ligase. The ligation product was transformed into DH5α, and the transformed cells were incubated at 30° C. on LB+ampicillin agar plates. Individual colonies were screened by colony PCR using two flanking plasmid primers pKR34-F (SEQ ID NO:36) and pKR51-R (SEQ ID NO:37) to amplify the plasmid inserts. The amplified products were analyzed by agarose gel electrophoresis, purified using QIAquick PCR Purification Kit, and sequenced with primers pKR34-F and pKR51-R. Based on the sequencing results, a clone designated as pKABT_2-D5/DH5α was identified. Miniprep plasmid DNA was prepared from an overnight culture of this clone, and the p15 gene insert was sequence confirmed. SEQ ID NO:51 shows the nucleotide sequence of the expressed p15 recombinant protein in clone pKABT_2-D5/DH5α. The non-fusion recombinant protein (p15-PL) encoded by pKABT_2-D5/DH5α consists of 129 amino acids (including the native viral N-terminal methionine) of gag p15 protein followed by six histidine residues (SEQ ID NO: 52).
B. Construction of pJABT_2-C3/XL1
As outlined in FIG. 5B, the gel-purified gag p15 gene insert from pUC57 was amplified using QIAGEN OneStep RT-PCR Kit (Qiagen) and primers ABT2-p15cks-F (SEQ ID NO:53) and ABT2-p15cks-R (SEQ ID NO:54) according to the manufacturer's protocol. Amplified product was analyzed by agarose gel electrophoresis and purified using QIAquick PCR Purification Kit. The purified PCR product and pJO200 vector DNA were digested with Eco RI+Bam HI, purified on Chroma Spin Columns, and ligated using T4 DNA ligase. The ligation product was transformed into XL1-Blue, and the transformed cells were incubated at 37° C. on LB+ampicillin+1% glucose agar plates. Individual colonies were screened by colony PCR using two flanking plasmid primers JF19 (SEQ ID NO:20) and JR20 (SEQ ID NO:21) to amplify the plasmid inserts. The amplified insert products were evaluated by agarose gel electrophoresis, purified using QIAquick PCR Purification Kit, and sequenced with primers JF19 and JR20. Based on the sequencing results, a desired clone designated as pJABT_2-C3/XL1 was identified. Miniprep plasmid DNA was prepared from an overnight culture of this clone, and the p15 gene insert was confirmed once again by sequencing with primers JF19 and JR20. SEQ ID NO:55 shows the nucleotide sequence of the expressed gag p15-CKS fusion protein in clone pJABT_2-C3/XL1. The recombinant fusion protein (p15-CKS) encoded by pJABT_2-C3/XL1 is comprised of 246 amino acids of CKS and polylinker fused to 129 amino acids of gag p15 viral protein followed by six histidine residues (SEQ ID NO:56).

EXAMPLE 7

Construction of Plasmid Clones Carrying a Synthetic XMRV Gag p12 Gene

A full-length XMRV gag p12 gene was synthesized by GenScript Corporation (Piscataway, N.J.) and was inserted into pUC57 as described in Example 5. In this synthetic gag p12 gene, the native XMRV viral codons were changed to conform to *E. coli* codon bias in an effort to boost the expression level of the p12 recombinant protein in *E. coli* host. The pUC57-based plasmid clone was used as a source of DNA to make the following two gag p12 expression clones.
A. Construction of pJABT_3-E4/XL1
As illustrated in FIG. 5B, the gel-purified gag p12 gene insert from pUC57 was amplified using QIAGEN OneStep RT-PCR Kit (Qiagen) and primers ABT3-p12cks-F (SEQ ID NO:57) and ABT3-p12cks-R (SEQ ID NO:58) according to the manufacturer's protocol. Amplified product was analyzed by agarose gel electrophoresis and purified using QIAquick PCR Purification Kit. The purified PCR product and pJO200 vector DNA were digested with Eco RI+Bam HI, purified on Chroma Spin Columns, and ligated with T4 DNA ligase. The ligation product was transformed into XL1-Blue, and the transformed cells were incubated at 37° C. on LB+ampicillin+1% glucose agar plates. Individual colonies were screened by colony PCR using two flanking plasmid primers JF19 (SEQ ID NO:20) and JR20 (SEQ ID NO:21) to amplify the plasmid inserts. The amplified products were analyzed by agarose gel electrophoresis, purified using QIAquick PCR Purification Kit, and sequenced with primers JF19 and JR20. Based on the sequencing results, a desired clone designated as pJABT_3-E4/XL1 was identified. Miniprep plasmid DNA was prepared from an overnight culture of this clone, and the gag p12 gene insert was sequence confirmed. SEQ ID NO:59 shows the nucleotide sequence of the expressed p12-CKS fusion protein in clone pJABT_3-E4/XL1. The recombinant fusion protein (p12-CKS) encoded by pJABT_3-E4/XL1 is composed of 246 amino acids of CKS/polylinker fused to 84 amino acids of gag p12 viral protein followed by six histidine residues (SEQ ID NO:60).
B. Construction of pEABT_3-B3/DH5α
As diagrammed in FIG. 5C, the gel-purified p12 gene insert from pUC57 was amplified using QIAGEN OneStep RT-PCR Kit (Qiagen) and primers ABT3-p12cks-F (SEQ ID NO:57) and ABT3-p12xho-R (SEQ ID NO:61). Amplified product was analyzed by agarose gel electrophoresis and purified using a QIAquick PCR Purification Kit. The purified PCR product and pET-28b(+) vector DNA were digested with Eco RI+Xho I, purified on Chroma Spin Columns, and ligated using T4 DNA ligase. The ligation product was transformed into DH5α, and the transformed cells were incubated at 37° C. on LB+kanamycin agar plates. Individual colonies were screened by colony PCR using two flanking plasmid primers T7 promoter (SEQ ID NO:34) and T7 terminator (SEQ ID NO:35) to amplify the plasmid inserts. The amplified insert products were evaluated by agarose gel electrophoresis, purified using QIAquick PCR Purification Kit, and sequenced with primers T7 promoter and T7 terminator. Based on the sequencing results, a desired clone designated as pEABT_3-B3/DH5α was identified. Miniprep plasmid DNA was prepared from an overnight culture of this clone, and the gag p12 gene insert was sequence confirmed using primers T7 promoter and T7 terminator. SEQ ID NO:62 shows the nucleotide sequence of the expressed gag p12-PET fusion protein in clone pEABT_3-B3/DH5α. The recombinant fusion protein (p12-PET) encoded by pEABT_3-B3/DH5α consists of 36 amino acids of plasmid his-tag/polylinker followed by 84 amino acids of gag p12 viral protein (SEQ ID NO:63).

EXAMPLE 8

Construction of Plasmid Clones Carrying an XMRV Gag P30 Gene

A full-length XMRV gag p30 gene was synthesized by GenScript Corporation (Piscataway, N.J.) where the native XMRV viral codons were altered to conform to *E. coli* codon bias in an effort to increase the expression level of the p30 recombinant protein in a bacterial host. This synthetic gene was used to generate a CKS fusion expression construct (A).

A. Construction of pJABT_4-G1/XL1

As outlined in FIG. 5B, the synthetic gag p30 gene was excised out of pUC57 with Eco RI+Bam HI, gel-purified using QIAquick Gel Extraction Kit (Qiagen), and amplified using a QIAGEN OneStep RT-PCR Kit (Qiagen) and primers ABT4-p30cks-F (SEQ ID NO:64) and ABT4-p30cks-R (SEQ ID NO:65). The amplified product was analyzed by agarose gel electrophoresis and purified with QIAquick PCR Purification Kit. The purified PCR product and pJO200 vector DNA were digested with Eco RI+Bam HI, purified on Chroma Spin Columns, and ligated with T4 DNA ligase. The ligation product was transformed into XL1-Blue, and the transformed cells were incubated at 37° C. on LB+ampicillin+1% glucose agar plates. Individual colonies were screened by colony PCR using two flanking plasmid primers JF19 (SEQ ID NO:20) and JR20 (SEQ ID NO:21) to amplify the plasmid inserts. The amplified insert products were examined by agarose gel electrophoresis, purified using QIAquick PCR Purification Kit, and sequenced with primers JF19, JR20, ABT4-p30cks-F and ABT4-p30cks-R. Based on the sequencing results, a desired clone designated as pJABT_4-G1/XL1 was identified. Miniprep plasmid DNA was prepared from an overnight culture of this clone, and the synthetic gag p30 gene insert was sequence confirmed. SEQ ID NO:66 shows the nucleotide sequence of the expressed p30-CKS fusion protein in clone pJABT_4-G1/XL1. The recombinant fusion protein (p30-CKS) encoded by pJABT_4-G1/XL1 consists of 246 amino acids of CKS/polylinker fused to the entire 263 amino acids of gag p30 viral protein followed by six histidine residues (SEQ ID NO:67).

B. Construction of pKp30-B2/DH5α

A plasmid clone AM-2-9 carrying the entire gag gene and 5' portion of the pol gene of XMRV strain VP62 was constructed and described by A. Urisman et al., *PloS Pathogens* 2:e25 (2006). The nearly 4 kb VP62 DNA insert was generated by RT-PCR of viral RNA and cloned into vector pCR2.1. As illustrated in FIG. 5A, the native gag p30 gene was amplified from clone AM-2-9 using QIAGEN OneStep RT-PCR Kit (Qiagen) and primers p30E-EcoR1metb (SEQ ID NO:68) and p30R-His (SEQ ID NO:69) according to the manufacturer's protocol. The gag p30 gene PCR product was gel-purified. The purified gene insert and pKRR826 vector DNA were digested with Eco RI+Bam HI, purified on Chroma Spin columns, and ligated using T4 DNA ligase. The ligation product was transformed into DH5α, and the transformed cells were incubated at 30° C. on LB+ampicillin agar plates. Individual colonies were screened by colony PCR using two flanking plasmid primers pKR34-F (SEQ ID NO:36) and pKR51-R (SEQ ID NO:37) to amplify the plasmid inserts. The amplified insert products were analyzed by agarose gel electrophoresis, purified using QIAquick PCR Purification Kit, and sequenced with primers pKR34-F, pKR51-R, p30E-seq2 (SEQ ID NO:70) and p30R-seq2 (SEQ ID NO:71). Based on the sequencing results, a desired clone designated as pKp30-B2/DH5α was identified. Miniprep plasmid DNA was prepared from an overnight culture of this clone, and the native gag p30 gene insert was sequence confirmed. SEQ ID NO:72 shows the nucleotide sequence of the expressed gag p30 recombinant protein in clone pKp30-B2/DH5α. The recombinant protein (p30-PL) encoded by pKp30-B2/DH5α is composed of an N-terminal methionine followed by two C-terminal amino acids of gag p12 fused to the entire 263 amino acids of gag p30 viral protein and six carboxy-terminal histidine residues (SEQ ID NO: 73).

EXAMPLE 9

Construction of Plasmid Clones Carrying a Synthetic XMRV Gag p10 Gene

A full-length XMRV gag p10 gene was synthesized by GenScript Corporation (Piscataway, N.J.) and was inserted into pUC57 as described in Example 5. In this synthetic gag p10 gene, the native XMRV viral codons were modified to conform to *E. coli* codon bias in an effort to raise the expression level of the p10 recombinant protein in *E. coli*. The pUC57-based plasmid clone was used as a source of DNA to make the following two gag p10 expression clones.

A. Construction of pJABT_5-D5/XL1

As depicted in FIG. 5B, the gel-purified gag p10 gene insert from pUC57 was amplified using QIAGEN OneStep RT-PCR Kit (Qiagen) and primers ABT5-p10cks-F (SEQ ID NO:74) and ABT5-p10cks-R (SEQ ID NO:75) according to the manufacturer's protocol. Amplified product was analyzed by agarose gel electrophoresis and purified using QIAquick PCR Purification Kit. The purified PCR product and pJO200 vector DNA were digested with Eco RI+Bam HI, purified on Chroma Spin Columns, and ligated with T4 DNA ligase. The ligation product was transformed into XL1-Blue, and the transformed cells were incubated at 37° C. on LB+ampicillin+1% glucose agar plates. Individual colonies were screened by colony PCR using two flanking plasmid primers JF19 (SEQ ID NO:20) and JR20 (SEQ ID NO:21) to amplify the plasmid inserts. The amplified insert products were analyzed by agarose gel electrophoresis, purified using QIAquick PCR Purification Kit, and sequenced with primers JF19 and JR20. Based on the sequencing results, a desired clone designated as pJABT_5-D5/XL1 was identified. Miniprep plasmid DNA was prepared from an overnight culture of this clone, and the gag p10 gene insert was sequence confirmed. SEQ ID NO:76 shows the nucleotide sequence of the expressed gag p10-CKS fusion protein in clone pJABT_5-D5/XL1. The recombinant fusion protein (p10-CKS) encoded by pJABT_5-D5/XL1 contains 246 amino acids of CKS/polylinker fused to 56 amino acids of gag p10 viral protein followed by six histidine residues (SEQ ID NO:77).

B. Construction of pEABT_5-E4/DH5α

As diagrammed in FIG. 5C, the gel-purified gag p10 gene insert from pUC57 was amplified using QIAGEN OneStep RT-PCR Kit (Qiagen) and primers ABT5-p10cks-F (SEQ ID NO:74) and ABT5-p10xho-R (SEQ ID NO:78). Amplified product was analyzed by agarose gel electrophoresis and purified using QIAquick PCR Purification Kit. The purified PCR product and pET-28b(+) vector DNA were digested with Eco RI+Xho I, purified on Chroma Spin Columns, and ligated with T4 DNA ligase. The ligation product was transformed into DH5α, and the transformed cells were incubated at 37° C. on LB+kanamycin agar plates. Individual colonies were screened by colony PCR using two flanking plasmid primers T7 promoter (SEQ ID NO:34) and T7 terminator (SEQ ID NO:35) to amplify the plasmid inserts. The amplified insert products were evaluated by agarose gel electrophoresis, purified using QIAquick PCR Purification Kit, and sequenced with primers T7 promoter and T7 terminator. Based on the sequencing results, a desired clone designated as pEABT_5-E4/DH5α was identified. Miniprep plasmid DNA was prepared from an overnight culture of this clone, and the gag p10 gene insert was sequence verified with primers T7 promoter and T7 terminator. SEQ ID NO:79 shows the nucleotide sequence of the expressed gag p10-PET fusion protein in clone pEABT_5-E4/DH5α. The recombinant protein (p10-PET) encoded by pEABT_5-E4/DH5α consists of 36 amino acids of plasmid his-tag/polylinker followed by 56 amino acids of gag p10 viral protein (SEQ ID NO:80).

EXAMPLE 10

Preparation and Purification of XMRV Recombinant Proteins Expressed in *E. coli* Strains Unless specified otherwise, the following is a general protocol to prepare and purify XMRV recombinant proteins expressed from the plasmid constructs in *E. coli*.

A. Growth and Induction of *E. coli* Strains with XMRV Recombinant Protein Constructs (1) pKRR826-Based Constructs A culture of DH5α harboring a pKRR826-based construct was prepared by inoculating a single colony from an agar plate into a 125 ml Erlenmeyer flask (Corning Inc., Corning, N.Y.) containing 10 ml LB Broth (Sigma-Aldrich) supplemented with 100 µg/ml ampicillin. The flask was placed in a shaking orbital incubator and incubated overnight (~16 hours) at 30° C. Four ml of the overnight culture was transferred to a sterile 2-liter flask (Bellco, Vineland, N.J.) containing 400 ml of LB Broth+100 µg/ml ampicillin. The culture was incubated in a shaking orbital air incubator at 30° C. until reaching a cell density of $OD_{600}$=0.7-0.9. Cells were then induced at 42° C. for 6-8 hours. After the induction period, cells were harvested by centrifugation and the LB supernatant was discarded. Cell pellets were stored at −70° C. until further processing.

(2) pJO200-based Constructs

An overnight culture of XL1-Blue having a pJO200-based construct was prepared by inoculating a single colony from an agar plate into a 125 ml Erlenmeyer flask containing 10 ml LB Broth supplemented with 100 µg/ml ampicillin+1% glucose. The flask was placed in a shaking orbital incubator at 37° C. and was incubated overnight (~16 hours). Four ml of the overnight culture was transferred to a sterile 2-liter Bellco flask containing 400 ml of LB Broth+100 µg/ml ampicillin without the addition of glucose. The culture was incubated in a shaking orbital air incubator at 37° C. until reaching a cell density of $OD_{600}$=0.7-0.9. Cells were then induced with a final concentration of 1 mM IPTG (isopropylthiogalactopyranoside) (Sigma-Aldrich) for 6-8 hours. After the induction period, cells were harvested by centrifugation and the LB supernatant was discarded. Cell pellets were stored at −70° C. until further processing.

(3) pET-28b(+) Based Constructs

Miniprep plasmid DNA prepared from an overnight culture of DH5α having a pET-28b(+)based construct was used to transform *E. coli* BL21(DE3) competent cells (Novagen). The transformed cells, such as pET28b-p15E/BL21(DE3), were incubated at 37° C. on LB+50 µg/ml kanamycin agar plates supplemented with 1% glucose. Colonies were restreaked three times for isolation. An overnight culture of BL21(DE3) having a pET-28b(+) based construct was prepared by inoculating a single colony from an agar plate into a 125 ml Erlenmeyer flask containing 10 ml LB Broth supplemented with 50 µg/ml kanamycin+1% glucose. The flask was placed in a shaking orbital incubator at 37° C. and was incubated overnight (~16 hours). Four ml of the overnight culture was transferred to a sterile 2-liter Bellco flask containing 400 ml of LB Broth+50 µg/ml kanamycin without the addition of glucose. The culture was incubated in a shaking orbital air incubator at 37° C. until the cell density reached an $OD_{600}$=0.7-0.9. Cells were then induced with a final concentration of 1 mM IPTG for 6-8 hours. After the induction period, cells were harvested by centrifugation and the LB supernatant was discarded. Cell pellets were stored at −70° C. until further processing.

B. Isolation and Solubilization of XMRV Recombinant Proteins Produced as Insoluble Inclusion Bodies in *E. Coli*

Frozen cell pellets were thawed and resuspended thoroughly with lysis buffer containing 50 mM Tris-HCl, pH 8.0, 10 mM EDTA, 150 mM NaCl, 5% Triton X-100, 8% sucrose and 1 mM PMSF (phenylmethanesulfonyl fluoride) (Sigma-Aldrich) using 10 ml of lysis buffer per gram of pellet. Lysozyme was added to the cell suspension at a final concentration of 0.3 mg/ml, and the mixture was incubated for 30 min on ice to lyse the cells. $MgCl_2$ and DNase I were later added to the lysed viscous solution at a final concentration of 15 mM and 6 units/ml, respectively, and the mixture was incubated for 1 hour at 37° C. to digest the genomic DNA. Recombinant protein produced as insoluble inclusion bodies within *E. coli* was separated from soluble cellular proteins by centrifugation. The pelleted inclusion bodies were washed and centrifuged sequentially in (1) lysis buffer; (2) water; (3) a solution containing 50 mM sodium phosphate buffer, pH7.0, 1 M NaCl, 5% Triton X-100 and 2% sodium deoxycholate; and (4) 50 mM sodium phosphate buffer, pH7.0. Finally, the washed inclusion bodies were solubilized in a solution of 6 M guanidine-HCl, 50 mM Tris-HCl, pH 8.0 and 0.1% β-mercaptoethanol overnight at 4° C. The solubilized recombinant protein was then clarified by centrifugation.

C. Purification of XMRV Recombinant Proteins by S-200 Size Exclusion Chromatography The solubilized recombinant protein was loaded onto a Sephacryl S-200 size exclusion column (Pharmacia, Piscataway, N.J.) equilibrated with a buffer containing 50 mM Tris-HCl, pH 8.0, 6 M urea and 0.1% β-mercaptoethanol. SDS-polyacrylamide gel electrophoresis was used to evaluate the fractions from the S-200 column, and fractions containing the recombinant protein were pooled and stored at 4° C.

D. Purification of XMRV Recombinant Proteins by His-Bind Nickel Affinity Chromatography The pooled recombinant protein from the 5-200 column was loaded onto a His-Bind nickel column (Novagen) equilibrated with binding buffer containing 20 mM Tris-HCl, pH 7.9, 0.5 M NaCl, 5 mM imidazole, 6 M urea and 1 mM THP (Trishydroxypropylphosphine) (Novagen). The bound protein was washed with 10 column volumes of binding buffer followed by 6 column volumes of wash buffer (20 mM Tris-HCl, pH 7.9, 0.5 M NaCl, 20 mM imidazole, 6 M urea and 1 mM THP) (Novagen), and finally eluted with elution buffer (20 mM Tris-HCl, pH 7.9, 0.5 M NaCl, 1 M imidazole, 6 M urea and 1 mM THP) (Novagen). SDS-polyacrylamide gel electrophoresis was used to assess the fractions eluted from the nickel column, and fractions containing the recombinant protein were pooled. The pooled purified recombinant protein was dialyzed at room temperature overnight (16-18 hours) against a buffer of 1× phosphate buffered saline (PBS; Invitrogen), pH 7.4, 1% SDS and 5 mM β-mercaptoethanol, followed by a second overnight dialysis against a buffer containing 1×PBS, pH 7.4, 0.1% SDS and 5 mM β-mercaptoethanol. The dialyzed solution containing the purified protein was aliquoted and stored at −70° C. for future use.

E. Preparation of XMRV env p15EΔ-CKS Recombinant Protein

XL1-Blue cells carrying the plasmid construct pJ10B9A (Example 3, Section D), expressing XMRV recombinant protein env p15EΔ-CKS, were grown at 37° C. in LB Broth ampicillin and induced with 1 mM IPTG as described in this Example, Section A2. Cells were lysed and inclusion bodies were processed as described in this Example, Section B. The pelleted proteins were solubilized in 6 M guanidine-HCl solution followed by fractionation on a Sephacryl S-200 size exclusion column as described in this example, Section C. After S-200 column chromatography, the pooled purified p15EΔ-CKS fusion proteins were dialysed against PBS SDS buffers as described in section D of this Example. The dialysed proteins were aliquoted and stored at −70° C. for future use.

EXAMPLE 11

Characterization of XMRV Virions and Viral Proteins

Figure 6:
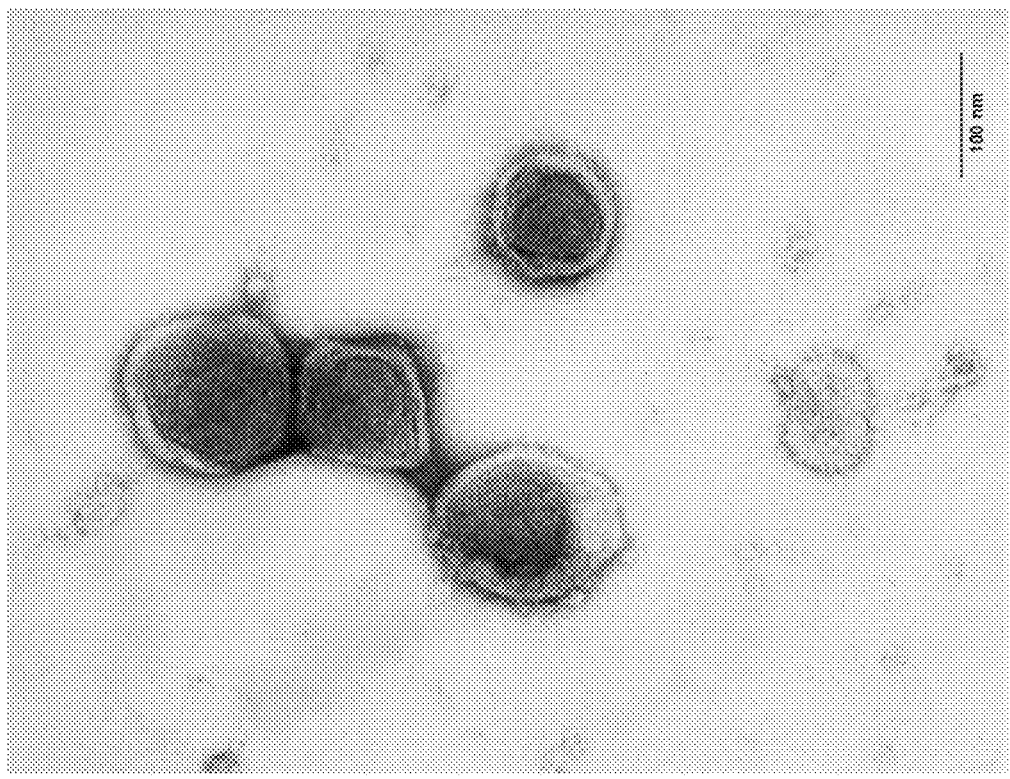
FIG. 6 is an electron micrograph of purified XMRV enveloped virions.

Electron microscopy analysis showed that XMRV particles produced from DU145 prostate cancer cells are approximately 100 to 120 nm diameter. Morphology of the viral particles is typical for gamma-retroviruses including a condensed central core and an envelope with barely visible spikes (FIG. 6).

Figure 7:
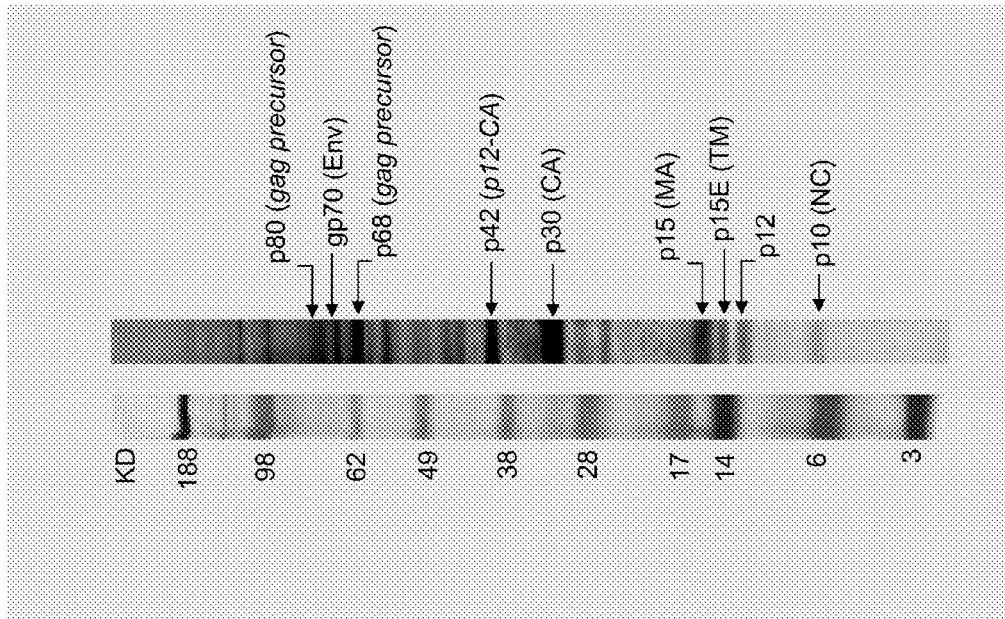
FIG. 7 shows the XMRV viral protein bands identified by goat anti-Friend MuLV polyclonal antibody on Western Blot. Env, Envelope protein; TM, Transmembrane protein; MA, Matrix protein; CA, Capsid protein; and NC, Nucleocapsid protein. The gag precursor (p68/p80) and proteolysis intermediate (p12-CA) are italicized.
Figure 8:
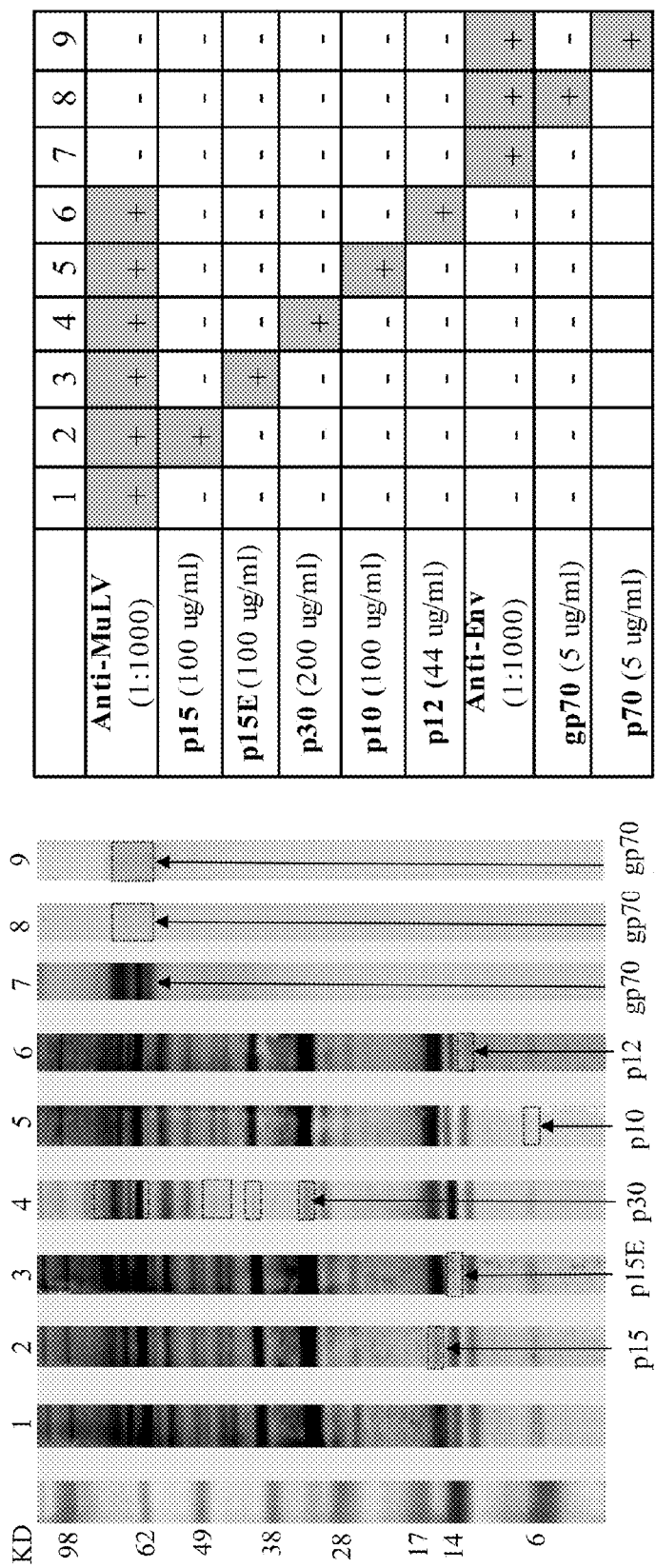
FIG. 8 shows competitive inhibition of anti-MulV and anti-Env polyclonal antibodies binding to native XMRV proteins by recombinant XMRV proteins. Recombinant proteins and concentrations for specific strips are listed in the tables.

FIG. 7 shows the antigenic proteins of XMRV identified by the present invention. Because XMRV shares ~95% overall nucleotide sequence identity with known MuLVs, goat polyclonal antibodies to Friend MuLV (anti-MuLV pAb; abbreviated as α-F) from ATCC (VR-1537AS-Gt™) and to envelope glycoprotein gp69/71 of Rauscher-MuLV (anti-Env pAb, ATCC, VR-1521) were used for Western Blot (WB) analysis. The anti-MuLV pAb was able to detect all structural proteins of XMRV including four gag proteins (p30, p15, p12, and p10) and the two env proteins (p15E and gp70) on the WB strips. Based on WB analysis, clearly resolvable bands were evident for all of the viral proteins (FIG. 7), with the exception of env gp70 which was not visible by the anti-MuLV pAb due to antibody binding to the gag precursor p68/p80 obscuring the region between 62 and 80 kDa (FIG. 7). However, gp70 was clearly detected by the anti-Env pAb, showing doublet bands at 70 kDa (FIG. 8, strip 7). Each protein band was identified using a combination of WB and WB inhibition with recombinant XMRV antigens as described below.

WB strips were prepared from the sucrose gradient purified XMRV viral particles (ABI). The viral particles were lysed with 10 mM Tris-HCl (pH 7.5) buffer containing 150 mM NaCl and 0.5% Triton at 100° C. for 10 min. The viral lysate proteins were separated by electrophoresis on a 4-12% NuPAGE Bis-Tris 2-dimension gel (Invitrogen, Carlsbad, Calif.) in the presence of sodium dodecylsulfate (SDS). The protein bands on the gel were electrophoretically transferred to a polyvinylidene difluoride (PDVF) membrane (Invitrogen) according to the manufacture's instructions. The PVDF membrane was blocked with buffer containing Casein, then cut into 2 mm strips and stored at 2-8° C.

WB was performed using WesternBreeze kit reagents (Invitrogen) per the manufacturer's instructions. Briefly, the viral protein strips were incubated with 2 ml of goat anti-MuLV pAb or anti-Env pAb (diluted 1:1000) at room temperature for 1 hour. After 4 successive 5 min washes with kit antibody wash solution, the strips were then incubated with Alkaline Phosphatase conjugated anti-goat antibody for 30 minutes at room temperature. The strips were washed as described and chromogenic substrate solution was added. XMRV lysate proteins that were cross reactive with goat anti-MuLV pAb developed purple bands. As depicted in FIG. 7, four major proteins were detected at 62, 40, 30 and 15 kD as well as some minor proteins at 14 kD and 6 kD.

The nature of the antigenic proteins was further defined by WB inhibition using purified recombinant XMRV proteins (construction and production of the recombinant proteins were described in Examples 3-10). Recombinant XMRV proteins, any gp70, p70, p15E, gag p30, p15, p12 and p10, were incubated individually with goat anti-MuLV pAb (diluted 1:2000) or anti-Env pAb (diluted 1:3000) at room temperature for 30 min to block specific antibodies. WB strips containing native viral proteins were then added into the mixture and incubated for 1 hr at room temperature. Subsequent washing, addition of anti-goat-AP conjugate and color development steps were as described above. XMRV proteins were identified based on a reduction (reduced intensity) or elimination of specific bands on WB in the presence of XMRV recombinant proteins as shown in FIG. 8.

Strip 2 in FIG. 8 shows the specific inhibition of antibody binding in the presence of the recombinant protein, gag p15 (p15-CKS=SEQ ID NO:56). At a concentration of 100 ug/ml, recombinant protein p15-CKS specifically inhibited the binding of anti-gag p15 antibodies to native gag p15 protein, resulting in ~90% decreased intensity of the major band at 15 kD as compared to Strip 1. Thus, the major 15 kD band was identified as the gag p15 protein of XMRV. The data also demonstrated that the recombinant gag p15-CKS is similar to the native gag p15 protein in terms of epitope presentation and binding to anti-gag p15 specific antibodies.

Strip 3 in FIG. 8 shows specific inhibition by recombinant protein env p15E (p15E-PET=SEQ ID NO:33). At 100 ug/ml concentration, recombinant env p15E-PET specifically inhibited binding of antibodies to native env p15E protein, resulting in complete disappearance of the band at 14 kD as compared to Strip 1. Thus, the 14 kD band represents XMRV env p15E protein. The data also demonstrate that the recombinant env p15E-PET is similar to the native env p15E protein in terms of epitope presentation and binding to anti-env p15E specific antibodies.

Strip 4 in FIG. 8 shows specific inhibition by purified recombinant gag p30 (p30-PL=SEQ ID NO:73) protein. At a concentration of 200 ug/ml, the recombinant gag p30-PL specifically inhibited binding of anti-gag p30 antibodies to native gag p30 protein and its precursors, resulting in substantial reduction or disappearance of multiple bands (30 kD, 40-48 kD and 65-75 kD) as compared to Strip 1. Thus, the major 30 kD band and other bands (40-48 kD and 65-75 kD) were identified as XMRV gag p30 protein and precursors. These data also suggest that the recombinant gag p30-PL is similar to native gag p30 in terms of epitope presentation and binding to anti-gag p30 specific antibodies.

Strip 5 in FIG. 8 shows specific inhibition by recombinant gag p10 (p10-CKS=SEQ ID NO:77) protein. At a concentration of 100 ug/ml concentration, recombinant gag p10-CKS specifically inhibited binding of anti-gag p10 antibodies to native gag p10 protein, resulting in the complete disappearance of the band at 6 kD as compared to Strip 1. Thus, the 6 kD band was identified as the gag p10 protein of XMRV. These data also demonstrate that the recombinant gag p10-CKS is essentially equivalent to native gag p10 protein in terms of epitope presentation and binding to anti-gag p10 specific antibodies.

Strip 6 in FIG. 8 shows specific inhibition by recombinant gag p12 (p12-CKS; SEQ ID NO:60) protein. At a concentration of 44 ug/ml, the recombinant gag p12-CKS specifically inhibited binding of anti-gag p12 specific antibodies to the native gag p12 viral protein, resulting complete disappearance of the band at 12 kD as compared to Strip 1. Thus, the 12 kD band was identified as the gag p12 protein of XMRV. These data also demonstrate that the recombinant gag p12-CKS is similar to the native gag p12 protein in terms of epitope presentation and binding to specific anti-gag p12 antibodies.

Strips 8 and 9 in FIG. 8 show specific inhibition of the anti-Env pAb binding to the gp70 protein by recombinant gp70 (gp70; SEQ ID NO:102) and env p70 (p70-PET; SEQ ID NO:50). Addition of recombinant gp70 or p70 at a concentration of 5 ug/ml resulted in specific inhibition of anti-Env pAb binding to the native env gp70 viral protein, resulting in disappearance of the doublet bands at 70 kD as compared to Strip 7 (the gp70 showed better inhibition than the p70-PET). This confirmed that the doublet bands were env gp70 of XMRV. This data also demonstrated that the recombinant gp70 and p70 appear to be fairly equivalent to the native env gp70 protein in terms of epitope presentation and specific binding to anti-env gp70 antibody.

In summary, the data herein demonstrate that the XMRV particles produced from prostate cancer cell line DU145 contain the four mature core (gag) proteins (p30, p15, p12, and p10) and the two any proteins (p15E and gp70). In addition, the present invention demonstrates that the WB method using XMRV lysate proteins has the capacity to detect antibodies to the two any proteins (p15E and gp70) and four gag proteins (p15, p12, p30 and p10).

Moreover, the present invention demonstrates that epitopes presented by the recombinant XMRV antigens, two env proteins (p15E and gp70) and four gag proteins (p15, p12, p30 and p10) appear to be fairly equivalent to the corresponding native viral proteins.

The identified XMRV native viral proteins can be further isolated in substantially pure form following standard purification techniques, such as affinity chromatography, HPLC, preparative gel electrophoresis, and the like. The purified XMRV native viral proteins can then be used as diagnostic reagents for detection of the presence of anti-XMRV antibodies in a biological sample by reacting said sample with the antigenic viral proteins, a positive, antigen-antibody complex formation being indicative of XMRV infection. Antigen-antibody reactions can be detected by any standard immunological techniques well-known to one of ordinary skill in the art, such as Western blot, ELISA, immunofluorescence, histoimmunological tests and the like.

EXAMPLE 12

Experimental Infection of Rhesus Macaques with XMRV

A. Selection of Rhesus Macaques.

Three young adult rhesus macaques (>3 years old; >6 kg body weight) were selected from the Yerkes National Primate Research Center colony of Emory University. These included two males (RIl-10 and RLq-10) and one female (RYh-10). All three monkeys were documented (based on serology) to be free from exposure to SIV, SRV and STLV and lacked cross-reactive antibodies to XMRV. Based on partial MHC typing, the animals did not contain the Mamu B.08 allele or combined Mamu A.01/B.17 associated with improved control of another retrovirus, simian immunodeficiency virus. Following quarantine prior to admittance to the Yerkes main station, the animals were housed in the Biosafety Level 2+ area.

B. Experimental Infection with XMRV

After collection of baseline samples, each of the 3 animals was inoculated intravenously with 10 ml of culture supernatant containing $3.67 \times 10^5$ $TCID_{50}$/ml XMRV on day 0. One macaque (RLq-10) was sacrificed on day 144. To ensure persistent infections, 2 macaques (RIl-10 and RYh-10) were re-inoculated on day 158 with $3.67 \times 10^5$ $TCID_{50}$/ml of purified XMRV virus. The XMRV was cultured in DU-145 (human prostate cancer cell line) as described previously [Dong et al., PNAS104: 1655-1660 (2007)]

C. Sample Collection

Blood was collected from each primate on days 3, 4, 5, 7, 9, 11, 14, 18, 21, 28, 35, 42, 56, 73, 93, 113, 132, 158 post $1^{st}$ inoculation (PI) and on day 3, 5, 7, 9, 11, 13, 21, 28, 34, 52, 117 post $2^{nd}$ inoculation. Blood samples were obtained by venipuncture using tubes containing the anticoagulent, EDTA. The tubes were first centrifuged at 250 g for 10 min/room temperature, the plasma were collected in 0.5 ml aliquots and stored at −80° C. for subsequent analysis by quantitative RT-PCR, Western Blot and EIA.

EXAMPLE 13

Western Blot Analysis of XMRV Inoculated Rhesus Macaques

A. Western Blot analysis using native XMRV viral proteins

Serial bleeds from XMRV inoculated macaques (RIl-10, RLq-10 and RYh-10) were first analyzed using native viral proteins. The WB strips were prepared as described in Example 11 using the lysed XMRV particles. Goat anti-human IgM and IgG specific Alkaline Phosphatase conjugates (Southern Biotech, Birmingham, Ala.) were used to individually detect IgM and IgG responses to XMRV infection in the rhesus macaques. Other reagents used in the WB were from Invitrogen's WesternBreeze kit. WB was performed as the following. The viral protein strips were incubated with 2 ml of primate plasma (diluted 1:250) overnight at 2-8° C. After 4 successive 5 minute washes, the strips were then incubated with specific anti-human IgM or IgG Alkaline Phosphatase (AP) conjugate for 1 hour at room temperature. The strips were washed as described and chromogenic substrate solution was added to develop purple bands. FIG. 9 shows WB results of plasma samples from pre and post inoculation (PI) with XMRV.

FIG. 9A shows IgG and IgM responses of RIl-10 detected by the native XMRV viral proteins. Primate RIl-10 developed a detectable IgG response to env p15E (14 kD band) on the 11th day PI, followed 3 days later by an IgG response to gag p30. Both IgG responses were persistent up to 93 days PI. There was also a weak transient anti-env p15E IgM response from day 9 to 18 PI. Of note, several major bands between 49 to 80 kD that became apparent on day 9 PT were subsequently confirmed to be specific for human cellular proteins derived form the prostate cancer cell line DU145, thus were unrelated to XMRV. Due to interference of anti-human protein response in the range of 49-98 kD, it was difficult to detect anti-env gp70 response using the viral lysate strips. Nevertheless, detectable anti-env p15E and anti-gag p30 IgG responses demonstrate successful XMRV infection and seroconversion in RIl-10.

FIG. 9B shows the IgG and IgM antibody responses by the rhesus macaque, RLq-10, detected by native XMRV proteins. RLq-10 developed a persistent IgG antibody response to env p15E (14 kD band) detectable from days 9-93 PI and to gag p30 (30 kD band) from days 14-93 PI. In addition, RLq-10 exhibited weak IgG response to gag p15 and a transient response to gag p10 (detectable from day 14 to 35 PI). The IgM antibody response of RLq-10 is similar to RIl-10, only a weak and transient anti-env p15E (9-28 PI) response was detected. The RLq-10 also developed strong IgG response to DU-145 human cellular proteins, exhibiting multiple intensive bands between 49 to 98 kD from day 9 to 93 PI, which precluded visualization of an anti-env gp70 response. However, the detectable anti-env p15E and anti-gag p30 IgG antibody responses indicate successful XMRV infection and seroconversion in RLq-10.

FIG. 9C shows IgG and IgM antibody responses in the rhesus macaque, RYh-10, detected by native XMRV proteins. Similar to RIl-10 and RLq-10, RYh-10 developed a persistent IgG antibody response to env p15E (14 kD band) from day 11-93 PI and to gag p30 (30 kD band) from day 14 to 93 PI. The IgM antibody response of RYh-10 is too weak to be detected by the viral lysate strip. Similar to RIl-10 and RLq-10, RYh-10 developed strong IgG response to human cellular proteins, exhibiting multiple intensive bands between 49 to 98 kD. In addition, two bands, one below gag p30 (28 kD) and the other below env p15E (~13 kD), were detected in all samples including the sample prior to XMRV inoculation indicating that this reactivity is unrelated to XMRV infection. Consistent with the two male macaques, the female macaque, RYh-10, also exhibits detectable anti-env p15E and anti-gag p30 IgG antibody responses indicating successful XMRV infection and seroconversion.

B. Western Blot Analysis Using Recombinant XMRV Proteins

Two purified recombinant XMRV proteins, env p15EΔ-CKS (SEQ ID NO:29) and gag p30-PL (SEQ ID NO:73) were selected to confirm the anti-env p15E and anti-gag p30 IgG antibody responses detected by native viral proteins as described above. In addition, recombinant env p70-CKS (SEQ ID NO:43) was used to detect an anti-gp70 response that could not be readily detected by the native viral proteins due to interference of human cellular proteins. WB strips were prepared by electrophoresis of individual recombinant proteins on a 4-12% NuPAGE Bis-Tris 2 dimension gel (Invitrogen) in the presence of SDS. The protein gel was electrophoretically transferred to a PDVF membrane. After blocking with buffer containing Casein, the PDVF membrane was cut into 2 mm strips and stored at 2-8° C. WB was performed by incubating the recombinant protein strips with 2 ml of primate plasma (diluted 1:250) overnight at 2-8° C. After 4 successive 5 minute washes, the strips were then incubated with anti-human IgG Alkaline Phosphatase conjugate for 1 hour at room temperature. The strips were washed as described and chromogenic substrate solution was added to develop purple bands. FIG. 10 shows WB results for RIl-10 with recombinant proteins env p15EΔ-CKS (A), env p70-CKS (B) and gag p30-PL (C).

Figure 10A:
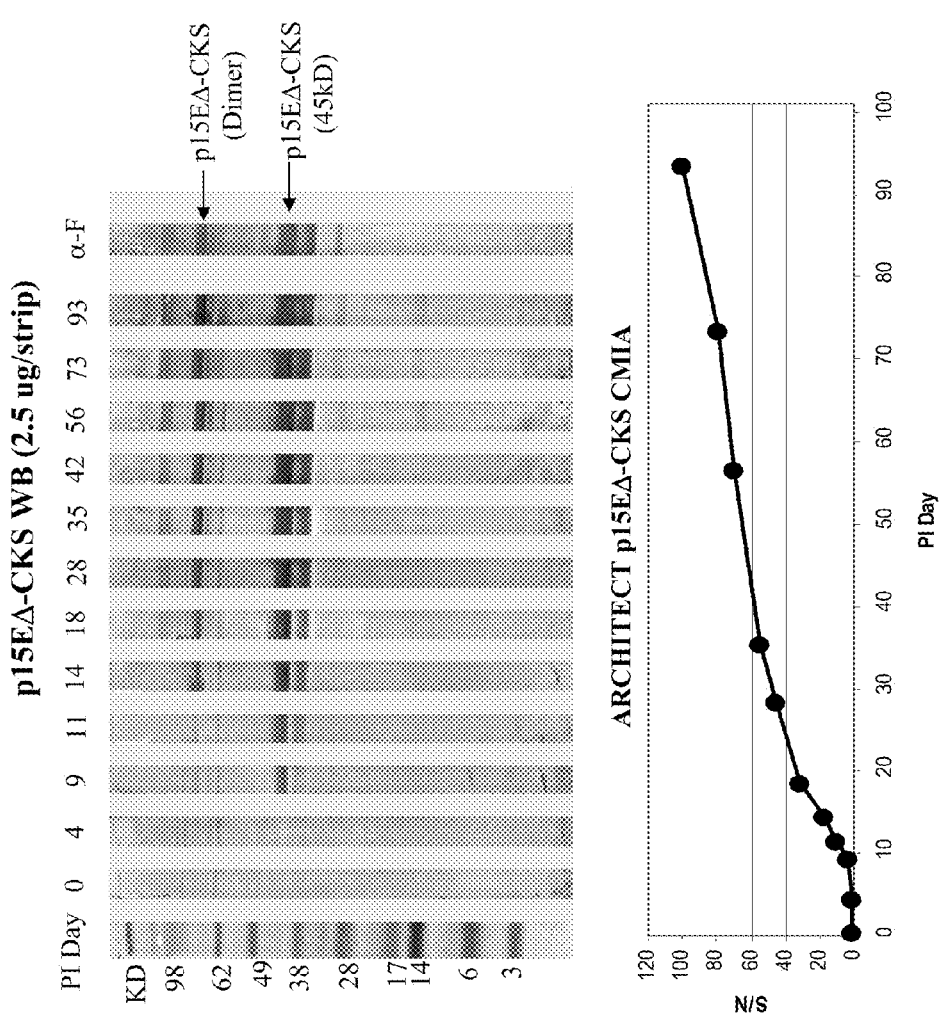
FIGS. 10A-10C show the detection of IgG antibody responses in the rhesus macaque, RIl-10, by recombinant XMRV protein based Western Blots and ARCHITECT® chemiluminescent immunoassays (CMIA). Blood samples were listed on strips as days PI with XMRV (0-93). The goat anti-Friend MuLV (α-F) was used as a positive control in the Western Blots.

With recombinant p15EΔ-CKS WB strips, RIl-10 samples from day 9 to 93 PI showed a major WB band at 45 kD, which is the monomer form of recombinant p15EΔ-CKS (strips 9-93 in FIG. 10A). The other two bands at 90 and 135 kD are the dimer and trimer forms of p15EΔ-CKS. Thus, the recombinant protein p15EΔ-CKS at 2.5 ug/strip detected not only the samples that were anti-p15E positive against the native viral protein, but also the sample (Strip 9 in FIG. 10A) that was barely detected by the native viral protein. The data confirmed anti-p15E response developed in RIl-10 after XMRV infection. Furthermore, these data demonstrates the utility of recombinant p15EΔ-CKS for detection of specific anti-p15E antibodies.

Figure 10B:
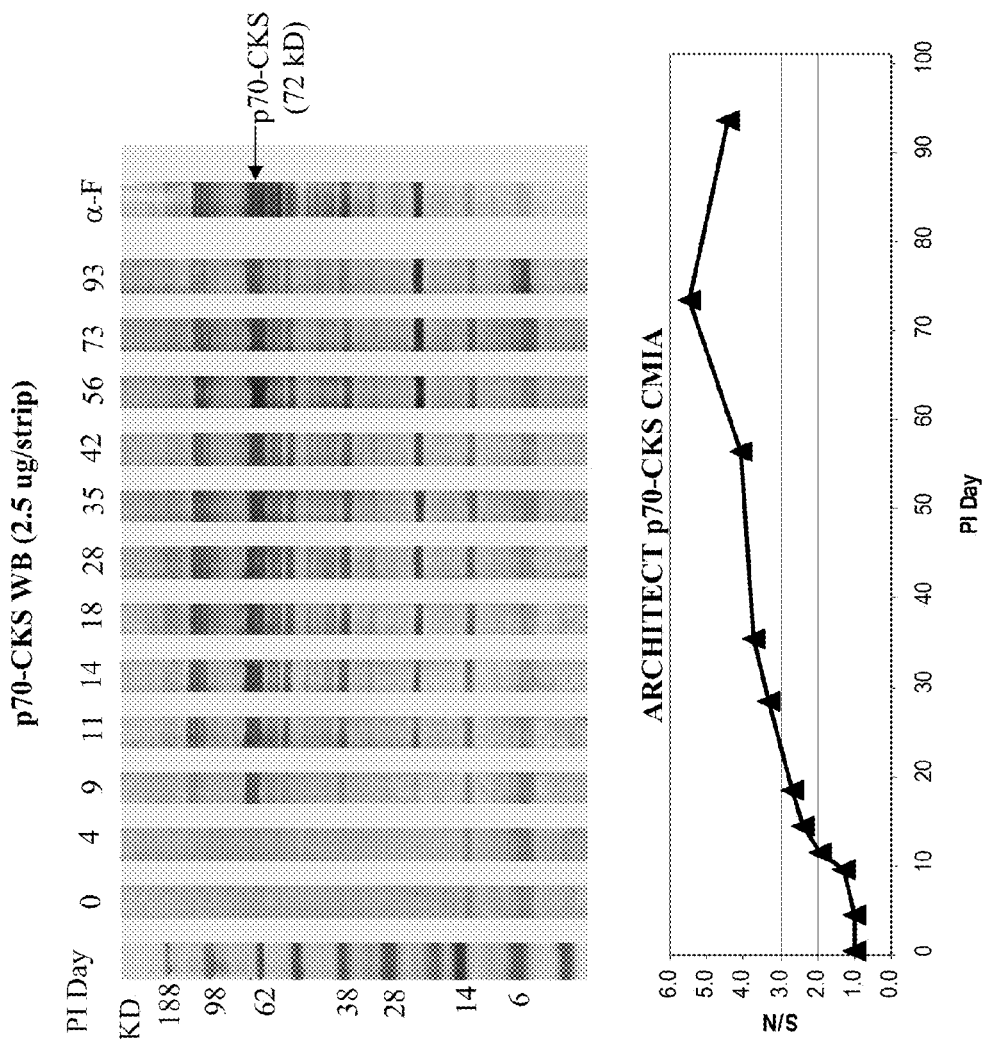

With recombinant p70-CKS WB strips, RIl-10 samples from day 9 to 93 PI showed a major band at 72 kD, which is the monomer form of recombinant p70-CKS (strips 9-93 in FIG. 10B). The band at ~140 kD is the dimer form of p70-CKS, other minor bands at 38 kD and 20 kD probably are the breakdown proteins of the p70-CKS. The specific binding to recombinant p70-CKS indicated that RIl-10 developed anti-gp70 antibodies in addition to the anti-p15E and anti-p30 antibodies after infection with XMRV. Moreover, these data demonstrate that the recombinant p70-CKS can be used to detect an anti-gp70 specific antibody response.

Figure 10C:
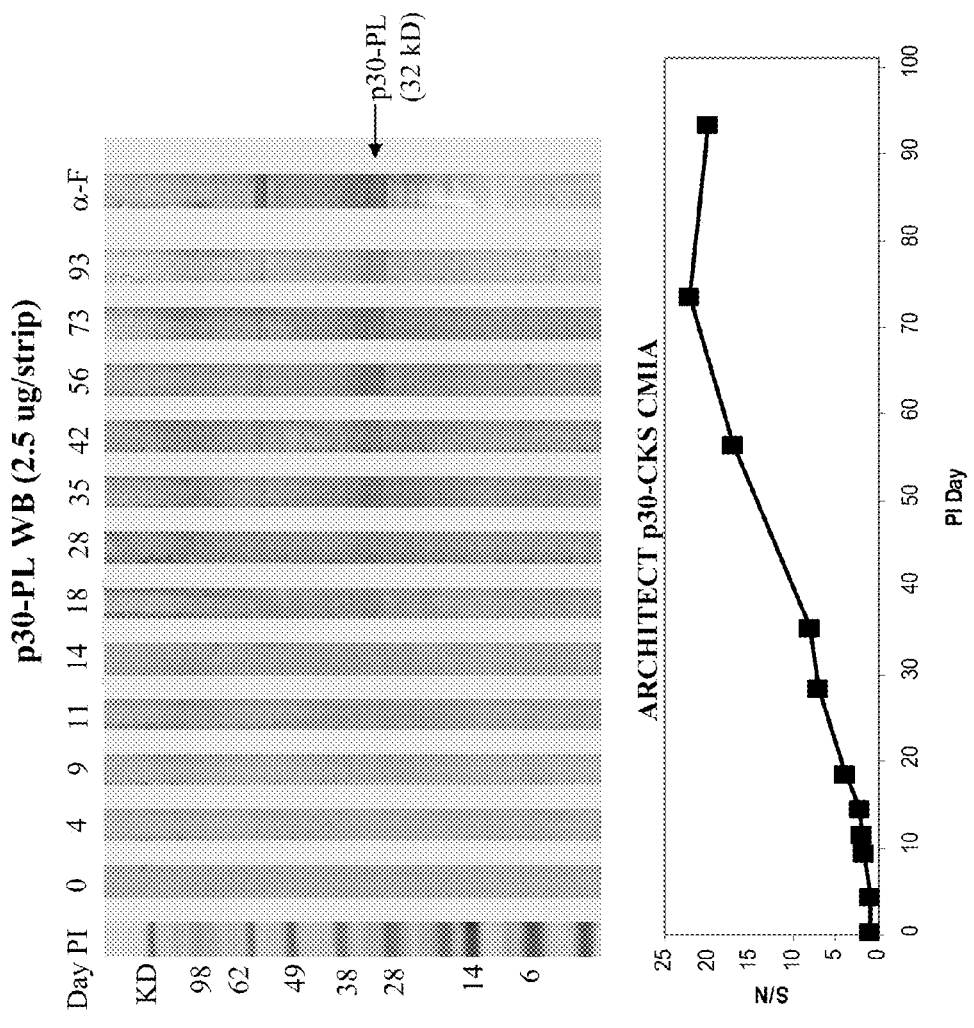

Although the recombinant p30-PL protein strips appeared to be less potent than the native viral protein strips, they detected 7 of the 8 primate RIl-10 samples that were anti-p30 positive against the viral lysate strips (FIG. 10C). Thus the data confirmed a specific anti-p30 antibody response developed in primate RIl-10 after XMRV infection; it also demonstrated utility of recombinant p30-PL for detection of anti-p30 antibodies.

C. Summary

All three primates developed detectable anti-p15E, anti-p70 and anti-p30 antibody responses providing direct evidence of XMRV infection and seroconversion. Thus, the data presented herein demonstrate the utility of the recombinant XMRV proteins, p15EΔ-CKS, p70-CKS and p30-CKS, as diagnostic reagents for detection and/or confirmation of XMRV infection. WBs using these recombinant proteins detected all of the samples with reactivity against the corresponding native viral proteins. This represents the first demonstration of seroconversion patterns elicited by infection with XMRV.

EXAMPLE 14

Western Blot Analysis of Human Prostate Cancer Samples

Figure 11:
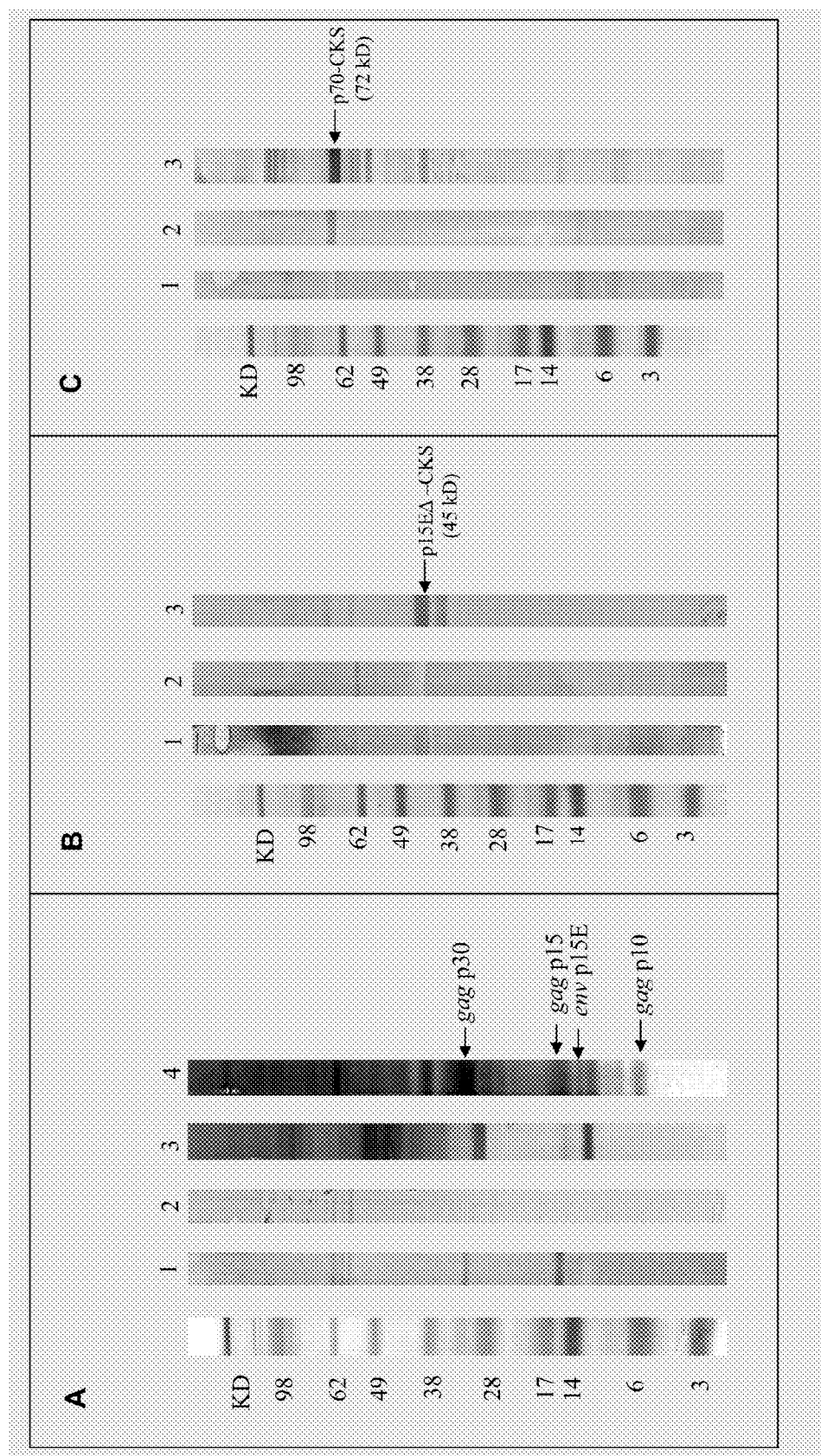
FIG. 11A through 11C illustrate Western Blot analysis of the human prostate cancer sample VP234 with native viral protein strips (A), recombinant p15EΔ-CKS strips (B) and recombinant p70-CKS strips. (Sample keys, 1: VP234, 2: normal human plasma #85 as negative control, 3: Day 93 bleed of primate RIl-10 PI with XMRV 4: goat anti-Friend MuLV polyclonal antibody as the positive control).

To confirm that antibody responses in humans are similar to those observed in non-human primates after XMRV infection, a plasma sample from a prostate cancer patient, VP234, was selected for WB analysis. This patient had germ-line mutations (R462Q) in both alleles of RNAseL and was identified as XMRV-infected based on RT-PCR analysis of prostate cancer tissue [Dong et al., *PNAS* 104:1655 (2007)]. Moreover, XMRV provirus integration sites were identified in prostate genomic DNA of VP234 [Dong et al., *PNAS* 104:1655 (2007)]. Plasma collected from VP234 was analyzed with WB strips containing viral lysate proteins, recombinant p15EΔ-CKS, and recombinant p70-CKS. WB strips preparation and procedures were as same as described in Example 13, sections A and B. Briefly, WB strips were incubated with 2 ml of VP 234 sample (diluted 1:250) in diluent that contained 5% goat serum and 0.15% Tween 20. After overnight incubation at 2-8° C., the bound anti-XMRV antibodies were detected by goat anti-human IgG Alkaline Phosphatase conjugate followed by the development of a purple colored AP reaction product. The results obtained are presented in FIG. 11.

The VP234 sample showed two major bands at 30 kD and 15 kD and three minor bands in the 62 kD range on the viral lysate protein strip (FIG. 11A). WB inhibition using recombinant XMRV proteins (gag p30, env p15E and gag p15) confirmed that the two major bands are antibodies against the gag p30 and gag p15 viral proteins. The minor bands in the 62 kD range were considered non-specific binding because they were also shown in the normal blood donor sample #85. Although the viral lysate strip did not detect anti-p15E response in the VP234 sample, the recombinant p15E strip detected such response showing a weak anti-p15E band at 45 kD (FIG. 11B). There was no visible band at 72 kD range on the recombinant p70-CKS WB strip (FIG. 11C) suggesting no detectable anti-gp70 response in the VP234 sample. In summary, the VP234 sample showed detectable antibodies against env p15E, gag p30 and gag p15 of XMRV viral proteins, and the anti-gag p15 appeared to be the dominant response.

EXAMPLE 15

ARCHITECT® Chemiluminescent Immunoassay for Detection of Antibodies to XMRV (Anti-Human Assay Format)

Figure 12:
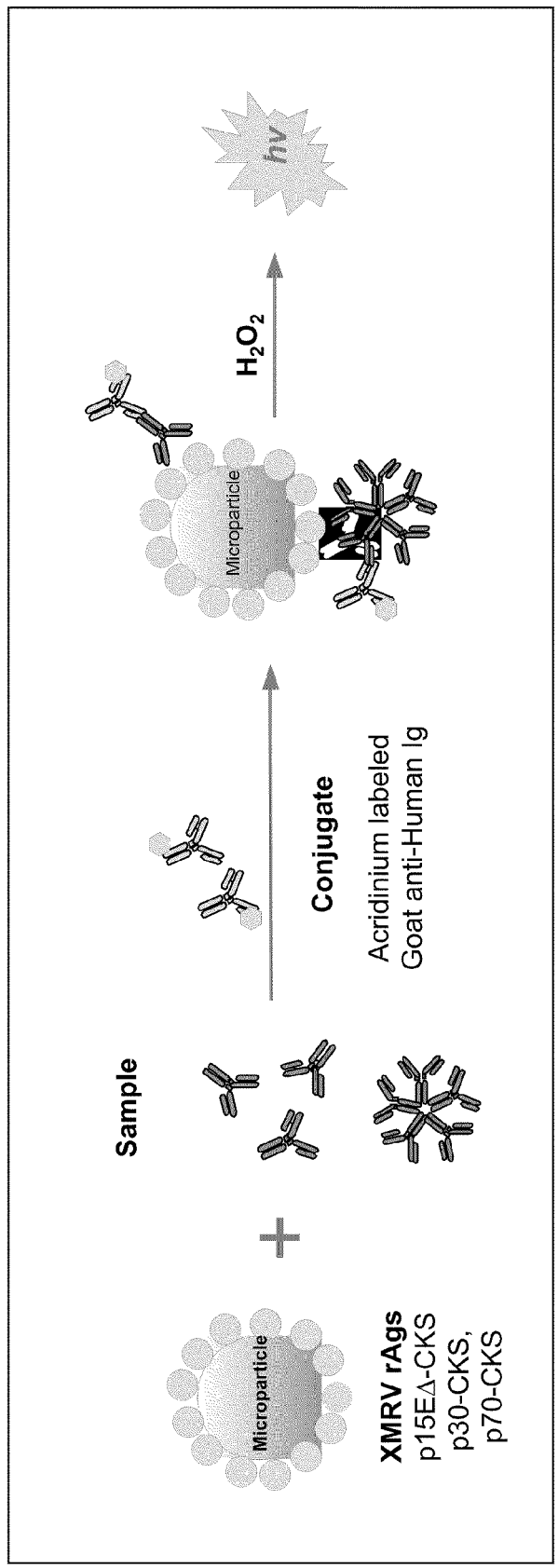
FIG. 12 shows a schematic diagram of indirect Anti-human based ARCHITECT® CMIA format using recombinant protein to detect antibodies to XMRV.

Using the potential diagnostic reagents identified (i.e., p15EΔ-CKS (SEQ ID NO:29), p70-CKS (SEQ ID NO:43) and gag p30-CKS (SEQ ID NO:67), three prototype chemiluminescent immunoassays (CMIA) were developed on the automated ARCHITECT® instrument system (Abbott Laboratories, Abbott Park, Ill.). All three ARCHITECT® CMIAs are two-step immunoassays which utilize an indirect anti-human assay format as illustrated in FIG. 12. The first step combines sample (10 ul), assay diluent (90 ul) and paramagnetic microparticles. Anti-XMRV antibodies present in the sample are captured on paramagnetic particles coated with individual recombinant proteins p15EΔ-CKS, p70-CKS or gag p30-CKS. The microparticles are washed to remove unbound proteins. In the second step, anti-XMRV antibodies captured by the microparticles are incubated with acridinium-labeled goat anti-human IgG conjugate. Following an additional wash cycle, alkaline hydrogen peroxide solution is added to release acridinium chemiluminescence signal. The intensity of the chemiluminescence, measured as relative light unite (RLU), is proportional to the amount of specific antibody captured by the individual recombinant proteins p15EΔ-CKS, p70-CKS, p30-CKS or p30-PL.

Figure 13:
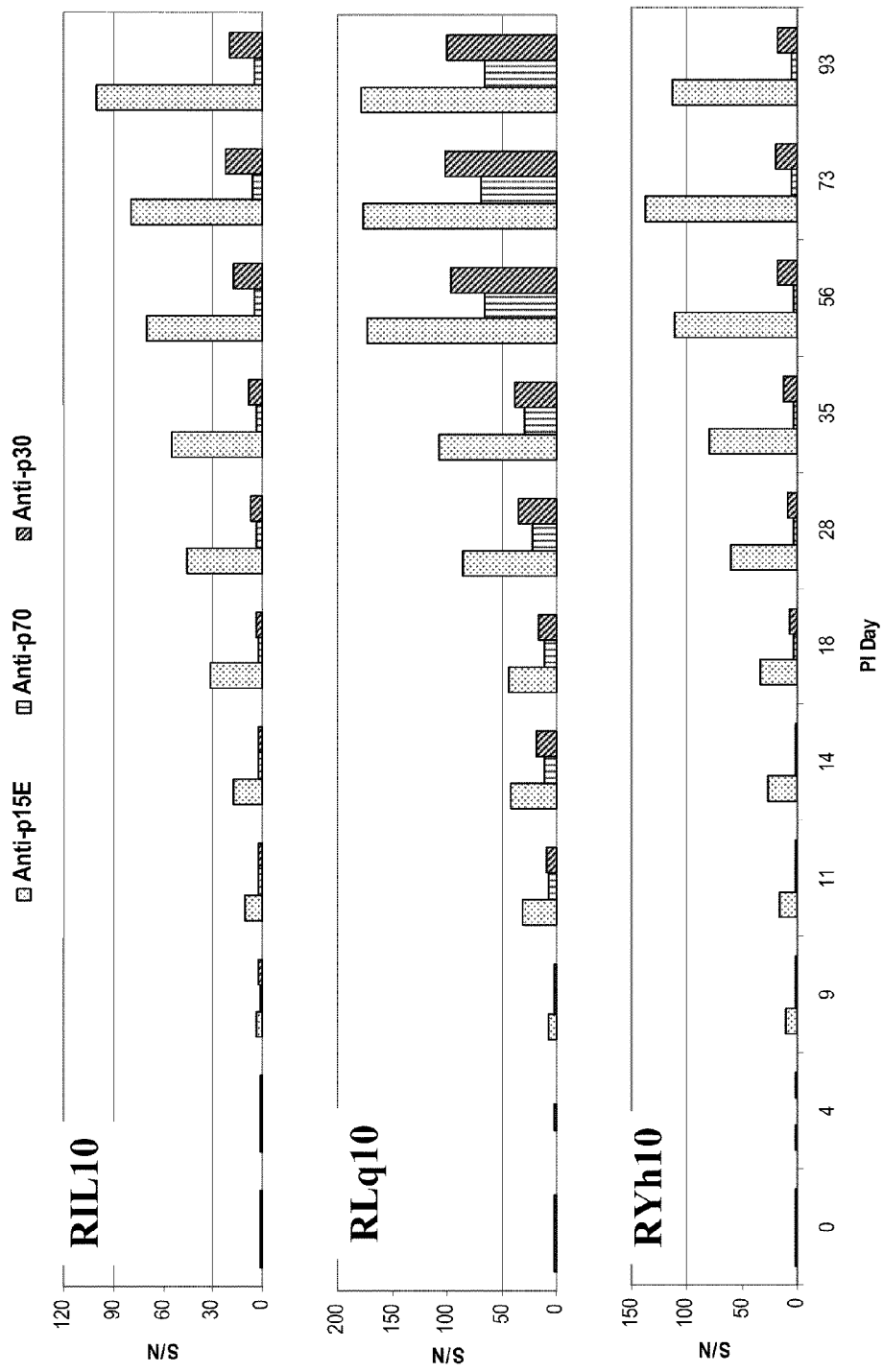
FIG. 13 shows detection of XMRV-specific antibodies in rhesus macaques using the indirect anti-human based ARCHITECT® CMIA format with recombinant proteins (p15E, p70 and p30). S/N signal of sample/signal of the day 0 sample.

Sensitivity of the CMIAs was evaluated with serial bleeds from the XMRV infected rhesus macaques, RIl-10, RLq-10 and RYh-10. FIG. 13 summarizes the results obtained with the ARCHITECT assays. To facilitate comparison of the CMIA and WB results, CMIA testing results obtained for samples from RIl-10 were also inserted into FIG. 10 under the WB images of the corresponding recombinant proteins. As shown in FIG. 10A, the p15EΔ-CKS based CMIA detected all samples that were anti-p15E positive by WB with high signals ranging from 4 to 100 S/N(S/N=signal of sample/signal of sample at Day 0). Furthermore, the p15EΔ-CKS based ARCHITECT CMIA provided qualitative results showing that the anti-p15E response appeared on day 9 PI (S/N=4) and continued to increase on day 93 PI (S/N=100). Similar results were obtained for the p70 and p30-based CMIAs (FIGS. 10B and 10C). These data demonstrate the capacity of the CMIAs to detect antibodies to XMRV with high sensitivity and formally establish the utility of these rare reagents to detect infection with XMRV.

EXAMPLE 16

ARCHITECT® Chemiluminescent Immunoassay for Detection of Antibodies to p15E Protein of XMRV (Sandwich Assay Format)

Figure 14:
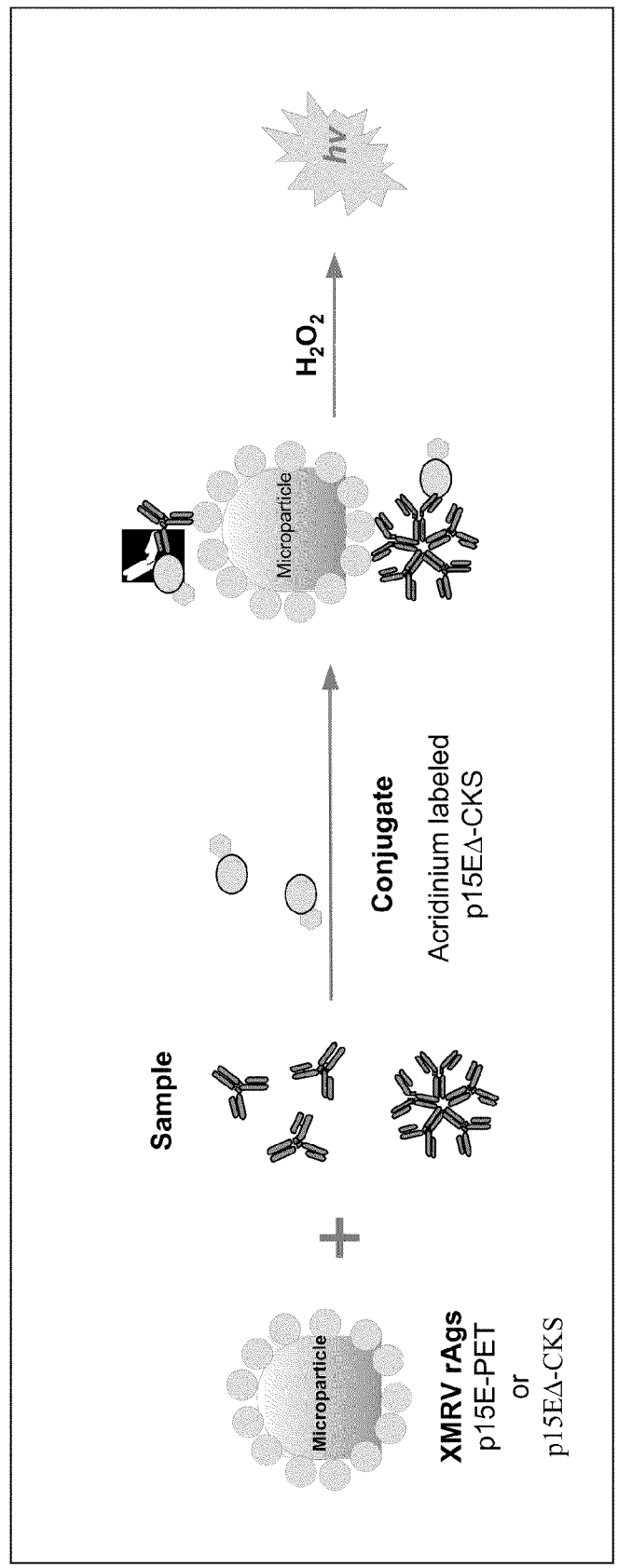
FIG. 14 shows a schematic diagram of the direct double p15E antigen sandwich based ARCHITECT® CMIA format designed to detect antibodies to XMRV-p15E protein.

To further improve assay performance, a direct double antigen sandwich assay was developed on the automated ARCHITECT® instrument system (Abbott Laboratories, Abbott Park, Ill.). The ARCHITECT® CMIA is a two-step immunoassay that utilizes two p15E antigens (i.e., p15E-PET=SEQ ID NO:33, and p15EΔ-CKS=SEQ ID NO:29) to form a double antigen sandwich with the anti-p15E antibody. As illustrated in FIG. 14, in the first step, sample (100 ul), assay diluent (50 ul) and paramagnetic microparticles (50 ul) are combined. Anti-p15E antibodies, present in the sample are captured on paramagnetic particles coated with either p15E-PET or p15EΔ-CKS recombinant protein. The microparticles are washed to remove unbound proteins. In the second step, anti-p15E antibodies captured by the microparticles are incubated with acridinium-labeled p15EΔ-CKS recombinant antigen. Following an additional wash cycle, alkaline hydrogen peroxide solution is added to release acridinium chemiluminescence signal. The intensity of the chemiluminescence, measured as relative light unite (RLU), is proportional to the amount of anti-p15E antibody captured by the p15E-PET recombinant protein.

Figure 15:
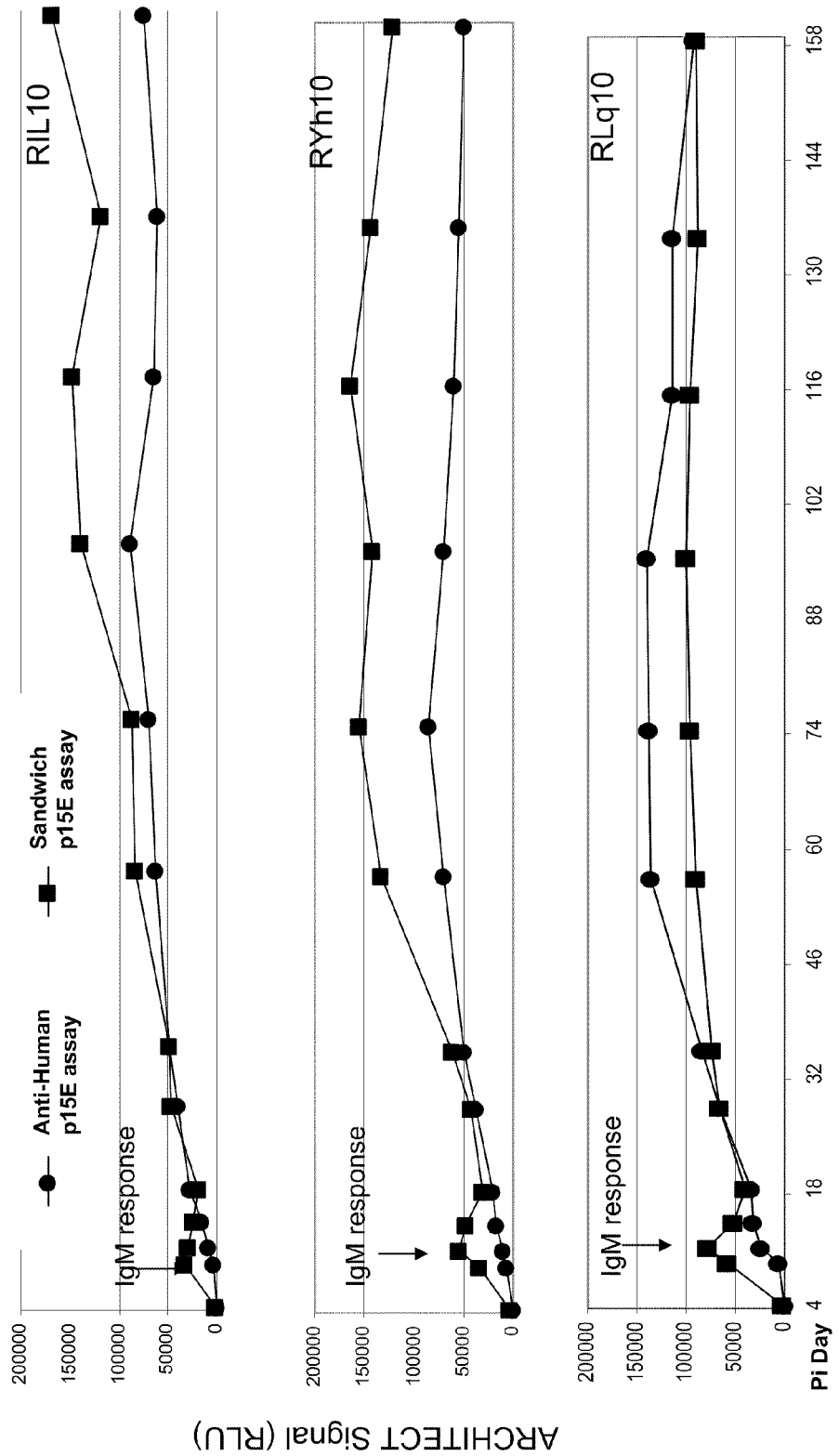
FIG. 15 shows detection of XMRV-p15E specific antibodies in rhesus macaques using both anti-human assay format and double antigen sandwich assay format based CMIAs.

Sensitivity of the sandwich p15E CMIA was evaluated with 39 serial bleeds from the XMRV infected rhesus macaques, RIl-10, RLq-10 and RYh-10. FIG. 15 summarizes the results obtained with the sandwich assay format of p15E CMIA. To facilitate comparison between assay formats, the anti-human p15E CMIA results obtained on the same serial bleeds were also plotted in FIG. 15. The sandwich p15E assay detected all 36 samples that were anti-p15E positive by WB. Compared to the anti-human p15E assay, the sandwich p15E assay demonstrated better seroconversion sensitivity by generating much higher signals on the early IgM response (Day 9-14 PI) from all three primates; it also showed better or equivalent sensitivity for the rest of serial bleeds of RIl-10 and RYh-10.

In addition, sensitivity of the sandwich p15E CMIA on an alternative mammalian species was evaluated using the goat polyclonal antibody to Friend MuLV (anti-MuLV pAb) obtained from ATCC (VR-1537AS-Gt™). The sandwich p15E CMIA showed excellent detection of anti-p15E antibody from the goat anti-MuLV pAb with an end-point dilution at 1:32,000. As anticipated, these data confirm that the sandwich p15E CMIA is capable of detecting anti-p15E antibody from alternative mammalian species.

Figure 16:
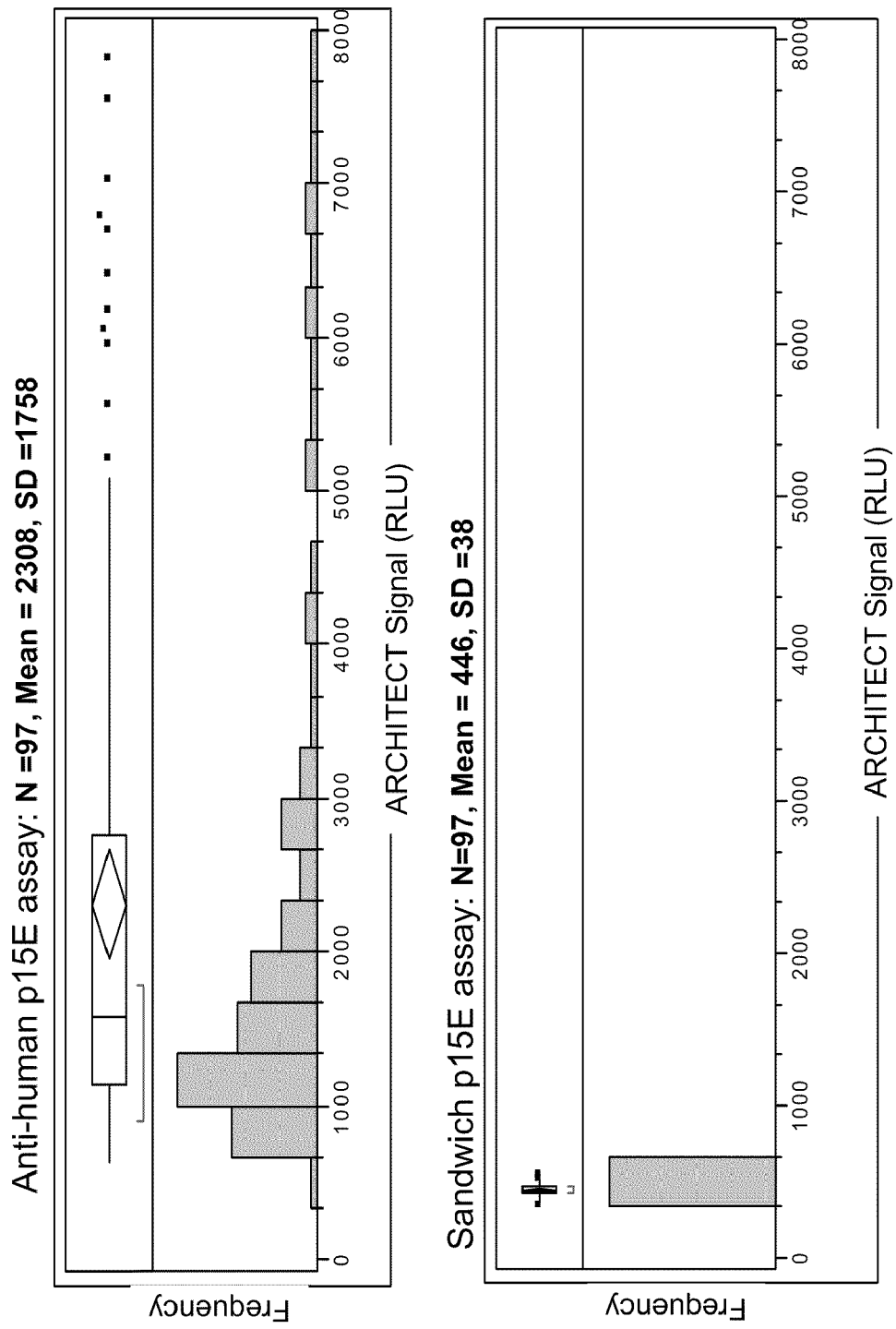
FIG. 16 compares signal distribution patterns between anti-human and sandwich p15E assay format based CMIAs on 97 blood donor samples.

The most significant improvement is that the sandwich p15E assay increases separation between the negative and positive populations. Evaluation of specificity utilizing 97 blood donors (see FIG. 16) showed that signals of this presumed negative population (negative for other known blood-borne pathogens) were substantially reduced, and the distribution was also tightened by the sandwich p15E assay as compared to the anti-human p15E assay. Consequently, the 36 XMRV positive primate bleeds were clearly separated from the 880 negative blood donors by the sandwich p15E assay, resulting in 100% (36/36) sensitivity and 99% (879/

880) specificity (FIG. 17). These data demonstrate the utility of the sandwich p15E assay to detect and/or screen for XMRV infection.

EXAMPLE 17

Epitope Mapping of p15E Using Synthetic Peptides

Immunogenic regions of the p15E antigen were mapped by specific binding of p15E synthetic peptides to anti-p15E positive sera from XMRV infected primates. Eight peptides were designed to cover various regions of the p15E antigen as shown in FIG. 18. The peptides were manufactured by GenScript Co. (Piscataway, N.J.). They were synthesized by solid-phase methodology using Fmoc chemistry. Biotin was added at the N-terminus to facilitate attachment to immobilized streptavidin. All peptides were determined to be at least 85% pure.

Specific binding of the mapping peptides to anti-p15E antibodies was determined by an indirect ELISA assay. Briefly, biotinylated synthetic peptides (~2 ug/well/100 ul assay buffer) were immobilized on streptavidin coated microtiter plate (Thermo Fisher Scientific, Waltham, Mass.) by incubating overnight at 2-8° C. After washing (2 times), primate samples diluted 1:100 with sample diluent (100 ul/well) were incubated with immobilized peptides for 3 hours at room temperature. After washing (4 times), the bound anti-p15E antibodies were detected by goat anti-human IgG Alkaline Phosphatase conjugates (Southern Biotech, Birmingham, Ala.). All samples were run in duplicate and continuously shaken during the incubations.

Figure 19:
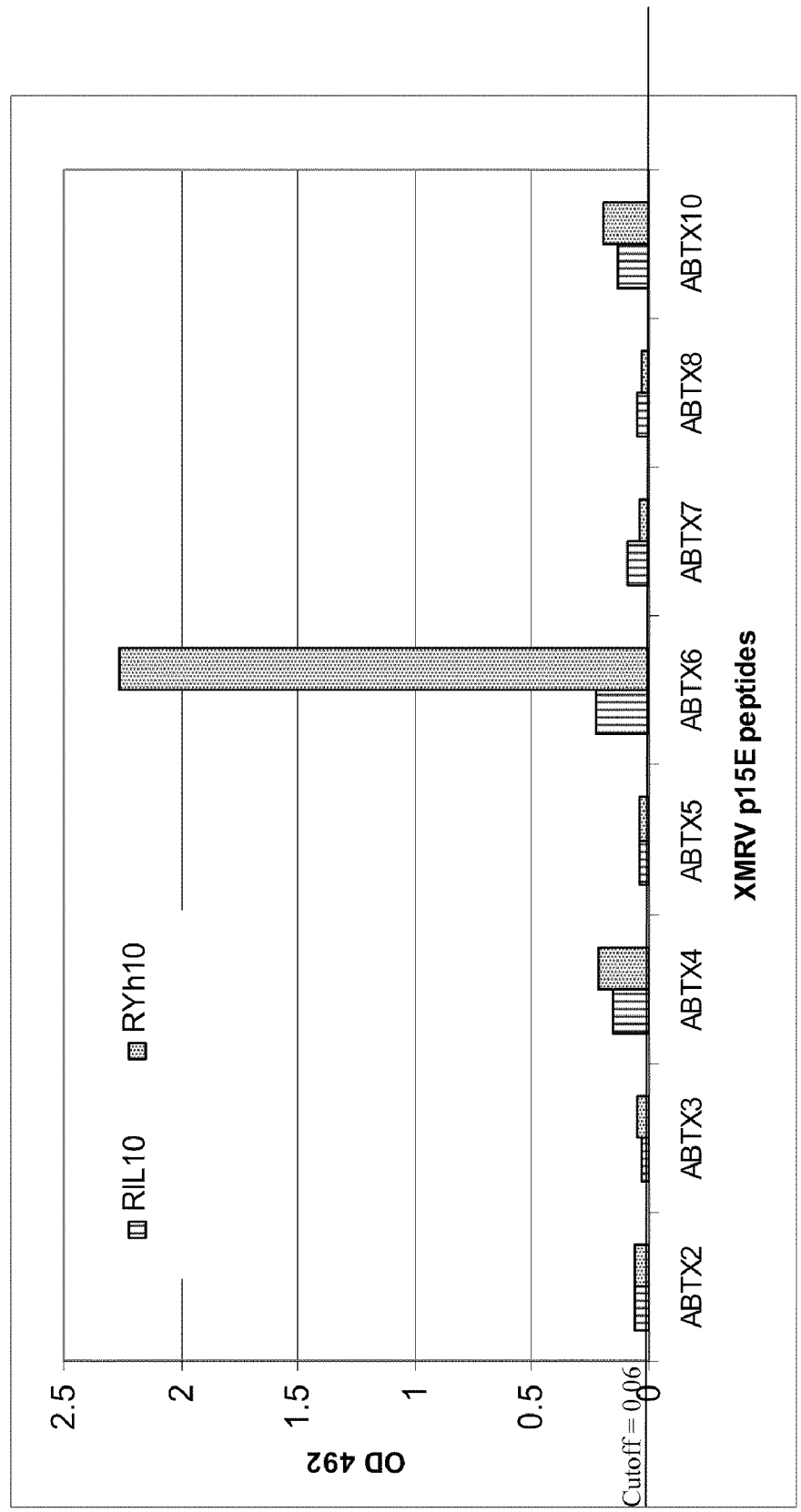
FIG. 19 shows binding of p15E synthetic peptides to antibodies present in plasma samples from XMRV infected primates RIL-10 and RYh-10. Binding was considered significant when signal was greater than the cutoff value of 0.06.

Results of the epitope mapping analysis are depicted in FIG. 19. Both primate RII-10 and RYh-10 samples (bleeds on day 93 PI) showed specific binding to three peptides, ABTX-6, (SEQ ID NO:83) ABTX-4 (SEQ ID NO:84) and ABTX-10 (SEQ ID NO:85). All three peptides had signals that were greater than 2 times the cutoff value of 0.06. The ABTX-6 peptide (SEQ ID NO:83) showed strong binding to the primate RYh-10 sample with signal that was 37 times greater than the cutoff value (0.06), indicating it is an immunodominant epitope within the p15E antigen.

EXAMPLE 18

Figure 20:
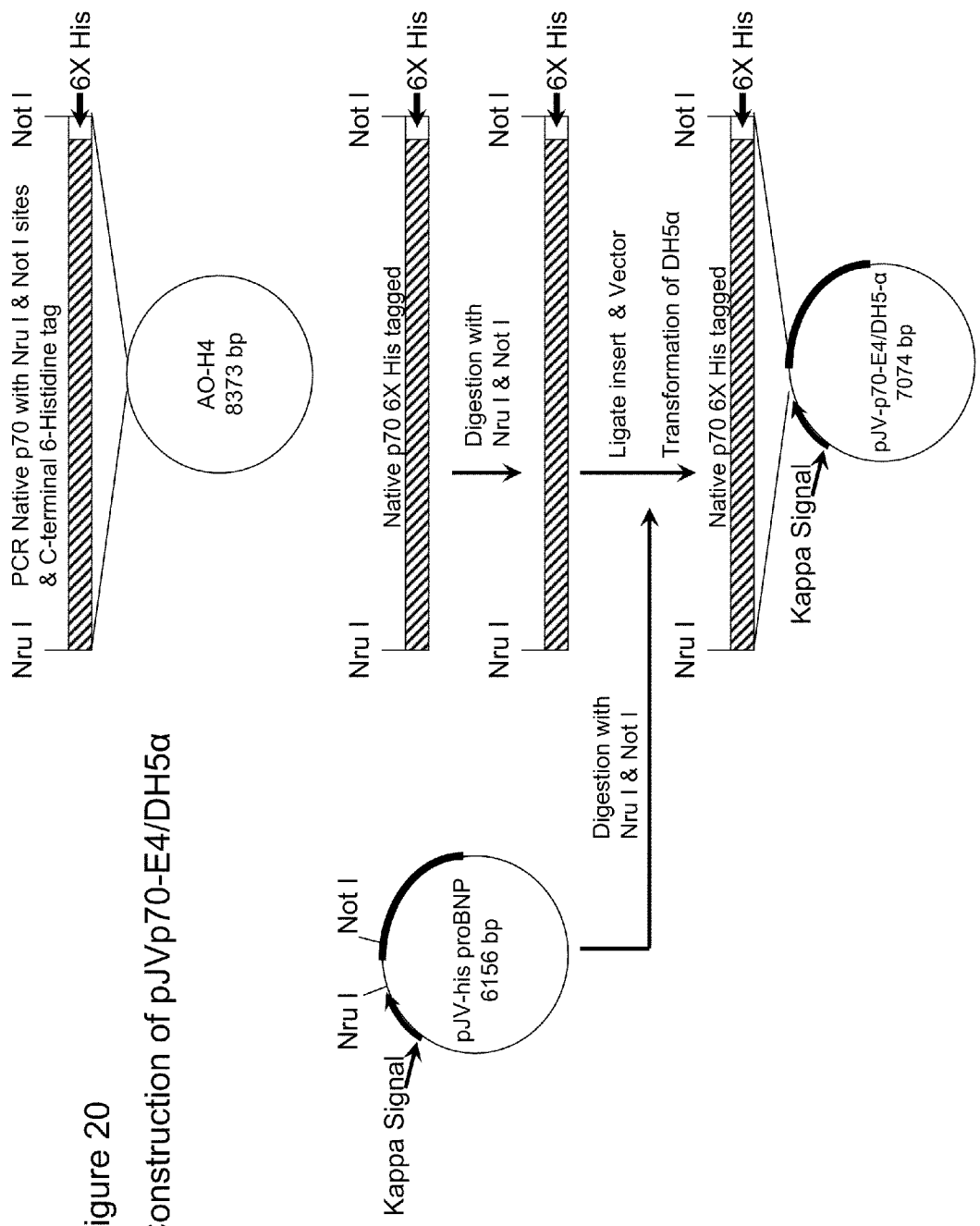
FIG. 20 shows construction of a plasmid clone carrying a native XMRV env gp70 gene for mammalian expression.

Construction of Plasmid Clones Carrying a Native XMRV Env gp70 or Gag p30 Gene for Mammalian Expression A. Construction of a Plasmid Clone (pJVp70-E4) Carrying a Native XMRV Env gp70 Gene for Mammalian Cell Expression A plasmid clone AO-H4 encompassing the 3' end of XMRV strain VP62 and carrying the entire env gene was constructed as described by A. Urisman et al., *PloS Pathogens* 2:e25 (2006). An approximately 4.4 kb VP62 DNA insert was generated by RT-PCR of viral RNA and cloned into vector pCR2.1. As illustrated in FIG. 20, the full-length native env gp70 gene was amplified from AO-H4 plasmid DNA using the Qiagen One-Step RT-PCR Kit (Qiagen, Valencia, Calif.) according to the manufacturer's protocol and primers p70-F-NruI (SEQ ID NO: 90) and p70-R-NotI (SEQ ID NO: 91) to introduce restriction enzyme sites as well as six histidine residues at the C-terminus. Amplified product was analyzed by agarose gel electrophoresis and purified using QIAquick PCR Purification Kit (Qiagen). The Abbott Laboratories vector pJV-his-proBNP (Abbott Bioresearch Center, Worchester, Mass.) was used as the cloning vector for mammalian expression. The purified env gp70 PCR product and pJV-his-proBNP vector DNA were digested with Nru I and Not I, purified on Chroma Spin Columns and ligated with T4 DNA ligase. The ligation product was transformed into DH5α competent cells, and the transformed cells were incubated at 37° C. on LB+ampicillin agar plates. Individual colonies were screened by colony PCR using primers p70-F-NruI (SEQ ID NO: 90) and p70-R-NotI (SEQ ID NO: 91) to amplify the plasmid inserts. The amplified insert products were analyzed by agarose gel electrophoresis, purified using QIAquick PCR Purification Kit and sequenced with primers Vector1-F (SEQ ID NO: 92), Vector1-R (SEQ ID NO: 93), Vector2-F (SEQ ID NO: 94), Vector2-R (SEQ ID NO: 95), p70-seq1-F (SEQ ID NO: 96), p70-seq1-R (SEQ ID NO: 97), p70-seq3-F (SEQ ID NO: 98), p70-seq3-R (SEQ ID NO: 99), p70-F-NruI (SEQ ID NO: 90) and p70-R-NotI (SEQ ID NO: 91). Based on the sequencing results, a desired clone designated as pJVp70-E4 was identified. Miniprep plasmid DNA was prepared from an overnight culture of this clone, and the env gp70 gene insert was sequence verified. Colonies were restreaked three times for isolation and preparation of glycerol stocks.

The env gp70 plasmid construct for mammalian expression produces a recombinant protein pJVp70-E4/DH5α, the amino acid sequence of which is shown in SEQ ID NO: 100. The recombinant protein (pJVp70) encoded by pJVp70-E4/DH5α contains 22 amino acids of plasmid kappa signal sequence fused to 413 amino acids of env gp70 viral protein and six amino acids of histidine. SEQ ID NO: 101 shows the nucleotide sequence of the env gp70 protein in clone pJVp70-E4/DH5α and contains 66 base pairs from the plasmid kappa signal sequence followed by 1239 base pairs of the env gp70 gene derived from native XMRV viral RNA and 18 base pairs of histidine. SEQ ID NO: 102 shows the expressed/processed env gp70 protein that consists of 413 amino acids of env gp70 viral protein and six amino acids of histidine.

Figure 21:
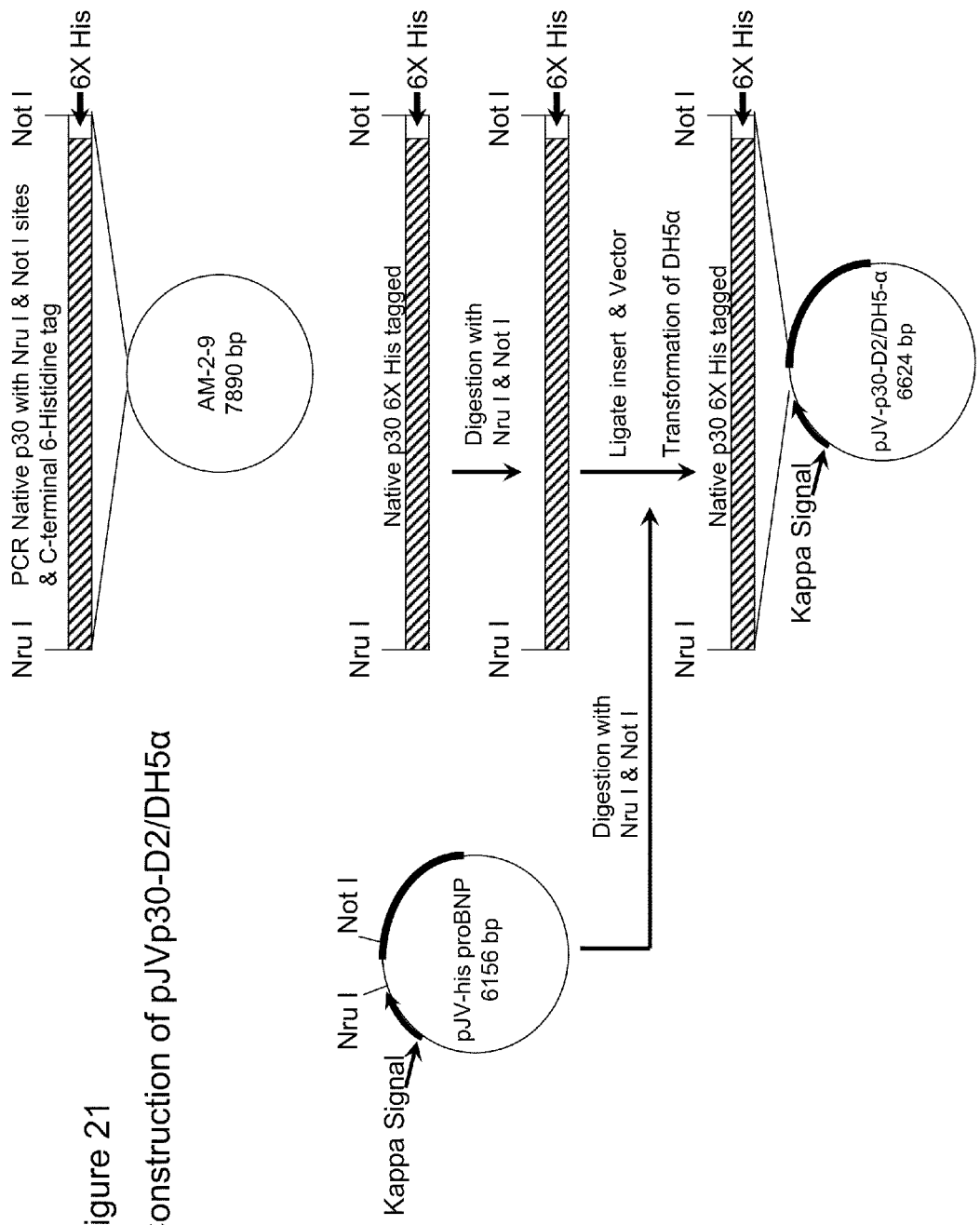
FIG. 21 shows construction of a plasmid clone carrying a native XMRV gag p30 gene for mammalian expression.

B. Construction of a Plasmid Clone (pJVp30-D2) Carrying a Native XMRV Gag p30 Gene for Mammalian Cell Expression A plasmid clone AM-2-9 encompassing the entire gag gene and 5' portion of the pol gene of XMRV strain VP62 was constructed as described by A. Urisman et al., *PloS Pathogens* 2:e25 (2006). An approximately 4 kb VP62 DNA insert was generated by RT-PCR of viral RNA and cloned into vector pCR2.1. As illustrated in FIG. 21, the full-length native gag p30 gene was amplified from AO-H4 plasmid DNA using the Qiagen (Qiagen, Valencia, Calif.) One-Step RT-PCR Kit according to the manufacturer's protocol and primers p30-F-NruI (SEQ ID NO: 103) and p30-R-NotI (SEQ ID NO: 104) to introduce enzyme restriction sites as well as six histidine residues at the C-terminus. Amplified product was analyzed by agarose gel electrophoresis and purified using QIAquick PCR Purification Kit (Qiagen). The Abbott Laboratories vector pJV-his-proBNP (Abbott Bioresearch Center, Worchester, Mass.) was used as the cloning vector for mammalian expression. The purified gag p30 PCR product and pJV-his-proBNP vector DNA were digested with Nru I and Not I, purified on Chroma Spin Columns, and ligated with T4 DNA ligase. The ligation product was transformed into DH5α competent cells, and the transformed cells were incubated at 37° C. on LB ampicillin agar plates. Individual colonies were screened by colony PCR using primers p30-F-NruI (SEQ ID NO: 103) and p30-R—NotI (SEQ ID NO: 104) to amplify the plasmid inserts. The amplified insert products were analyzed by agarose gel electrophoresis, purified using QIAquick PCR Purification Kit and sequenced with primers Vector2-F (SEQ ID NO: 94), Vector2-R (SEQ ID NO: 95), p30F-seq2 (SEQ ID NO: 105), p30R-seq2 (SEQ ID NO: 106), p30-F-NruI (SEQ ID NO: 103) and p30-R-NotI (SEQ ID NO: 104). Based on the sequencing results, a desired clone designated as pJVp30-D2 was identified. Miniprep plasmid DNA was prepared from an overnight culture of this clone, and the gag p30 gene insert was sequence verified. Colonies were restreaked three times for isolation and preparation of glycerol stocks.

The gag p30 plasmid construct for mammalian expression produces a recombinant protein pJVp30-D2/DH5α, the amino acid sequence of which is shown in SEQ ID NO: 107. The recombinant protein (pJVp30) encoded by pJVp30-D2/DH5α contains 22 amino acids of plasmid kappa signal sequence fused to 263 amino acids of gag p30 viral protein and six amino acids of histidine. SEQ ID NO: 108 shows the nucleotide sequence of the pJVp30 protein in clone pJVp30-D2/DH5α. The DNA sequence contains 66 base pairs from the plasmid kappa signal sequence followed by 789 base pairs of the gag p30 gene derived from native XMRV viral RNA and 18 base pairs of histidine. SEQ ID NO: 109 shows the expressed/processed gag p30 protein that contains 263 amino acids of gag p30 viral protein and six histidines.

EXAMPLE 19

Preparation and Purification of XMRV Recombinant Proteins Expressed in Mammalian Cells A. Preparation of Plasmid DNA from XMRV Constructs for Mammalian Expression One culture each of DH5α competent cells harboring pJV-his-proBNP-based env gp70 (pJVp70-E4) or gag p30 (pJVp30-D2) construct was prepared by inoculating one loop of glycerol stock into each of three tubes containing 10 ml LB Broth (Invitrogen) supplemented with 100 µg/ml ampicillin. The tubes were placed in a shaking orbital incubator and incubated overnight (~16 hours) at 37° C. Five ml of overnight culture was transferred to each of five sterile 2-liter shake flasks (Bellco, Vineland, N.J.) containing 500 ml of LB Broth 100 µg/ml ampicillin. The flasks were placed in a shaking orbital incubator and incubated overnight (~16 hours) at 37° C. Cells were harvested by centrifugation and the LB supernatant was discarded. Cell pellets were stored at −70° C. until further processing.

Frozen cell pellets were thawed, and plasmid DNA was prepared from 5 to 7 gm of cell paste using Endo Free Plasmid Giga Kit (Qiagen) according to instructions of the manufacturer. Plasmid DNA was stored at −20° C. until further use.

B. Transfection of HEK Mammalian cells with XMRV Recombinant Protein Constructs

HEK293 cells (Invitrogen) were resuspended in 1.2 Lt Freestyle 293 Expression Medium (Gibco) at a final concentration of $1 \times 10^6$ viable cells/ml. Cells were incubated for 3 hours on a shaker table at 100 rpm in a 37° C. incubator with 8% $CO_2$. A plasmid DNA:PEI complex was formed by combining 1.2 mg plasmid DNA in 15 ml transfection media 2.4 mg PEI in 15 ml transfection media. The complex was vortexed for 10 seconds, incubated at room temperature for 15 minutes and added to 1.2 Lt HEK293 cell suspension. In addition, 20% tryptone was added to achieve a final concentration of 0.5% in the cell suspension. Cells were incubated on a shaker table at 100 rpm in a 37° C. incubator with 8% $CO_2$ for four days. The cells were harvested by centrifugation at 8000 rpm for 20 minutes followed by filtration of the supernatant through a 0.22 micron filter and storage at 4° C. until protein purification.

C. Purification of XMRV Recombinant Proteins by His-Bind Nickel Affinity Chromatography XMRV env gp70 and gag p30 proteins were purified using fast protein liquid chromatography (FPLC) and binding of the C-terminal His tag to Ni-NTA superflow resin (Qiagen). A 10 ml column of His-bind resin was washed with 30 ml of water and 50 ml of imidazole buffer (20 mM imidazole, 50 mM $NaH_2PO_4$, 300 mM NaCl, 0.05% Tween 20, pH 8.0) at a flow rate of 1 ml/min. The 1.2 Lt filtered supernatant fluid from HEK293 cell culture was applied to the column at a flow rate of 1 ml/min followed by washing with 60 ml imidizole buffer. To elute the His-tagged protein, the column was washed with 25 ml of a 0-100% gradient of imidazole buffer (250 mM imidazole, 50 mM $NaH_2PO_4$, 300 mM NaCl, 0.05% Tween 20, pH 8.0) and 20 ml of 100% imidazole buffer at a flow rate of 1 ml/min and collection of 1 ml fractions. The column fractions were stored at 2-8° C. until protein analysis by SDS-polyacrylamide electrophoresis (SDS-PAGE). The column fractions containing recombinant proteins were pooled and dialyzed at 2-8° C. for 24 hours against a buffer of phosphate buffered saline (PBS; Invitrogen). The dialyzed solution containing the purified protein was aliquoted and stored at −20° C. for future use.

EXAMPLE 20

Figure 22:
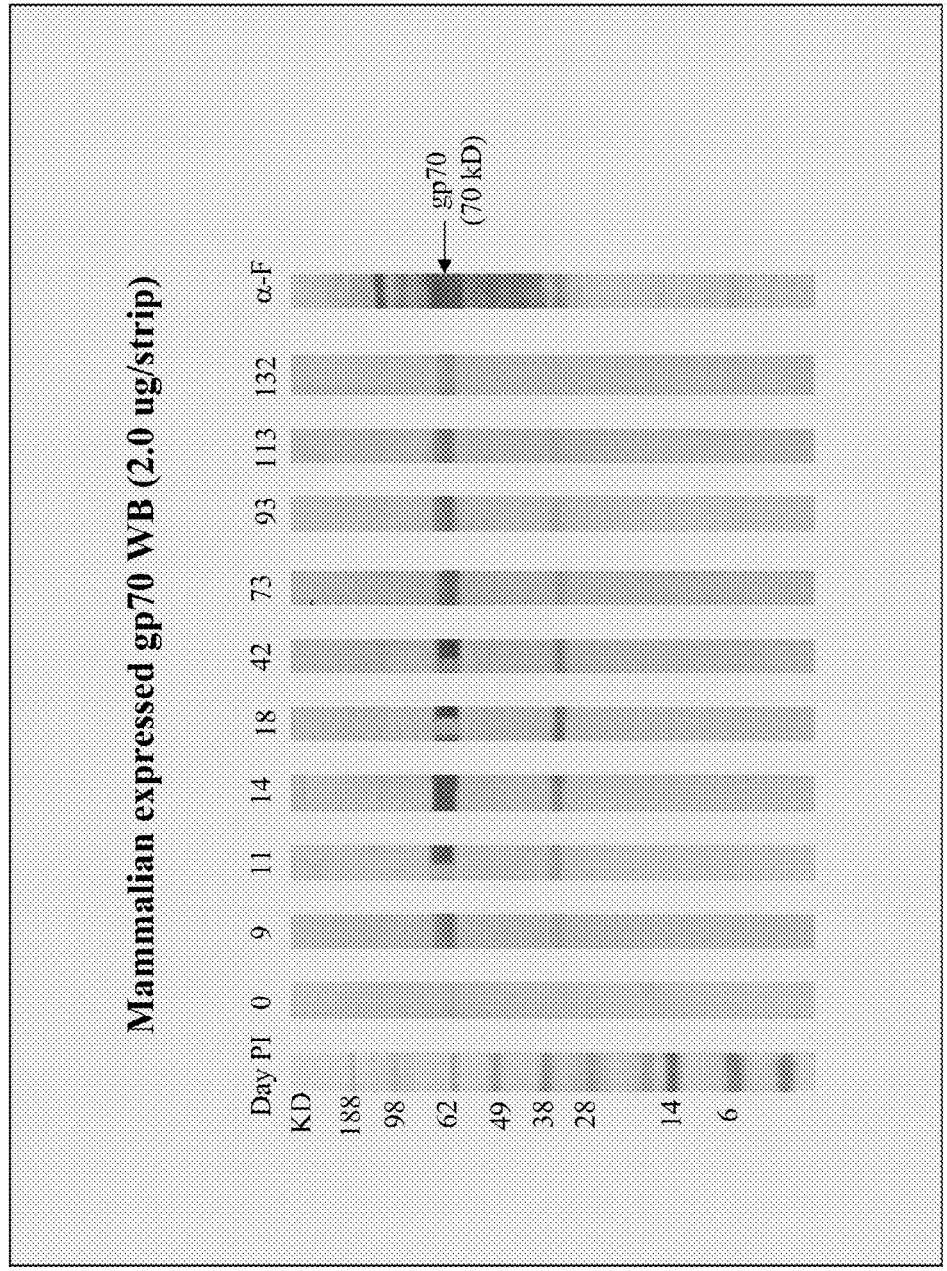
FIG. 22 shows the detection of IgG antibody responses in rhesus macaque RIl-10 by mammalian expressed XMRV gp70 protein-based Western Blot (WB). Plasma samples are listed on WB strips as PI days 0-132. Goat anti-Friend MuLV (α-F) was used as a positive control.

Characterization of XMRV Recombinant gp70 Protein Expressed in Mammalian Cells Using Western Blot Analysis The mammalian expressed gp70 (SEQ ID NO: 102) was used to detect an anti-gp70 response in plasma of XMRV inoculated rhesus macaque RIl-10 that could not be readily detected by native viral proteins due to interference of human cellular proteins. WB strips were prepared by electrophoresis of the gp70 proteins on a 4-12% NuPAGE Bis-Tris 2 dimension gel (Invitrogen) in the presence of SDS. The protein gel was electrophoretically transferred to a PDVF membrane. After blocking with buffer containing casein, the PDVF membrane was cut into 2 mm strips and stored at 2-8° C. WB was performed using the WesternBreeze Kit reagents (Invitrogen) per the manufacturer's instructions as described in Example 11. The gp70 protein strips were incubated overnight at 2-8° C. with 1.0 ml of primate plasma (diluted 1:250 in kit primary antibody diluent). After 4 successive 5 minute washes with kit antibody wash solution, the strips were then incubated with anti-human IgG Alkaline Phosphatase conjugate for 1 hour at room temperature. The strips were washed as described previously and chromogenic substrate solution was added to develop immunoreactive bands. FIG. 22 shows WB results for RIl-10 with the gp70 protein.

As compared to the E. coli expressed gp70-CKS (FIG. 10B), the mammalian expressed gp70 WB had substantially reduced background results with the RIl-10 samples. RIl-10 bleeds from days 9 to 132 PI showed a diffuse band at 70 kD, which is the monomer form of gp70 (strips 9-132 in FIG. 22). The weak minor band near 38 kD is likely due to reactivity with breakdown proteins of gp70. The specific binding to gp70 indicates that RIl-10 developed anti-gp70 specific antibodies in addition to the anti-p15E (FIG. 10A) and anti-p30 (FIG. 10C) antibodies observed after infection with XMRV. Moreover, these data indicate that the mammalian expressed gp70 may be advantageous relative to the E. coli expressed gp70-CKS for the detection of anti-gp70 specific antibody responses.

EXAMPLE 21

ARCHITECT® Chemiluminescent Immunoassay (CMIA) for Detection of Antibodies to XMRV 9p70 Protein (Sandwich Assay Format)

To improve detection sensitivity of anti-gp70 antibody response, the mammalian expressed env gp70 protein (SEQ ID NO: 102) was used to develop a direct double antigen sandwich assay on the automated ARCHITECT® instrument system (Abbott Laboratories, Abbott Park, Ill.). In order to enhance conjugate potency, the mammalian expressed gp70 protein was first biotinylated and subsequently incubated with chemiluminescent acridinium labeled streptavidin to form an avidin-biotin complex (ABC) gp70 conjugate. The ABC gp70 conjugate is comprised of multiple gp70 antigen and streptavidin complexes resulting in signal amplification and avidity improvement. In addition, a one-step assay format was designed for the gp70 ARCHITECT® CMIA that provided a longer incubation time of the ABC gp70 conjugate with anti-gp70 antibodies. In the ARCHITECT® gp70 CMIA protocol, sample (100 ul), ABC gp70 conjugate (50 ul) and paramagnetic microparticles (50 ul) are combined in one step. Anti-gp70 antibodies present in the sample simultaneously bind to the ABC gp70 conjugate and the gp70 antigen-coated paramagnetic particles. The microparticles are washed to remove unbound proteins and ABC gp70 conjugate. Following the wash cycle, alkaline hydrogen peroxide solution is added to release acridinium chemiluminescent signal. The intensity of the chemiluminescence, measured as relative light units (RLU), is proportional to the amount of anti-gp70 antibody captured by the gp70 recombinant protein.

Figure 23:
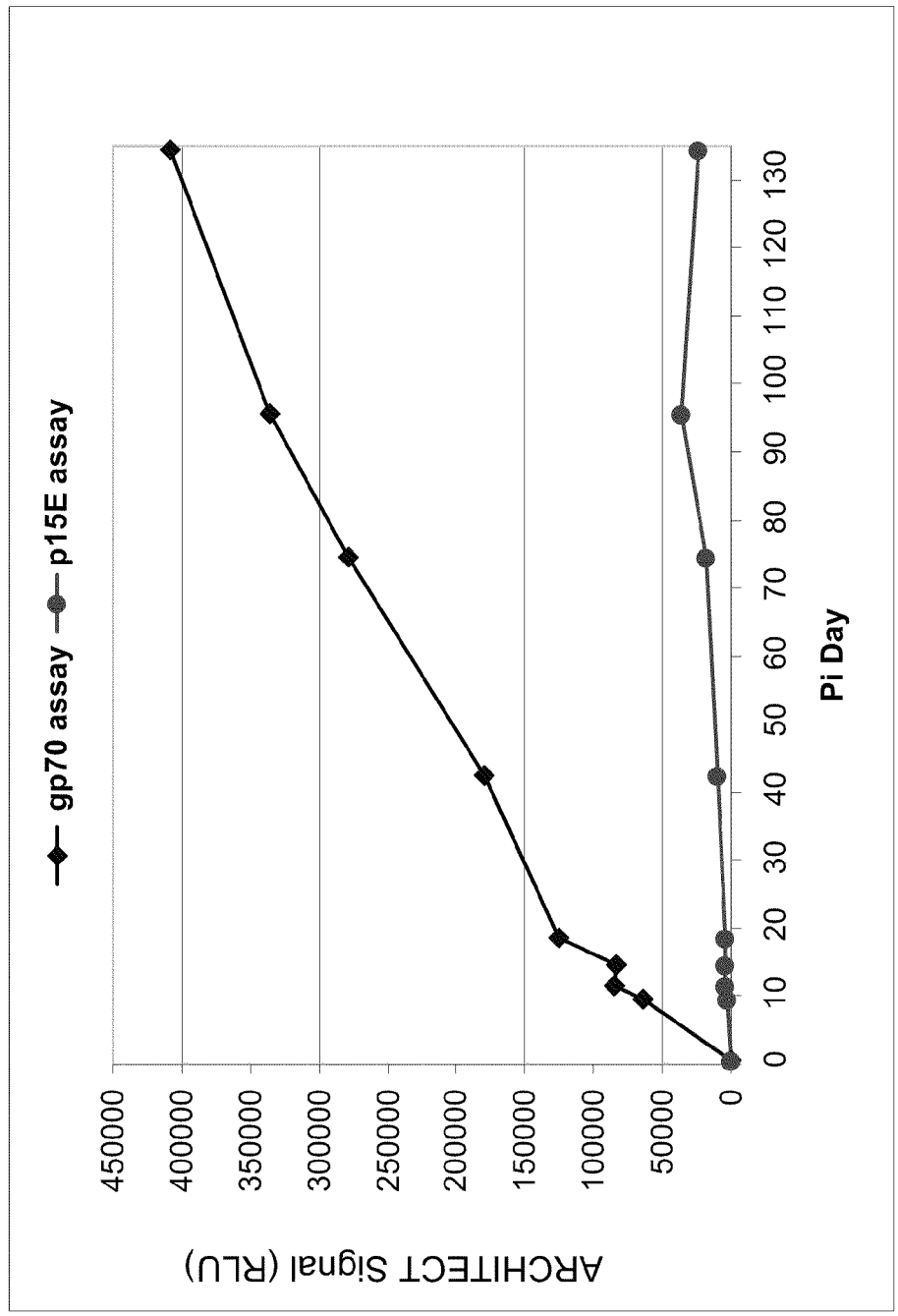
FIG. 23 compares anti-gp70 and anti-p15E responses in rhesus macaque RIl-10 using the direct gp70 and p15E ARCHITECT® CMIAs. Serial bleeds were diluted 1:10 in normal human plasma.

Sensitivity of the sandwich gp70 CMIA was evaluated with 1:10 dilutions of 8 serial bleeds from XMRV infected rhesus macaque RIl-10 (days 9, 11, 14, 18, 42, 73, 93, and 132 PI), summarized in FIG. 23. To facilitate comparison of the gp70 and p15E assays, direct p15E CMIA results obtained on the same 1:10 diluted serial bleeds were also plotted (FIG. 23). The gp70 sandwich assay format detected all 8 samples that were anti-gp70 and anti-p15E positive by WB. Compared to the direct p15E assay, the sandwich gp70 assay demonstrated approximately 10 to 28-fold higher signals on the serial bleeds and approximately 3-fold lower background signal on the pre-bleed (Day 0) sample. The combination of lower background and higher positive signal in the one-step gp70 CMIA contributes to a more sensitive assay than the p15E CMIA. It should be noted that the difference in signal intensity between the two CMIAs is likely due to assay design and may not reflect comparative antibody concentrations.

Figure 24:
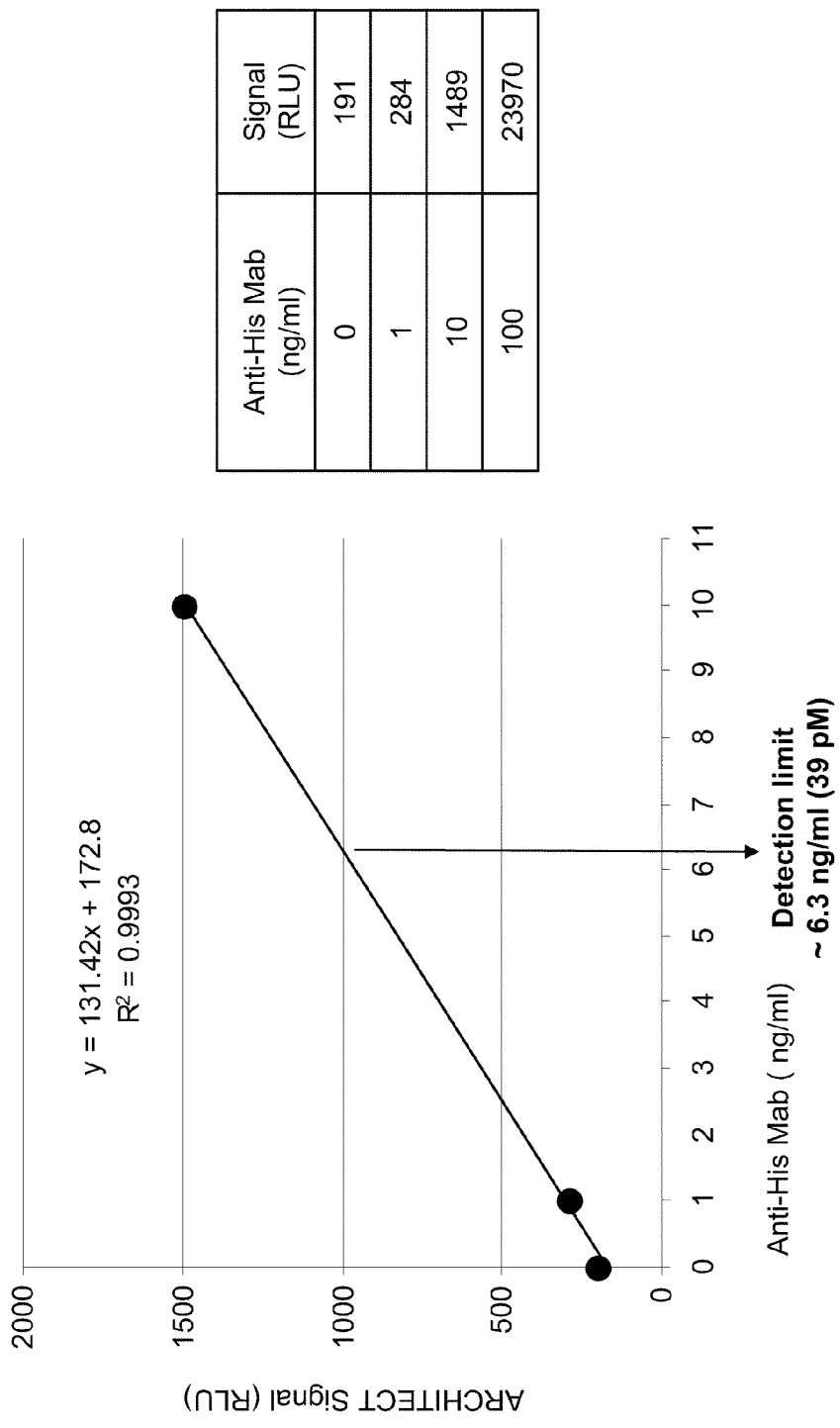
FIG. 24 shows detection of anti-His monoclonal antibody (Mab) in the gp70 ARCHITECT® CMIA. Anti-His Mab was diluted with normal human plasma to achieve concentrations of 100, 10, 1 and 0 ng/ml. By linear regression analysis using a cutoff of 1000 RLU (equivalent to background RLU+17 standard deviations), the detection limit was estimated at 6.3 ng/ml.

Since the recombinant gp70 protein contains a 6-histidine tag sequence, sensitivity of the sandwich gp70 CMIA was also quantified using anti-His monoclonal antibody (anti-His Mab, Abcam plc, Cambridge, UK). Anti-His Mab was diluted in normal human plasma at concentrations of 100, 10 and 1 ng/ml and tested in the one-step gp70 CMIA. As shown in FIG. 24, anti-His could be detected at a level of 6.3 ng/ml or 39 pM.

In addition, sensitivity of the sandwich gp70 CMIA on an alternative mammalian species was evaluated using goat polyclonal antibodies to Friend Murine Leukemia Virus (anti-MuLV pAb) obtained from ATCC (VR-1537AS-Gt™) and to envelope glycoprotein gp69/71 of Rauscher-MuLV (anti-Env pAb, ATCC, VR-1521). In the sandwich gp70 CMIA, the end-pint dilutions were 1:16,000 for anti-MuLV pAb and 1:10,000 for the ant-Env pAb. These data confirm that the sandwich gp70 CMIA is capable of detecting gp70 antibodies from an alternative mammalian species.

Figure 25:
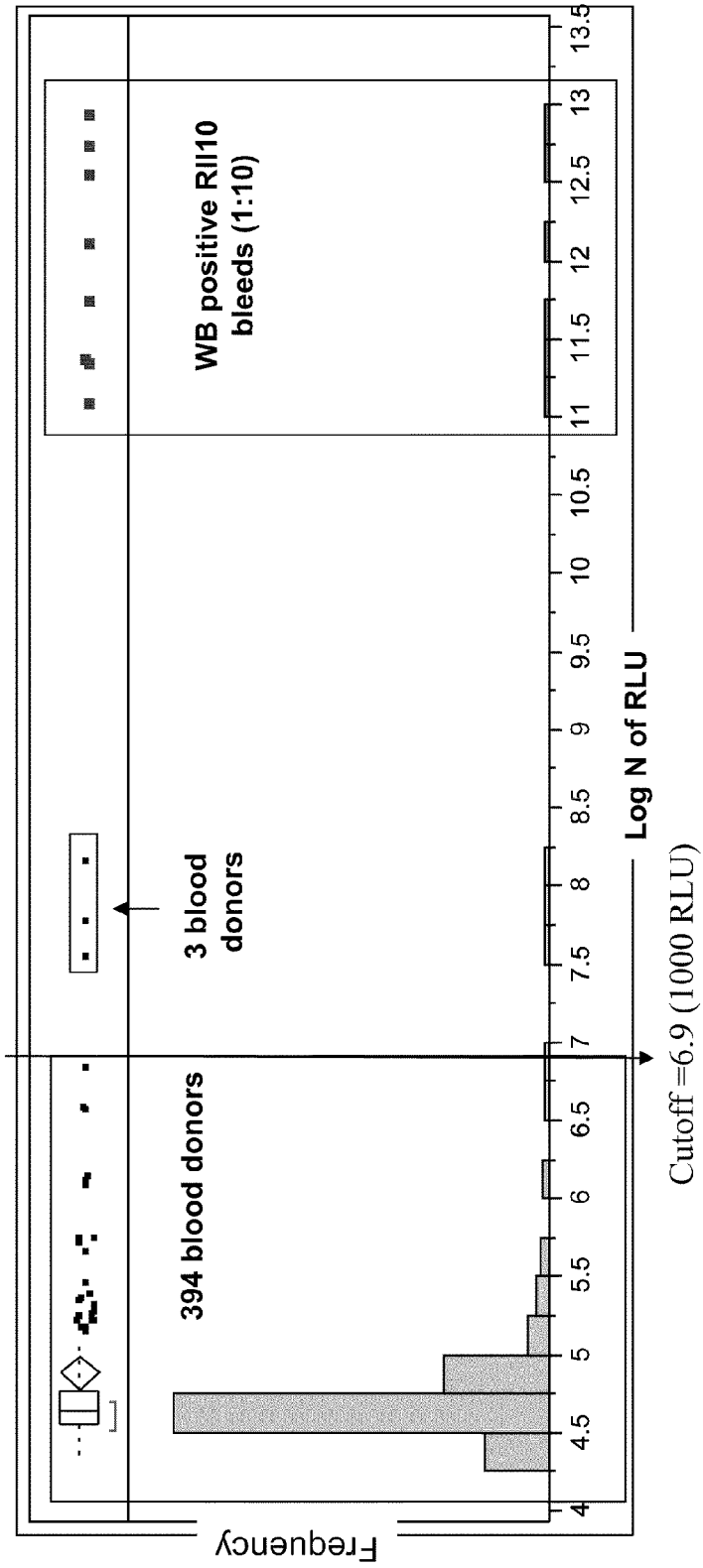
FIG. 25 shows the distribution of normal blood donors and XMRV WB positive primate bleeds tested in the direct gp70 sandwich CMIA assay.

Specificity of the sandwich gp70 CMIA assay was also evaluated on 397 blood donors (Gulf Coast Regional Blood Center). Three blood donors were above the assay cutoff value of 1000 RLU. One of the three CMIA reactive donor samples had WB confirmed specific gp70 reactivity. Excluding the WB confirmed sample, specificity of the direct gp70 CMIA assay was estimated at 99.5% (394/396). This assay also showed substantial discrimination between the blood donor negative population and the 1:10 dilutions of primate RIl-10 WB confirmed serial bleeds (FIG. 25). These data demonstrate the utility and value of the one-step gp70 CMIA for detection and screening of XMRV infection.

EXAMPLE 22

Figure 26:
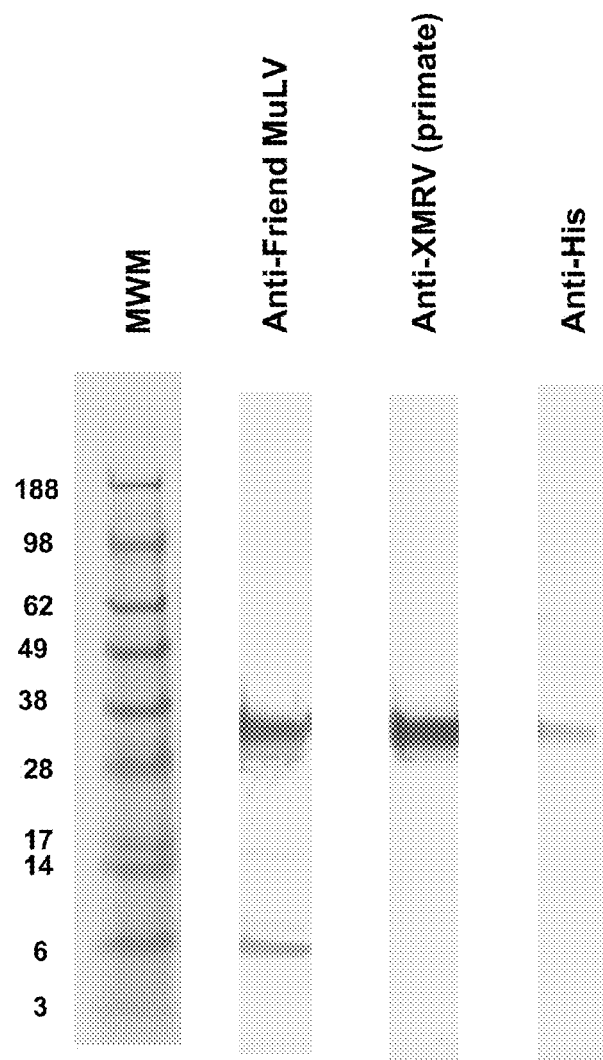
FIG. 26 shows the antibody reactivity of goat anti-MuLV pAb and anti-XMRV rhesus macaque RIl-10 plasma as well as mouse anti-His Mab by mammalian expressed XMRV p30 protein-based WB.

Characterization of XMRV Recombinant p30 Protein Expressed in Mammalian Cells Using Western Blot Analysis The mammalian expressed gag p30 (SEQ ID NO: 109) was used to detect anti-p30 reactivity in goat polyclonal antibody to Friend Murine Leukemia Virus (anti-MuLV pAb) obtained from ATCC (VR-1537AS-Gt™), plasma of XMRV inoculated rhesus macaque RIl-10 and mouse monoclonal antibody to histidine (anti-His Mab, Abcam). WB strips were prepared by electrophoresis of the p30 proteins on a 4-12% NuPAGE Bis-Tris (Invitrogen) in the presence of SDS. The protein gel was electrophoretically transferred to a PDVF membrane. WB was performed using the WesternBreeze Kit reagents (Invitrogen) per the manufacturer's instructions as described in Example 11. The PVDF membrane was divided and incubated for 1 hour at room temperature with either a 1:500 dilution of anti-MuLV pAb, a 1:250 dilution of anti-XMRV primate plasma RIl-10 or a 1:500 dilution of anti-His Mab (diluted in kit primary antibody diluent). After removing unbound protein by 4 successive 5 minute washes with kit antibody wash solution, the membranes were incubated with either anti-goat IgG Alkaline Phosphatase conjugate (goat anti-MuLV pAb WB), anti-human IgG Alkaline Phosphatase conjugate (anti-XMRV primate plasma RIl-10 WB) or anti-mouse IgG Alkaline Phosphatase conjugate (anti-His Mab WB) for 1 hour at room temperature. The blots were washed as described previously and chromogenic substrate solution was added to develop purple bands. FIG. 26 shows WB reactivity of all antisera with the p30 protein. These results demonstrate the utility of gag p30 protein as a diagnostic reagent for detection or confirmation of XMRV infection.

EXAMPLE 23

ARCHITECT® Chemiluminescent Immunoassay for Detection of Antibodies to p30 Protein of XMRV (Sandwich Assay Format)

A direct double antigen sandwich p30 assay was developed on the automated ARCHITECT® instrument system (Abbott Laboratories, Abbott Park, Ill.). The ARCHITECT® CMIA is a two-step immunoassay that utilizes two p30 antigens (i.e., p30-CKS=SEQ ID NO:67, and p30-PL=SEQ ID NO:73) to form a double antigen sandwich with the anti-p30 antibody. In the first step, sample (100 ul), assay diluent (50 ul) and paramagnetic microparticles (50 ul) are combined. Anti-p30 antibodies, present in the sample are captured on paramagnetic particles coated with p30-CKS recombinant protein. The microparticles are washed to remove unbound proteins. In the second step, anti-p30 antibodies captured by the microparticles are incubated with acridinium-labeled p30-PL recombinant antigen. Following an additional wash cycle, alkaline hydrogen peroxide solution is added to release acridinium chemiluminescence signal. The intensity of the chemiluminescence, measured as relative light unite (RLU), is proportional to the amount of anti-p30 antibody captured by the p30-CKS recombinant protein.

Sensitivity of the direct p30 CMIA was initially evaluated using serial 10-fold dilutions of monoclonal antibody to gag p30 MuLV (anti-p30 Mab, ATCC, CRL-1912) or H is (anti-His Mab, Abcam plc, Cambridge, UK). By linear regression, the detection limits were estimated to be 0.56 nM for the anti-p30 Mab and 1.18 nM for the anti-His Mab. Seroconversion sensitivity was subsequently evaluated with 9 serial bleeds of RIl-10 from days 14 to 158 post the 1$^{st}$ infection. Due to the delayed kinetics of the anti-p30 response, the assay failed to detect the two early bleeds (days 14 and 18). However, it detected the remaining 7 bleeds. An additional 16 serial bleeds from RIl-10 and RYh-10 (days 5 to 52 post the 2$^{nd}$ infection) were detected at a 1:10 dilution. Thus, the overall seroconversion sensitivity was 92% (23/25). In addition, the sandwich p30 CMIA showed excellent detection of anti-p30 antibody of the goat polyclonal antibody to Friend Murine Leukemia Virus (anti-MuLV pAb) obtained from ATCC (VR-1537AS-Gt™) with an end-point dilution at 1:64,000. As anticipated, the detection of mouse anti-p30 Mab and goat anti-MuLV pAb confirmed that the sandwich p30 CMIA is capable of detecting anti-p30 antibody from alternative mammalian species.

Specificity of the direct p30 CMIA was evaluated with 985 blood donor samples. Distribution of the assay values for the donor population had a mean of 420 RLU with SD of 195 RLU. Eight samples had values above the assay cutoff of 2000 RLU. Two of the 8 reactive donor samples had WB confirmed p30 reactivity. Excluding the 2 WB confirmed samples, specificity of the direct p30 CMIA was estimated at 99.4% (977/983).

Notably, the p30 assay detects antibody to the core protein distinct from envelope proteins, thus, has value for confirmation of XMRV infection.

What is claimed is:

1. An isolated human, chimeric or humanized antibody that selectively binds to a polypeptide consisting of an amino acid sequence selected from SEQ ID NO: 83, SEQ ID NO: 84, and SEQ ID NO: 85.

2. The isolated antibody of claim 1, wherein said antibody selectively binds a polypeptide consisting of SEQ ID NO: 83.

3. The isolated antibody of claim 1, wherein said antibody selectively binds a polypeptide consisting of SEQ ID NO: 84.

4. The isolated antibody of claim 1, wherein said antibody selectively binds a polypeptide consisting of SEQ ID NO: 85.

* * * * *